US011529395B2

(12) United States Patent
Chapman et al.

(10) Patent No.: US 11,529,395 B2
(45) Date of Patent: *Dec. 20, 2022

(54) TREATMENT OF GASTROINTESTINAL BLEEDING IN PATIENTS WITH SEVERE VON WILLEBRAND DISEASE BY ADMINISTRATION OF RECOMBINANT VWF

(71) Applicant: Takeda Pharmaceutical Company Limited, Osaka (JP)

(72) Inventors: Miranda Chapman, Wellesley, MA (US); Bruce Ewenstein, Brookline, MA (US); Bettina Ploder, Vienna (AT)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/108,562

(22) Filed: Dec. 1, 2020

(65) Prior Publication Data

US 2021/0169989 A1   Jun. 10, 2021

Related U.S. Application Data

(63) Continuation of application No. 16/802,118, filed on Feb. 26, 2020, now Pat. No. 10,905,746, which is a continuation of application No. 16/030,659, filed on Jul. 9, 2018, now Pat. No. 10,632,176.

(60) Provisional application No. 62/530,027, filed on Jul. 7, 2017.

(51) Int. Cl.
| | |
|---|---|
| *A61K 38/00* | (2006.01) |
| *A61K 38/37* | (2006.01) |
| *A61K 38/36* | (2006.01) |
| *A61P 7/04* | (2006.01) |

(52) U.S. Cl.
CPC .............. *A61K 38/37* (2013.01); *A61K 38/36* (2013.01); *A61P 7/04* (2018.01)

(58) Field of Classification Search
CPC .................................. A61K 38/37; A61P 7/04
See application file for complete search history.

(56) References Cited

U.S. PATENT DOCUMENTS

| | | | |
|---|---|---|---|
| 4,179,337 A | 12/1979 | Davis et al. |
| 4,301,144 A | 11/1981 | Iwashita et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 5,854,403 A | 12/1998 | Bernhard et al. |
| 6,531,577 B1 | 3/2003 | Kaergaard et al. |
| 7,005,502 B1 | 2/2006 | Schwarz et al. |
| 7,335,634 B2 | 2/2008 | Walter et al. |
| 8,173,597 B2 | 5/2012 | Schwarz et al. |
| 8,597,910 B1 | 12/2013 | Ginsburg et al. |
| 8,852,888 B2 | 10/2014 | Grillberger et al. |
| 9,409,971 B2 | 8/2016 | Grillberger et al. |
| 2005/0239171 A1 | 10/2005 | Mitterer et al. |
| 2006/0094104 A1 | 5/2006 | Grillberger et al. |
| 2006/0160948 A1 | 7/2006 | Scheiflinger et al. |
| 2007/0212770 A1 | 9/2007 | Grillberger et al. |
| 2008/0009040 A1 | 1/2008 | Grillberger et al. |
| 2010/0099603 A1 | 4/2010 | Schnecker et al. |
| 2010/0286047 A1 | 11/2010 | Kronthaler |
| 2012/0035110 A1 | 2/2012 | Grillberger et al. |
| 2012/0316116 A1 | 12/2012 | Scheiflinger et al. |
| 2016/0129090 A1 | 5/2016 | Schnecker et al. |
| 2019/0091299 A1 | 3/2019 | Chapman et al. |

FOREIGN PATENT DOCUMENTS

| | | |
|---|---|---|
| EP | 1593390 A1 | 11/2005 |
| JP | 2005/320330 A | 11/2005 |
| WO | WO 1986/006096 A1 | 10/1986 |
| WO | WO 1996/10584 A1 | 4/1996 |
| WO | WO 1997/034930 A1 | 9/1997 |
| WO | WO 1998/38219 A1 | 9/1998 |
| WO | WO 2005/012354 A1 | 2/2005 |
| WO | WO 2006/071801 A2 | 7/2006 |
| WO | WO 2008/151817 A1 | 12/2008 |
| WO | WO 2009/062100 A1 | 5/2009 |
| WO | WO 2009/086400 A3 | 7/2009 |
| WO | WO 2009/156137 A1 | 12/2009 |
| WO | WO 2011/017414 A2 | 2/2011 |
| WO | WO 2012/006591 A1 | 1/2012 |
| WO | WO 2019/010497 A1 | 1/2019 |

OTHER PUBLICATIONS

U.S. Appl. No. 13/493,926, filed Jun. 11, 2012.
U.S. Appl. No. 14/985,212, filed Dec. 30, 2015.
U.S. Appl. No. 16/030,653, filed Jul. 9, 2018.
U.S. Appl. No. 17/545,870, filed Dec. 8, 2021.
U.S. Appl. No. 16/030,659, filed Jul. 9, 2018.
U.S. Appl. No. 16/802,118, filed Feb. 26, 2020.
U.S. Appl. No. 17/108,562, filed Dec. 1, 2020.
U.S. Appl. No. 16/778,771, filed Jan. 31, 2020.
U.S. Appl. No. 17/362,191, filed Jun. 29, 2021.
"rVWF in Prophylaxis—Full Text View—ClinicalTrials.gov", Mar. 6, 2018, URL:https://clinicaltrials.gov/ct2/show/NCT02973087.
Abshire, T. C. "The Role of Prophylaxis in the Management of von Willebrand Disease: Today and Tomorrow." Thrombosis Research, vol. 124 Suppl 1, Nov. 2009, pp. S15-S19.
Abshire, T. C., et al. "Prophylaxis in Severe Forms of von Willebrand's Disease: Results from the von Willebrand Disease Prophylaxis Network (VWD PN)." Haemophilia: The Official Journal of the World Federation of Hemophilia, vol. 19, No. 1, Jan. 2013, pp. 76-81.

(Continued)

*Primary Examiner* — Jeanette M Lieb
(74) *Attorney, Agent, or Firm* — Morgan, Lewis & Bockius LLP

(57) ABSTRACT

The present invention relates to a method for treating gastrointestinal bleeding in a subject with severe von Willebrand Disease comprising administering to the subject at least one dose of recombinant von Willebrand Factor (rVWF) ranging from about 40 IU/kg to about 100 IU/kg, wherein the first dose further comprises recombinant Factor VIII (rFVIII).

20 Claims, 21 Drawing Sheets

Specification includes a Sequence Listing.

(56) References Cited

OTHER PUBLICATIONS

Abshire, T., et al. "Prophylaxis Escalation in Severe von Willebrand Disease: A Prospective Study from the von Willebrand Disease Prophylaxis Network." Journal of Thrombosis and Haemostasis: JTH, vol. 13, No. 9, Sep. 2015, pp. 1585-1589.

Abuchowski, A. et al., "Soluble Polymer-Enzyme Adducts," Chapter 13 in Enzymes as Drugs, Holcenberg, J.S. et al., ed., John Wiley and Sons, New York, 1981:367-383.

Andersson, L.-O. et al., "Isolation and characterization of human factor VIII: Molecular forms in commercial factor VIII concentrate, cryoprecipitate, and plasma," Proc. Natl. Acad. Sci. USA, May 1986, vol. 83, pp. 2979-2983.

Berntorp, E. "Prophylaxis in von Willebrand Disease." Haemophilia, vol. 14, No. s5, 2008, pp. 47-53.

Berntorp, E. et al., "Treatment and prevention of acute bleedings in von Willebrand disease—efficacy and safety of Wilate®, a new generation von Willebrand factor/factor VIII concentrate," Haemophilia, 2009;15(1):122-130.

Berntorp, E., "Prophylaxis and Treatment of Bleeding Complications in von Willebrand Disease Type 3." Seminars in Thrombosis and Hemostasis, vol. 32, No. 6, Sep. 2006, pp. 621-625.

Berntorp, E., et al. "Long-Term Prophylaxis in von Willebrand Disease." Blood Coagulation & Fibrinolysis, vol. 16, Apr. 2005, p. S23.

Brown, J.E. et al., "An ELISA test for the binding of von Willebrand antigen to collagen," Thromb. Res., 1986;43:303-311.

Carpenter, J.F. et al., "Interactions of Stabilizing Additives With Proteins During Freeze-Thawing and Freeze-Drying," Develop. Biol. Standard, 1991;225-239.

Castaman, G. et al., "von Willebrand's disease in the year 2003: towards the complete identification of gene defects for correct diagnosis and treatment," Haematological/Journal of Hematology, Jan. 2003, vol. 88, No. 1, pp. 94-108.

Chang, B.S. et al., "Development of a stable freeze-dried formulation of recombinant human interleukin-1 receptor antagonist," Pharm Res., 1996;13(2):243-249.

Chang, B.S. et al., "Surface-Induced Denaturation of Proteins during Freezing and its Inhibition by Surfactants," Pharm Sci., 1996;85(12):1325-1330.

Chen, B. et al., "Influence of calcium ions on the structure and stability of recombinant human deoxyribonuclease I in the aqueous and lyophilized states," Pharm. Sci., 1999;88(4):477-482.

Chen, B. et al., "Influence of histidine on the stability and physical properties of a fully human antibody in aqueous and solid forms," Pharm Res., 2003;20(12):1952-60.

Chen, T., "Formulation concerns of protein drugs," Drug Development and Industrial Pharmacy, 1992;18:1311-1354.

Cumming, A.M. et al., "Analysis of von Willebrand factor multimers using a commercially available enhanced chemiluminescence kit," J. Clin. Pathol., May 1993;46(5):470-473.

Denis, C.V. et al., "Clearance of von Willebrand factor," Thromb. Haemost., 2008, vol. 99, pp. 271-278.

Derrick, T.S. et al., "Effect of metal cations on the conformation and inactivation of recombinant human factor VIII," Pharm. Sci., 2004;93(10):2549-57.

Eikenboom, J. C., et al. "The inheritance and molecular genetics of von Willebrand's disease." Haemophilia : the official journal of the World Federation of Hemophilia vol. 1,2 (1995): 77-90.

Fatouros, A. et al., "Recombinant factor VIII SQ—influence of oxygen, metal ions, pH and ionic strength on its stability in aqueous solution," Int. J. Pharm., 1997;155:121-131.

Favaloro, E. J. "Towards Personalised Therapy for von Willebrand Disease: A Future Role for Recombinant Products." Blood Transfusion = Trasfusione Del Sangue, vol. 14, No. 2, 2016, pp. 262-276.

Favaloro, E.J. et al., "Collagen binding assay for von Willebrand factor (VWF:CBA):detection of von VVillebrands Disease (VWD), and discrimination of VWD subtypes, depends on collagen source," Thromb. Haemost., 2000;83:127-135.

Favaloro, E.J. et al., "Laboratory assays for von Willebrand factor: relative contribution to the diagnosis of von Willebrand's disease," Pathology, 1997;29(4):385-91.

Fernandes, A.I. et al., "Polysialyated asparaginase: preparation, activity and pharmacokinetics," Biochim. Biophys. Acta., 1997;1341:26-34.

Fijnvandraat, K. et al., "Inter-individual variation in half-life of infused recombinant factor VIII is related to pre-infusion von Willebrand factor antigen levels," British Journal of Haematology, 1995, vol. 91, pp. 474-476.

Fischer, B.E. et al., "Effect of Multimerization of Human Recombinant von Willebrand Factor on Platelet Aggregation, Binding to Collagen and Binding of Coagulation Factor VIII," Thrombosis Research, 1996, vol. 84, No. 1, pp. 55-66.

Fischer, B.E. et al., "Structural Analysis of Recombinant von Willebrand Factor Produced at Industrial Scale Fermentation of Transformed CHO Cells Co-Expressing Recombinant Furin," FEBS Letters, Nov. 20, 1995, vol. 375, pp. 259-262.

Fischer, B.E., "Recombinant von Willebrand factor: potential therapeutic use," Journal of Thrombosis and Thrombolysis, Jan. 1, 1999, vol. 8, pp. 197-205.

Franchini, M. et al., "Gastrointestinal angiodysplasia and bleeding in von Willebrand disease," Thromb Haemost., 2014;112(3):427-431.

Franchini, M. et al., "Von Willebrand disease-associated angiodysplasia: a few answers, still many questions," Br J Haemost., 2013;161(2):177-182.

Franchini, M. et al., "Von Willebrand factor (Vonvendi®): the first recombinant product licensed for the treatment of von Willebrand disease," Expert Rev Hematol., 2016;9(9):825-830.

GenBank Accession No. NM_000543, "*Homo sapiens* sphingomyelin phosphodiesterase 1 (SMPD1), transcript variant 1, mRNA," 2018, 5 pages.

GenBank Accession No. NM_000552, "*Homo sapiens* von Willebrand factor (VWF), mRNA," 2018, 10 pages.

Gill Joan Cox et al: "Recombinant Von Willebrand Factor Administration: Dosing Considerations and Rapid Stabilization of Endogenous Plasma FVIII Levels in Patients with Severe Von Willebrand Disease", XP002784853, Database accession No. REV201800668643 abstract, Blood, vol. 130, Suppl. 1, Dec. 7, 2017 (Dec. 7, 2017), p. 3682, 59th Annual Meeting of the American-Society-of-Hematology (ASH).

Gill, J.C. et al., "Hemostatic efficacy, safety, and pharmacokinetics of a recombinant von Willebrand factor in severe von Willebrand disease," Blood, 2015;126(17):2038-2046.

Hollander-Rodriguez, J.C. et al., "Hyperkalemia," Am. Fam. Physician., 2006;73(2):283-90.

International Search Report dated Sep. 7, 2012, for International Patent Application No. PCT/US2012/041957, 6 pages.

Kappelgaard, A.M. et al., "Liquid Growth Hormone: Preservatives and Buffers," Horm Res., 2004;3(suppl 1):98-103.

Keeling, D. et al., "Guideline on the selection and use of therapeutic products to treat hemophilia and other hereditary bleeding disorders," Haemophilia, 2008, vol. 14, pp. 671-684.

Lam, X.M. et al., "Antioxidants for Prevention of Methionine Oxidation in Recombinant Monoclonal Antibody HER2," J. Pharm. Sci., 1997;86(11):1250-5.

Lankhof, H. et al., "von Willebrand Factor without the A2 Domain Is Resistant to Proteolysis," Thromb. Haemost., 1997;77:1008-1013.

Laursen, T. et al., "Pain Perception after Subcutaneous Injections of Media Containing Different Buffers," Basic Clin Pharmacol Toxicol., 2006;98(2):21821.

Leebeek, F. W. G., et al. "Von Willebrand's Disease." The New England journal of medicine vol. 375,21 (2016): 2067-2080.

Macfarlane, D.E. et al., "Letter: A method for assaying von Willebrand factor (ristocetin cofactor)," Thromb. Diath. Haemorrh., 1975;34:306-308.

Mackenzie, A.P., "Non-equilibrium freezing behavior of aqueous systems," Phil Trans R Soc London, Ser B, Biol, 1977;278:167-189.

Mannucci, P. M., et al. "Proteolysis of von Willebrand Factor in Therapeutic Plasma Concentrates." Blood, vol. 83, No. 10, May 1994, pp. 3018-3027.

(56) References Cited

OTHER PUBLICATIONS

Mannucci, P.M. et al., "Laboratory monitoring of replacement therapy for major surgery in von Willebrand disease," Haemophilia, 2017, 23(2):182-187.
Mannucci, P.M. et al., "Pharmacokinetics and safety of a novel recombinant human von Willebrand factor manufactured with a plasma-free method: a prospective clinical trial," Blood, 2013;122(5):648-657.
Meulien, P. et al., "Processing and characterization of recombinant von Willebrand factor expressed in different cell types using a vaccinia virus vector," Thromb. Haemost., Jan. 23, 1992; 67(1):154-160.
Migneault, I. et al., "Glutaraldehyde: behavior in aqueous solution, reaction with proteins, and application to enzyme crosslinking," Biotechniques, 2004;37:790-802.
Minogue, S.C. et al., "Bacteriostatic Saline Containing Benzyl Alcohol Decreases the Pain Associated with the Injection of Propofol," Anesth Analg., 2005;100(3):683-6.
National Institutes of Health, Lung and Blood Institute, "The Diagnosis, Evaluation, and Management of von Willebrand Disease," NIH Publication No. 08-5832, Dec. 2007, 116 pages.
Nichols, W. L., et al. "Von Willebrand Disease (VWD): Evidence-Based Diagnosis and Management Guidelines, the National Heart, Lung, and Blood Institute (NHLBI) Expert Panel Report (USA)1." Haemophilia, vol. 14, No. 2, 2008, pp. 171-232.
Piétu, G. et al., "Production in *Escherichia coli* of a biologically active subfragment of von Willebrand factor corresponding to the platelet glycoprotein Ib, collagen and heparin binding domains," Biochem. Biophys. Res. Commun., 1989;164:1339-1347.
Randi, A.M. et al., "Von Willebrand factor and angiogenesis: basic and applied issues," J Thromb Haemost., 2017;15(1):13-20.
Randi, A.M., "Endothelial dysfunction in von Willebrand disease: angiogenesis and angiodysplasia," Thromb Res., 2016;141(suppl 2):S55-S58.
Reininger, A. J. "The Function of Ultra-Large von Willebrand Factor Multimers in High Shear Flow Controlled by ADAMTS13." Hamostaseologie, vol. 35, No. 3, 2015, pp. 225-233.
Remmele, R.L. Jr et al., "Minimization of Recombinant Human Flt3 Ligand Aggregation at the Tm Plateau: a Matter of Thermal Reversibility," Biochemistry, 1999;38(16):5241-7.
Remmele, R.L. Jr. et al., "Interleukin-1 receptor (IL-1R) liquid formulation development using differential scanning calorimetry," Pharm Res., 1998;15(2):2008.
Rodeghiero, F. et al., "Treatment of von Willebrand disease," Semin Heamtol., Jan. 2005;42(1):29-35.
Roy, S. et al., "Effects of Benzyl Alcohol on Aggregation of Recombinant Human Interleukin-1-Receptor Antagonist in Reconstituted Lyophilized Formulations," J Pharm Sci., 2005;94(2):382-96.
Sadler, J.E., "Biochemistry and Genetics of von Willebrand Factor," Annu. Rev. Biochem., 1998;67:395-424.
Saenko, E.L. et al., "Strategies towards a longer acting factor VIII," Haemophilia, 2006;12:42-51.
Schlokat, E. et al., "Production of Highly Homogenous and Structurally Intact Recombinant von Willebrand Factor Multimers by Furin-Mediated Propeptide Removal in Vitro," Dec. 1, 1996, vol. 24, Part 3, pp. 257-267.
Selvam, S. et al., "Angiodysplasia in von Willibrand Disease: Understanding the Clinical and Basic Science," Semin Thromb Hemost., 2017.
Singal et al., "Recombinant von Willebrand Factor: a first-of-its kind product for von Willebrand disease", Drugs of Today, Dec. 1, 2016 (Dec. 1, 2016), pp. 653-664.
Sobieraj, D.M. et al., "Venous Thromboembolism Prophylaxis in Orthopedic Surgery," Rockville (MD): Agency for Healthcare Research and Quality (US); Mar. 2012, Comparative Effectiveness Reviews, No. 49, 949 pages.
Tang, X. et al., "Design of freeze-drying processes for pharmaceuticals: practical advice," Pharm. Res., 2004;21:191-200.
Tomita, M. et al., "Sensitized photooxidation if histidine and its derivatives. Products and mechanism of the reaction," Biochemistry, 1969;8(12):5149-60.
Turecek, P.L. et al., "Biochemical and Functional Characterization of a Serum-Free rVWF Drug Candidate," Blood, Nov. 1, 2006, vol. 108, No. 11, p. 303A., Abstract.
Turecek, P.L. et al., "Biochemical and Functional Characterization of Chemically Modified Recombinant von Willebrand Factor (rVWF) as a Carrier Prolonging Survival of RFVIII in Hemophilia a Knock-Out Mice," J. Thromb. Haemost., Aug. 2007; vol. 5 Supplement 2: O-M-018, 3 pages.
Turecek, P.L. et al., "Comparative Study on Collagen-Binding Enzyme-Linked Immunosorbent Assay and Ristocetin Cofactor Activity Assays for Detection of Functional Activity of von Willebrand Factor," Semin. Thromb. Hemost., 2002;28:149-160.
Turecek, P.L. et al., "Development of a plasma- and albumin-free recombinant von Willebrand factor," Hamostaseologie, 2009;29(suppl 1):S32-38.
Turecek, P.L. et al., "In Vivo Characterization of Recombinant von Willebrand Factor in Dogs With von Willebrand Disease," Blood, Nov. 1, 1997, vol. 90, No. 9, pp. 3555-3567.
Turecek, P.L. et al., "PEG Modified rVWF Prolongs the Survival of Native rFVIII in Hemophilia A Knock-Out Mice," Blood, 2006, vol. 108: Abstract 1002, 1 page.
Turecek, P.L. et al., "Structure and Function of a Recombinant von Willebrand Factor Drug Candidate," Semin, Thromb. Hemost., 2010;36(5):510-521.
Turecek, P.L., "The role of ultralarge multimers in recombinant human von Willebrand factor—a review of physico- and biochemical studies and findings in in vivo models and in humans with von Willebrand disease," Hämostaseologie, 2017;37(suppl 1):S15-S25.
Van Wezel, A.L., "Growth of Cell-strains and Primary Cells on Micro-carriers in Homogeneous Culture," Nature, Oct. 7, 1967, vol. 216, pp. 64-65.
Varadi, K. et al., "In Vivo Cleavage of Recombinant VWF Upon Intravenous Administration in Preclinical and Clinical Setting," Blood, Nov. 1, 2011, vol. 118, No. 21, p. 549.
Veyradier, A. et al., "A Laboratory Phenotype/Genotype Correlation of 1167 French Patients From 670 Families With von Willebrand Disease: A New Epidemiologic Picture," Medicine, Mar. 2016;95(11):1-11.
Veyvondi Summary of Product Characteristics. European Medicines Agency. https://www.ema.europa.eu/en/documents/product-information/veyvondi-epar-product-information_en.pdf.
Vicky Mcdonald: "Inherited bleeding disorders", Medicine, Apr. 1, 2017 (Apr. 1, 2017), XP055507424.
Weiss, H.J. et al., "Quantitative Assay of a Plasma Factor Deficient in von Willebrand's Disease that is Necessary for Platelet Aggregation. Relationship to Factor VIII Procoagulant Activity and Antigen Content," J. Clin. Invest., 1973;52:2708-2716.
Wells, G. et al., "Safety, Effectiveness, and Cost-Effectiveness of New Oral Anticoagulants Compared with Warfarin in Preventing Stroke and Other Cardiovascular Events in Patients with Atrial Fibrillation," Ottawa(On): Canadian Agency for Drugs and Technologies in Health; Apr. 9, 2012, Clinical Review, 189 pages.
Wen, L.T. et al., "Chemiluminographic Detection of von Willebrand Factor Multimeric Composition," J. Clin. Lab. Anal., 1993;7:317-323.

BE=bleeding event; GI=gastrointestinal,
*4 patients experienced a total of 6 GI bleeds.

FIG. 2A

SEQ ID NO:1

```
agctcacagc tattgtggtg ggaaagggag ggtggttggt ggatgtcaca gcttgggctt      60
tatctccccc agcagtgggg actccacagc ccctgggcta cataacagca agacagtccg     120
gagctgtagc agacctgatt gagcctttgc agcagctgag agcatggcct agggtgggcg     180
gcaccattgt ccagcagctg agtttcccag ggaccttgga gatagccgca gccctcattt     240
gcagggaag atgattcctg ccagatttgc cggggtgctg cttgctctgg ccctcatttt      300
gccagggacc ctttgtgcag aaggaactcg cggcaggtca tccacgccc gatgcagcct      360
tttcggaagt gacttcgtca acacctttga tgggagcatg tacagctttg cgggatactg     420
cagttacctc ctggcagggg gctgccagaa acgctccttc tcgattattg gggacttcca     480
gaatggcaag agagtgagcc tctccgtgta tcttggggaa tttttttgaca tccatttgtt    540
tgtcaatggt accgtgacac aggggggacca aagagtctcc atgccctatg cctccaaagg    600
gctgtatcta gaaactgagg ctgggtacta caagctgtcc ggtgaggcct atggctttgt     660
ggccaggatc gatggcagcg gcaactttca agtcctgctg tcagacagat acttcaacaa     720
gacctgcggg ctgtgtggca acttttaacat ctttgctgaa gatgacttta tgacccaaga    780
agggaccttg acctcggacc cttatgactt tgccaactca tgggctctga gcagtggaga    840
acagtggtgt gaacggcat ctcctcccag cagctcatgc aacatctcct ctggggaaat      900
gcagaagggc ctgtgggagc agtgccagct tctgaagagc acctcggtgt tgcccgctg     960
ccaccctctg gtggacccg agccttttgt ggccctgtgt gagaagactt tgtgtgagtg     1020
tgctggggg ctggagtgcg cctgccctgc cctcctggag tacgcccgga cctgtgccca     1080
ggagggaatg gtgctgtacg gctggaccga ccacagcgcg tgcagcccag tgtgccctgc    1140
tggtatggag tataggcagt gtgtgtcccc ttgcgccagg acctgccaga gcctgcacat    1200
caatgaaatg tgtcaggagc gatgcgtgga tggctgcagc tgccctgagg acagctcct    1260
ggatgaaggc ctctgcgtgg agagcaccga gtgtcctgc gtgcattccg aaagcgcta    1320
ccctccggc acctccctct ctcgagactg caacacctgc atttgccgaa acagccagtg   1380
gatctgcagc aatgaagaat gtccagggga gtgccttgtc acaggtcaat cacacttcaa    1440
gagctttgac aacagatact tcaccttcag tgggatctgc cagtacctgc tggcccggga    1500
ttgccaggac cactccttct ccattgtcat tgagactgtc cagtgtgctg atgaccgcga    1560
cgctgtgtgc acccgctccg tcaccgtccg gctgcctggc ctgcacaaca gccttgtgaa    1620
actgaagcat ggggcaggag ttgccatgga tggccaggac gtccagctcc cctcctgaa    1680
aggtgacctc cgcatccagc atacagtgac ggcctccgtg cgcctcagct acggggagga    1740
cctgcagatg gactgggatg ccgcgggag gctgctggtg aagctgtccc cgtctatgc     1800
cgggaagacc tgcggcctgt gtgggaatta caatggcaac cagggcgacg acttccttac    1860
cccctctggg ctggcggagc cccggggtgga ggacttcggg aacgcctgga agctgcacgg    1920
ggactgccag gacctgcaga agcagcacag cgatccctgc gccctcaacc cgcgcatgac    1980
caggttctcc gaggaggcgt gcgcggtcct gacgtccccc acattcgagg cctgccatcg    2040
tgccgtcagc ccgctgccct acctgcggaa ctgccgctac gacgtgtgct cctgctcgga    2100
cggccgcgag tgcctgtgcg gcgccctggc cagctatgcc gcggcctgcg cggggagagg    2160
cgtgcgcgtc gcgtggcgcg agccaggccg ctgtgagctg aactgcccga aggccaggt    2220
gtacctgcag tgcgggaccc cctgcaacct gacctgccgc tctctctctt acccggatga    2280
ggaatgcaat gaggcctgcc tggagggctg cttctgcccc caggctct acatggatga     2340
gagggggggac tgcgtgccca aggcccagtg cccctgttac tatgacggtg agatcttcca    2400
gccagaagac atcttctcag accatcacac catgtgctac tgtgaggatg gcttcatgca    2460
ctgtaccatg agtggagtcc ccggaagctt gctgcctgac gctgtcctca gcagtcccct    2520
gtctcatcgc agcaaaagga gcctatcctg tcggccccccc atggtcaagc tggtgtgtcc    2580
cgctgacaac ctgcgggctg aagggctcga gtgtaccaaa acgtgccaga actatgacct    2640
ggagtgcatg agcatgggct gtgtctctgg ctgcctctgc ccccccggca tggtccggca    2700
tgagaacaga tgtgtggccc tggaaaggtg tccctgcttc catcagggca aggagtatgc    2760
ccctggagaa acagtgaaga ttggctgcaa cacttgtgtc tgtcgggacc ggaagtggaa    2820
ctgcacagac catgtgtgtg atgccacgtg ctccacgatc ggcatggccc actacctcac    2880
cttcgacggg ctcaaatacc tgttccccgg ggagtgccag tacgttctgg tgcaggatta    2940
ctgcggcagt aaccctggga cctttcggat cctagtgggg aataagggat gcagccaccc    3000
ctcagtgaaa tgcaagaaac gggtcaccat cctggtggag ggaggagaga ttgagctgtt    3060
tgacggggag gtgaatgtga agaggcccat gaaggatgag actcactttg aggtggtgga    3120
gtctggccgg tacatcattc tgctgctggg caaagccctc tccgtggtct ggaccgcca    3180
cctgagcatc tccgtggtcc tgaagcagac ataccaggag aaagtgtgtg gcctgtgtgg    3240
gaattttgat ggcatccaga caatgacct caccagcagc aacctccaag tggaggaaga    3300
ccctgtggac tttgggaact cctggaaagt gagctcgcag tgtgctgaca ccagaaaagt    3360
gcctctggac tcatcccctg ccacctgcca taacaacatc atgaagcaga cgatggtgga    3420
```

FIG. 2B

```
ttcctcctgt agaatcctta ccagtgacgt cttccaggac tgcaacaagc tggtggaccc    3480
cgagccatat ctggatgtct gcatttacga cacctgctcc tgtgagtcca ttggggactg    3540
cgcctgcttc tgcgacacca ttgctgccta tgcccacgtg tgtgcccagc atggcaaggt    3600
ggtgacctgg aggacggcca cattgtgccc ccagagctgc gaggagagga atctccggga    3660
gaacgggtat gagtgtgagt ggcgctataa cagctgtgca cctgcctgtc aagtcacgtg    3720
tcagcaccct gagccactgg cctgccctgt gcagtgtgtg gagggctgcc atgccactg     3780
ccctccaggg aaaatcctgg atgagctttt gcagacctgc gttgaccctg aagactgtcc    3840
agtgtgtgag gtggctggcc ggcgttttgc ctcaggaaag aaagtcacct tgaatcccag    3900
tgaccctgag cactgccaga tttgccactg tgatgttgtc aacctcacct gtgaagcctg    3960
ccaggagccg ggaggcctgg tggtgcctcc cacagatgcc ccggtgagcc ccaccactct    4020
gtatgtggag gacatctcgg aaccgccgtt gcacgatttc tactgcagca ggctactgga    4080
cctggtcttc ctgctggatg gctcctccag gctgtccgag gctgagtttg aagtgctgaa    4140
ggcctttgtg gtggacatga tggagcggct gcgcatctcc cagaagtggg tccgcgtggc    4200
cgtggtggag taccacgacg gctcccacgc ctacatcggg ctcaaggacc ggaagcgacc    4260
gtcagagctg cggcgcattg ccagccaggt gaagtatgcg ggcagccagg tggcctccac    4320
cagcgaggtc ttgaaataca cactgttcca aatcttcagc aagatcgacc gccctgaagc    4380
ctcccgcatc accctgctcc tgatggccag ccaggagccc aacggatgt cccggaactt     4440
tgtccgctac gtccagggcc tgaagaagaa gaaggtcatt gtgatcccgg tgggcattgg    4500
gccccatgcc aacctcaagc agatccgcct catcgagaag caggcccctg agaacaaggc    4560
cttcgtgctg agcagtgtgg atgagctgga gcagcaaagg gacgagatcg ttagctacct    4620
ctgtgacctt gcccctgaag cccctcctcc tactctgccc ccgacatgg cacaagtcac      4680
tgtgggccg gggctcttgg gggtttcgac cctggggccc aagaggaact ccatggttct      4740
ggatgtggcg ttcgtcctgg aaggatcgga caaaattggt gaagccgact caacaggag      4800
caaggagttc atggaggagg tgattcagcg gatggatgtg ggccaggaca gcatccacgt    4860
cacggtgctg cagtactcct acatggtgac tgtggagtac cccttcagcg aggcacagtc    4920
caaaggggac atcctgcagc gggtgcgaga gatccgctac cagggcggca acaggaccaa    4980
cactgggctg gccctgcggt acctctctga ccacagcttc ttggtcagcc agggtgaccg    5040
ggagcaggcg cccaacctgg tctacatggt caccggaaat cctgcctctg atgagatcaa    5100
gaggctgcct ggagacatcc aggtggtgcc cattggagtg ggcccaatg ccaacgtgca     5160
ggagctggag aggattggct ggcccaatgc cctatcctc atccaggact ttgagacgct     5220
ccccgagag gctcctgacc tggtgctgca gaggtgctgc tccggagagg gctgcagat     5280
cccccaccctc tccctgcac ctgactgcag ccagccctg gacgtgatcc ttctcctgga      5340
tggctcctcc agtttcccag cttcttattt tgatgaaatg aagagtttcg ccaaggcttt    5400
catttcaaaa gccaatatag gcctcgtct cactcaggtg tcagtgctgc agtatggaag     5460
catcaccacc attgacgtgc catggaacgt ggtcccggag aaagcccatt gctgagcct     5520
tgtggacgtc atgcagcggg agggaggccc cagccaaatc ggggatgcct tgggctttgc    5580
tgtgcgatac ttgacttcag aaatgcatgg tgccaggccg ggagcctcaa aggcggtggt    5640
catcctggtc acggacgtct ctgtggattc agtggatgca gcagctgatg ccgccaggtc    5700
caacagagtg acagtgttcc ctattggaat tggagatcgc tacgatgcag cccagctacg    5760
gatcttggca ggcccagcag gcgactccaa cgtggtgaag ctccagcgaa tcgaagacct    5820
ccctaccatg gtcaccttgg gcaattcctt cctccacaaa ctgtgctctg gatttgttag    5880
gatttgcatg gatgaggatg ggaatgagaa gaggcccggg gacgtctgga ccttgccaga    5940
ccagtgccac accgtgactt gccagccaga tggccagacc ttgctgaaga gtcatcgggt    6000
caactgtgac cgggggctga ggccttcgtg cctaacagc cagtccctg ttaaagtgga      6060
agagacctgt ggctgccgct ggacctgccc ctgcgtgtgc acaggcagct ccactcggca    6120
catcgtgacc tttgatgggc agaatttcaa gctgactggc agctgttctt atgtcctatt    6180
tcaaaacaag gagcaggacc tggaggtgat tctccataat ggtgcctgca gccctggagc    6240
aaggcagggc tgcatgaaat ccatcgaggt gaagcacagt gccctctccg tcgagctgca    6300
cagtgacatg gaggtgacgg tgaatgggag actggtctct gttccttacg tgggtgggaa    6360
catggaagtc aacgtttatg tgccatcat gcatgaggtc agattcaatc accttggtca    6420
catcttcaca ttcactccac aaaacaatga gttccaactg cagctcagcc caagactttt    6480
tgcttcaaag acgtatggtc tgtgtgggat ctgtgatgag aacggagcca atgacttcat    6540
gctgagggat ggcacagtca ccacagactg gaaaacactt gttcaggaat ggactgtgca    6600
gcggccaggg cagacgtgcc agcccatcct ggaggagcag tgtcttgtcc ccgacagctc    6660
ccactgccag gtcctcctct taccactgtt tgctgaatgc cacaaggtcc tggctccagc    6720
cacattctat gccatctgcc agcaggacag ttgccaccag gagcaagtgt gtgaggtgat    6780
cgcctcttat gcccacctct gtcggaccaa cggggtctgc gttgactgga gacacctga    6840
tttctgtgct atgtcatgcc caccatctct ggtctacaac cactgtgagc atggctgtcc    6900
ccggcactgt gatggcaacg tgagctcctg tgggaccat ccctccgaag gctgtttctg    6960
```

FIG. 2C

```
ccctccagat aaagtcatgt tggaaggcag ctgtgtccct gaagaggcct gcactcagtg    7020
cattggtgag gatggagtcc agcaccagtt cctggaagcc tgggtcccgg accaccagcc    7080
ctgtcagatc tgcacatgcc tcagcgggcg gaaggtcaac tgcacaacgc agccctgccc    7140
cacggccaaa gctcccacgt gtggcctgtg tgaagtagcc cgcctccgcc agaatgcaga    7200
ccagtgctgc cccgagtatg agtgtgtgtg tgacccagtg agctgtgacc tgccccagt     7260
gcctcactgt gaacgtggcc tccagcccac actgaccaac cctggcgagt gcagacccaa    7320
cttcacctgc gcctgcagga aggaggagtg caaaagagtg tccccaccct cctgccccc     7380
gcaccgtttg cccacccttc ggaagaccca gtgctgtgat gagtatgagt gtgcctgcaa    7440
ctgtgtcaac tccacagtga gctgtccct tgggtacttg gcctcaactg ccaccaatga     7500
ctgtggctgt accacaacca cctgccttcc cgacaaggtg tgtgtccacc gaagcaccat    7560
ctaccctgtg ggccagttct gggaggaggg ctgcgatgtg tgcacctgca ccgacatgga    7620
ggatgccgtg atgggcctcc gcgtggccca gtgctcccag aagccctgtg aggacagctg    7680
tcggtcgggc ttcacttacg ttctgcatga aggcgagtgc tgtggaaggt gcctgccatc    7740
tgcctgtgag gtggtgactg gctcaccgcg ggggactcc cagtcttcct ggaagagtgt     7800
cggctcccag tgggcctccc cggagaaccc ctgcctcatc aatgagtgtg tccgagtgaa    7860
ggaggaggtc tttatacaac aaaggaacgt ctcctgcccc cagctggagg tccctgtctg    7920
ccctcgggc tttcagctga gctgtaagac ctcagcgtgc tgcccaagct gtcgctgtga     7980
gcgcatggag gcctgcatgc tcaatggcac tgtcattggg cccgggaaga ctgtgatgat    8040
cgatgtgtgc acgacctgcc gctgcatggt gcaggtgggg gtcatctctg gattcaagct    8100
ggagtgcagg aagaccacct gcaaccctg cccctgggt tacaaggaag aaaataacac       8160
aggtgaatgt tgtgggagat gtttgcctac ggcttgcacc attcagctaa gaggaggaca    8220
gatcatgaca ctgaagcgtg atgagacgct ccaggatggc tgtgatactc acttctgcaa    8280
ggtcaatgag agaggagagt acttctggga aagagggtc acaggctgcc caccctttga     8340
tgaacacaag tgtctggctg agggaggtaa aattatgaaa attccaggca cctgctgtga    8400
cacatgtgag gagcctgagt gcaacgacat cactgccagg ctgcagtatg tcaaggtggg    8460
aagctgtaag tctgaagtag aggtggatat ccactactgc cagggcaaat gtgccagcaa    8520
agccatgtac tccattgaca tcaacgatgt gcaggaccag tgctcctgct gctctccgac    8580
acggacggag cccatgcagg tggccctgca ctgcaccaat ggctctgttg tgtaccatga    8640
ggttctcaat gccatggagt gcaaatgctc cccaggaag tgcagcaagt gaggctgctg      8700
cagctgcatg ggtgcctgct gctgcctgcc ttggcctgat ggccaggcca gagtgctgcc    8760
agtcctctgc atgttctgct cttgtgccct tctgagccca caataaaggc tgagctctta    8820
tcttgcaaaa ggc                                                        8833
```

FIG. 3A

SEQ ID NO:2

```
Met Ile Pro Ala Arg Phe Ala Gly Val Leu Leu Leu Ile Leu Pro Gly
1               5                   10                  15

Thr Leu Cys Ala Glu Gly Thr Arg Gly Arg Ser Ser Thr Ala Arg Cys
            20                  25                  30

Ser Leu Phe Gly Ser Asp Phe Val Asn Thr Phe Asp Gly Ser Met Tyr
        35                  40                  45

Ser Phe Ala Gly Tyr Cys Ser Tyr Leu Leu Ala Gly Gly Cys Gln Lys
    50                  55                  60

Arg Ser Phe Ser Ile Ile Gly Asp Phe Gln Asn Gly Lys Arg Val Ser
65                  70                  75                  80

Leu Ser Val Tyr Leu Gly Glu Phe Phe Asp Ile His Leu Phe Val Asn
                85                  90                  95

Gly Thr Val Thr Gln Gly Asp Gln Arg Val Ser Met Pro Tyr Ala Ser
            100                 105                 110

Lys Leu Glu Thr Glu Ala Gly Tyr Tyr Lys Leu Ser Gly Glu Ala Tyr
            115                 120                 125

Gly Phe Val Ala Arg Ile Asp Gly Ser Gly Asn Phe Gln Val Leu Leu
    130                 135                 140

Ser Asp Arg Tyr Phe Asn Lys Thr Cys Gly Leu Cys Gly Asn Phe Asn
145                 150                 155                 160

Ile Phe Ala Glu Asp Asp Phe Met Thr Gln Glu Gly Thr Leu Thr Ser
                165                 170                 175

Asp Pro Tyr Asp Phe Ala Asn Ser Trp Ala Leu Ser Ser Gly Glu Gln
            180                 185                 190

Trp Cys Glu Arg Pro Ser Ser Ser Cys Asn Ile Ser Ser Gly Glu Met
            195                 200                 205

Gln Lys Gly Leu Trp Glu Gln Cys Gln Leu Leu Lys Ser Thr Ser Val
            210                 215                 220

Phe Ala Arg Cys His Pro Leu Val Asp Pro Glu Pro Phe Cys Glu Lys
225                 230                 235                 240

Thr Leu Cys Glu Cys Ala Gly Gly Leu Glu Cys Ala Cys Pro Ala Leu
                245                 250                 255

Leu Glu Tyr Ala Arg Thr Cys Ala Gln Glu Gly Met Val Leu Tyr Gly
            260                 265                 270

Trp Thr Asp His Ser Ala Cys Ser Pro Val Cys Pro Ala Gly Met Glu
            275                 280                 285

Tyr Arg Gln Cys Val Ser Pro Cys Ala Arg Thr Cys Gln Ser Leu His
            290                 295                 300
```

FIG. 3B

```
Ile Asn Glu Met Cys Gln Glu Arg Cys Val Asp Gly Cys Ser Cys Pro
305                 310                 315                 320

Glu Gly Gln Leu Leu Asp Glu Gly Leu Cys Val Glu Ser Thr Glu Cys
                325                 330                 335

Pro Cys Val His Ser Gly Lys Arg Tyr Pro Pro Gly Thr Ser Leu Ser
                340                 345                 350

Arg Asp Cys Asn Thr Cys Ile Cys Arg Asn Ser Gln Trp Ile Cys Ser
                355                 360                 365

Asn Glu Glu Cys Pro Gly Glu Cys Leu Val Thr Gly Gln Ser His Phe
        370                 375                 380

Lys Ser Phe Asp Asn Arg Tyr Phe Thr Phe Ser Gly Ile Cys Gln Tyr
385                 390                 395                 400

Leu Leu Ala Arg Asp Cys Gln Asp His Ser Phe Ser Ile Val Ile Glu
                405                 410                 415

Thr Val Gln Cys Ala Asp Asp Arg Asp Ala Val Cys Thr Arg Ser Val
                420                 425                 430

Thr Val Arg Leu Pro Gly Leu His Asn Ser Leu Val Lys Leu Lys His
                435                 440                 445

Gly Ala Gly Val Ala Met Asp Gly Gln Asp Val Gln Leu Pro Leu Leu
        450                 455                 460

Lys Gly Asp Leu Arg Ile Gln His Thr Val Thr Ala Ser Val Arg Leu
465                 470                 475                 480

Ser Tyr Gly Glu Asp Leu Gln Met Asp Trp Asp Gly Arg Gly Arg Leu
                485                 490                 495

Leu Val Lys Leu Ser Pro Val Tyr Ala Gly Lys Thr Cys Gly Leu Cys
                500                 505                 510

Gly Asn Tyr Asn Gly Asn Gln Gly Asp Asp Phe Leu Thr Pro Ser Gly
                515                 520                 525

Leu Ala Glu Pro Arg Val Glu Asp Phe Gly Asn Ala Trp Lys Leu His
        530                 535                 540

Gly Asp Cys Gln Asp Leu Gln Lys Gln His Ser Asp Pro Cys Ala Leu
545                 550                 555                 560

Asn Pro Arg Met Thr Arg Phe Ser Glu Ala Cys Ala Val Leu Thr
                565                 570                 575

Ser Pro Thr Phe Glu Ala Cys His Arg Ala Val Ser Pro Leu Pro Tyr
                580                 585                 590

Leu Arg Asn Cys Arg Tyr Asp Val Cys Ser Cys Ser Asp Gly Arg Glu
                595                 600                 605

Cys Leu Cys Gly Ser Tyr Ala Ala Ala Cys Ala Gly Arg Gly Val Arg
        610                 615                 620
```

FIG. 3C

```
Val Ala Trp Arg Glu Pro Gly Arg Cys Glu Leu Asn Cys Pro Lys Gly
625                 630                 635                 640

Gln Val Tyr Leu Gln Cys Gly Thr Pro Cys Asn Leu Thr Cys Arg Ser
                645                 650                 655

Leu Ser Tyr Pro Asp Glu Glu Cys Asn Glu Ala Cys Leu Glu Gly Cys
                660                 665                 670

Phe Cys Pro Pro Met Asp Glu Arg Gly Asp Cys Val Pro Lys Ala Gln
            675                 680                 685

Cys Pro Cys Tyr Tyr Asp Gly Glu Ile Phe Gln Pro Glu Asp Ile Phe
        690                 695                 700

Ser Asp His His Thr Met Cys Tyr Cys Glu Asp Gly Phe Met His Cys
705                 710                 715                 720

Thr Met Ser Gly Val Pro Gly Ser Leu Leu Pro Asp Ala Val Leu Ser
                725                 730                 735

Ser Pro Leu Ser His Arg Ser Lys Arg Ser Leu Ser Cys Arg Pro Pro
                740                 745                 750

Met Val Lys Leu Val Cys Pro Ala Asp Asn Leu Arg Ala Glu Gly Leu
            755                 760                 765

Glu Cys Thr Lys Thr Cys Gln Asn Tyr Asp Leu Glu Cys Met Ser Met
        770                 775                 780

Gly Cys Val Ser Gly Cys Leu Cys Pro Pro Gly Met Val Arg His Glu
785                 790                 795                 800

Asn Arg Cys Glu Arg Cys Pro Cys Phe His Gln Gly Lys Glu Tyr Ala
                805                 810                 815

Pro Gly Glu Thr Val Lys Ile Gly Cys Asn Thr Cys Val Cys Arg Asp
            820                 825                 830

Arg Lys Trp Asn Cys Thr Asp His Val Cys Asp Ala Thr Cys Ser Thr
            835                 840                 845

Ile Gly Met Ala His Tyr Leu Thr Phe Asp Gly Leu Lys Tyr Leu Phe
    850                 855                 860

Pro Gly Glu Cys Gln Tyr Val Leu Val Gln Asp Tyr Cys Gly Ser Asn
865                 870                 875                 880

Pro Gly Thr Phe Arg Ile Leu Val Gly Asn Lys Gly Cys Ser His Pro
                885                 890                 895

Ser Val Lys Cys Lys Lys Arg Val Thr Ile Leu Val Glu Gly Gly Glu
                900                 905                 910

Ile Glu Leu Phe Asp Gly Glu Val Asn Val Lys Arg Pro Met Lys Asp
        915                 920                 925
```

FIG. 3D

```
Glu Thr His Phe Glu Val Val Glu Ser Gly Arg Tyr Ile Ile Leu Leu
    930             935             940
Leu Gly Lys Ala Leu Ser Val Val Trp Asp Arg His Leu Ser Ile Ser
945             950             955                 960
Val Val Leu Lys Gln Thr Tyr Gln Glu Lys Val Cys Gly Leu Cys Gly
            965             970                 975
Asn Phe Asp Gly Ile Gln Asn Asp Leu Thr Ser Ser Asn Leu Gln
        980             985             990
Val Glu Glu Asp Pro Val Asp Phe Gly Asn Ser Trp Lys Val Ser Ser
        995             1000            1005
Gln Cys Ala Asp Thr Arg Lys Val Pro Leu Asp Ser Ser Pro Ala
    1010            1015            1020
Thr Cys His Asn Asn Ile Met Lys Gln Thr Met Val Asp Ser Ser
    1025            1030            1035
Cys Arg Ile Leu Thr Ser Asp Val Phe Gln Asp Cys Asn Lys Leu
    1040            1045            1050
Val Asp Pro Glu Pro Tyr Leu Asp Val Cys Ile Tyr Asp Thr Cys
    1055            1060            1065
Ser Cys Glu Ser Ile Gly Asp Cys Ala Cys Phe Cys Asp Thr Ile
    1070            1075            1080
Ala Ala Tyr Ala His Val Cys Ala Gln His Gly Lys Val Val Thr
    1085            1090            1095
Trp Arg Thr Ala Thr Leu Cys Pro Gln Ser Cys Glu Glu Arg Asn
    1100            1105            1110
Leu Arg Glu Asn Gly Tyr Glu Cys Glu Trp Arg Tyr Asn Ser Cys
    1115            1120            1125
Ala Pro Ala Cys Gln Val Thr Cys Gln His Pro Glu Pro Leu Ala
    1130            1135            1140
Cys Pro Val Gln Cys Val Glu Gly Cys His Ala His Cys Pro Pro
    1145            1150            1155
Gly Lys Ile Leu Asp Glu Leu Leu Gln Thr Cys Val Asp Pro Glu
    1160            1165            1170
Asp Cys Pro Val Cys Glu Val Ala Gly Arg Arg Phe Ala Ser Gly
    1175            1180            1185
Lys Lys Val Thr Leu Asn Pro Ser Asp Pro Glu His Cys Gln Ile
    1190            1195            1200
Cys His Cys Asp Val Val Asn Leu Thr Cys Glu Ala Cys Gln Glu
    1205            1210            1215
Pro Gly Gly Leu Val Val Pro Pro Thr Asp Ala Pro Val Ser Pro
    1220            1225            1230
```

FIG. 3E

```
Thr Thr Leu Tyr Val Glu Asp Ile Ser Glu Pro Pro Leu His Asp
    1235            1240            1245
Phe Tyr Cys Ser Arg Leu Leu Asp Leu Val Phe Leu Leu Asp Gly
    1250            1255            1260
Ser Ser Arg Leu Ser Glu Ala Glu Phe Glu Val Leu Lys Ala Phe
    1265            1270            1275
Val Val Asp Met Met Glu Arg Leu Arg Ile Ser Gln Lys Trp Val
    1280            1285            1290
Arg Val Ala Val Val Glu Tyr His Asp Gly Ser His Ala Tyr Ile
    1295            1300            1305
Gly Leu Lys Asp Arg Lys Arg Pro Ser Glu Leu Arg Arg Ile Ala
    1310            1315            1320
Ser Gln Val Lys Tyr Ala Gly Ser Gln Val Ala Ser Thr Ser Glu
    1325            1330            1335
Val Leu Lys Tyr Thr Leu Phe Gln Ile Phe Ser Lys Ile Asp Arg
    1340            1345            1350
Pro Glu Ala Ser Arg Ile Thr Leu Leu Leu Met Ala Ser Gln Glu
    1355            1360            1365
Pro Gln Arg Met Ser Arg Asn Phe Val Arg Tyr Val Gln Gly Leu
    1370            1375            1380
Lys Lys Lys Lys Val Ile Val Ile Pro Val Gly Ile Gly Pro His
    1385            1390            1395
Ala Asn Leu Lys Gln Ile Arg Leu Ile Glu Lys Gln Ala Pro Glu
    1400            1405            1410
Asn Lys Ala Phe Val Leu Ser Ser Val Asp Glu Leu Glu Gln Gln
    1415            1420            1425
Arg Asp Glu Ile Val Ser Tyr Leu Cys Asp Leu Ala Pro Glu Ala
    1430            1435            1440
Pro Pro Pro Thr Leu Pro Pro Asp Met Ala Gln Val Thr Val Gly
    1445            1450            1455
Pro Gly Leu Leu Gly Val Ser Thr Leu Gly Pro Lys Arg Asn Ser
    1460            1465            1470
Met Val Leu Asp Val Ala Phe Val Leu Glu Gly Ser Asp Lys Ile
    1475            1480            1485
Gly Glu Ala Asp Phe Asn Arg Ser Lys Glu Phe Met Glu Glu Val
    1490            1495            1500
Ile Gln Arg Met Asp Val Gly Gln Asp Ser Ile His Val Thr Val
    1505            1510            1515
Leu Gln Tyr Ser Tyr Met Val Thr Val Glu Tyr Pro Phe Ser Glu
    1520            1525            1530
```

FIG. 3F

```
Ala Gln Ser Lys Gly Asp Ile Leu Gln Arg Val Arg Glu Ile Arg
    1535                1540                1545

Tyr Gln Gly Gly Asn Arg Thr Asn Thr Gly Leu Ala Leu Arg Tyr
    1550                1555                1560

Leu Ser Asp His Ser Phe Leu Val Ser Gln Gly Asp Arg Glu Gln
    1565                1570                1575

Ala Pro Asn Leu Val Tyr Met Val Thr Gly Asn Pro Ala Ser Asp
    1580                1585                1590

Glu Ile Lys Arg Leu Pro Gly Asp Ile Gln Val Val Pro Ile Gly
    1595                1600                1605

Val Gly Pro Asn Ala Asn Val Gln Glu Leu Glu Arg Ile Gly Trp
    1610                1615                1620

Pro Asn Ala Pro Ile Leu Ile Gln Asp Phe Glu Thr Leu Pro Arg
    1625                1630                1635

Glu Ala Pro Asp Leu Val Leu Gln Arg Cys Cys Ser Gly Glu Gly
    1640                1645                1650

Leu Gln Ile Pro Thr Leu Ser Pro Ala Pro Asp Cys Ser Gln Pro
    1655                1660                1665

Leu Asp Val Ile Leu Leu Leu Asp Gly Ser Ser Ser Phe Pro Ala
    1670                1675                1680

Ser Tyr Phe Asp Glu Met Lys Ser Phe Ala Lys Ala Phe Ile Ser
    1685                1690                1695

Lys Ala Asn Ile Gly Pro Arg Leu Thr Gln Val Ser Val Leu Gln
    1700                1705                1710

Tyr Gly Ser Ile Thr Thr Ile Asp Val Pro Trp Asn Val Val Pro
    1715                1720                1725

Glu Lys Ala His Leu Leu Ser Leu Val Asp Val Met Gln Arg Glu
    1730                1735                1740

Gly Gly Pro Ser Gln Ile Gly Asp Ala Leu Gly Phe Ala Val Arg
    1745                1750                1755

Tyr Leu Thr Ser Glu Met His Gly Ala Arg Pro Gly Ala Ser Lys
    1760                1765                1770

Ala Val Val Ile Leu Val Thr Asp Val Ser Val Asp Ser Val Asp
    1775                1780                1785

Ala Ala Ala Asp Ala Ala Arg Ser Asn Arg Val Thr Val Phe Pro
    1790                1795                1800

Ile Gly Ile Gly Asp Arg Tyr Asp Ala Ala Gln Leu Arg Ile Leu
    1805                1810                1815
```

FIG. 3G

Ala Gly Pro Ala Gly Asp Ser Asn Val Val Lys Leu Gln Arg Ile
1820                    1825                1830

Glu Asp Leu Pro Thr Met Val Thr Leu Gly Asn Ser Phe Leu His
1835                    1840                1845

Lys Leu Cys Ser Gly Phe Val Arg Ile Cys Met Asp Glu Asp Gly
1850                    1855                1860

Asn Glu Lys Arg Pro Gly Asp Val Trp Thr Leu Pro Asp Gln Cys
1865                    1870                1875

His Thr Val Thr Cys Gln Pro Asp Gly Gln Thr Leu Leu Lys Ser
1880                    1885                1890

His Arg Val Asn Cys Asp Arg Gly Leu Arg Pro Ser Cys Pro Asn
1895                    1900                1905

Ser Gln Ser Pro Val Lys Val Glu Glu Thr Cys Gly Cys Arg Trp
1910                    1915                1920

Thr Cys Pro Cys Val Cys Thr Gly Ser Ser Thr Arg His Ile Val
1925                    1930                1935

Thr Phe Asp Gly Gln Asn Phe Lys Leu Thr Gly Ser Cys Ser Tyr
1940                    1945                1950

Val Leu Phe Gln Asn Lys Glu Gln Asp Leu Glu Val Ile Leu His
1955                    1960                1965

Asn Gly Ala Cys Ser Pro Gly Ala Arg Gln Gly Cys Met Lys Ser
1970                    1975                1980

Ile Glu Val Lys His Ser Ala Leu Ser Val Glu Leu His Ser Asp
1985                    1990                1995

Met Glu Val Thr Val Asn Gly Arg Leu Val Ser Val Pro Tyr Val
2000                    2005                2010

Gly Gly Asn Met Glu Val Asn Val Tyr Gly Ala Ile Met His Glu
2015                    2020                2025

Val Arg Phe Asn His Leu Gly His Ile Phe Thr Phe Thr Pro Gln
2030                    2035                2040

Asn Asn Glu Phe Gln Leu Gln Leu Ser Pro Lys Thr Phe Ala Ser
2045                    2050                2055

Lys Thr Tyr Gly Leu Cys Gly Ile Cys Asp Glu Asn Gly Ala Asn
2060                    2065                2070

Asp Phe Met Leu Arg Asp Gly Thr Val Thr Thr Asp Trp Lys Thr
2075                    2080                2085

Leu Val Gln Glu Trp Thr Val Gln Arg Pro Gly Gln Thr Cys Gln
2090                    2095                2100

Pro Glu Gln Cys Leu Val Pro Asp Ser Ser His Cys Gln Val Leu
2105                    2110                2115

FIG. 3H

```
Leu Leu Pro Leu Phe Ala Glu Cys His Lys Val Leu Ala Pro Ala
    2120            2125            2130
Thr Phe Tyr Ala Ile Cys Gln Gln Asp Ser Cys His Gln Glu Gln
    2135            2140            2145
Val Cys Glu Val Ile Ala Ser Tyr Ala His Leu Cys Arg Thr Asn
    2150            2155            2160
Gly Val Cys Val Asp Trp Arg Thr Pro Asp Phe Cys Ala Met Ser
    2165            2170            2175
Cys Pro Pro Ser Leu Val Tyr Asn His Cys Glu His Gly Cys Pro
    2180            2185            2190
Arg His Cys Asp Gly Asn Val Ser Ser Cys Gly Asp His Pro Ser
    2195            2200            2205
Glu Gly Cys Phe Cys Pro Pro Asp Lys Val Met Leu Glu Gly Ser
    2210            2215            2220
Cys Val Pro Glu Glu Ala Cys Thr Gln Cys Ile Gly Glu Asp Gly
    2225            2230            2235
Val Gln His Gln Phe Leu Glu Ala Trp Val Pro Asp His Gln Pro
    2240            2245            2250
Cys Gln Ile Cys Thr Cys Leu Ser Gly Arg Lys Val Asn Cys Thr
    2255            2260            2265
Thr Gln Pro Cys Pro Thr Ala Lys Ala Pro Thr Cys Gly Leu Cys
    2270            2275            2280
Glu Val Ala Arg Leu Arg Gln Asn Ala Asp Gln Cys Cys Pro Glu
    2285            2290            2295
Tyr Glu Cys Val Cys Asp Pro Val Ser Cys Asp Leu Pro Pro Val
    2300            2305            2310
Pro His Cys Glu Arg Gly Leu Gln Pro Thr Leu Thr Asn Pro Gly
    2315            2320            2325
Glu Cys Arg Pro Asn Phe Thr Cys Ala Cys Arg Lys Glu Glu Cys
    2330            2335            2340
Lys Arg Val Ser Pro Pro Ser Cys Pro Pro His Arg Leu Pro Thr
    2345            2350            2355
Leu Arg Lys Thr Gln Cys Cys Asp Glu Tyr Glu Cys Ala Cys Asn
    2360            2365            2370
Cys Val Asn Ser Thr Val Ser Cys Pro Leu Gly Tyr Leu Ala Ser
    2375            2380            2385
Thr Ala Thr Asn Asp Cys Gly Cys Thr Thr Thr Thr Cys Leu Pro
    2390            2395            2400
```

FIG. 3I

```
Asp Lys Val Cys Val His Arg Ser Thr Ile Tyr Pro Val Gly Gln
    2405            2410                2415
Phe Trp Glu Glu Gly Cys Asp Val Cys Thr Cys Thr Asp Met Glu
    2420            2425                2430
Asp Ala Val Met Gly Leu Arg Val Ala Gln Cys Ser Gln Lys Pro
    2435            2440                2445
Cys Glu Asp Ser Cys Arg Ser Gly Phe Thr Tyr Val Leu His Glu
    2450            2455                2460
Gly Glu Cys Cys Gly Arg Cys Leu Pro Ser Ala Cys Glu Val Val
    2465            2470                2475
Thr Gly Ser Pro Arg Gly Asp Ser Gln Ser Ser Trp Lys Ser Val
    2480            2485                2490
Gly Ser Gln Trp Glu Asn Pro Cys Leu Ile Asn Glu Cys Val Arg
    2495            2500                2505
Val Lys Glu Glu Val Phe Ile Gln Gln Arg Asn Val Ser Cys Pro
    2510            2515                2520
Gln Leu Glu Val Pro Val Cys Pro Ser Gly Phe Gln Leu Ser Cys
    2525            2530                2535
Lys Thr Ser Ala Cys Cys Pro Ser Cys Arg Cys Glu Arg Met Glu
    2540            2545                2550
Ala Cys Met Leu Asn Gly Thr Val Ile Gly Pro Gly Lys Thr Val
    2555            2560                2565
Met Ile Asp Val Cys Thr Thr Cys Arg Cys Met Val Gln Val Gly
    2570            2575                2580
Val Ile Ser Gly Phe Lys Leu Glu Cys Arg Lys Thr Thr Cys Asn
    2585            2590                2595
Pro Cys Pro Leu Gly Tyr Lys Glu Glu Asn Asn Thr Gly Glu Cys
    2600            2605                2610
Cys Gly Arg Cys Leu Pro Thr Ala Cys Thr Ile Gln Leu Arg Gly
    2615            2620                2625
Gly Gln Ile Met Thr Leu Lys Arg Asp Glu Thr Leu Gln Asp Gly
    2630            2635                2640
Cys Asp Thr His Phe Cys Lys Val Asn Glu Arg Gly Glu Tyr Phe
    2645            2650                2655
Trp Glu Lys Arg Val Thr Gly Cys Pro Pro Phe Asp Glu His Lys
    2660            2665                2670
Cys Leu Ala Glu Gly Gly Lys Ile Met Lys Ile Pro Gly Thr Cys
    2675            2680                2685
Cys Asp Thr Cys Glu Glu Pro Glu Cys Asn Asp Ile Thr Ala Arg
    2690            2695                2700
```

FIG. 3J

```
Leu Gln  Tyr Val Lys Val Gly  Ser Cys Lys Ser Glu  Val Glu Val
    2705              2710              2715

Asp Ile  His Tyr Cys Gln Gly  Lys Cys Ala Ser Lys  Ala Met Tyr
    2720              2725              2730

Ser Ile  Asp Ile Asn Asp Val  Gln Asp Gln Cys Ser  Cys Cys Ser
    2735              2740              2745

Pro Thr  Arg Thr Glu Pro Met  Gln His Cys Thr Asn  Gly Ser Val
    2750              2755              2760

Val Tyr  His Glu Val Leu Asn  Ala Met Glu Cys Lys  Cys Ser Pro
    2765              2770              2775

Arg Lys  Cys Ser Lys
    2780
```

FIG. 4A

SEQ ID NO:3

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65              70                  75                      80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
            195                 200                 205

Val Val Trp Asp Arg His Leu Ser Ile Ser Val Val Leu Lys Gln Thr
            210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
            245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
            290                 295                 300

FIG. 4B

```
Phe Gln Asp Cys Asn Lys Leu Val Asp Pro Glu Pro Tyr Leu Asp Val
305                     310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
                340                 345                 350

Lys Val Val Thr Trp Arg Thr Ala Thr Leu Cys Pro Gln Ser Cys Glu
                355                 360                 365

Glu Arg Asn Leu Arg Glu Asn Gly Tyr Glu Cys Glu Trp Arg Tyr Asn
                370                 375                 380

Ser Cys Ala Pro Ala Cys Gln Val Thr Cys Gln His Pro Glu Pro Leu
385                     390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
                435                 440                 445

Val Thr Leu Asn Pro Ser Asp Pro Glu His Cys Gln Ile Cys His Cys
450                     455                 460

Asp Val Val Asn Leu Thr Cys Glu Ala Cys Gln Glu Pro Gly Gly Leu
465                     470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp Phe Tyr Cys Ser Arg Leu
                500                 505                 510

Leu Asp Leu Val Phe Leu Leu Asp Gly Ser Ser Arg Leu Ser Glu Ala
                515                 520                 525

Glu Phe Glu Val Leu Lys Ala Phe Val Val Asp Met Met Glu Arg Leu
                530                 535                 540

Arg Ile Ser Gln Lys Trp Val Arg Val Ala Val Val Glu Tyr His Asp
545                     550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
                580                 585                 590

Ser Thr Ser Glu Val Leu Lys Tyr Thr Leu Phe Gln Ile Phe Ser Lys
                595                 600                 605

Ile Asp Arg Pro Glu Ala Ser Arg Ile Thr Leu Leu Leu Met Ala Ser
610                     615                 620
```

FIG. 4C

```
Gln Glu Pro Gln Arg Met Ser Arg Asn Phe Val Arg Tyr Val Gln Gly
625                 630             635                 640

Leu Lys Lys Lys Lys Val Ile Val Ile Pro Val Gly Ile Gly Pro His
                645             650                 655

Ala Asn Leu Lys Gln Ile Arg Leu Ile Glu Lys Gln Ala Pro Glu Asn
            660             665             670

Lys Ala Phe Val Leu Ser Ser Val Asp Glu Leu Glu Gln Gln Arg Asp
        675             680             685

Glu Ile Val Ser Tyr Leu Cys Asp Leu Ala Pro Glu Ala Pro Pro Pro
    690             695             700

Thr Leu Pro Pro Asp Met Ala Gln Val Thr Val Gly Pro Gly Leu Leu
705             710             715                 720

Gly Val Ser Thr Leu Gly Pro Lys Arg Asn Ser Met Val Leu Asp Val
            725             730             735

Ala Phe Val Leu Glu Gly Ser Asp Lys Ile Gly Glu Ala Asp Phe Asn
            740             745             750

Arg Ser Lys Glu Phe Met Glu Glu Val Ile Gln Arg Met Asp Val Gly
        755             760             765

Gln Asp Ser Ile His Val Thr Val Leu Gln Tyr Ser Tyr Met Val Thr
    770             775             780

Val Glu Tyr Pro Phe Ser Glu Ala Gln Ser Lys Gly Asp Ile Leu Gln
785             790             795                 800

Arg Val Arg Glu Ile Arg Tyr Gln Gly Gly Asn Arg Thr Asn Thr Gly
                805             810             815

Leu Ala Leu Arg Tyr Leu Ser Asp His Ser Phe Leu Val Ser Gln Gly
            820             825             830

Asp Arg Glu Gln Ala Pro Asn Leu Val Tyr Met Val Thr Gly Asn Pro
        835             840             845

Ala Ser Asp Glu Ile Lys Arg Leu Pro Gly Asp Ile Gln Val Val Pro
    850             855             860

Ile Gly Val Gly Pro Asn Ala Asn Val Gln Glu Leu Glu Arg Ile Gly
865             870             875                 880

Trp Pro Asn Ala Pro Ile Leu Ile Gln Asp Phe Glu Thr Leu Pro Arg
                885             890             895

Glu Ala Pro Asp Leu Val Leu Gln Arg Cys Cys Ser Gly Glu Gly Leu
            900             905             910

Gln Ile Pro Thr Leu Ser Pro Ala Pro Asp Cys Ser Gln Pro Leu Asp
            915             920             925
```

FIG. 4D

```
Val Ile Leu Leu Leu Asp Gly Ser Ser Ser Phe Pro Ala Ser Tyr Phe
    930                 935                 940
Asp Glu Met Lys Ser Phe Ala Lys Ala Phe Ile Ser Lys Ala Asn Ile
945                 950                 955                 960
Gly Pro Arg Leu Thr Gln Val Ser Val Leu Gln Tyr Gly Ser Ile Thr
                965                 970                 975
Thr Ile Asp Val Pro Trp Asn Val Val Pro Glu Lys Ala His Leu Leu
            980                 985                 990
Ser Leu Val Asp Val Met Gln Arg Glu Gly Gly Pro Ser Gln Ile Gly
        995                 1000                1005
Asp Ala Leu Gly Phe Ala Val Arg Tyr Leu Thr Ser Glu Met His
    1010                1015                1020
Gly Ala Arg Pro Gly Ala Ser Lys Ala Val Val Ile Leu Val Thr
    1025                1030                1035
Asp Val Ser Val Asp Ser Val Asp Ala Ala Ala Asp Ala Ala Arg
    1040                1045                1050
Ser Asn Arg Val Thr Val Phe Pro Ile Gly Ile Gly Asp Arg Tyr
    1055                1060                1065
Asp Ala Ala Gln Leu Arg Ile Leu Ala Gly Pro Ala Gly Asp Ser
    1070                1075                1080
Asn Val Val Lys Leu Gln Arg Ile Glu Asp Leu Pro Thr Met Val
    1085                1090                1095
Thr Leu Gly Asn Ser Phe Leu His Lys Leu Cys Ser Gly Phe Val
    1100                1105                1110
Arg Ile Cys Met Asp Glu Asp Gly Asn Glu Lys Arg Pro Gly Asp
    1115                1120                1125
Val Trp Thr Leu Pro Asp Gln Cys His Thr Val Thr Cys Gln Pro
    1130                1135                1140
Asp Gly Gln Thr Leu Leu Lys Ser His Arg Val Asn Cys Asp Arg
    1145                1150                1155
Gly Leu Arg Pro Ser Cys Pro Asn Ser Gln Ser Pro Val Lys Val
    1160                1165                1170
Glu Glu Thr Cys Gly Cys Arg Trp Thr Cys Pro Cys Val Cys Thr
    1175                1180                1185
Gly Ser Ser Thr Arg His Ile Val Thr Phe Asp Gly Gln Asn Phe
    1190                1195                1200
Lys Leu Thr Gly Ser Cys Ser Tyr Val Leu Phe Gln Asn Lys Glu
    1205                1210                1215
Gln Asp Leu Glu Val Ile Leu His Asn Gly Ala Cys Ser Pro Gly
    1220                1225                1230
```

FIG. 4E

```
Ala Arg Gln Gly Cys Met Lys Ser Ile Glu Val Lys His Ser Ala
    1235            1240            1245

Leu Ser Val Glu Leu His Ser Asp Met Glu Val Thr Val Asn Gly
    1250            1255            1260

Arg Leu Val Ser Val Pro Tyr Val Gly Gly Asn Met Glu Val Asn
    1265            1270            1275

Val Tyr Gly Ala Ile Met His Glu Val Arg Phe Asn His Leu Gly
    1280            1285            1290

His Ile Phe Thr Phe Thr Pro Gln Asn Asn Glu Phe Gln Leu Gln
    1295            1300            1305

Leu Ser Pro Lys Thr Phe Ala Ser Lys Thr Tyr Gly Leu Cys Gly
    1310            1315            1320

Ile Cys Asp Glu Asn Gly Ala Asn Asp Phe Met Leu Arg Asp Gly
    1325            1330            1335

Thr Val Thr Thr Asp Trp Lys Thr Leu Val Gln Glu Trp Thr Val
    1340            1345            1350

Gln Arg Pro Gly Gln Thr Cys Gln Pro Ile Leu Glu Glu Gln Cys
    1355            1360            1365

Leu Val Pro Asp Ser Ser His Cys Gln Val Leu Leu Leu Pro Leu
    1370            1375            1380

Phe Ala Glu Cys His Lys Val Leu Ala Pro Ala Thr Phe Tyr Ala
    1385            1390            1395

Ile Cys Gln Gln Asp Ser Cys His Gln Glu Gln Val Cys Glu Val
    1400            1405            1410

Ile Ala Ser Tyr Ala His Leu Cys Arg Thr Asn Gly Val Cys Val
    1415            1420            1425

Asp Trp Arg Thr Pro Asp Phe Cys Ala Met Ser Cys Pro Pro Ser
    1430            1435            1440

Leu Val Tyr Asn His Cys Glu His Gly Cys Pro Arg His Cys Asp
    1445            1450            1455

Gly Asn Val Ser Ser Cys Gly Asp His Pro Ser Glu Gly Cys Phe
    1460            1465            1470

Cys Pro Pro Asp Lys Val Met Leu Glu Gly Ser Cys Val Pro Glu
    1475            1480            1485

Glu Ala Cys Thr Gln Cys Ile Gly Glu Asp Gly Val Gln His Gln
    1490            1495            1500

Phe Leu Glu Ala Trp Val Pro Asp His Gln Pro Cys Gln Ile Cys
    1505            1510            1515
```

FIG. 4F

Thr Cys Leu Ser Gly Arg Lys Val Asn Cys Thr Thr Gln Pro Cys
1520                    1525              1530

Pro Thr Ala Lys Ala Pro Thr Cys Gly Leu Cys Glu Val Ala Arg
1535                    1540              1545

Leu Arg Gln Asn Ala Asp Gln Cys Cys Pro Glu Tyr Glu Cys Val
1550                    1555              1560

Cys Asp Pro Val Ser Cys Asp Leu Pro Pro Val Pro His Cys Glu
1565                    1570              1575

Arg Gly Leu Gln Pro Thr Leu Thr Asn Pro Gly Glu Cys Arg Pro
1580                    1585              1590

Asn Phe Thr Cys Ala Cys Arg Lys Glu Glu Cys Lys Arg Val Ser
1595                    1600              1605

Pro Pro Ser Cys Pro Pro His Arg Leu Pro Thr Leu Arg Lys Thr
1610                    1615              1620

Gln Cys Cys Asp Glu Tyr Glu Cys Ala Cys Asn Cys Val Asn Ser
1625                    1630              1635

Thr Val Ser Cys Pro Leu Gly Tyr Leu Ala Ser Thr Ala Thr Asn
1640                    1645              1650

Asp Cys Gly Cys Thr Thr Thr Thr Cys Leu Pro Asp Lys Val Cys
1655                    1660              1665

Val His Arg Ser Thr Ile Tyr Pro Val Gly Gln Phe Trp Glu Glu
1670                    1675              1680

Gly Cys Asp Val Cys Thr Cys Thr Asp Met Glu Asp Ala Val Met
1685                    1690              1695

Gly Leu Arg Val Ala Gln Cys Ser Gln Lys Pro Cys Glu Asp Ser
1700                    1705              1710

Cys Arg Ser Gly Phe Thr Tyr Val Leu His Glu Gly Glu Cys Cys
1715                    1720              1725

Gly Arg Cys Leu Pro Ser Ala Cys Glu Val Val Thr Gly Ser Pro
1730                    1735              1740

Arg Gly Asp Ser Gln Ser Ser Trp Lys Ser Val Gly Ser Gln Trp
1745                    1750              1755

Ala Ser Pro Glu Asn Pro Cys Leu Ile Asn Glu Cys Val Arg Val
1760                    1765              1770

Lys Glu Glu Val Phe Ile Gln Gln Arg Asn Val Ser Cys Pro Gln
1775                    1780              1785

Leu Glu Val Pro Val Cys Pro Ser Gly Phe Gln Leu Ser Cys Lys
1790                    1795              1800

Thr Ser Ala Cys Cys Pro Ser Cys Arg Cys Glu Arg Met Glu Ala
1805                    1810              1815

FIG. 4G

```
Cys Met Leu Asn Gly Thr Val Ile Gly Pro Gly Lys Thr Val Met
    1820            1825            1830

Ile Asp Val Cys Thr Thr Cys Arg Cys Met Val Gln Val Gly Val
    1835            1840            1845

Ile Ser Gly Phe Lys Leu Glu Cys Arg Lys Thr Thr Cys Asn Pro
    1850            1855            1860

Cys Pro Leu Gly Tyr Lys Glu Glu Asn Asn Thr Gly Glu Cys Cys
    1865            1870            1875

Gly Arg Cys Leu Pro Thr Ala Cys Thr Ile Gln Leu Arg Gly Gly
    1880            1885            1890

Gln Ile Met Thr Leu Lys Arg Asp Glu Thr Leu Gln Asp Gly Cys
    1895            1900            1905

Asp Thr His Phe Cys Lys Val Asn Glu Arg Gly Glu Tyr Phe Trp
    1910            1915            1920

Glu Lys Arg Val Thr Gly Cys Pro Pro Phe Asp Glu His Lys Cys
    1925            1930            1935

Leu Ala Glu Gly Gly Lys Ile Met Lys Ile Pro Gly Thr Cys Cys
    1940            1945            1950

Asp Thr Cys Glu Glu Pro Glu Cys Asn Asp Ile Thr Ala Arg Leu
    1955            1960            1965

Gln Tyr Val Lys Val Gly Ser Cys Lys Ser Glu Val Glu Val Asp
    1970            1975            1980

Ile His Tyr Cys Gln Gly Lys Cys Ala Ser Lys Ala Met Tyr Ser
    1985            1990            1995

Ile Asp Ile Asn Asp Val Gln Asp Gln Cys Ser Cys Cys Ser Pro
    2000            2005            2010

Thr Arg Thr Glu Pro Met Gln Val Ala Leu His Cys Thr Asn Gly
    2015            2020            2025

Ser Val Val Tyr His Glu Val Leu Asn Ala Met Glu Cys Lys Cys
    2030            2035            2040

Ser Pro Arg Lys Cys Ser Lys
    2045            2050
```

TREATMENT OF GASTROINTESTINAL BLEEDING IN PATIENTS WITH SEVERE VON WILLEBRAND DISEASE BY ADMINISTRATION OF RECOMBINANT VWF

CROSS-REFERENCE TO RELATED APPLICATIONS

This application is a continuation of U.S. patent application Ser. No. 16/802,118 filed Feb. 26, 2020, which is a continuation of U.S. patent application Ser. No. 16/030,659 filed Jul. 9, 2018, which claims priority to U.S. Provisional Patent Application No. 62/530,027, filed on Jul. 7, 2017, which is hereby incorporated by reference in its entirety.

REFERENCE TO A "SEQUENCE LISTING," A TABLE, OR A COMPUTER PROGRAM, LISTING APPENDIX SUBMITTED ON A COMPACT DISK

This disclosure incorporates by reference the Sequence Listing text copy submitted herewith via EFS-Web, which was created on Feb. 18, 2021, entitled 008073-5201-US02_Sequence_Listing.txt which is 78,326 bytes in size.

BACKGROUND OF THE INVENTION

Coagulation diseases, such as von Willebrand Disease (VWD) generally result from a deficiency in the coagulation cascade. von Willebrand Disease (VWD) refers to the group of diseases caused by a deficiency of von Willebrand factor. Von Willebrand factor helps blood platelets clump together and stick to the blood vessel wall, which is necessary for normal blood clotting.

von Willebrand disease (VWD) is the most common inherited bleeding disorder, with an estimated prevalence rate of 1% (Veyradier A, et al., Medicine (Baltimore). 2016, 95(11):e3038). However, excluding milder forms of the disease, only about 1/10,000 patients actually require treatment. Current treatment for these coagulopathies includes a replacement therapy using pharmaceutical preparations comprising the normal coagulation factor.

VWF is a glycoprotein circulating in plasma as a series of multimers ranging in size from about 500 to 20,000 kD. The full length of cDNA of VWF has been cloned; the propolypeptide corresponds to amino acid residues 23 to 764 of the full length prepro-VWF (Eikenboom et al (1995) Haemophilia 1, 77 90). Multimeric forms of VWF are composed of 250 kD polypeptide subunits linked together by disulfide bonds. VWF mediates the initial platelet adhesion to the sub-endothelium of the damaged vessel wall, with the larger multimers exhibiting enhanced hemostatic activity. Multimerized VWF binds to the platelet surface glycoprotein Gp1bα, through an interaction in the A1 domain of VWF, facilitating platelet adhesion. Other sites on VWF mediate binding to the blood vessel wall. Thus, VWF forms a bridge between the platelet and the vessel wall that is essential to platelet adhesion and primary hemostasis under conditions of high shear stress. Normally, endothelial cells secrete large polymeric forms of VWF and those forms of VWF that have a lower molecular weight arise from proteolytic cleavage. The multimers of exceptionally large molecular masses are stored in the Weibel-Pallade bodies of the endothelial cells and liberated upon stimulation by agonists such as thrombin and histamine.

For patients with VWD, it is recommended that they be treated with von Willebrand factor (VWF) replacement given the need for prolonged hemostasis, particularly in major surgery (Mannucci P M and Franchini M., Haemophilia, 2017, 23(2):182-187; National Institutes of Health. National Heart, Lung, and Blood Institute. The Diagnosis, Evaluation, and Management of von Willebrand Disease NIH Publication No. 08-5832; December, 2007). Plasma-derived VWF therapies contain factor VIII (FVIII) and have the potential for FVIII accumulation with repeated dosing. VONVENDI® (von Willebrand factor [recombinant], Shire, Westlake Village, Calif.) is the first and only recombinant VWF (rVWF) concentrate (Turecek P L, et al. Hamostaseologie. 2009; 29(suppl 1):S32-38; Mannucci P M, et al. Blood, 2013; 122(5):648-657; Gill J C, et al. Blood, 2015; 126(17):2038-2046).

Gastrointestinal (GI) bleeding events occur in up to 20% of patients with von Willebrand disease (VWD) and have been observed in association with angiodysplastic lesions in 2%-4% of patients with VWD. GI bleeds are closely associated with the absence of higher molecular weight and ultra-large multimers (ULMs) of von Willebrand factor (VWF), which are most often seen in patients with type 2A and type 3 VWD. Higher doses and longer durations of therapy with plasma-derived VWF replacement concentrates are usually needed to resolve GI bleeds compared with bleeds at other sites, and treatment may still be unsuccessful.

BRIEF SUMMARY OF THE INVENTION

The present invention provides a method for treating gastrointestinal bleeding in a patient with severe von Willebrand Disease (VWD). The method comprises administering to the subject at least one dose of recombinant von Willebrand Factor (rVWF) ranging from about 40 IU/kg to about 100 IU/kg, wherein the first dose further comprises recombinant Factor VIII (rFVIII).

In some embodiments, the rFVIII is administered at a dose of about 20 IU/kg to about 50 IU/kg.

In some embodiments, the method further comprises administering to the subject a second dose of recombinant von Willebrand Factor (rVWF) ranging from about 40 IU/kg to about 100 IU/kg, wherein the second dose does not comprise recombinant Factor VIII (rFVIII).

In some embodiments, the rVWF to FVIII ratio is about 1.5:0.8. In some embodiments, the rVWF to FVIII ratio is about 1.3:1. In some embodiments, the rVWF to FVIII ratio is about 1.1:0.8. In some embodiments, the rVWF to FVIII ratio is about 1.5:1. In some embodiments, the rVWF to FVIII ratio is about 1.1:1.2.

In some embodiments, the rVWF is administered every 8 to 12 hours.

In some embodiments, the 40-60 IU/kg rVWF of said rVWF is administered and wherein said gastrointestinal bleeding is minor or moderate gastrointestinal bleeding.

In some embodiments, the 40-80 IU/kg rVWF of said rVWF and wherein said gastrointestinal bleeding is major or severe gastrointestinal bleeding.

In some embodiments, the rVWF is administered every 8 to 12 hours for about 3 days to about 7 days.

In some embodiments, the 40-60 IU/kg rVWF of said rVWF is administered every 8 to 12 hours for about 3 days to about 7 days, wherein said gastrointestinal bleeding is minor or moderate gastrointestinal bleeding.

In some embodiments, the 40-80 IU/kg rVWF of said rVWF is administered every 8 to 12 hours for about 3 days to about 7 days, wherein said gastrointestinal bleeding is major or severe gastrointestinal bleeding.

In some embodiments, the subject has Type 3 VWD. In some embodiments, the subject has severe type 1 VWD. In some embodiments, the subject has severe type 2 VWD.

In some embodiments, the e subject had been treated for at least 1 bleeding event within the previous 12 months. In some embodiments, the subject had been treated for more than 1 bleeding event within the previous 12 months.

Other objects, advantages and embodiments of the invention will be apparent from the detailed description following.

BRIEF DESCRIPTION OF THE DRAWINGS

FIG. 2A-2C show the nucleic acid sequence of VWF.

FIG. 3A-3J show the amino acid sequence of VWF.

FIG. 4A-4G show the amino acid sequence of mature VWF.

DETAILED DESCRIPTION OF THE INVENTION

Introduction

Figure 1:
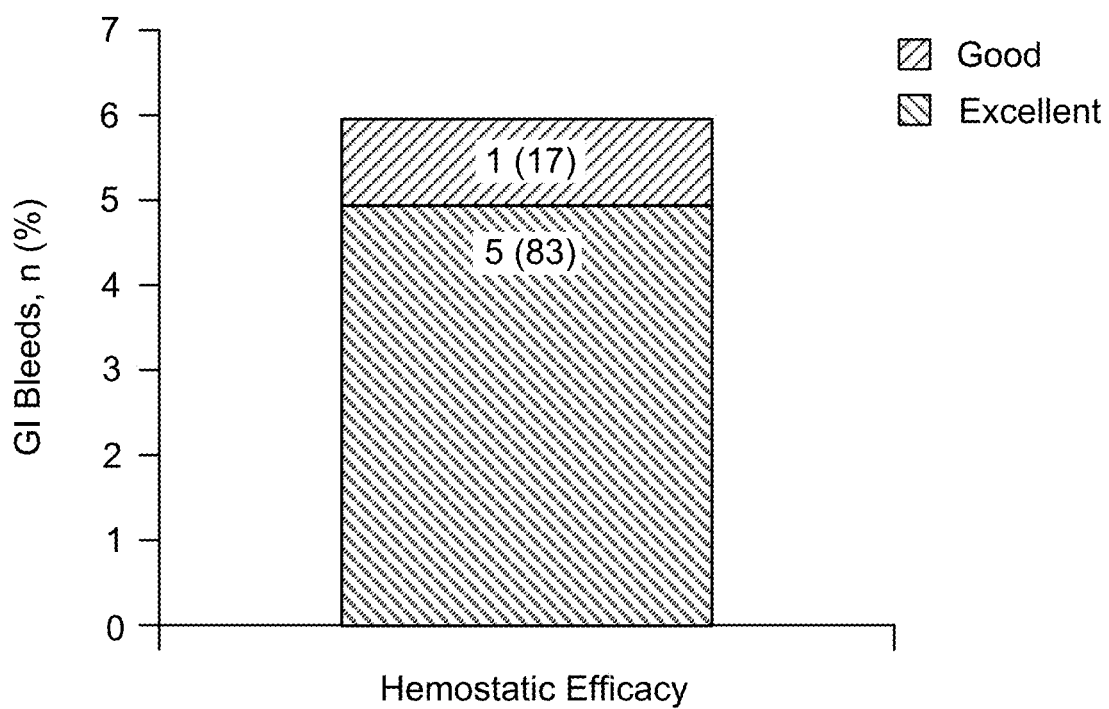
FIG. 1 shows hemostatic efficiency of rVWF for treatment in GI bleeds. BE=bleeding event; GI=gastrointestinal. 4 patients experienced a total of 6 GI bleeds. Minor and moderate BEs were rated as "Good" if 1-2 infusions more than estimated were required to control that bleeing episode and no additional VWF-containing product was required. Major BEs were rated as "Good" if <1.5 times more infusions than estimated were required to control that bleeding episode and no additional VWF-containing product was required. Minor, moderate, and major BEs were rated as "Excellent" if the actual number of infusions was less than or equal to the estimated number required to treat the BE, and no additional VWF-containing product was required.

The present invention provides methods for treating gastrointestinal bleeding in a patient with severe von Willebrand Disease (VWD) comprising administering to the subject at least one dose of recombinant von Willebrand Factor (rVWF) ranging from about 40 IU/kg to about 100 IU/kg, wherein the first dose further comprises recombinant Factor VIII (rFVIII).

The disclosure of PCT Application Publication No. WO2012/171031 is herein incorporated by reference in its entirety for all purposes.

Definitions

As used herein and in the appended claims, the singular forms "a," "an," and "the" include plural referents unless the context clearly dictates otherwise. Thus, for example, reference to "an antibody" includes a plurality of such antibodies and reference to "a host cell" includes reference to one or more host cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Before the invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

As used herein. "rVWF" refers to recombinant VWF.

As used herein, "rFVIII" refers to recombinant FVIII.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, "recombinant VWF" includes VWF obtained via recombinant DNA technology. In certain embodiments, VWF proteins of the invention can comprise a construct, for example, prepared as in WO 1986/06096 published on Oct. 23, 1986 and U.S. patent application Ser. No. 07/559,509, filed on Jul. 23, 1990, in the name of Ginsburg et al., which is incorporated herein by reference with respect to the methods of producing recombinant VWF. The VWF in the present invention can include all potential forms, including the monomeric and multimeric forms. It should also be understood that the present invention encompasses different forms of VWF to be used in combination. For example, the VWF of the present invention may include different multimers, different derivatives and both biologically active derivatives and derivatives not biologically active.

In the context of the present invention, the recombinant VWF embraces any member of the VWF family from, for example, a mammal such as a primate, human, monkey, rabbit, pig, rodent, mouse, rat, hamster, gerbil, canine, feline, and biologically active derivatives thereof. Mutant and variant VWF proteins having activity are also embraced, as are functional fragments and fusion proteins of the VWF proteins. Furthermore, the VWF of the invention may further comprise tags that facilitate purification, detection, or both. The VWF described herein may further be modified with a therapeutic moiety or a moiety suitable imaging in vitro or in vivo.

As used herein, "plasma-derived VWF (pdVWF)" includes all forms of the protein found in blood including the mature VWF obtained from a mammal having the property of in vivo-stabilizing, e.g. binding, of at least one FVIII molecule.

The term "highly multimeric VWF" or "high molecular weight VWF" refers to VWF comprising at least 10 subunits, or 12, 14, or 16 subunits, to about 20, 22, 24 or 26 subunits or more. The term "subunit" refers to a monomer of VWF. As is known in the art, it is generally dimers of VWF that polymerize to form the larger order multimers (see Turecek et al., Semin. Thromb. Hemost. 2010, 36(5): 510-521 which is hereby incorporated by reference in its entirety for all purposes and in particular for all teachings regarding multimer analysis of VWF).

As used herein, the term "factor VIII" or "FVIII" refers to any form of factor VIII molecule with the typical characteristics of blood coagulation factor VIII, whether endogenous to a patient, derived from blood plasma, or produced through the use of recombinant DNA techniques, and including all modified forms of factor VIII. Factor VIII (FVIII) exists naturally and in therapeutic preparations as a heterogeneous distribution of polypeptides arising from a single gene product (see, e.g., Andersson et al., Proc. Natl.

Acad. Sci. USA, 83:2979-2983 (1986)). Commercially available examples of therapeutic preparations containing Factor VIII include those sold under the trade names of HEMOFIL M, ADVATE, and RECOMBINATE (available from Baxter Healthcare Corporation, Deerfield, Ill., U.S.A.).

As used herein, "plasma FVIII activity" and "in vivo FVIII activity" are used interchangeably. The in vivo FVIII activity measured using standard assays may be endogenous FVIII activity, the activity of a therapeutically administered FVIII (recombinant or plasma derived), or both endogenous and administered FVIII activity. Similarly, "plasma FVIII" refers to endogenous FVIII or administered recombinant or plasma derived FVIII.

As used herein "von Willebrand Disease" refers to the group of diseases caused by a deficiency of von Willebrand factor. Von Willebrand factor helps blood platelets clump together and stick to the blood vessel wall, which is necessary for normal blood clotting. As described in further detail herein, there are several types of Von Willebrand disease including type 1, 2A, 2B, 2M and 3.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. VWF is the predominant species present in a preparation is substantially purified. The term "purified" in some embodiments denotes that a nucleic acid or protein gives rise to essentially one band in an electrophoretic gel. In other embodiments, it means that the nucleic acid or protein is at least 50% pure, more preferably at least 60%, 65%, 70%, 75%, 80%, 85%, 90%, 95%, 96%, 97%, 98%, 99% or more pure. "Purify" or "purification" in other embodiments means removing at least one contaminant from the composition to be purified. In this sense, purification does not require that the purified compound be homogenous, e.g., 100% pure.

As used herein, "administering" (and all grammatical equivalents) includes intravenous administration, intramuscular administration, subcutaneous administration, oral administration, administration as a suppository, topical contact, intraperitoneal, intralesional, or intranasal administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "therapeutically effective amount or dose" or "therapeutically sufficient amount or dose" or "effective or sufficient amount or dose" refer to a dose that produces therapeutic effects for which it is administered. For example, a therapeutically effective amount of a drug useful for treating hemophilia can be the amount that is capable of preventing or relieving one or more symptoms associated with hemophilia. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, the terms "patient" and "subject" are used interchangeably and refer to a mammal (preferably human) that has a disease or has the potential of contracting a disease.

As used herein, the term "about" denotes an approximate range of plus or minus 10% from a specified value. For instance, the language "about 20%" encompasses a range of 18-22%.

As used herein, the term "half-life" refers to the period of time it takes for the amount of a substance undergoing decay (or clearance from a sample or from a patient) to decrease by half.

I. Recombinant Von Willebrand Factor (rVWF)

The present invention utilizes compositions comprising von Willebrand Factor (rVWF) for pretreatment of subject with severe VWD who are undergoing a surgical procedure, such as, but not limited to, major surgery, minor surgery, or oral surgery.

In certain embodiments, VWF proteins of the invention may comprise a construct, for example, prepared as in WO 1986/06096 published on Oct. 23, 1986 and U.S. patent application Ser. No. 07/559,509, filed on Jul. 23, 1990, in the name of Ginsburg et al., which is incorporated herein by reference with respect to the methods of producing recombinant VWF. The VWF useful for the present invention includes all potential forms, including the monomeric and multimeric forms. One particularly useful form of VWF are homo-multimers of at least two VWFs. The VWF proteins may be either a biologically active derivative, or when to be used solely as a stabilizer for FVIII the VWF may be of a form not biologically active. It should also be understood that the present invention encompasses different forms of VWF to be used in combination. For example, a composition useful for the present invention may include different multimers, different derivatives and both biologically active derivatives and derivatives not biologically active.

In primary hemostasis VWF serves as a bridge between platelets and specific components of the extracellular matrix, such as collagen. The biological activity of VWF in this process can be measured by different in vitro assays (Turecek et al., Semin. Thromb. Hemost. 28: 149-160, 2002). The ristocetin cofactor assay is based on the agglutination of fresh or formalin-fixed platelets induced by the antibiotic ristocetin in the presence of VWF.

The degree of platelet agglutination depends on the VWF concentration and can be measured by the turbidimetric method, e.g. by use of an aggregometer (Weiss et al., J. Clin. Invest. 52: 2708-2716, 1973; Macfarlane et al., Thromb. Diath. Haemorrh. 34: 306-308, 1975). The second method is the collagen binding assay, which is based on ELISA technology (Brown et Bosak, Thromb. Res. 43: 303-311, 1986; Favaloro, Thromb. Haemost. 83: 127-135, 2000). A microtiter plate is coated with type I or III collagen. Then the VWF is bound to the collagen surface and subsequently detected with an enzyme-labeled polyclonal antibody. The last step is the substrate reaction, which can be photometrically monitored with an ELISA reader. As provided herein, the specific Ristocetin Cofactor activity of the VWF (VWF: RCo) of the present invention is generally described in terms of mU/µg of VWF, as measured using in vitro assays.

An advantage of the rVWF compositions of the present invention over pdVWF is that rVWF exhibits a higher specific activity than pdVWF. In some embodiments, the rVWF of the invention has a specific activity of at least about 20, 22.5, 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, 82.5, 85, 87.5, 90, 92.5, 95, 97.5, 100, 105, 110, 115, 120, 125, 130, 135, 140, 145, 150 or more mU/µg.

The rVWF of the present invention is highly multimeric comprising about 10 to about 40 subunits. In further embodiments, the multimeric rVWF produced using methods of the present invention comprise about 10-30, 12-28, 14-26, 16-24, 18-22, 20-21 subunits. In further embodiments, the rVWF is present in multimers varying in size from dimers to multimers of over 40 subunits (>10 million Daltons). The largest multimers provide multiple binding sites that can interact with both platelet receptors and subendothelial matrix sites of injury, and are the most hemostatically active form of VWF. Application of ADAMTS13 will cleave the ultra-large rVWF multimers over time, but during production (generally through expression in cell culture), rVWF compositions of the present invention are generally not exposed to ADAMTS13 and retain their highly multimeric structure.

In one embodiment, a rVWF composition used in the methods described herein has a distribution of rVWF oligomers characterized in that 95% of the oligomers have between 6 subunits and 20 subunits. In other embodiments, the a rVWF composition has a distribution of rVWF oligomers characterized in that 95% of the oligomers have a range of subunits selected from variations 458 to 641 found in Table 2 of WO 2012/171031, which is herein incorporated by reference in its entirety for all purposes.

In one embodiment, a rVWF composition can be characterized according to the percentage of rVWF molecules that are present in a particular higher order rVWF multimer or larger multimer. For example, in one embodiment, at least 20% of rVWF molecules in a rVWF composition used in the methods described herein are present in an oligomeric complex of at least 10 subunits. In another embodiment, at least 20% of rVWF molecules in a rVWF composition used in the methods described herein are present in an oligomeric complex of at least 12 subunits. In yet other embodiments, a rVWF composition used in the methods provided herein has a minimal percentage (e.g., has at least X %) of rVWF molecules present in a particular higher-order rVWF multimer or larger multimer (e.g., a multimer of at least Y subunits) according to any one of variations 134 to 457 found in Table 3 to Table 5, which is herein incorporated by reference in its entirety for all purposes.

In accordance with the above, the rVWF composition administered to the subject (with or without FVIII) generally comprises a significant percentage of high molecular weight (HMW) rVWF multimers. In further embodiments, the HMW rVWF multimer composition comprises at least 10%-80% rVWF decamers or higher order multimers. In further embodiments, the composition comprises about 10-95%, 20-90%, 30-85%, 40-80%, 50-75%, 60-70% decamers or higher order multimers. In further embodiments, the HMW rVWF multimer composition comprises at least about 10%, 20%, 30%, 40%, 50%, 60%, 70%, 80%, 90% decamers or higher order multimers.

Assessment of the number and percentage of rVWF multimers can be conducted using methods known in the art, including without limitation methods using electrophoresis and size exclusion chromatography methods to separate VWF multimers by size, for example as discussed by Cumming et al, (J Clin Pathol. 1993 May; 46(5): 470-473, which is hereby incorporated by reference in its entirety for all purposes and in particular for all teachings related to assessment of VWF multimers). Such techniques may further include immunoblotting techniques (such as Western Blot), in which the gel is immunoblotted with a radiolabeled antibody against VWF followed by chemiluminescent detection (see for example Wen et al., (1993), J. Clin. Lab. Anal., 7: 317-323, which is hereby incorporated by reference in its entirety for all purposes and in particular for all teachings related to assessment of VWF multimers). Further assays for VWF include VWF:Antigen (VWF:Ag), VWF:Ristocetin Cofactor (VWF:RCof), and VWF:Collagen Binding Activity assay (VWF:CBA), which are often used for diagnosis and classification of Von Willebrand Disease. (see for example Favaloro et al., Pathology, 1997, 29(4): 341-456, which is hereby incorporated by reference in its entirety for all purposes and in particular for all teachings related to assays for VWF).

In further embodiments, higher order rVWF multimers of the invention are stable for about 1 to about 90 hours post-administration. In still further embodiments, the higher order rVWF multimers are stable for about 5-80, 10-70, 15-60, 20-50, 25-40, 30-35 hours post-administration. In yet further embodiments, the higher order rVWF multimers are stable for at least 3, 6, 12, 18, 24, 36, 48, 72 hours post-administration. In certain embodiments the stability of the rVWF multimers is assessed in vitro.

In one embodiment, higher order rVWF multimers used in the compositions and methods provided herein have a half-life of at least 12 hour post administration. In another embodiment, the higher order rVWF multimers have a half-life of at least 24 hour post administration. In yet other embodiments, the higher order rVWF multimers have a half-life selected from variations 642 to 1045 found in Table 6 of WO 2012/171031, which is herein incorporated by reference in its entirety for all purposes.

In specific aspects, the rVWF (recombinant or plasma derived) used in accordance with the present invention are not modified with any conjugation, post-translation or covalent modifications. In particular embodiments, the rVWF of the present invention is not modified with a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

In other aspects, the rVWF (recombinant or plasma derived) used in accordance with the present invention is modified through conjugation, post-translation modification, or covalent modification, including modifications of the N- or C-terminal residues as well as modifications of selected side chains, for example, at free sulfhydryl-groups, primary amines, and hydroxyl-groups. In one embodiment, a water soluble polymer is linked to the protein (directly or via a linker) by a lysine group or other primary amine. In one embodiment, the rVWF proteins of the present invention may be modified by conjugation of a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

Water soluble polymers that may be used to modify the rVWF and/or FVIII include linear and branched structures. The conjugated polymers may be attached directly to the coagulation proteins of the invention, or alternatively may be attached through a linking moiety. Non-limiting examples of protein conjugation with water soluble polymers can be found in U.S. Pat. Nos. 4,640,835; 4,496,689; 4,301,144; 4,670,417; 4,791,192, and 4,179,337, as well as in Abuchowski and Davis "Enzymes as Drugs," Holcenberg and Roberts, Eds., pp. 367 383, John Wiley and Sons, New York (1981), and Hermanson G., Bioconjugate Techniques 2nd Ed., Academic Press, Inc. 2008.

Protein conjugation may be performed by a number of well-known techniques in the art, for example, see Hermanson G., Bioconjugate Techniques 2nd Ed., Academic Press, Inc. 2008. Examples include linkage through the peptide bond between a carboxyl group on one of either the coagulation protein or water-soluble polymer moiety and an amine group of the other, or an ester linkage between a carboxyl group of one and a hydroxyl group of the other. Another linkage by which a coagulation protein of the invention could be conjugated to a water-soluble polymer compound is via a Schiff base, between a free amino group on the polymer moiety being reacted with an aldehyde group formed at the non-reducing end of the polymer by periodate oxidation (Jennings and Lugowski, J. Immunol. 1981; 127: 1011-8; Fernandes and Gregonradis, Biochim Biophys Acta. 1997; 1341; 26-34). The generated Schiff Base can be stabilized by specific reduction with $NaCNBH_3$ to form a secondary amine. An alternative approach is the generation of terminal free amino groups on the polymer by reductive amination with $NH_4Cl$ after prior oxidation. Bifunctional reagents can be used for linking two amino or two hydroxyl groups. For example a polymer containing an amino group can be coupled to an amino group of the coagulation protein with reagents like BS3 (Bis(sulfosuccinimidyl)suberate/Pierce, Rockford, Ill.). In addition heterobifunctional cross linking reagents like Sulfo-EMCS (N-.epsilon.-Maleimidocaproyloxy) sulfosuccinimide ester/Pierce) can be used for instance to link amine and thiol groups. In other embodiments, an aldehyde reactive group, such as PEG alkoxide plus diethyl acetal of bromoacetaldehyde; PEG plus DMSO and acetic anhydride, and PEG chloride plus the phenoxide of 4-hydroxybenzaldehyde, succinimidyl active esters, activated dithiocarbonate PEG, 2,4,5-trichlorophenylcloroformate and P-nitrophenylcloroformate activated PEG, may be used in the conjugation of a coagulation protein.

In some aspects, the rVWF used in methods of the present invention has been matured in vitro with furin. In further embodiments, the furin is recombinant furin.

In further aspects, the rVWF used in the methods of the present invention are produced by expression in a mammalian cell culture using methods known in the art. In particular embodiments, the mammalian culture comprises CHO cells. In an exemplary embodiment, the rVWF of the invention comprises rVWF protein isolated from a CHO cell expression system. In a further embodiment, the propeptide removal is mediated in vitro through exposure of the pro-VWF to furin—in a still further embodiment, the Furin used for propeptide removal is recombinant furin. In as yet further embodiment, fully glycosylated/ABO blood group glycans are absent.

In yet further embodiments, the rVWF used in methods and compositions of the present invention by expression in a suitable eukaryotic host system. Examples of eukaryotic cells include, without limitation, mammalian cells, such as CHO, COS, HEK 293, BHK, SK-Hep, and HepG2; insect cells, e.g., SF9 cells, SF21 cells, S2 cells, and High Five cells; and yeast cells, e.g., *Saccharomyces* or *Schizosaccharomyces* cells. In one embodiment, the VWF can be expressed in yeast cells, insect cells, avian cells, mammalian cells, and the like. For example, in a human cell line, a hamster cell line, or a murine cell line. In one particular embodiment, the cell line is a CHO, BHK, or HEK cell line. Typically, mammalian cells, e.g., CHO cell from a continuous cell line, can be used to express the VWF of the present invention.

In certain embodiments, the nucleic acid sequence comprising a sequence coding for VWF can be a vector. The vector can be delivered by a virus or can be a plasmid. The nucleic acid sequence coding for the protein can be a specific gene or a biologically functional part thereof. In one embodiment, the protein is at least a biologically active part of VWF. A wide variety of vectors can be used for the expression of the VWF and can be selected from eukaryotic expression vectors. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

In some embodiments of the present invention, the nucleic acid sequence further comprises other sequences suitable for a controlled expression of a protein such as promoter sequences, enhancers, TATA boxes, transcription initiation sites, polylinkers, restriction sites, poly-A-sequences, protein processing sequences, selection markers, and the like which are generally known to a person of ordinary skill in the art.

In certain embodiments, the cell-culture methods of the invention may comprise the use of a microcarrier. In some embodiments, the cell-cultures of the embodiments can be performed in large bioreactors under conditions suitable for providing high volume-specific culture surface areas to achieve high cell densities and protein expression. One means for providing such growth conditions is to use microcarriers for cell-culture in stirred tank bioreactors. The concept of cell-growth on microcarriers was first described by van Wezel (van Wezel, A. L., Nature 216:64-5 (1967)) and allows for cell attachment on the surface of small solid particles suspended in the growth medium. These methods provide for high surface-to-volume ratios and thus allow for efficient nutrient utilization. Furthermore, for expression of secreted proteins in eukaryotic cell lines, the increased surface-to-volume ratio allows for higher levels of secretion and thus higher protein yields in the supernatant of the culture. Finally, these methods allow for the easy scale-up of eukaryotic expression cultures.

The cells expressing VWF can be bound to a spherical or a porous microcarrier during cell culture growth. The microcarrier can be a microcarrier selected from the group of microcarriers based on dextran, collagen, plastic, gelatine and cellulose and others as described in Butler (1988. In: Spier & Griffiths, Animal Cell Biotechnology 3:283-303). It is also possible to grow the cells to a biomass on spherical microcarriers and subculture the cells when they have reached final fermenter biomass and prior to production of the expressed protein on a porous microcarrier or vice versa. Suitable spherical microcarriers can include smooth surface microcarriers, such as Cytodex™ 1, Cytodex™ 2, and Cytode™ 3 (GE Healthcare) and macroporous microcarriers such as Cytopore™. 1, Cytopore™ 2, Cytoline™ 1, and Cytoline™ 2 (GE Healthcare).

In certain embodiments, rVWF is expressed in cells cultured in cell culture media that produces high molecular weight rVWF. The terms "cell culture solution," "cell culture medium or media," and "cell culture supernatant" refer to aspects of cell culture processes generally well known in the art. In the context of the present invention, a cell culture solution can include cell culture media and cell culture supernatant. The cell culture media are externally added to the cell culture solution, optionally together with supplements, to provide nutrients and other components for culturing the cells expressing VWF. The cell culture supernatant refers to a cell culture solution comprising the nutrients and other components from the cell culture medium as well as products released, metabolized, and/or excreted from the cells during culture. In further embodiments, the media can be animal protein-free and chemically defined. Methods of preparing animal protein-free and chemically defined culture media are known in the art, for example in US 2008/0009040 and US 2007/0212770, which are both incorporated herein for all purposes and in particular for all teachings related to cell culture media. "Protein free" and related terms refers to protein that is from a source exogenous to or other than the cells in the culture, which naturally shed proteins during growth. In another embodiment, the culture medium is polypeptide free. In another embodiment, the culture medium is serum free. In another embodiment the culture medium is animal protein free. In another embodiment the culture medium is animal component free. In another embodiment, the culture medium contains protein, e.g., animal protein from serum such as fetal calf serum. In another embodiment, the culture has recombinant proteins exogenously added. In another embodiment, the proteins are from a certified pathogen free animal. The term "chemically defined" as used herein shall mean, that the medium does not comprise any undefined supplements, such as, for example, extracts of animal components, organs, glands, plants, or yeast. Accordingly, each component of a chemically defined medium is accurately defined. In a preferred embodiment, the media are animal-component free and protein free.

In further embodiments, subsequent to purification from a mammalian cell culture, rFVIII is reconstituted prior to administration. In still further embodiments, the rVWF is treated with furin prior to or subsequent to reconstitution. In further embodiments, the Furin is recombinant furin. In still further embodiments, the rVWF of the invention is not exposed to ADAMTS13, with the result that ultra large (i.e., comprising 10 or more subunits) are present in rVWF compositions of the invention.

In specific aspects, the rVWF used in methods of the present invention is contained in a formulation containing a buffer, a sugar and/or a sugar alcohol (including without limitation trehalose and mannitol), a stabilizer (such as glycine), and a surfactant (such as polysorbate 80). In further embodiments, for formulations containing rFVIII, the formulation may further include sodium, histidine, calcium, and glutathione.

In one aspect, the formulations comprising rVWF is lyophilized prior to administration. Lyophilization is carried out using techniques common in the art and should be optimized for the composition being developed [Tang et al., Pharm Res. 21:191-200. (2004) and Chang et al., Pharm Res. 13:243-9 (1996)].

Methods of preparing pharmaceutical formulations can include one or more of the following steps: adding a stabilizing agent as described herein to said mixture prior to lyophilizing, adding at least one agent selected from a bulking agent, an osmolarity regulating agent, and a surfactant, each of which as described herein, to said mixture prior to lyophilization. A lyophilized formulation is, in one aspect, at least comprised of one or more of a buffer, a bulking agent, and a stabilizer. In this aspect, the utility of a surfactant is evaluated and selected in cases where aggregation during the lyophilization step or during reconstitution becomes an issue. An appropriate buffering agent is included to maintain the formulation within stable zones of pH during lyophilization.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration [Chen, Drug Development and Industrial Pharmacy, 18:1311-1354 (1992)]. Accordingly, methods are provided for preparation of reconstituted recombinant VWF compositions comprising the step of adding a diluent to a lyophilized recombinant VWF composition of the invention.

The lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum acacia; dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example and without limitation, polyethylene sorbitan monooleate. In various aspects, the aqueous suspensions also contain one or more preservatives, for example and without limitation, ethyl, or n-propyl, p-hydroxybenzoate.

In certain embodiments, compositions of the present invention are liquid formulations for administration with the use of a syringe or other storage vessel. In further embodiments, these liquid formulations are produced from lyophilized material described herein reconstituted as an aqueous solution.

In a further aspect, the compositions of the invention further comprise one or more pharmaceutically acceptable carriers. The phrases "pharmaceutically" or "pharmacologically" acceptable refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

II. Production of Recombinant VWF

The free mature recombinant von Willebrand Factor (rVWF) of the present invention can be produced recombinantly. One skilled in the art recognizes useful methods for expressing a recombinant protein in a host cell. In some instances, the method includes expressing a nucleic acid sequence encoding rVWF in a host cell such as a CHO cell and culturing the resulting host cell under certain conditions to produce rVWF, prepro-VWF, pro-VWF, and the like.

In certain embodiments, the nucleic acid sequence comprising a sequence coding for VWF can be an expression vector. The vector can be delivered by a virus or can be a plasmid. The nucleic acid sequence coding for the protein can be a specific gene or a biologically functional part thereof. In one embodiment, the protein is at least a biologically active part of VWF. The nucleic acid sequence can further comprise other sequences suitable for a controlled expression of a protein such as promoter sequences, enhancers, TATA boxes, transcription initiation sites, polylinkers, restriction sites, poly-A-sequences, protein processing sequences, selection markers, and the like which are generally known to a person of ordinary skill in the art.

A wide variety of vectors can be used for the expression of the VWF and can be selected from eukaryotic expression vectors. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

In some aspects, the rVWF used in the methods of the present invention is produced by expression in a mammalian cell culture using methods known in the art. In particular embodiments, the mammalian culture comprises CHO cells. In further embodiments, the rVWF is co-expressed with recombinant Factor VIII (rFVIII) in the same culture. In such embodiments, the rVWF and the rFVIII are purified together (co-purified) or separately using methods known in the art. In other embodiments, the rVWF is expressed in a culture that does not contain rFVIII.

In some embodiments, rVWF is expressed and isolated from a suitable eukaryotic host system. Examples of eukaryotic cells include, without limitation, mammalian cells, such as CHO, COS, HEK 293, BHK, SK-Hep, and HepG2; insect cells, e.g., SF9 cells, SF21 cells, S2 cells, and High Five cells; and yeast cells, e.g., *Saccharomyces* or *Schizosaccharomyces* cells. In one embodiment, the VWF can be expressed in yeast cells, insect cells, avian cells, mammalian cells, and the like. For example, in a human cell line, a hamster cell line, or a murine cell line. In one particular embodiment, the cell line is a CHO, BHK, or HEK cell line. Typically, mammalian cells, e.g., CHO cell from a continuous cell line, can be used to express the VWF of the present invention. In certain instances, VWF protein is expressed and isolated from a CHO cell expression system.

VWF can be produced in a cell culture system or according to any cell culture method recognized by those in the art. In some embodiments, the cell cultures can be performed in large bioreactors under conditions suitable for providing high volume-specific culture surface areas to achieve high cell densities and protein expression. One means for providing such growth conditions is to use microcarriers for cell-culture in stirred tank bioreactors. The concept of cell-growth on microcarriers was first described by van Wezel (van Wezel, A. L., Nature, 1967, 216:64-5) and allows for cell attachment on the surface of small solid particles suspended in the growth medium. These methods provide for high surface-to-volume ratios and thus allow for efficient nutrient utilization. Furthermore, for expression of secreted proteins in eukaryotic cell lines, the increased surface-to-volume ratio allows for higher levels of secretion and thus higher protein yields in the supernatant of the culture. Finally, these methods allow for the easy scale-up of eukaryotic expression cultures.

The cells expressing VWF can be bound to a spherical or a porous microcarrier during cell culture growth. The microcarrier can be a microcarrier selected from the group of microcarriers based on dextran, collagen, plastic, gelatine and cellulose and others as described in Butler (1988. In: Spier & Griffiths, Animal Cell Biotechnology 3:283-303). I t is also possible to grow the cells to a biomass on spherical microcarriers and subculture the cells when they have reached final fermenter biomass and prior to production of the expressed protein on a porous microcarrier or vice versa. Suitable spherical microcarriers can include smooth surface microcarriers, such as Cytodex™ 1, Cytodex™ 2, and Cytodex™ 3 (GE Healthcare) and macroporous microcarriers such as Cytopore™ 1, Cytopore™ 2, Cytoline™ 1, and Cytoline™ 2 (GE Healthcare).

In a further embodiment, the VWF propeptide is cleaved from the non-mature VWF in vitro through exposure of the pro-VWF to furin. In some embodiments, the furin used for propeptide cleavage is recombinant furin.

In certain embodiments, rVWF is expressed in cells cultured in cell culture media that produces high molecular weight rVWF. The terms "cell culture solution," "cell culture medium or media," and "cell culture supernatant" refer to aspects of cell culture processes generally well known in the art. In the context of the present invention, a cell culture solution can include cell culture media and cell culture supernatant. The cell culture media are externally added to the cell culture solution, optionally together with supplements, to provide nutrients and other components for culturing the cells expressing VWF. The cell culture supernatant refers to a cell culture solution comprising the nutrients and other components from the cell culture medium as well as products released, metabolized, and/or excreted from the cells during culture. In further embodiments, the media can be animal protein-free and chemically defined. Methods of preparing animal protein-free and chemically defined culture media are known in the art, for example in US 2006/0094104, US 2007/0212770, and US 2008/0009040, which are both incorporated herein for all purposes and in particular for all teachings related to cell culture media. "Protein free" and related terms refers to protein that is from a source exogenous to or other than the cells in the culture, which naturally shed proteins during growth. In another embodiment, the culture medium is polypeptide free. In another embodiment, the culture medium is serum free. In another embodiment the culture medium is animal protein free. In another embodiment the culture medium is animal component free. In another embodiment, the culture medium contains protein, e.g., animal protein from serum such as fetal calf serum. In another embodiment, the culture has recombinant proteins exogenously added. In another embodiment, the proteins are from a certified pathogen free animal. The term "chemically defined" as used herein shall mean, that the medium does not comprise any undefined supplements, such as, for example, extracts of animal components, organs, glands, plants, or yeast. Accordingly, each component of a chemically defined medium is accurately defined. In a preferred embodiment, the media are animal-component free and protein free.

In certain embodiments, the culture of cells expressing VWF can be maintained for at least about 7 days, or at least about 14 days, 21 days, 28 days, or at least about 5 weeks, 6 weeks, 7 weeks, or at least about 2 months, or 3, 4, 5, 6, 7, 8, 9, 10, 11, 12, 13, 14, 15, 16, 17, 18 months or longer. The cell density at which a cell-culture is maintained at for production of a recombinant VWF protein will depend upon the culture-conditions and medium used for protein expression. One of skill in the art will readily be able to determine the optimal cell density for a cell-culture producing an VWF. In one embodiment, the culture is maintained at a cell density of between about $0.5\times10^6$ and $4\times10^7$ cells/ml for an extended period of time. In other embodiments, the cell density is maintained at a concentration of between about $1.0\times10^6$ and about $1.0\times10^7$ cells/ml for an extended period of time. In other embodiments, the cell density is maintained at a concentration of between about $1.0\times10^6$ and about $4.0\times10^6$ cells/ml for an extended period of time. In other embodiments, the cell density is maintained at a concentration of between about $1.0\times10^6$ and about $4.0\times10^6$ cells/ml for an extended period of time. In yet other embodiments, the cell density may be maintained at a concentration between about $2.0\times10^6$ and about $4.0\times10^6$, or between about $1.0\times10^6$ and about $2.5\times10^6$, or between about $1.5\times10^6$ and about $3.5\times10^6$, or any other similar range, for an extended period of time. After an appropriate time in cell culture, the rVWF can be isolated from the expression system using methods known in the art.

In a specific embodiment, the cell density of the continuous cell culture for production of rVWF is maintained at a concentration of no more than $2.5\times10^6$ cells/mL for an extended period. In other specific embodiments, the cell density is maintained at no more than $2.0\times10^6$ cells/mL, $1.5\times10^6$ cells/mL, $1.0\times10^6$ cells/mL, $0.5\times10^6$ cells/mL, or less. In one embodiment, the cell density is maintained at between $1.5\times10^6$ cells/mL and $2.5\times10^6$ cells/mL.

In one embodiment of the cell cultures described above, the cell culture solution comprises a medium supplement comprising copper. Such cell culture solutions are described, for example, in U.S. Pat. Nos. 8,852,888 and 9,409,971, which is hereby incorporated by reference in its entirety for all purposes and in particular for all teachings related to cell culture methods and compositions for producing recombinant VWF.

The polynucleotide and amino acid sequences of prepro-VWF are set out in SEQ ID NO:1 and SEQ ID NO:2, respectively, and are available at GenBank Accession Nos. NM_000552 (*Homo sapiens* von Willebrand factor (VWF) mRNA) and NP 000543, respectively. The amino acid sequence corresponding to the mature VWF protein is set out in SEQ ID NO: 3 (corresponding to amino acids 764-2813 of the full length prepro-VWF amino acid sequence). In some embodiments, the VWF exhibits at least 80%, at least 85%, at least 90%, at least 95%, at least 96%, at least 97%, at least 98%, at least 99%, or at least 100% identity to the sequence of SEQ ID NO:3. In some embodiments, the rVWF of the invention exhibits at least 80%, at least 85%, at least 90%, at least 95%, at least 96%, at least 97%, at least 98%, at least 99%, or at least 100% identity to the sequence of SEQ ID NO:3. See, for example, U.S. Pat. No. 8,597,910, U.S. Patent Publication No. 2016/0129090, as well as FIG. 6.

One form of useful rVWF has at least the property of in vivo-stabilizing, e.g. binding, of at least one Factor VIII (FVIII) molecule and having optionally a glycosylation pattern which is pharmacologically acceptable. Specific examples thereof include VWF without the A2 domain thus resistant to proteolysis (Lankhof et al., Thromb. Haemost. 77: 1008-1013, 1997), and a VWF fragment from Val 449 to Asn 730 including the glycoprotein 1b-binding domain and binding sites for collagen and heparin (Pietu et al., Biochem. Biophys. Res. Commun. 164: 1339-1347, 1989). The determination of the ability of a VWF to stabilize at least one FVIII molecule is, in one aspect, carried out in VWF-deficient mammals according to methods known in the state in the art.

The rVWF of the present invention can be produced by any method known in the art. One specific example is disclosed in WO86/06096 published on Oct. 23, 1986 and U.S. patent application Ser. No. 07/559,509, filed on Jul. 23, 1990, which is incorporated herein by reference with respect to the methods of producing recombinant VWF. Thus, methods are known in the art for (i) the production of recombinant DNA by genetic engineering, e.g. via reverse transcription of RNA and/or amplification of DNA, (ii) introducing recombinant DNA into prokaryotic or eukaryotic cells by transfection, e.g. via electroporation or microinjection, (iii) cultivating the transformed cells, e.g. in a continuous or batchwise manner, (iv) expressing VWF, e.g. constitutively or upon induction, and (v) isolating the VWF, e.g. from the culture medium or by harvesting the transformed cells, in order to (vi) obtain purified rVWF, e.g. via anion exchange chromatography or affinity chromatography. A recombinant VWF is, in one aspect, made in transformed host cells using recombinant DNA techniques well known in the art. For instance, sequences coding for the polypeptide could be excised from DNA using suitable restriction enzymes. Alternatively, the DNA molecule is, in another aspect, synthesized using chemical synthesis techniques, such as the phosphoramidate method. Also, in still another aspect, a combination of these techniques is used.

The invention also provides vectors encoding polypeptides of the invention in an appropriate host. The vector comprises the polynucleotide that encodes the polypeptide operatively linked to appropriate expression control sequences. Methods of effecting this operative linking, either before or after the polynucleotide is inserted into the vector, are well known. Expression control sequences include promoters, activators, enhancers, operators, ribosomal binding sites, start signals, stop signals, cap signals, polyadenylation signals, and other signals involved with the control of transcription or translation. The resulting vector having the polynucleotide therein is used to transform an appropriate host. This transformation may be performed using methods well known in the art.

Any of a large number of available and well-known host cells are used in the practice of this invention. The selection of a particular host is dependent upon a number of factors recognized by the art, including, for example, compatibility with the chosen expression vector, toxicity of the peptides encoded by the DNA molecule, rate of transformation, ease of recovery of the peptides, expression characteristics, biosafety and costs. A balance of these factors must be struck with the understanding that not all host cells are equally effective for the expression of a particular DNA sequence. Within these general guidelines, useful microbial host cells include, without limitation, bacteria, yeast and other fungi, insects, plants, mammalian (including human) cells in culture, or other hosts known in the art.

Transformed host cells are cultured under conventional fermentation conditions so that the desired compounds are expressed. Such fermentation conditions are well known in the art. Finally, the polypeptides are purified from culture media or the host cells themselves by methods well known in the art.

Depending on the host cell utilized to express a compound of the invention, carbohydrate (oligosaccharide) groups are optionally attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids not counting proline. The structures of N-linked and O-linked oligosaccharides and the sugar residues found in each type are different. One type of sugar that is commonly found on both N-linked and O-linked oligosaccharides is N-acetylneuraminic acid (referred to as sialic acid). Sialic acid is usually the terminal residue of both N-linked and O-linked oligosaccharides and, by virtue of its negative charge, in one aspect, confers acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). In other aspects, such sites are glycosylated by synthetic or semi-synthetic procedures known in the art.

In some embodiments, sialysation (also referred to as sialylation), can be performed on the column as part of the purification procedures described herein (including the anion exchange, cation exchange, size exclusion, and/or immunoaffinity methods). In some embodiments, the sialylation results in increased stability of the rVWF as compared to rVWF that has not undergone sialylation. In some embodiments, the sialylation results in increased stability of the rVWF in blood circulation (for example, after administration to a subject) as compared to rVWF that has not undergone sialylation. In some embodiments, the increased stability of salivated rVWF results in an increase of 10%, 20%, 30%, 40%, 50%, 60%, 70%, 80%, 90%, or more as compared rVWF that has not undergone sialylation. In some embodiments, the sialylation results in increased half-life for the rVWF as compared to rVWF that has not undergone sialylation. In some embodiments, the sialylation results in increased half-life for the rVWF in blood circulation (for example, after administration to a subject) as compared to rVWF that has not undergone sialylation. In some embodiments, the increased half-life of sialylated rVWF results in an increase of 10%, 20%, 30%, 40%, 50%, 60%, 70%, 80%, 90%, or more as compared rVWF that has not undergone sialylation. In some embodiments, the increased half-life of sialylated rVWF results in rVWF that is stable for 1 hour, 2 hours, 3 hours, 4 hours, 6 hours, 12 hours, 24 hours or more in blood circulation (for example, after administration to a subject) as compared to rVWF that has not undergone sialylation. In some embodiments, sialylation increases the number of 2,3 sialylation and/or 2,6 sialylation. In some embodiments, sialylation is increased by the addition of 2,3 sialyltransferase and/or 2,6 sialyltransferase and CMP-NANA (Cytidine-5'-monophospho-N-acetylneuraminic acid sodium salt) as an additional buffer step. In some embodiments, sialylation is increased by the addition of 2,3 sialyltransferase and CMP-NANA (Cytidine-5'-monophospho-N-acetylneuraminic acid sodium salt) as an additional buffer step. In some embodiments, 2,3 sialylation is increased by the addition of 2,3 sialyltransferase and CMP-NANA (Cytidine-5'-monophospho-N-acetylneuraminic acid sodium salt) as an additional buffer step. In some embodiments, 2,6 sialylation is increased by the addition of 2,6 sialyltransferase and CMP-NANA (Cytidine-5'-monophospho-N-acetylneuraminic acid sodium salt) as an additional buffer step. In some embodiments, 2,3 sialylation and/or 2,6 sialylation are increased by the addition of 2,3 sialyltransferase and/or 2,6 sialyltransferase and CMP-NANA (Cytidine-5'-monophospho-N-acetylneuraminic acid sodium salt) as an additional buffer step. In some embodiments, CMP-NANA is chemically or enzymatic modified to transfer modified sialic acid to potential free position. In some embodiments, sialylation is performed by loading rVWF onto the resin, washing with one or more buffers as described herein to deplete unwanted impurities, apply one or more buffers containing sialyltransferase and CMP-NANA at conditions that allow additional sialylation, and washing with one or more buffers to deplete excess of the sialylation reagents, and eluting with one or more buffers the enhanced rVWF (e.g., the rVWF with increased sialylation). In some embodiments, the sialylation process is performed as part of a cation exchange method, an anion exchange method, a size exclusion method, or an immunoaffinity purification method, as described herein.

Alternatively, the compounds are made by synthetic methods using, for example, solid phase synthesis techniques. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527'. Solid phase synthesis is the preferred technique of making individual peptides since it is the most cost-effective method of making small peptides Fragments, variants and analogs of VWF can be produced according to methods that are well-known in the art. Fragments of a polypeptide can be prepared using, without limitation, enzymatic cleavage (e.g., trypsin, chymotrypsin) and also using recombinant means to generate a polypeptide fragments having a specific amino acid sequence. Polypeptide fragments may be generated comprising a region of the protein having a particular activity, such as a multimerization domain or any other identifiable VWF domain known in the art.

Methods of making polypeptide analogs are also well-known. Amino acid sequence analogs of a polypeptide can be substitutional, insertional, addition or deletion analogs. Deletion analogs, including fragments of a polypeptide, lack one or more residues of the native protein which are not essential for function or immunogenic activity. Insertional analogs involve the addition of, e.g., amino acid(s) at a non-terminal point in the polypeptide. This analog may include, for example and without limitation, insertion of an immunoreactive epitope or simply a single residue. Addition analogs, including fragments of a polypeptide, include the addition of one or more amino acids at either or both termini of a protein and include, for example, fusion proteins. Combinations of the aforementioned analogs are also contemplated.

Substitutional analogs typically exchange one amino acid of the wild-type for another at one or more sites within the protein, and may be designed to modulate one or more properties of the polypeptide without the complete loss of other functions or properties. In one aspect, substitutions are conservative substitutions. "Conservative amino acid substitution" is substitution of an amino acid with an amino acid having a side chain or a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine).

In one aspect, analogs are substantially homologous or substantially identical to the recombinant VWF from which they are derived. Analogs include those which retain at least some of the biological activity of the wild-type polypeptide, e.g. blood clotting activity.

Polypeptide variants contemplated include, without limitation, polypeptides chemically modified by such techniques as ubiquitination, glycosylation, including polysialation (or polysialylation), conjugation to therapeutic or diagnostic agents, labeling, covalent polymer attachment such as pegylation (derivatization with polyethylene glycol), introduction of non-hydrolyzable bonds, and insertion or substitution by chemical synthesis of amino acids such as ornithine, which do not normally occur in human proteins. Variants retain the same or essentially the same binding properties of non-modified molecules of the invention. Such chemical modification may include direct or indirect (e.g., via a linker) attachment of an agent to the VWF polypeptide. In the case of indirect attachment, it is contemplated that the linker may be hydrolyzable or non-hydrolyzable.

Preparing pegylated polypeptide analogs will in one aspect comprise the steps of (a) reacting the polypeptide with polyethylene glycol (such as a reactive ester or aldehyde derivative of PEG) under conditions whereby the binding construct polypeptide becomes attached to one or more PEG groups, and (b) obtaining the reaction product(s). In general, the optimal reaction conditions for the acylation reactions are determined based on known parameters and the desired result. For example, the larger the ratio of PEG:protein, the greater the percentage of poly-pegylated product. In some embodiments, the binding construct has a single PEG moiety at the N-terminus. Polyethylene glycol (PEG) may be attached to the blood clotting factor to, for example, provide a longer half-life in vivo. The PEG group may be of any convenient molecular weight and is linear or branched. The average molecular weight of the PEG ranges from about 2 kiloDalton ("kD") to about 100 kDa, from about 5 kDa to about 50 kDa, or from about 5 kDa to about 10 kDa. In certain aspects, the PEG groups are attached to the blood clotting factor via acylation or reductive alkylation through a natural or engineered reactive group on the PEG moiety (e.g., an aldehyde, amino, thiol, or ester group) to a reactive group on the blood clotting factor (e.g., an aldehyde, amino, or ester group) or by any other technique known in the art.

Methods for preparing polysialylated polypeptide are described in United States Patent Publication 20060160948, Fernandes et Gregoriadis; Biochim. Biophys. Acta 1341: 26-34, 1997, and Saenko et al., Haemophilia 12:42-51, 2006. Briefly, a solution of colominic acid (CA) containing 0.1 M NaIO$_4$ is stirred in the dark at room temperature to oxidize the CA. The activated CA solution is dialyzed against, e.g., 0.05 M sodium phosphate buffer, pH 7.2 in the dark and this solution was added to a rVWF solution and incubated for 18 h at room temperature in the dark under gentle shaking. Free reagents are optionally be separated from the rVWF-polysialic acid conjugate by, for example, ultrafiltration/diafiltration. Conjugation of rVWF with polysialic acid is achieved using glutaraldehyde as cross-linking reagent (Migneault et al., Biotechniques 37: 790-796, 2004).

It is also contemplated in another aspect that prepro-VWF and pro-VWF polypeptides will provide a therapeutic benefit in the formulations of the present invention. For example, U.S. Pat. No. 7,005,502 describes a pharmaceutical preparation comprising substantial amounts of pro-VWF that induces thrombin generation in vitro. In addition to recombinant, biologically active fragments, variants, or other analogs of the naturally-occurring mature VWF, the present invention contemplates the use of recombinant biologically active fragments, variants, or analogs of the pre-pro-VWF (set out in SEQ ID NO:2) or pro-VWF polypeptides (amino acid residues 23 to 764 of SEQ ID NO: 2) in the formulations described herein.

Polynucleotides encoding fragments, variants and analogs may be readily generated by a worker of skill to encode biologically active fragments, variants, or analogs of the naturally-occurring molecule that possess the same or similar biological activity to the naturally-occurring molecule. In various aspects, these polynucleotides are prepared using PCR techniques, digestion/ligation of DNA encoding molecule, and the like. Thus, one of skill in the art will be able to generate single base changes in the DNA strand to result in an altered codon and a missense mutation, using any method known in the art, including, but not limited to site-specific mutagenesis. As used herein, the phrase "moderately stringent hybridization conditions" means, for example, hybridization at 42° C. in 50% formamide and washing at 60° C. in 0.1×SSC, 0.1% SDS. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47-9.51 in Molecular Cloning, Cold Spring Harbor Laboratory Press, Cold Spring Harbor, N.Y. (1989).

A. VWF Multimers

Assessment of the number and percentage of rVWF multimers can be conducted using methods known in the art, including without limitation methods using electrophoresis and size exclusion chromatography methods to separate VWF multimers by size, for example as discussed by Cumming et al., (J Clin Pathol., 1993 May; 46(5): 470-473, which is hereby incorporated by reference in its entirety for all purposes and in particular for all teachings related to assessment of VWF multimers). Such techniques may further include immunoblotting techniques (such as Western Blot), in which the gel is immunoblotted with a radiolabelled antibody against VWF followed by chemiluminescent detection (see, for example, Wen et al., J. Clin. Lab. Anal., 1993, 7: 317-323, which is hereby incorporated by reference in its entirety for all purposes and in particular for all teachings related to assessment of VWF multimers). Further assays for VWF include VWF:Antigen (VWF:Ag), VWF:Ristocetin Cofactor (VWF:RCof), and VWF:Collagen Binding Activity assay (VWF:CBA), which are often used for diagnosis and classification of Von Willebrand Disease (see, for example, Favaloro et al., Pathology, 1997, 29(4): 341-456; Sadler, J E, Annu Rev Biochem, 1998, 67:395-424; and Turecek et al., Semin Thromb Hemost, 2010, 36:510-521, which are hereby incorporated by reference in their entirety for all purposes and in particular for all teachings related to assays for VWF). In some embodiments, the rVWF obtained using the present methods includes any multimer pattern present in the loading sample of the rVWF. In some embodiments, the rVWF obtained using the present methods includes physiological occurring multimer patters as well as ultralarge VWF-multimer patterns.

b. VWF Assays

In primary hemostasis VWF serves as a bridge between platelets and specific components of the extracellular matrix, such as collagen. The biological activity of VWF in this process can be measured by different in vitro assays (Turecek et al., Semin Thromb Hemost, 2010, 36: 510-521).

The VWF:Ristocetin Cofactor (VWF:RCof) assay is based on the agglutination of fresh or formalin-fixed platelets induced by the antibiotic ristocetin in the presence of VWF. The degree of platelet agglutination depends on the VWF concentration and can be measured by the turbidimetric method, e.g., by use of an aggregometer (Weiss et al., J. Clin. Invest., 1973, 52: 2708-2716; Macfarlane et al., Thromb. Diath. Haemorrh., 1975, 34: 306-308). As provided herein, the specific ristocetin cofactor activity of the VWF (VWF:RCo) of the present invention is generally described in terms of mU/µg of VWF, as measured using in vitro assays.

In some embodiments, the rVWF purified according to the methods of the present invention has a specific activity of at least about 20, 22.5, 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, 82.5, 85, 87.5, 90, 92.5, 95, 97.5, 100, 105, 110, 115, 120, 125, 130, 135, 140, 145, 150 or more mU/µg. In some embodiments, rVWF used in the methods described herein has a specific activity of from 20 mU/µg to 150 mU/µg. In some embodiments, the rVWF has a specific activity of from 30 mU/µg to 120 mU/µg. In some embodiments, the rVWF has a specific activity from 40 mU/µg to 90 mU/µg. In some embodiments, the rVWF has a specific activity selected from variations 1 to 133 found in Table 3, below.

TABLE 3

Exemplary embodiments for the specific activity of rVWF found in the compositions and used in the methods provided herein.

| (mU/µg) | |
| --- | --- |
| 20 | Var. 1 |
| 22.5 | Var. 2 |
| 25 | Var. 3 |
| 27.5 | Var. 4 |
| 30 | Var. 5 |
| 32.5 | Var. 6 |
| 35 | Var. 7 |
| 37.5 | Var. 8 |
| 40 | Var. 9 |
| 42.5 | Var. 10 |
| 45 | Var. 11 |
| 47.5 | Var. 12 |
| 50 | Var. 13 |
| 52.5 | Var. 14 |
| 55 | Var. 15 |
| 57.5 | Var. 16 |
| 60 | Var. 17 |
| 62.5 | Var. 18 |
| 65 | Var. 19 |
| 67.5 | Var. 20 |
| 70 | Var. 21 |
| 72.5 | Var. 22 |
| 75 | Var. 23 |
| 77.5 | Var. 24 |
| 80 | Var. 25 |
| 82.5 | Var. 26 |
| 85 | Var. 27 |
| 87.5 | Var. 28 |
| 90 | Var. 29 |
| 92.5 | Var. 30 |
| 95 | Var. 31 |
| 97.5 | Var. 32 |
| 100 | Var. 33 |
| 105 | Var. 34 |

TABLE 3-continued

Exemplary embodiments for the specific activity of rVWF found in the compositions and used in the methods provided herein.

| (mU/µg) | |
| --- | --- |
| 110 | Var. 35 |
| 115 | Var. 36 |
| 120 | Var. 37 |
| 125 | Var. 38 |
| 130 | Var. 39 |
| 135 | Var. 40 |
| 140 | Var. 41 |
| 145 | Var. 42 |
| 150 | Var. 43 |
| 20-150 | Var. 44 |
| 20-140 | Var. 45 |
| 20-130 | Var. 46 |
| 20-120 | Var. 47 |
| 20-110 | Var. 48 |
| 20-100 | Var. 49 |
| 20-90 | Var. 50 |
| 20-80 | Var. 51 |
| 20-70 | Var. 52 |
| 20-60 | Var. 53 |
| 20-50 | Var. 54 |
| 20-40 | Var. 55 |
| 30-150 | Var. 56 |
| 30-140 | Var. 57 |
| 30-130 | Var. 58 |
| 30-120 | Var. 59 |
| 30-110 | Var. 60 |
| 30-100 | Var. 61 |
| 30-90 | Var. 62 |
| 30-80 | Var. 63 |
| 30-70 | Var. 64 |
| 30-60 | Var. 65 |
| 30-50 | Var. 66 |
| 30-40 | Var. 67 |
| 40-150 | Var. 68 |
| 40-140 | Var. 69 |
| 40-130 | Var. 70 |
| 40-120 | Var. 71 |
| 40-110 | Var. 72 |
| 40-100 | Var. 73 |
| 40-90 | Var. 74 |
| 40-80 | Var. 75 |
| 40-70 | Var. 76 |
| 40-60 | Var. 77 |
| 40-50 | Var. 78 |
| 50-150 | Var. 79 |
| 50-140 | Var. 80 |
| 50-130 | Var. 81 |
| 50-120 | Var. 82 |
| 50-110 | Var. 83 |
| 50-100 | Var. 84 |
| 50-90 | Var. 85 |
| 50-80 | Var. 86 |
| 50-70 | Var. 87 |
| 50-60 | Var. 88 |
| 60-150 | Var. 89 |
| 60-140 | Var. 90 |
| 60-130 | Var. 91 |
| 60-120 | Var. 92 |
| 60-110 | Var. 93 |
| 60-100 | Var. 94 |
| 60-90 | Var. 95 |
| 60-80 | Var. 96 |
| 60-70 | Var. 97 |
| 70-150 | Var. 98 |
| 70-140 | Var. 99 |
| 70-130 | Var. 100 |
| 70-120 | Var. 101 |
| 70-110 | Var. 102 |
| 70-100 | Var. 103 |
| 70-90 | Var. 104 |
| 70-80 | Var. 105 |
| 80-150 | Var. 106 |
| 80-140 | Var. 107 |
| 80-130 | Var. 108 |
| 80-120 | Var. 109 |

TABLE 3-continued

Exemplary embodiments for the specific activity of rVWF found in the compositions and used in the methods provided herein.

| (mU/µg) | |
|---|---|
| 80-110 | Var. 110 |
| 80-100 | Var. 111 |
| 80-90 | Var. 112 |
| 90-150 | Var. 113 |
| 90-140 | Var. 114 |
| 90-130 | Var. 115 |
| 90-120 | Var. 116 |
| 90-110 | Var. 117 |
| 90-100 | Var. 118 |
| 100-150 | Var. 119 |
| 100-140 | Var. 120 |
| 100-130 | Var. 121 |
| 100-120 | Var. 122 |
| 100-110 | Var. 123 |
| 110-150 | Var. 124 |
| 110-140 | Var. 125 |
| 110-130 | Var. 126 |
| 110-120 | Var. 127 |
| 120-150 | Var. 128 |
| 120-140 | Var. 129 |
| 120-130 | Var. 130 |
| 130-150 | Var. 131 |
| 130-140 | Var. 132 |
| 140-150 | Var. 133 |

Var. = Variation

The rVWF of the present invention is highly multimeric comprising about 10 to about 40 subunits. In further embodiments, the multimeric rVWF produced using methods of the present invention comprise about 10-30, 12-28, 14-26, 16-24, 18-22, 20-21 subunits. In some embodiments, the rVWF is present in multimers varying in size from dimers to multimers of over 40 subunits (>10 million Daltons). The largest multimers provide multiple binding sites that can interact with both platelet receptors and subendothelial matrix sites of injury, and are the most hemostatically active form of VWF. In some embodiments, the rVWF of the present invention comprises ultralarge multimers (ULMs). Generally, high and ultralarge multimers are considered to be hemostatically most effective (see, for example, Turecek, P., Hamostaseologie, (Vol. 37): Supplement 1, pages S15-S25 (2017)). In some embodiments, the rVWF is between 500 kDa and 20,000 kDa. In some embodiments, any desired multimer pattern can be obtained using the methods described. In some embodiments, when anion exchange and/or cation exchanger methods are employed, the pH, conductivity, and/or counterion concentration of the buffers in the one or more wash step(s) or the gradient buffers can be manipulated to obtain the desired multimer pattern. In some embodiments, then size exclusion chromatography methods are employed, the collection criteria can be employed to obtain the desired multimer pattern. In some embodiments, the described multimer pattern comprises ultralarge multimers. In some embodiments, the ultralarge multimers are at least 10,000 kDa, at least 11,000 kDa, at least 12,000 kDa, at least 13,000 kDa, at least 14,000 kDa, at least 15,000 kDa, at least 16,000 kDa, at least 17,000 kDa, at least 18,000 kDa, at least 19,000 kDa, at least 20,000 kDa. In some embodiments, the ultralarge multimers are between about 10,000 kDa and 20,000 kDa. In some embodiments, the ultralarge multimers are between about 11,000 kDa and 20,000 kDa. In some embodiments, the ultralarge multimers are between about 12,000 kDa and 20,000 kDa. In some embodiments, the ultralarge multimers are between about 13,000 kDa and 20,000 kDa. In some embodiments, the ultralarge multimers are between about 14,000 kDa and 20,000 kDa. In some embodiments, the ultralarge multimers are between about 15,000 kDa and 20,000 kDa. In some embodiments, the ultralarge multimers are between about 16,000 kDa and 20,000 kDa. In some embodiments, the ultralarge multimers are between about 17,000 kDa and 20,000 kDa. In some embodiments, the ultralarge multimers are between about 18,000 kDa and 20,000 kDa. In some embodiments, the ultralarge multimers are between about 19,000 kDa and 20,000 kDa. In some embodiments, the rVWF obtained using the present methods includes any multimer pattern present in the loading sample of the rVWF. In some embodiments, the rVWF obtained using the present methods includes physiolocical occurring multimer patters as well as ultra large VWF-multimer patterns.

In some embodiments, the rVWF composition prepared by the purification method described herein has a distribution of rVWF oligomers characterized in that 95% of the oligomers have between 6 subunits and 20 subunits. In some embodiments, the rVWF composition has a distribution of rVWF oligomers characterized in that 95% of the oligomers have a range of subunits selected from variations 458 to 641 found in 4.

TABLE 4

Exemplary embodiments for the distribution of rVWF oligomers found in the compositions and used in the methods provided herein.

| Subunits | |
|---|---|
| 2-40 | Var. 458 |
| 2-38 | Var. 459 |
| 2-36 | Var. 460 |
| 2-34 | Var. 461 |
| 2-32 | Var. 462 |
| 2-30 | Var. 463 |
| 2-28 | Var. 464 |
| 2-26 | Var. 465 |
| 2-24 | Var. 466 |
| 2-22 | Var. 467 |
| 2-20 | Var. 468 |
| 2-18 | Var. 469 |
| 2-16 | Var. 470 |
| 2-14 | Var. 471 |
| 2-12 | Var. 472 |
| 2-10 | Var. 473 |
| 2-8 | Var. 474 |
| 4-40 | Var. 475 |
| 4-38 | Var. 476 |
| 4-36 | Var. 477 |
| 4-34 | Var. 478 |
| 4-32 | Var. 479 |
| 4-30 | Var. 480 |
| 4-28 | Var. 481 |
| 4-26 | Var. 482 |
| 4-24 | Var. 483 |
| 4-22 | Var. 484 |
| 4-20 | Var. 485 |
| 4-18 | Var. 486 |
| 4-16 | Var. 487 |
| 4-14 | Var. 488 |
| 4-12 | Var. 489 |
| 4-10 | Var. 490 |
| 4-8 | Var. 491 |
| 6-40 | Var. 492 |
| 6-38 | Var. 493 |
| 6-36 | Var. 494 |
| 6-34 | Var. 495 |
| 6-32 | Var. 496 |
| 6-30 | Var. 497 |
| 6-28 | Var. 498 |
| 6-26 | Var. 499 |
| 6-24 | Var. 500 |
| 6-22 | Var. 501 |

TABLE 4-continued

Exemplary embodiments for the distribution of rVWF oligomers found in the compositions and used in the methods provided herein.

| Subunits | |
|---|---|
| 6-20 | Var. 502 |
| 6-18 | Var. 503 |
| 6-16 | Var. 504 |
| 6-14 | Var. 505 |
| 6-12 | Var. 506 |
| 6-10 | Var. 507 |
| 6-8 | Var. 508 |
| 8-40 | Var. 509 |
| 8-38 | Var. 510 |
| 8-36 | Var. 511 |
| 8-34 | Var. 512 |
| 8-32 | Var. 513 |
| 8-30 | Var. 514 |
| 8-28 | Var. 515 |
| 8-26 | Var. 516 |
| 8-24 | Var. 517 |
| 8-22 | Var. 518 |
| 8-20 | Var. 519 |
| 8-18 | Var. 520 |
| 8-16 | Var. 521 |
| 8-14 | Var. 522 |
| 8-12 | Var. 523 |
| 8-10 | Var. 524 |
| 10-40 | Var. 525 |
| 10-38 | Var. 526 |
| 10-36 | Var. 527 |
| 10-34 | Var. 528 |
| 10-32 | Var. 529 |
| 10-30 | Var. 530 |
| 10-28 | Var. 531 |
| 10-26 | Var. 532 |
| 10-24 | Var. 533 |
| 10-22 | Var. 534 |
| 10-20 | Var. 535 |
| 10-18 | Var. 536 |
| 10-16 | Var. 537 |
| 10-14 | Var. 538 |
| 10-12 | Var. 539 |
| 12-40 | Var. 540 |
| 12-38 | Var. 541 |
| 12-36 | Var. 542 |
| 12-34 | Var. 543 |
| 12-32 | Var. 544 |
| 12-30 | Var. 545 |
| 12-28 | Var. 546 |
| 12-26 | Var. 547 |
| 12-24 | Var. 548 |
| 12-22 | Var. 549 |
| 12-20 | Var. 550 |
| 12-18 | Var. 551 |
| 12-16 | Var. 552 |
| 12-14 | Var. 553 |
| 14-40 | Var. 554 |
| 14-38 | Var. 555 |
| 14-36 | Var. 556 |
| 14-34 | Var. 557 |
| 14-32 | Var. 558 |
| 14-30 | Var. 559 |
| 14-28 | Var. 560 |
| 14-26 | Var. 561 |
| 14-24 | Var. 562 |
| 14-22 | Var. 563 |
| 14-20 | Var. 564 |
| 14-18 | Var. 565 |
| 14-16 | Var. 566 |
| 16-40 | Var. 567 |
| 16-38 | Var. 568 |
| 16-36 | Var. 569 |
| 16-34 | Var. 570 |
| 16-32 | Var. 571 |
| 16-30 | Var. 572 |
| 16-28 | Var. 573 |
| 16-26 | Var. 574 |
| 16-24 | Var. 575 |
| 16-22 | Var. 576 |
| 16-20 | Var. 577 |
| 16-18 | Var. 578 |
| 18-40 | Var. 579 |
| 18-38 | Var. 580 |
| 18-36 | Var. 581 |
| 18-34 | Var. 582 |
| 18-32 | Var. 583 |
| 18-30 | Var. 584 |
| 18-28 | Var. 585 |
| 18-26 | Var. 586 |
| 18-24 | Var. 587 |
| 18-22 | Var. 588 |
| 18-20 | Var. 589 |
| 20-40 | Var. 590 |
| 20-38 | Var. 591 |
| 20-36 | Var. 592 |
| 20-34 | Var. 593 |
| 20-32 | Var. 594 |
| 20-30 | Var. 595 |
| 20-28 | Var. 596 |
| 20-26 | Var. 597 |
| 20-24 | Var. 598 |
| 20-22 | Var. 599 |
| 22-40 | Var. 600 |
| 22-38 | Var. 601 |
| 22-36 | Var. 602 |
| 22-34 | Var. 603 |
| 22-32 | Var. 604 |
| 22-30 | Var. 605 |
| 22-28 | Var. 606 |
| 22-26 | Var. 607 |
| 22-24 | Var. 608 |
| 24-40 | Var. 609 |
| 24-38 | Var. 610 |
| 24-36 | Var. 611 |
| 24-34 | Var. 612 |
| 24-32 | Var. 613 |
| 24-30 | Var. 614 |
| 24-28 | Var. 615 |
| 24-26 | Var. 616 |
| 26-40 | Var. 617 |
| 26-38 | Var. 618 |
| 26-36 | Var. 619 |
| 26-34 | Var. 620 |
| 26-32 | Var. 621 |
| 26-30 | Var. 622 |
| 26-28 | Var. 623 |
| 28-40 | Var. 624 |
| 28-38 | Var. 625 |
| 28-36 | Var. 626 |
| 28-34 | Var. 627 |
| 28-32 | Var. 628 |
| 28-30 | Var. 629 |
| 30-40 | Var. 630 |
| 30-38 | Var. 631 |
| 30-36 | Var. 632 |
| 30-34 | Var. 633 |
| 30-32 | Var. 634 |
| 32-40 | Var. 635 |
| 32-38 | Var. 636 |
| 32-36 | Var. 637 |
| 32-34 | Var. 638 |
| 34-40 | Var. 639 |
| 36-38 | Var. 640 |
| 38-40 | Var. 641 |

Var. = Variation

In some embodiments, the rVWF composition prepared by the methods provided herein can be characterized according to the percentage of rVWF molecules that are present in a particular higher order rVWF multimer or larger multimer. For example, in one embodiment, at least 20% of rVWF molecules in a rVWF composition used in the methods described herein are present in an oligomeric complex of at least 10 subunits. In another embodiment, at least 20% of rVWF molecules in a rVWF composition used in the methods described herein are present in an oligomeric complex of at least 12 subunits. In yet other embodiments, a rVWF composition used in the methods provided herein has a minimal percentage (e.g., has at least X %) of rVWF molecules present in a particular higher-order rVWF multimer or larger multimer (e.g., a multimer of at least Y subunits) according to any one of variations 134 to 457 found in Table 5 to Table 7.

TABLE 5

Exemplary embodiments for the percentage of rVWF molecules that are present in a particular higher order rVWF multimer or larger multimer found in the compositions and used in the methods provided herein.

| | | Minimal Number of Subunits in rVWF Multimer | | | | | |
|---|---|---|---|---|---|---|---|
| | | 6 | 8 | 10 | 12 | 14 | 16 |
| Minimal | 10% | Var. 134 | Var. 152 | Var. 170 | Var. 188 | Var. 206 | Var. 224 |
| Percentage of | 15% | Var. 135 | Var. 153 | Var. 171 | Var. 189 | Var. 207 | Var. 225 |
| rVWF | 20% | Var. 136 | Var. 154 | Var. 172 | Var. 190 | Var. 208 | Var. 226 |
| Molecules | 25% | Var. 137 | Var. 155 | Var. 173 | Var. 191 | Var. 209 | Var. 227 |
| | 30% | Var. 138 | Var. 156 | Var. 174 | Var. 192 | Var. 210 | Var. 228 |
| | 35% | Var. 139 | Var. 157 | Var. 175 | Var. 193 | Var. 211 | Var. 229 |
| | 40% | Var. 140 | Var. 158 | Var. 176 | Var. 194 | Var. 212 | Var. 230 |
| | 45% | Var. 141 | Var. 159 | Var. 177 | Var. 195 | Var. 213 | Var. 231 |
| | 50% | Var. 142 | Var. 160 | Var. 178 | Var. 196 | Var. 214 | Var. 232 |
| | 55% | Var. 143 | Var. 161 | Var. 179 | Var. 197 | Var. 215 | Var. 233 |
| | 60% | Var. 144 | Var. 162 | Var. 180 | Var. 198 | Var. 216 | Var. 234 |
| | 65% | Var. 145 | Var. 163 | Var. 181 | Var. 199 | Var. 217 | Var. 235 |
| | 70% | Var. 146 | Var. 164 | Var. 182 | Var. 200 | Var. 218 | Var. 236 |
| | 75% | Var. 147 | Var. 165 | Var. 183 | Var. 201 | Var. 219 | Var. 237 |
| | 80% | Var. 148 | Var. 166 | Var. 184 | Var. 202 | Var. 220 | Var. 238 |
| | 85% | Var. 149 | Var. 167 | Var. 185 | Var. 203 | Var. 221 | Var. 239 |
| | 90% | Var. 150 | Var. 168 | Var. 186 | Var. 204 | Var. 222 | Var. 240 |
| | 95% | Var. 151 | Var. 169 | Var. 187 | Var. 205 | Var. 223 | Var. 241 |

Var. = Variation

TABLE 6

Exemplary embodiments for the percentage of rVWF molecules that are present in a particular higher order rVWF multimer or larger multimer found in the compositions and used in the methods provided herein.

| | | Minimal Number of Subunits in rVWF Multimer | | | | | |
|---|---|---|---|---|---|---|---|
| | | 18 | 20 | 22 | 24 | 26 | 28 |
| Minimal Percentage | 10% | Var. 242 | Var. 260 | Var. 278 | Var. 296 | Var. 314 | Var. 332 |
| of rVWF Molecules | 15% | Var. 243 | Var. 261 | Var. 279 | Var. 297 | Var. 315 | Var. 333 |
| | 20% | Var. 244 | Var. 262 | Var. 280 | Var. 298 | Var. 316 | Var. 334 |
| | 25% | Var. 245 | Var. 263 | Var. 281 | Var. 299 | Var. 317 | Var. 335 |
| | 30% | Var. 246 | Var. 264 | Var. 282 | Var. 300 | Var. 318 | Var. 336 |
| | 35% | Var. 247 | Var. 265 | Var. 283 | Var. 301 | Var. 319 | Var. 337 |
| | 40% | Var. 248 | Var. 266 | Var. 284 | Var. 302 | Var. 320 | Var. 338 |
| | 45% | Var. 249 | Var. 267 | Var. 285 | Var. 303 | Var. 321 | Var. 339 |
| | 50% | Var. 250 | Var. 268 | Var. 286 | Var. 304 | Var. 322 | Var. 340 |
| | 55% | Var. 251 | Var. 269 | Var. 287 | Var. 305 | Var. 323 | Var. 341 |
| | 60% | Var. 252 | Var. 270 | Var. 288 | Var. 306 | Var. 324 | Var. 342 |
| | 65% | Var. 253 | Var. 271 | Var. 289 | Var. 307 | Var. 325 | Var. 343 |
| | 70% | Var. 254 | Var. 272 | Var. 290 | Var. 308 | Var. 326 | Var. 344 |
| | 75% | Var. 255 | Var. 273 | Var. 291 | Var. 309 | Var. 327 | Var. 345 |
| | 80% | Var. 256 | Var. 274 | Var. 292 | Var. 310 | Var. 328 | Var. 346 |
| | 85% | Var. 257 | Var. 275 | Var. 293 | Var. 311 | Var. 329 | Var. 347 |
| | 90% | Var. 258 | Var. 276 | Var. 294 | Var. 312 | Var. 330 | Var. 348 |
| | 95% | Var. 259 | Var. 277 | Var. 295 | Var. 313 | Var. 331 | Var. 349 |

Var. = Variation

TABLE 7

Exemplary embodiments for the percentage of rVWF molecules that are present in a particular higher order rVWF multimer or larger multimer found in the compositions and used in the methods provided herein.

| | | Minimal Number of Subunits in rVWF Multimer | | | | | |
|---|---|---|---|---|---|---|---|
| | | 30 | 32 | 34 | 36 | 38 | 40 |
| Minimal | 10% | Var. 350 | Var. 368 | Var. 386 | Var. 404 | Var. 422 | Var. 440 |
| Percentage of | 15% | Var. 351 | Var. 369 | Var. 387 | Var. 405 | Var. 423 | Var. 441 |
| rVWF | 20% | Var. 352 | Var. 370 | Var. 388 | Var. 406 | Var. 424 | Var. 442 |
| Molecules | 25% | Var. 353 | Var. 371 | Var. 389 | Var. 407 | Var. 425 | Var. 443 |
| | 30% | Var. 354 | Var. 372 | Var. 390 | Var. 408 | Var. 426 | Var. 444 |
| | 35% | Var. 355 | Var. 373 | Var. 391 | Var. 409 | Var. 427 | Var. 445 |
| | 40% | Var. 356 | Var. 374 | Var. 392 | Var. 410 | Var. 428 | Var. 446 |
| | 45% | Var. 357 | Var. 375 | Var. 393 | Var. 411 | Var. 429 | Var. 447 |
| | 50% | Var. 358 | Var. 376 | Var. 394 | Var. 412 | Var. 430 | Var. 448 |
| | 55% | Var. 359 | Var. 377 | Var. 395 | Var. 413 | Var. 431 | Var. 449 |
| | 60% | Var. 360 | Var. 378 | Var. 396 | Var. 414 | Var. 432 | Var. 450 |
| | 65% | Var. 361 | Var. 379 | Var. 397 | Var. 415 | Var. 433 | Var. 451 |
| | 70% | Var. 362 | Var. 380 | Var. 398 | Var. 416 | Var. 434 | Var. 452 |
| | 75% | Var. 363 | Var. 381 | Var. 399 | Var. 417 | Var. 435 | Var. 453 |
| | 80% | Var. 364 | Var. 382 | Var. 400 | Var. 418 | Var. 436 | Var. 454 |
| | 85% | Var. 365 | Var. 383 | Var. 401 | Var. 419 | Var. 437 | Var. 455 |
| | 90% | Var. 366 | Var. 384 | Var. 402 | Var. 420 | Var. 438 | Var. 456 |
| | 95% | Var. 367 | Var. 385 | Var. 403 | Var. 421 | Var. 439 | Var. 457 |

Var. = Variation

In accordance with the above, the rVWF comprises a significant percentage of high molecular weight (HMW) rVWF multimers. In further embodiments, the HMW rVWF multimer composition comprises at least 10%-80% rVWF decamers or higher order multimers. In further embodiments, the composition comprises about 10-95%, 20-90%, 30-85%, 40-80%, 50-75%, 60-70% decamers or higher order multimers. In further embodiments, the HMW rVWF multimer composition comprises at least about 10%, 20%, 30%, 40%, 50%, 60%, 70%, 80%, 90% decamers or higher order multimers.

Assessment of the number and percentage of rVWF multimers can be conducted using methods known in the art, including without limitation methods using electrophoresis and size exclusion chromatography methods to separate rVWF multimers by size, for example as discussed by Cumming et al, (J Clin Pathol. 1993 May; 46(5): 470-473, which is hereby incorporated by reference in its entirety for all purposes and in particular for all teachings related to assessment of rVWF multimers). Such techniques may further include immunoblotting techniques (such as Western Blot), in which the gel is immunoblotted with a radiolabelled antibody against VWF followed by chemiluminescent detection (see for example Wen et al., (1993), J. Clin. Lab. Anal., 7: 317-323, which is hereby incorporated by reference in its entirety for all purposes and in particular for all teachings related to assessment of rVWF multimers). Further assays for VWF include VWF:Antigen (VWF:Ag), VWF:Ristocetin Cofactor (VWF:RCof), and VWF:Collagen Binding Activity assay (VWF:CBA), which are often used for diagnosis and classification of Von Willebrand Disease. (see for example Favaloro et al., Pathology, 1997, 29(4): 341-456, which is hereby incorporated by reference in its entirety for all purposes and in particular for all teachings related to assays for VWF).

In some embodiments, the ratio of rFVIII procoagulant activity (IU rFVIII:C) to rVWF Ristocetin cofactor activity (IU rVWF:RCo) for the rVWF prepared according to the methods of the present invention is between 3:1 and 1:5. In further embodiments, the ratio is between 2:1 and 1:4. In still further embodiments, the ratio is between 5:2 and 1:4. In further embodiments, the ratio is between 3:2 and 1:3. In still further embodiments, the ratio is about 1:1, 1:2, 1:3, 1:4, 1:5, 2:1, 2:3, 2:4, 2:5, 3:1, 3:2, 3:4, or 3:5. In further embodiments, the ratio is between 1:1 and 1:2. In yet further embodiments, the ratio is 1.1:1, 1.2:1, 1.3:1, 1.4:1, 1.5:1, 1.6:1, 1.7:1, 1.8:1, 1.9:1, or 2:1. In certain embodiments, the ratio of rFVIII procoagulant activity (IU rFVIII:C) to rVWF Ristocetin cofactor activity (IU rVWF:RCo) in a composition useful for a method described herein is selected from variations 1988 to 2140 found in Table 8.

TABLE 8

Exemplary embodiments for the ratio of rFVIII procoagulant activity (IU rFVIII:C) to rVWF Ristocetin cofactor activity (IU rVWF:RCo) in compositions and used in methods provided herein.

| (IU rFVIII:C) to (IU rVWF:RCo) | |
|---|---|
| 4:1 | Var. 1988 |
| 3:1 | Var. 1989 |
| 2:1 | Var. 1990 |
| 3:2 | Var. 1991 |
| 4:3 | Var. 1992 |
| 1:1 | Var. 1993 |
| 5:6 | Var. 1994 |
| 4:5 | Var. 1995 |
| 3:4 | Var. 1996 |
| 2:3 | Var. 1997 |
| 3:5 | Var. 1998 |
| 1:2 | Var. 1999 |
| 2:5 | Var. 2000 |
| 1:3 | Var. 2001 |
| 1:4 | Var. 2002 |
| 1:5 | Var. 2003 |
| 1:6 | Var. 2004 |
| 4:1-1:6 | Var. 2005 |
| 4:1-1:5 | Var. 2006 |
| 4:1-1:4 | Var. 2007 |
| 4:1-1:3 | Var. 2008 |
| 4:1-2:5 | Var. 2009 |
| 4:1-1:2 | Var. 2010 |
| 4:1-3:5 | Var. 2011 |
| 4:1-2:3 | Var. 2012 |
| 4:1-3:4 | Var. 2013 |

TABLE 8-continued

Exemplary embodiments for the ratio of rFVIII procoagulant activity (IU rFVIII:C) to rVWF Ristocetin cofactor activity (IU rVWF:RCo) in compositions and used in methods provided herein.

| (IU rFVIII:C) to (IU rVWF:RCo) | |
|---|---|
| 4:1-4:5 | Var. 2014 |
| 4:1-5:6 | Var. 2015 |
| 4:1-1:1 | Var. 2016 |
| 4:1-4:3 | Var. 2017 |
| 4:1-3:2 | Var. 2018 |
| 4:1-2:1 | Var. 2019 |
| 4:1-3:1 | Var. 2020 |
| 3:1-1:6 | Var. 2021 |
| 3:1-1:5 | Var. 2022 |
| 3:1-1:4 | Var. 2023 |
| 3:1-1:3 | Var. 2024 |
| 3:1-2:5 | Var. 2025 |
| 3:1-1:2 | Var. 2026 |
| 3:1-3:5 | Var. 2027 |
| 3:1-2:3 | Var. 2028 |
| 3:1-3:4 | Var. 2029 |
| 3:1-4:5 | Var. 2030 |
| 3:1-5:6 | Var. 2031 |
| 3:1-1:1 | Var. 2032 |
| 3:1-4:3 | Var. 2033 |
| 3:1-3:2 | Var. 2034 |
| 3:1-2:1 | Var. 2035 |
| 2:1-1:6 | Var. 2036 |
| 2:1-1:5 | Var. 2037 |
| 2:1-1:4 | Var. 2038 |
| 2:1-1:3 | Var. 2039 |
| 2:1-2:5 | Var. 2040 |
| 2:1-1:2 | Var. 2041 |
| 2:1-3:5 | Var. 2042 |
| 2:1-2:3 | Var. 2043 |
| 2:1-3:4 | Var. 2044 |
| 2:1-4:5 | Var. 2045 |
| 2:1-5:6 | Var. 2046 |
| 2:1-1:1 | Var. 2047 |
| 2:1-4:3 | Var. 2048 |
| 2:1-3:2 | Var. 2049 |
| 3:2-1:6 | Var. 2050 |
| 3:2-1:5 | Var. 2051 |
| 3:2-1:4 | Var. 2052 |
| 3:2-1:3 | Var. 2053 |
| 3:2-2:5 | Var. 2054 |
| 3:2-1:2 | Var. 2055 |
| 3:2-3:5 | Var. 2056 |
| 3:2-2:3 | Var. 2057 |
| 3:2-3:4 | Var. 2058 |
| 3:2-4:5 | Var. 2059 |
| 3:2-5:6 | Var. 2060 |
| 3:2-1:1 | Var. 2061 |
| 3:2-4:3 | Var. 2062 |
| 4:3-1:6 | Var. 2063 |
| 4:3-1:5 | Var. 2064 |
| 4:3-1:4 | Var. 2065 |
| 4:3-1:3 | Var. 2066 |
| 4:3-2:5 | Var. 2067 |
| 4:3-1:2 | Var. 2068 |
| 4:3-3:5 | Var. 2069 |
| 4:3-2:3 | Var. 2070 |
| 4:3-3:4 | Var. 2071 |
| 4:3-4:5 | Var. 2072 |
| 4:3-5:6 | Var. 2073 |
| 4:3-1:1 | Var. 2074 |
| 1:1-1:6 | Var. 2075 |
| 1:1-1:5 | Var. 2076 |
| 1:1-1:4 | Var. 2077 |
| 1:1-1:3 | Var. 2078 |
| 1:1-2:5 | Var. 2079 |
| 1:1-1:2 | Var. 2080 |
| 1:1-3:5 | Var. 2081 |
| 1:1-2:3 | Var. 2082 |
| 1:1-3:4 | Var. 2083 |
| 1:1-4:5 | Var. 2084 |
| 1:1-5:6 | Var. 2085 |
| 5:6-1:6 | Var. 2086 |
| 5:6-1:5 | Var. 2087 |
| 5:6-1:4 | Var. 2088 |
| 5:6-1:3 | Var. 2089 |
| 5:6-2:5 | Var. 2090 |
| 5:6-1:2 | Var. 2091 |
| 5:6-3:5 | Var. 2092 |
| 5:6-2:3 | Var. 2093 |
| 5:6-3:4 | Var. 2094 |
| 5:6-4:5 | Var. 2095 |
| 4:5-1:6 | Var. 2096 |
| 4:5-1:5 | Var. 2097 |
| 4:5-1:4 | Var. 2098 |
| 4:5-1:3 | Var. 2099 |
| 4:5-2:5 | Var. 2100 |
| 4:5-1:2 | Var. 2101 |
| 4:5-3:5 | Var. 2102 |
| 4:5-2:3 | Var. 2103 |
| 4:5-3:4 | Var. 2104 |
| 3:4-1:6 | Var. 2105 |
| 3:4-1:5 | Var. 2106 |
| 3:4-1:4 | Var. 2107 |
| 3:4-1:3 | Var. 2108 |
| 3:4-2:5 | Var. 2109 |
| 3:4-1:2 | Var. 2110 |
| 3:4-3:5 | Var. 2111 |
| 3:4-2:3 | Var. 2112 |
| 2:3-1:6 | Var. 2113 |
| 2:3-1:5 | Var. 2114 |
| 2:3-1:4 | Var. 2115 |
| 2:3-1:3 | Var. 2116 |
| 2:3-2:5 | Var. 2117 |
| 2:3-1:2 | Var. 2118 |
| 2:3-3:5 | Var. 2119 |
| 3:5-1:6 | Var. 2120 |
| 3:5-1:5 | Var. 2121 |
| 3:5-1:4 | Var. 2122 |
| 3:5-1:3 | Var. 2123 |
| 3:5-2:5 | Var. 2124 |
| 3:5-1:2 | Var. 2125 |
| 1:2-1:6 | Var. 2126 |
| 1:2-1:5 | Var. 2127 |
| 1:2-1:4 | Var. 2128 |
| 1:2-1:3 | Var. 2129 |
| 1:2-2:5 | Var. 2130 |
| 2:5-1:6 | Var. 2131 |
| 2:5-1:5 | Var. 2132 |
| 2:5-1:4 | Var. 2133 |
| 2:5-1:3 | Var. 2134 |
| 1:3-1:6 | Var. 2135 |
| 1:3-1:5 | Var. 2136 |
| 1:3-1:4 | Var. 2137 |
| 1:4-1:6 | Var. 2138 |
| 1:4-1:5 | Var. 2139 |
| 1:5-1:6 | Var. 2140 |

Var. = Variation

In further embodiments, higher order rVWF multimers of the invention are stable for about 1 to about 90 hours post-administration. In still further embodiments, the higher order rVWF multimers are stable for about 5-80, 10-70, 15-60, 20-50, 25-40, 30-35 hours post-administration. In yet further embodiments, the higher order rVWF multimers are stable for at least 3, 6, 12, 18, 24, 36, 48, 72 hours post-administration. In certain embodiments the stability of the rVWF multimers is assessed in vitro.

In one embodiment, higher order rVWF multimers used in the compositions and methods provided herein have a half-life of at least 12 hour post administration. In another embodiment, the higher order rVWF multimers have a half-life of at least 24 hour post administration. In yet other embodiments, the higher order rVWF multimers have a half-life selected from variations 642 to 1045 found in Table 9.

TABLE 9

Exemplary embodiments for the half-life of higher order rVWF multimers found in the compositions prepared by the methods provided herein.

| Hours | |
|---|---|
| at least 1 | Var. 642 |
| at least 2 | Var. 643 |
| at least 3 | Var. 644 |
| at least 4 | Var. 645 |
| at least 5 | Var. 646 |
| at least 6 | Var. 647 |
| at least 7 | Var. 648 |
| at least 8 | Var. 649 |
| at least 9 | Var. 650 |
| at least 10 | Var. 651 |
| at least 11 | Var. 652 |
| at least 12 | Var. 653 |
| at least 14 | Var. 654 |
| at least 16 | Var. 655 |
| at least 18 | Var. 656 |
| at least 20 | Var. 657 |
| at least 22 | Var. 658 |
| at least 24 | Var. 659 |
| at least 27 | Var. 660 |
| at least 30 | Var. 661 |
| at least 33 | Var. 662 |
| at least 36 | Var. 663 |
| at least 39 | Var. 664 |
| at least 42 | Var. 665 |
| at least 45 | Var. 666 |
| at least 48 | Var. 667 |
| at least 54 | Var. 668 |
| at least 60 | Var. 669 |
| at least 66 | Var. 670 |
| at least 72 | Var. 671 |
| at least 78 | Var. 672 |
| at least 84 | Var. 673 |
| at least 90 | Var. 674 |
| 2-90 | Var. 675 |
| 2-84 | Var. 676 |
| 2-78 | Var. 677 |
| 2-72 | Var. 678 |
| 2-66 | Var. 679 |
| 2-60 | Var. 680 |
| 2-54 | Var. 681 |
| 2-48 | Var. 682 |
| 2-45 | Var. 683 |
| 2-42 | Var. 684 |
| 2-39 | Var. 685 |
| 2-36 | Var. 686 |
| 2-33 | Var. 687 |
| 2-30 | Var. 688 |
| 2-27 | Var. 689 |
| 2-24 | Var. 690 |
| 2-22 | Var. 691 |
| 2-20 | Var. 692 |
| 2-18 | Var. 693 |
| 2-16 | Var. 694 |
| 2-14 | Var. 695 |
| 2-12 | Var. 696 |
| 2-10 | Var. 697 |
| 2-8 | Var. 698 |
| 2-6 | Var. 699 |
| 2-4 | Var. 700 |
| 3-90 | Var. 701 |
| 3-84 | Var. 702 |
| 3-78 | Var. 703 |
| 3-72 | Var. 704 |
| 3-66 | Var. 705 |
| 3-60 | Var. 706 |
| 3-54 | Var. 707 |
| 3-48 | Var. 708 |
| 3-45 | Var. 709 |
| 3-42 | Var. 710 |
| 3-39 | Var. 711 |
| 3-36 | Var. 712 |
| 3-33 | Var. 713 |
| 3-30 | Var. 714 |
| 3-27 | Var. 715 |
| 3-24 | Var. 716 |
| 3-22 | Var. 717 |
| 3-20 | Var. 718 |
| 3-18 | Var. 719 |
| 3-16 | Var. 720 |
| 3-14 | Var. 721 |
| 3-12 | Var. 722 |
| 3-10 | Var. 723 |
| 3-8 | Var. 724 |
| 3-6 | Var. 725 |
| 3-4 | Var. 726 |
| 4-90 | Var. 727 |
| 4-84 | Var. 728 |
| 4-78 | Var. 729 |
| 4-72 | Var. 730 |
| 4-66 | Var. 731 |
| 4-60 | Var. 732 |
| 4-54 | Var. 733 |
| 4-48 | Var. 734 |
| 4-45 | Var. 735 |
| 4-42 | Var. 736 |
| 4-39 | Var. 737 |
| 4-36 | Var. 738 |
| 4-33 | Var. 739 |
| 4-30 | Var. 740 |
| 4-27 | Var. 741 |
| 4-24 | Var. 742 |
| 4-22 | Var. 743 |
| 4-20 | Var. 744 |
| 4-18 | Var. 745 |
| 4-16 | Var. 746 |
| 4-14 | Var. 747 |
| 4-12 | Var. 748 |
| 4-10 | Var. 749 |
| 4-8 | Var. 750 |
| 4-6 | Var. 751 |
| 6-90 | Var. 752 |
| 6-84 | Var. 753 |
| 6-78 | Var. 754 |
| 6-72 | Var. 755 |
| 6-66 | Var. 756 |
| 6-60 | Var. 757 |
| 6-54 | Var. 758 |
| 6-48 | Var. 759 |
| 6-45 | Var. 760 |
| 6-42 | Var. 761 |
| 6-39 | Var. 762 |
| 6-36 | Var. 763 |
| 6-33 | Var. 764 |
| 6-30 | Var. 765 |
| 6-27 | Var. 766 |
| 6-24 | Var. 767 |
| 6-22 | Var. 768 |
| 6-20 | Var. 769 |
| 6-18 | Var. 770 |
| 6-16 | Var. 771 |
| 6-14 | Var. 772 |
| 6-12 | Var. 773 |
| 6-10 | Var. 774 |
| 6-8 | Var. 775 |
| 8-90 | Var. 776 |
| 8-84 | Var. 777 |
| 8-78 | Var. 778 |
| 8-72 | Var. 779 |
| 8-66 | Var. 780 |
| 8-60 | Var. 781 |
| 8-54 | Var. 782 |

TABLE 9-continued

Exemplary embodiments for the half-life of higher
order rVWF multimers found in the compositions
prepared by the methods provided herein.

| Hours | |
|---|---|
| 8-48 | Var. 783 |
| 8-45 | Var. 784 |
| 8-42 | Var. 785 |
| 8-39 | Var. 786 |
| 8-36 | Var. 787 |
| 8-33 | Var. 788 |
| 8-30 | Var. 789 |
| 8-27 | Var. 790 |
| 8-24 | Var. 791 |
| 8-22 | Var. 792 |
| 8-20 | Var. 793 |
| 8-18 | Var. 794 |
| 8-16 | Var. 795 |
| 8-14 | Var. 796 |
| 8-12 | Var. 797 |
| 8-10 | Var. 798 |
| 10-90 | Var. 799 |
| 10-84 | Var. 800 |
| 10-78 | Var. 801 |
| 10-72 | Var. 802 |
| 10-66 | Var. 803 |
| 10-60 | Var. 804 |
| 10-54 | Var. 805 |
| 10-48 | Var. 806 |
| 10-45 | Var. 807 |
| 10-42 | Var. 808 |
| 10-39 | Var. 809 |
| 10-36 | Var. 810 |
| 10-33 | Var. 811 |
| 10-30 | Var. 812 |
| 10-27 | Var. 813 |
| 10-24 | Var. 814 |
| 10-22 | Var. 815 |
| 10-20 | Var. 816 |
| 10-18 | Var. 817 |
| 10-16 | Var. 818 |
| 10-14 | Var. 819 |
| 10-12 | Var. 820 |
| 12-90 | Var. 821 |
| 12-84 | Var. 822 |
| 12-78 | Var. 823 |
| 12-72 | Var. 824 |
| 12-66 | Var. 825 |
| 12-60 | Var. 826 |
| 12-54 | Var. 827 |
| 12-48 | Var. 828 |
| 12-45 | Var. 829 |
| 12-42 | Var. 830 |
| 12-39 | Var. 831 |
| 12-36 | Var. 832 |
| 12-33 | Var. 833 |
| 12-30 | Var. 834 |
| 12-27 | Var. 835 |
| 12-24 | Var. 836 |
| 12-22 | Var. 837 |
| 12-20 | Var. 838 |
| 12-18 | Var. 839 |
| 12-16 | Var. 840 |
| 12-14 | Var. 841 |
| 14-90 | Var. 842 |
| 14-84 | Var. 843 |
| 14-78 | Var. 844 |
| 14-72 | Var. 845 |
| 14-66 | Var. 846 |
| 14-60 | Var. 847 |
| 14-54 | Var. 848 |
| 14-48 | Var. 849 |
| 14-45 | Var. 850 |
| 14-42 | Var. 851 |
| 14-39 | Var. 852 |
| 14-36 | Var. 853 |
| 14-33 | Var. 854 |
| 14-30 | Var. 855 |
| 14-27 | Var. 856 |
| 14-24 | Var. 857 |
| 14-22 | Var. 858 |
| 14-20 | Var. 859 |
| 14-18 | Var. 860 |
| 14-16 | Var. 861 |
| 16-90 | Var. 862 |
| 16-84 | Var. 863 |
| 16-78 | Var. 864 |
| 16-72 | Var. 865 |
| 16-66 | Var. 866 |
| 16-60 | Var. 867 |
| 16-54 | Var. 868 |
| 16-48 | Var. 869 |
| 16-45 | Var. 870 |
| 16-42 | Var. 871 |
| 16-39 | Var. 872 |
| 16-36 | Var. 873 |
| 16-33 | Var. 874 |
| 16-30 | Var. 875 |
| 16-27 | Var. 876 |
| 16-24 | Var. 877 |
| 16-22 | Var. 878 |
| 16-20 | Var. 879 |
| 16-18 | Var. 880 |
| 18-90 | Var. 881 |
| 18-84 | Var. 882 |
| 18-78 | Var. 883 |
| 18-72 | Var. 884 |
| 18-66 | Var. 885 |
| 18-60 | Var. 886 |
| 18-54 | Var. 887 |
| 18-48 | Var. 888 |
| 18-45 | Var. 889 |
| 18-42 | Var. 890 |
| 18-39 | Var. 891 |
| 18-36 | Var. 892 |
| 18-33 | Var. 893 |
| 18-30 | Var. 894 |
| 18-27 | Var. 895 |
| 18-24 | Var. 896 |
| 18-22 | Var. 897 |
| 18-20 | Var. 898 |
| 20-90 | Var. 899 |
| 20-84 | Var. 900 |
| 20-78 | Var. 901 |
| 20-72 | Var. 902 |
| 20-66 | Var. 903 |
| 20-60 | Var. 904 |
| 20-54 | Var. 905 |
| 20-48 | Var. 906 |
| 20-45 | Var. 907 |
| 20-42 | Var. 908 |
| 20-39 | Var. 909 |
| 20-36 | Var. 910 |
| 20-33 | Var. 911 |
| 20-30 | Var. 912 |
| 20-27 | Var. 913 |
| 20-24 | Var. 914 |
| 20-22 | Var. 915 |
| 22-90 | Var. 916 |
| 22-84 | Var. 917 |
| 22-78 | Var. 918 |
| 22-72 | Var. 919 |
| 22-66 | Var. 920 |
| 22-60 | Var. 921 |
| 22-54 | Var. 922 |
| 22-48 | Var. 923 |
| 22-45 | Var. 924 |
| 22-42 | Var. 925 |
| 22-39 | Var. 926 |
| 22-36 | Var. 927 |
| 22-33 | Var. 928 |
| 22-30 | Var. 929 |
| 22-27 | Var. 930 |

TABLE 9-continued

Exemplary embodiments for the half-life of higher order rVWF multimers found in the compositions prepared by the methods provided herein.

| Hours | |
|---|---|
| 22-24 | Var. 931 |
| 24-90 | Var. 932 |
| 24-84 | Var. 933 |
| 24-78 | Var. 934 |
| 24-72 | Var. 935 |
| 24-66 | Var. 936 |
| 24-60 | Var. 937 |
| 24-54 | Var. 938 |
| 24-48 | Var. 939 |
| 24-45 | Var. 940 |
| 24-42 | Var. 941 |
| 24-39 | Var. 942 |
| 24-36 | Var. 943 |
| 24-33 | Var. 944 |
| 24-30 | Var. 945 |
| 24-27 | Var. 946 |
| 27-90 | Var. 947 |
| 27-84 | Var. 948 |
| 27-78 | Var. 949 |
| 27-72 | Var. 950 |
| 27-66 | Var. 951 |
| 27-60 | Var. 952 |
| 27-54 | Var. 953 |
| 27-48 | Var. 954 |
| 30-90 | Var. 955 |
| 30-84 | Var. 956 |
| 30-78 | Var. 957 |
| 30-72 | Var. 958 |
| 30-66 | Var. 959 |
| 30-60 | Var. 960 |
| 30-54 | Var. 961 |
| 30-48 | Var. 962 |
| 30-45 | Var. 963 |
| 30-42 | Var. 964 |
| 30-39 | Var. 965 |
| 30-36 | Var. 966 |
| 30-33 | Var. 967 |
| 33-90 | Var. 968 |
| 33-84 | Var. 969 |
| 33-78 | Var. 970 |
| 33-72 | Var. 971 |
| 33-66 | Var. 972 |
| 33-60 | Var. 973 |
| 33-54 | Var. 974 |
| 33-48 | Var. 975 |
| 33-45 | Var. 976 |
| 33-42 | Var. 977 |
| 33-29 | Var. 978 |
| 33-36 | Var. 979 |
| 36-90 | Var. 980 |
| 36-84 | Var. 981 |
| 36-78 | Var. 982 |
| 36-72 | Var. 983 |
| 36-66 | Var. 984 |
| 36-60 | Var. 985 |
| 36-54 | Var. 986 |
| 36-48 | Var. 987 |
| 36-45 | Var. 988 |
| 36-42 | Var. 989 |
| 36-39 | Var. 990 |
| 39-90 | Var. 991 |
| 39-84 | Var. 992 |
| 39-78 | Var. 993 |
| 39-72 | Var. 994 |
| 39-66 | Var. 995 |
| 39-60 | Var. 996 |
| 39-54 | Var. 997 |
| 39-48 | Var. 998 |
| 39-45 | Var. 999 |
| 39-42 | Var. 1000 |
| 42-90 | Var. 1001 |
| 42-84 | Var. 1002 |
| 42-78 | Var. 1003 |
| 42-72 | Var. 1004 |
| 42-66 | Var. 1005 |
| 42-60 | Var. 1006 |
| 42-54 | Var. 1007 |
| 42-48 | Var. 1008 |
| 42-45 | Var. 1009 |
| 45-90 | Var. 1010 |
| 45-84 | Var. 1011 |
| 45-78 | Var. 1012 |
| 45-72 | Var. 1013 |
| 45-66 | Var. 1014 |
| 45-60 | Var. 1015 |
| 45-54 | Var. 1016 |
| 45-48 | Var. 1017 |
| 48-90 | Var. 1018 |
| 48-84 | Var. 1019 |
| 48-78 | Var. 1020 |
| 48-72 | Var. 1021 |
| 48-66 | Var. 1022 |
| 48-60 | Var. 1023 |
| 48-54 | Var. 1024 |
| 54-90 | Var. 1025 |
| 54-84 | Var. 1026 |
| 54-78 | Var. 1027 |
| 54-72 | Var. 1028 |
| 54-66 | Var. 1029 |
| 54-60 | Var. 1030 |
| 60-90 | Var. 1031 |
| 60-84 | Var. 1032 |
| 60-78 | Var. 1033 |
| 60-72 | Var. 1034 |
| 60-66 | Var. 1035 |
| 66-90 | Var. 1036 |
| 66-84 | Var. 1037 |
| 66-78 | Var. 1038 |
| 66-72 | Var. 1039 |
| 72-90 | Var. 1040 |
| 72-84 | Var. 1041 |
| 72-78 | Var. 1042 |
| 78-90 | Var. 1043 |
| 78-84 | Var. 1044 |
| 84-90 | Var. 1045 |

Var. = Variation

In some embodiments, the pro-VWF and/or purified rVWF purified in accordance with the present invention is not modified with any conjugation, post-translation or covalent modifications. In particular embodiments, the pro-VWF and/or purified rVWF of the present invention is not modified with a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

In some embodiments, the pro-VWF and/or purified rVWF purified in accordance with the present invention is modified through conjugation, post-translation modification, or covalent modification, including modifications of the N- or C-terminal residues as well as modifications of selected side chains, for example, at free sulfhydryl-groups, primary amines, and hydroxyl-groups. In one embodiment, a water soluble polymer is linked to the protein (directly or via a linker) by a lysine group or other primary amine. In some embodiments, the pro-VWF and/or purified rVWF of the present invention may be modified by conjugation of a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

Water soluble polymers that may be used to modify the pro-VWF and/or purified rVWF include linear and branched structures. The conjugated polymers may be attached directly to the coagulation proteins of the invention, or alternatively may be attached through a linking moiety. Non-limiting examples of protein conjugation with water soluble polymers can be found in U.S. Pat. Nos. 4,640,835; 4,496,689; 4,301,144; 4,670,417; 4,791,192, and 4,179,337, as well as in Abuchowski and Davis "Enzymes as Drugs," Holcenberg and Roberts, Eds., pp. 367 383, John Wiley and Sons, New York (1981), and Hermanson G., Bioconjugate Techniques 2nd Ed., Academic Press, Inc. 2008.

Protein conjugation may be performed by a number of well-known techniques in the art, for example, see Hermanson G., Bioconjugate Techniques 2nd Ed., Academic Press, Inc. 2008. Examples include linkage through the peptide bond between a carboxyl group on one of either the coagulation protein or water-soluble polymer moiety and an amine group of the other, or an ester linkage between a carboxyl group of one and a hydroxyl group of the other. Another linkage by which a coagulation protein of the invention could be conjugated to a water-soluble polymer compound is via a Schiff base, between a free amino group on the polymer moiety being reacted with an aldehyde group formed at the non-reducing end of the polymer by periodate oxidation (Jennings and Lugowski, J. Immunol. 1981; 127: 1011-8; Fernandes and Gregonradis, Biochim Biophys Acta. 1997; 1341; 26-34). The generated Schiff Base can be stabilized by specific reduction with $NaCNBH_3$ to form a secondary amine. An alternative approach is the generation of terminal free amino groups on the polymer by reductive amination with $NH_4Cl$ after prior oxidation. Bifunctional reagents can be used for linking two amino or two hydroxyl groups. For example, a polymer containing an amino group can be coupled to an amino group of the coagulation protein with reagents like BS3 (Bis(sulfosuccinimidyl)suberate/ Pierce, Rockford, Ill.). In addition, heterobifunctional cross linking reagents like Sulfo-EMCS (N-ε-Maleimidocaproyloxy) sulfosuccinimide ester/Pierce) can be used for instance to link amine and thiol groups. In other embodiments, an aldehyde reactive group, such as PEG alkoxide plus diethyl acetal of bromoacetaldehyde; PEG plus DMSO and acetic anhydride, and PEG chloride plus the phenoxide of 4-hydroxybenzaldehyde, succinimidyl active esters, activated dithiocarbonate PEG, 2,4,5-trichlorophenylcloroformate and P-nitrophenylcloroformate activated PEG, may be used in the conjugation of a coagulation protein.

Another method for measuring the biological activity of VWF is the collagen binding assay, which is based on ELISA technology (Brown and Bosak, Thromb. Res., 1986, 43:303-311; Favaloro, Thromb. Haemost., 2000, 83 127-135). A microtiter plate is coated with type I or III collagen. Then the VWF is bound to the collagen surface and subsequently detected with an enzyme-labeled polyclonal antibody. The last step is a substrate reaction, which can be photometrically monitored with an ELISA reader.

Immunological assays of von Willebrand factors (VWF: Ag) are immunoassays that measure the concentration of the VWF protein in plasma. They give no indication as to VWF function. A number of methods exist for measuring VWF:Ag and these include both enzyme-linked immunosorbent assay (ELISA) or automated latex immunoassays (LIA.) Many laboratories now use a fully automated latex immunoassay. Historically laboratories used a variety of techniques including Laurell electroimmunoassay 'Laurell Rockets' but these are rarely used in most labs today.

III. Kits

As an additional aspect, the invention includes kits which comprise one or more lyophilized compositions packaged in a manner which facilitates their use for administration to subjects. In one embodiment, such a kit includes pharmaceutical formulation described herein (e.g., a composition comprising a therapeutic protein or peptide), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (e.g., almost none). In one embodiment, the kit contains a first container having a therapeutic protein or peptide composition and a second container having a physiologically acceptable reconstitution solution for the composition. In one aspect, the pharmaceutical formulation is packaged in a unit dosage form. The kit may further include a device suitable for administering the pharmaceutical formulation according to a specific route of administration. Preferably, the kit contains a label that describes use of the pharmaceutical formulations.

IV. rVWF for Methods of Treating GI Bleeding in Patient with Severe VWD

One of the advantages of administering rVWF to subjects with severe VWD to pretreat for surgery is that the higher specific activity of rVWF as compared to pdVWF allows flexibility in the amount of rVWF administered and the number of times the subject is re-dosed. As will be appreciated and as is discussed in further detail herein, the co-administered FVIII may be recombinant or plasma derived Single or multiple administrations of rVWF are carried out with the dose levels and pattern being selected by the treating physician. For the prevention or treatment of disease, the appropriate dosage depends on the type of disease to be treated (e.g., von Willebrand disease), the severity and course of the disease, whether drug is administered for preventive or therapeutic purposes, previous therapy, the patient's clinical history and response to the drug, and the discretion of the attending physician.

In some aspects, rVWF is administered prior to a surgical procedure to a subject at a range from 20-60 IU/kg, e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 20-60, 35-70, 20-40, 35-60, 45-60, 45-55, 45-50, 50-60, 55-60, or 50-55 IU/kg. In some embodiments, rVWF is administered between 12 hours and 24 hours, e.g., 12 hours, 13 hours, 14 hours, 15 hours, 16 hours, 17 hours, 18 hours, 19 hours, 20 hours, 21 hours, 22 hours, 23 hours, 24 hours, 12 hours and 24 hours, 14 hours and 24 hours, 16 and 24 hours, 18 hours and 24 hours, or 20 hours and 24 hours prior to the surgical procedure. In some aspects, Factor VIII (FVIII) is not administered with the rVWF prior to the surgical procedure.

In some embodiments, rVWF is administered to the subject at a range of 5-90 IU/kg, e.g., 5-90, 5-50, 10-90, 15-90, 20-90, 30-90, 40-90, 50-90, 60-90, 70-90, 80-90, 5-80, 10-70, 20-60, 30-50, 35-60, 5-50, 5-40, 5-30, 5-20, 10-90, 10-50, or 20-40 IU/kg 1 hour prior to surgery. In other embodiments, rVWF is administered at a dose of 70-200 IU/kg, e.g., 70-200, 80-200-, 90-200, 100-200, 110-200, 120-200, 130-200, 130-200, 140-200, 150-200, 160-200, 170-200, 180-200, 190-200, 70-170, 80-180, 60-160, 50-150, 40-140, 30, 130, 20-120, 10-110, 70-100, or 70-90 IU/kg after the surgery. In some cases, the surgical procedure is selected from a group consisting of major surgery, minor surgery, and oral surgery.

In some embodiments, the subject is administered 35-60 IU/kg rVWF between 12 hours and 24 hours prior to major surgery. In other embodiments, the subject is administered 15-90 IU/kg rVWF 1 hour prior to major surgery. In another embodiment, the subject is administered 150-220 IU/kg rVWF after major surgery. In some instances, the subject undergoing major surgery is administered a total dosage of 220-320 IU/kg.

In some embodiments, the subject is administered 50-60 IU/kg rVWF between 12 hours and 24 hours prior to minor surgery. In other embodiments, the subject is administered 5-50 IU/kg rVWF 1 hour prior to minor surgery. In another embodiment, the subject is administered 70-150 IU/kg rVWF after minor surgery. In some instances, the subject undergoing minor surgery is administered a total dosage of 100-220 IU/kg.

In some embodiments, the subject is administered 20-40 IU/kg rVWF between 12 hours and 24 hours prior to oral surgery. In other embodiments, the subject is administered 20-50 IU/kg rVWF 1 hour prior to oral surgery. In another embodiment, the subject is administered 10-50 IU/kg rVWF during oral surgery. In another embodiment, the subject is administered 20-50 IU/kg rVWF after oral surgery. In some instances, the subject undergoing oral surgery is administered a total dosage of 70-190 IU/kg.

Compositions of rVWF can be contained in pharmaceutical formulations, as described herein. Such formulations can be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

In one aspect, formulations of the invention are administered by an initial bolus followed by a continuous infusion to maintain therapeutic circulating levels of drug product. As another example, the inventive compound is administered as a one-time dose. Those of ordinary skill in the art will readily optimize effective dosages and administration regimens as determined by good medical practice and the clinical condition of the individual patient. The route of administration can be, but is not limited to, by intravenous, intraperitoneal, subcutaneous, or intramuscular administration. The frequency of dosing depends on the pharmacokinetic parameters of the agents and the route of administration. The optimal pharmaceutical formulation is determined by one skilled in the art depending upon the route of administration and desired dosage. See for example, Remington's Pharmaceutical Sciences, 18th Ed., 1990, Mack Publishing Co., Easton, Pa. 18042 pages 1435-1712, the disclosure of which is hereby incorporated by reference in its entirety for all purposes and in particular for all teachings related to formulations, routes of administration and dosages for pharmaceutical products. Such formulations influence the physical state, stability, rate of in vivo release, and rate of in vivo clearance of the administered agents. Depending on the route of administration, a suitable dose is calculated according to body weight, body surface area or organ size. Appropriate dosages may be ascertained through use of established assays for determining blood level dosages in conjunction with appropriate dose-response data. The final dosage regimen is determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. By way of example, a typical dose of a recombinant VWF of the present invention is approximately 50 IU/kg, equal to 500 µg/kg. As studies are conducted, further information will emerge regarding the appropriate dosage levels and duration of treatment for various diseases and conditions.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, Highly stabilized York, Gait, "Oligonucleotide Synthesis: A Practical Approach" 1984, IRL Press, London, Nelson and Cox (2000), Lehninger, Principles of Biochemistry 3rd Ed., W. H. Freeman Pub., Highly stabilized York, N.Y. and Berg et al. (2002) Biochemistry, 5th Ed., W. H. Freeman Pub., Highly stabilized York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the above description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive method.

a. Lyophilized VWF Formulations

The present method also provides formulations of rVWF for use in the treatment methods provided herein. In some embodiments, the rVWF composition is used for the production of a pharmaceutical composition. In some embodiments, the rVWF can be formulated into a lyophilized formulation.

In some embodiments, the formulations comprising a VWF polypeptide of the invention are lyophilized after purification and prior to administration to a subject. Lyophilization is carried out using techniques common in the art and should be optimized for the composition being developed (Tang et al., Pharm Res. 21:191-200, (2004) and Chang et al., Pharm Res. 13:243-9 (1996)).

A lyophilization cycle is, in one aspect, composed of three steps: freezing, primary drying, and secondary drying (A. P. Mackenzie, Phil Trans R Soc London, Ser B, Biol 278:167 (1977)). In the freezing step, the solution is cooled to initiate ice formation. Furthermore, this step induces the crystallization of the bulking agent. The ice sublimes in the primary drying stage, which is conducted by reducing chamber pressure below the vapor pressure of the ice, using a vacuum and introducing heat to promote sublimation. Finally, adsorbed or bound water is removed at the secondary drying stage under reduced chamber pressure and at an elevated shelf temperature. The process produces a material known as a lyophilized cake. Thereafter the cake can be reconstituted with either sterile water or suitable diluent for injection.

The lyophilization cycle not only determines the final physical state of excipients but also affects other parameters such as reconstitution time, appearance, stability and final moisture content. The composition structure in the frozen state proceeds through several transitions (e.g., glass transitions, wettings, and crystallizations) that occur at specific temperatures and the structure may be used to understand and optimize the lyophilization process. The glass transition temperature (Tg and/or Tg') can provide information about the physical state of a solute and can be determined by differential scanning calorimetry (DSC). Tg and Tg' are an important parameter that must be taken into account when designing the lyophilization cycle. For example, Tg' is important for primary drying. Furthermore, in the dried state, the glass transition temperature provides information on the storage temperature of the final product.

b. Pharmaceutical Formulations and Excipients in General

Excipients are additives that either impart or enhance the stability and delivery of a drug product (e.g., protein). Regardless of the reason for their inclusion, excipients are an integral component of a formulation and therefore need to be safe and well tolerated by patients. For protein drugs, the choice of excipients is particularly important because they can affect both efficacy and immunogenicity of the drug. Hence, protein formulations need to be developed with appropriate selection of excipients that afford suitable stability, safety, and marketability.

A lyophilized formulation is, in one aspect, at least comprised of one or more of a buffer, a bulking agent, and a stabilizer. In this aspect, the utility of a surfactant is evaluated and selected in cases where aggregation during the lyophilization step or during reconstitution becomes an issue. An appropriate buffering agent is included to maintain the formulation within stable zones of pH during lyophilization. A comparison of the excipient components contemplated for liquid and lyophilized protein formulations is provided in Table 10.

TABLE 1

Excipient components of lyophilized protein formulations

| Excipient component | Function in lyophilized formulation |
|---|---|
| Buffer | Maintain pH of formulation during lyophilization and upon reconstitution |
| Tonicity agent/stabilizer | Stabilizers include cryo and lycoprotectants<br>Examples include Polyols, sugars and polymers<br>Cryoprotectants protect proteins from freezing stresses<br>Lyoprotectants stabilize proteins in the freeze-dried state |
| Bulking agent | Used to enhance product elegance and to prevent blowout<br>Provides structural strength to the lyo cake<br>Examples include mannitol and glycine |
| Surfactant | Employed if aggregation during the lyophilization process is an issue<br>May serve to reduce reconstitution times<br>Examples include polysorbate 20 and 80 |
| Anti-oxidant | Usually not employed, molecular reactions in the lyo cake are generally retarded |
| Metal ions/chelating agent | May be included if a specific metal ion is included only as a co-factor of where the metal is required for protease activity<br>Chelating agents are generally not needed in lyo formulations |
| Preservative | For multi-dose formulations only<br>Provides protection against microbial growth in formulation<br>Is usually included in the reconstitution diluent (e.g., bWFI) |

The principal challenge in developing formulations for proteins is stabilizing the product against the stresses of manufacturing, shipping and storage. The role of formulation excipients is to provide stabilization against these stresses. Excipients are also be employed to reduce viscosity of high concentration protein formulations in order to enable their delivery and enhance patient convenience. In general, excipients can be classified on the basis of the mechanisms by which they stabilize proteins against various chemical and physical stresses. Some excipients are used to alleviate the effects of a specific stress or to regulate a particular susceptibility of a specific protein. Other excipients have more general effects on the physical and covalent stabilities of proteins. The excipients described herein are organized either by their chemical type or their functional role in formulations. Brief descriptions of the modes of stabilization are provided when discussing each excipient type.

Given the teachings and guidance provided herein, those skilled in the art will know what amount or range of excipient can be included in any particular formulation to achieve a biopharmaceutical formulation of the invention that promotes retention in stability of the biopharmaceutical (e.g., a protein). For example, the amount and type of a salt to be included in a biopharmaceutical formulation of the invention is selected based on the desired osmolality (e.g., isotonic, hypotonic or hypertonic) of the final solution as well as the amounts and osmolality of other components to be included in the formulation.

By way of example, inclusion of about 5% sorbitol can achieve isotonicity while about 9% of a sucrose excipient is needed to achieve isotonicity. Selection of the amount or range of concentrations of one or more excipients that can be included within a biopharmaceutical formulation of the invention has been exemplified above by reference to salts, polyols and sugars. However, those skilled in the art will understand that the considerations described herein and further exemplified by reference to specific excipients are equally applicable to all types and combinations of excipients including, for example, salts, amino acids, other tonicity agents, surfactants, stabilizers, bulking agents, cryoprotectants, lyoprotectants, anti-oxidants, metal ions, chelating agents and/or preservatives.

Further, where a particular excipient is reported in molar concentration, those skilled in the art will recognize that the equivalent percent (%) w/v (e.g., (grams of substance in a solution sample/mL of solution)×100%) of solution is also contemplated.

Of course, a person having ordinary skill in the art would recognize that the concentrations of the excipients described herein share an interdependency within a particular formulation. By way of example, the concentration of a bulking agent may be lowered where, e.g., there is a high protein concentration or where, e.g., there is a high stabilizing agent concentration. In addition, a person having ordinary skill in the art would recognize that, in order to maintain the isotonicity of a particular formulation in which there is no bulking agent, the concentration of a stabilizing agent would be adjusted accordingly (e.g., a "tonicifying" amount of stabilizer would be used). Common excipients are known in the art and can be found in Powell et al., Compendium of Excipients fir Parenteral Formulations (1998), PDA J. Pharm. Sci. Technology, 52:238-311.

c. Pharmaceutical Buffers and Buffering Agents

The stability of a pharmacologically active protein formulation is usually observed to be maximal in a narrow pH range. This pH range of optimal stability needs to be identified early during pre-formulation studies. Several approaches, such as accelerated stability studies and calorimetric screening studies, are useful in this endeavor (Remmele R. L. Jr., et al., Biochemistry, 38(16): 5241-7 (1999)). Once a formulation is finalized, the protein must be manufactured and maintained throughout its shelf-life. Hence, buffering agents are almost always employed to control pH in the formulation.

The buffer capacity of the buffering species is maximal at a pH equal to the pKa and decreases as pH increases or decreases away from this value. Ninety percent of the buffering capacity exists within one pH unit of its pKa. Buffer capacity also increases proportionally with increasing buffer concentration.

Several factors need to be considered when choosing a buffer. First and foremost, the buffer species and its concentration need to be defined based on its pKa and the desired formulation pH. Equally important is to ensure that the buffer is compatible with the protein and other formulation excipients, and does not catalyze any degradation reactions. A third important aspect to be considered is the sensation of stinging and irritation the buffer may induce upon administration. For example, citrate is known to cause stinging upon injection (Laursen T, et al., Basic Clin Pharmacol Toxicol., 98(2): 218-21 (2006)). The potential for stinging and irritation is greater for drugs that are administered via the subcutaneous (SC) or intramuscular (IM) routes, where the drug solution remains at the site for a relatively longer period of time than when administered by the IV route where the formulation gets diluted rapidly into the blood upon administration. For formulations that are administered by direct IV infusion, the total amount of buffer (and any other formulation component) needs to be monitored. One has to be particularly careful about potassium ions administered in the form of the potassium phosphate buffer, which can induce cardiovascular effects in a patient (Hollander-Rodriguez J C, et al., Am. Fam. Physician., 73(2): 283-90 (2006)).

Buffers for lyophilized formulations need additional consideration. Some buffers like sodium phosphate can crystallize out of the protein amorphous phase during freezing resulting in shifts in pH. Other common buffers such as acetate and imidazole may sublime or evaporate during the lyophilization process, thereby shifting the pH of formulation during lyophilization or after reconstitution.

The buffer system present in the compositions is selected to be physiologically compatible and to maintain a desired pH of the pharmaceutical formulation. In one embodiment, the pH of the solution is between pH 2.0 and pH 12.0. For example, the pH of the solution may be 2.0, 2.3, 2.5, 2.7, 3.0, 3.3, 3.5, 3.7, 4.0, 4.3, 4.5, 4.7, 5.0, 5.3, 5.5, 5.7, 6.0, 6.3, 6.5, 6.7, 7.0, 7.3, 7.5, 7.7, 8.0, 8.3, 8.5, 8.7, 9.0, 9.3, 9.5, 9.7, 10.0, 10.3, 10.5, 10.7, 11.0, 11.3, 11.5, 11.7, or 12.0.

The pH buffering compound may be present in any amount suitable to maintain the pH of the formulation at a predetermined level. In one embodiment, the pH buffering concentration is between 0.1 mM and 500 mM (1 M). For example, it is contemplated that the pH buffering agent is at least 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 25, 30, 40, 50, 60, 70, 80, 90, 100, 200, or 500 mM.

Exemplary pH buffering agents used to buffer the formulation as set out herein include, but are not limited to organic acids, glycine, histidine, glutamate, succinate, phosphate, acetate, citrate, Tris, HEPES, and amino acids or mixtures of amino acids, including, but not limited to aspartate, histidine, and glycine. In one embodiment of the present invention, the buffering agent is citrate.

d. Pharmaceutical Stabilizers and Bulking Agents

In one aspect of the present pharmaceutical formulations, a stabilizer (or a combination of stabilizers) is added to prevent or reduce storage-induced aggregation and chemical degradation. A hazy or turbid solution upon reconstitution indicates that the protein has precipitated or at least aggregated. The term "stabilizer" means an excipient capable of preventing aggregation or physical degradation, including chemical degradation (for example, autolysis, deamidation, oxidation, etc.) in an aqueous state. Stabilizers contemplated include, but are not limited to, sucrose, trehalose, mannose, maltose, lactose, glucose, raffinose, cellobiose, gentiobiose, isomaltose, arabinose, glucosamine, fructose, mannitol, sorbitol, glycine, arginine HCL, poly-hydroxy compounds, including polysaccharides such as dextran, starch, hydroxyethyl starch, cyclodextrins, N-methyl pyrollidene, cellulose and hyaluronic acid, sodium chloride, (Carpenter et al., Develop. Biol. Standard 74:225, (1991)). In the present formulations, the stabilizer is incorporated in a concentration of about 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, 900, or 1000 mM. In one embodiment of the present invention, mannitol and trehalose are used as stabilizing agents.

If desired, the formulations also include appropriate amounts of bulking and osmolality regulating agents. Bulking agents include, for example and without limitation, mannitol, glycine, sucrose, polymers such as dextran, polyvinylpyrolidone, carboxymethylcellulose, lactose, sorbitol, trehalose, or xylitol. In one embodiment, the bulking agent is mannitol. The bulking agent is incorporated in a concentration of about 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, 900, or 1000 mM.

e. Pharmaceutical Surfactants

Proteins have a high propensity to interact with surfaces making them susceptible to adsorption and denaturation at air-liquid, vial-liquid, and liquid-liquid (silicone oil) interfaces. This degradation pathway has been observed to be inversely dependent on protein concentration and results in either the formation of soluble and insoluble protein aggregates or the loss of protein from solution via adsorption to surfaces. In addition to container surface adsorption, surface-induced degradation is exacerbated with physical agitation, as would be experienced during shipping and handling of the product.

Surfactants are commonly used in protein formulations to prevent surface-induced degradation. Surfactants are amphipathic molecules with the capability of out-competing proteins for interfacial positions. Hydrophobic portions of the surfactant molecules occupy interfacial positions (e.g., air/liquid), while hydrophilic portions of the molecules remain oriented towards the bulk solvent. At sufficient concentrations (typically around the detergent's critical micellar concentration), a surface layer of surfactant molecules serves to prevent protein molecules from adsorbing at the interface. Thereby, surface-induced degradation is minimized. Surfactants contemplated herein include, without limitation, fatty acid esters of sorbitan polyethoxylates, e.g., polysorbate 20 and polysorbate 80. The two differ only in the length of the aliphatic chain that imparts hydrophobic character to the molecules, C-12 and C-18, respectively. Accordingly, polysorbate-80 is more surface-active and has a lower critical micellar concentration than polysorbate-20.

Detergents can also affect the thermodynamic conformational stability of proteins. Here again, the effects of a given detergent excipient will be protein specific. For example, polysorbates have been shown to reduce the stability of some proteins and increase the stability of others. Detergent destabilization of proteins can be rationalized in terms of the hydrophobic tails of the detergent molecules that can engage in specific binding with partially or wholly unfolded protein states. These types of interactions could cause a shift in the conformational equilibrium towards the more expanded protein states (e.g. increasing the exposure of hydrophobic portions of the protein molecule in complement to binding polysorbate). Alternatively, if the protein native state exhibits some hydrophobic surfaces, detergent binding to the native state may stabilize that conformation.

Another aspect of polysorbates is that they are inherently susceptible to oxidative degradation. Often, as raw materials, they contain sufficient quantities of peroxides to cause oxidation of protein residue side-chains, especially methionine. The potential for oxidative damage arising from the addition of stabilizer emphasizes the point that the lowest effective concentrations of excipients should be used in formulations. For surfactants, the effective concentration for a given protein will depend on the mechanism of stabilization.

Surfactants are also added in appropriate amounts to prevent surface related aggregation phenomenon during freezing and drying (Chang, B, J. Pharm. Sci. 85:1325, (1996)). Thus, exemplary surfactants include, without limitation, anionic, cationic, nonionic, zwitterionic, and amphoteric surfactants including surfactants derived from naturally-occurring amino acids. Anionic surfactants include, but are not limited to, sodium lauryl sulfate, dioctyl sodium sulfo succinate and dioctyl sodium sulfonate, chenodeoxycholic acid, N-lauroylsarcosine sodium salt, lithium dodecyl sulfate, 1-octanesulfonic acid sodium salt, sodium cholate hydrate, sodium deoxycholate, and glycodeoxycholic acid sodium salt. Cationic surfactants include, but are not limited to, benzalkonium chloride or benzethonium chloride, cetylpyridinium chloride monohydrate, and hexadecyltrimethylammonium bromide. Zwitterionic surfactants include, but are not limited to, CHAPS, CHAPSO, SB3-10, and SB3-12. Non-ionic surfactants include, but are not limited to, digitonin, Triton X-100, Triton X-114, TWEEN-20, and TWEEN-80. Surfactants also include, but are not limited to lauromacrogol 400, polyoxyl 40 stearate, polyoxyethylene hydrogenated castor oil 10, 40, 50 and 60, glycerol monostearate, polysorbate 40, 60, 65 and 80, soy lecithin and other phospholipids such as dioleyl phosphatidyl choline (DOPC), dimyristoylphosphatidyl glycerol (DMPG), dimyristoylphosphatidyl choline (DMPC), and (dioleyl phosphatidyl glycerol) DOPG; sucrose fatty acid ester, methyl cellulose and carboxymethyl cellulose. Compositions comprising these surfactants, either individually or as a mixture in different ratios, are therefore further provided. In one embodiment of the present invention, the surfactant is TWEEN-80. In the present formulations, the surfactant is incorporated in a concentration of about 0.01 to about 0.5 g/L. In formulations provided, the surfactant concentration is 0.005, 0.01, 0.02, 0.03, 0.05, 0.06, 0.07, 0.08, 0.09, 0.1, 0.2, 0.3, 0.4, 0.5, 0.6, 0.7, 0.8, 0.9 or 1.0 g/L.

f. Pharmaceutical Salts

Salts are often added to increase the ionic strength of the formulation, which can be important for protein solubility, physical stability, and isotonicity. Salts can affect the physical stability of proteins in a variety of ways. Ions can stabilize the native state of proteins by binding to charged residues on the protein's surface. Alternatively, salts can stabilize the denatured state by binding to peptide groups along the protein backbone (—CONH—). Salts can also stabilize the protein native conformation by shielding repulsive electrostatic interactions between residues within a protein molecule. Salts in protein formulations can also shield attractive electrostatic interactions between protein molecules that can lead to protein aggregation and insolubility. In formulations provided, the salt concentration is between 0.1, 1, 10, 20, 30, 40, 50, 80, 100, 120, 150, 200, 300, and 500 mM.

& Other Common Excipient Components: Pharmaceutical Amino Acids

Amino acids have found versatile use in protein formulations as buffers, bulking agents, stabilizers and antioxidants. Thus, in one aspect histidine and glutamic acid are employed to buffer protein formulations in the pH range of 5.5-6.5 and 4.0-5.5 respectively. The imidazole group of histidine has a pKa=6.0 and the carboxyl group of glutamic acid side chain has a pKa of 4.3 which makes these amino acids suitable for buffering in their respective pH ranges. Glutamic acid is particularly useful in such cases. Histidine is commonly found in marketed protein formulations, and this amino acid provides an alternative to citrate, a buffer known to sting upon injection. Interestingly, histidine has also been reported to have a stabilizing effect, with respect to aggregation when used at high concentrations in both liquid and lyophilized presentations (Chen B, et al., Pharm Res., 20(12): 1952-60 (2003)). Histidine was also observed by others to reduce the viscosity of a high protein concentration formulation. However, in the same study, the authors observed increased aggregation and discoloration in histidine containing formulations during freeze-thaw studies of the antibody in stainless steel containers. Another note of caution with histidine is that it undergoes photo-oxidation in the presence of metal ions (Tomita M, et al., Biochemistry, 8(12): 5149-60 (1969)). The use of methionine as an antioxidant in formulations appears promising; it has been observed to be effective against a number of oxidative stresses (Lam X M, et al., J Pharm ScL, 86(11): 1250-5 (1997)).

In various aspects, formulations are provided which include one or more of the amino acids glycine, proline, serine, arginine and alanine have been shown to stabilize proteins by the mechanism of preferential exclusion. Glycine is also a commonly used bulking agent in lyophilized formulations. Arginine has been shown to be an effective agent in inhibiting aggregation and has been used in both liquid and lyophilized formulations. In formulations provided, the amino acid concentration is between 0.1, 1, 10, 20, 30, 40, 50, 80, 100, 120, 150, 200, 300, and 500 mM. In one embodiment of the present invention, the amino acid is glycine.

h. Other Common Excipient Components: Pharmaceutical Antioxidants

Oxidation of protein residues arises from a number of different sources. Beyond the addition of specific antioxidants, the prevention of oxidative protein damage involves the careful control of a number of factors throughout the manufacturing process and storage of the product such as atmospheric oxygen, temperature, light exposure, and chemical contamination. The invention therefore contemplates the use of the pharmaceutical antioxidants including, without limitation, reducing agents, oxygen/free-radical scavengers, or chelating agents. Antioxidants in therapeutic protein formulations are, in one aspect, water-soluble and remain active throughout the product shelf-life. Reducing agents and oxygen/free-radical scavengers work by ablating active oxygen species in solution. Chelating agents such as EDTA are effective by binding trace metal contaminants that promote free-radical formation. For example, EDTA was utilized in the liquid formulation of acidic fibroblast growth factor to inhibit the metal ion catalyzed oxidation of cysteine residues.

In addition to the effectiveness of various excipients to prevent protein oxidation, the potential for the antioxidants themselves to induce other covalent or physical changes to the protein is of concern. For example, reducing agents can cause disruption of intramolecular disulfide linkages, which can lead to disulfide shuffling. In the presence of transition metal ions, ascorbic acid and EDTA have been shown to promote methionine oxidation in a number of proteins and peptides (Akers M J, and Defelippis M R. Peptides and Proteins as Parenteral Solutions. In: Pharmaceutical Formulation Development of Peptides and Proteins. Sven Frokjaer, Lars Hovgaard, editors. Pharmaceutical Science. Taylor and Francis, UK (1999)); Fransson J. R., /. Pharm. Sci. 86(9): 4046-1050 (1997); Yin J, et al., Pharm Res., 21(12): 2377-83 (2004)). Sodium thiosulfate has been reported to reduce the levels of light and temperature induced methionine-oxidation in rhuMab HER2; however, the formation of a thiosulfate-protein adduct was also reported in this study (Lam X M, Yang J Y, et al., J Pharm Sci. 86(11): 1250-5 (1997)). Selection of an appropriate antioxidant is made according to the specific stresses and sensitivities of the protein. Antioxidants contemplated in certain aspects include, without limitation, reducing agents and oxygen/free-radical scavengers, EDTA, and sodium thiosulfate.

i. Other Common Excipient Components: Pharmaceutical Metal Ions

In general, transition metal ions are undesired in protein formulations because they can catalyze physical and chemical degradation reactions in proteins. However, specific metal ions are included in formulations when they are co-factors to proteins and in suspension formulations of proteins where they form coordination complexes (e.g., zinc suspension of insulin). Recently, the use of magnesium ions (10-120-mM) has been proposed to inhibit the isomerization of aspartic acid to isoaspartic acid (WO 2004039337).

Two examples where metal ions confer stability or increased activity in proteins are human deoxyribonuclease (rhDNase, Pulmozyme®), and Factor VIII. In the case of rhDNase, $Ca^{+2}$ ions (up to 100 mM) increased the stability of the enzyme through a specific binding site (Chen B, et al., I Pharm Sci., 88(4): 477-82 (1999)). In fact, removal of calcium ions from the solution with EGTA caused an increase in deamidation and aggregation. However, this effect was observed only with $Ca^{+2}$ ions; other divalent cations $Mg^{+2}$, $Mn^{+2}$ and $Zn^{+2}$ were observed to destabilize rhDNase. Similar effects were observed in Factor VIII. $Ca^{+2}$ and $Sr^{+2}$ ions stabilized the protein while others like $Mg^{+2}$, $Mn^{+2}$ and $Zn^{+2}$, $Cu^{+2}$ and $Fe^{+2}$ destabilized the enzyme (Fatouros, A., et al., Int. J. Pharm., 155, 121-131 (1997). In a separate study with Factor VIII, a significant increase in aggregation rate was observed in the presence of $Al^{+3}$ ions (Derrick T S, et al., I. Pharm. Sci., 93(10): 2549-57 (2004)). The authors note that other excipients like buffer salts are often contaminated with $Al^{+3}$ ions and illustrate the need to use excipients of appropriate quality in formulated products.

j. Other Common Excipient Components: Pharmaceutical Preservatives

Preservatives are necessary when developing multi-use parenteral formulations that involve more than one extraction from the same container. Their primary function is to inhibit microbial growth and ensure product sterility throughout the shelf-life or term of use of the drug product. Commonly used preservatives include, without limitation, benzyl alcohol, phenol and m-cresol. Although preservatives have a long history of use, the development of protein formulations that includes preservatives can be challenging. Preservatives almost always have a destabilizing effect (aggregation) on proteins, and this has become a major factor in limiting their use in multi-dose protein formulations (Roy S, et al., J Pharm ScL, 94(2): 382-96 (2005)).

To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market.

Norditropin® (liquid, Novo Nordisk), Nutropin AQ® (liquid, Genentech) & Genotropin (lyophilized—dual chamber cartridge, Pharmacia & Upjohn) contain phenol while Somatrope® (Eli Lilly) is formulated with m-cresol.

Several aspects need to be considered during the formulation development of preserved dosage forms. The effective preservative concentration in the drug product must be optimized. This requires testing a given preservative in the dosage form with concentration ranges that confer antimicrobial effectiveness without compromising protein stability. For example, three preservatives were successfully screened in the development of a liquid formulation for interleukin-1 receptor (Type I), using differential scanning calorimetry (DSC). The preservatives were rank ordered based on their impact on stability at concentrations commonly used in marketed products (Remmele R L Jr., et al., Pharm Res., 15(2): 200-8 (1998)).

Development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein significantly minimizing the associated stability risks. With liquid formulations, preservative effectiveness and stability have to be maintained over the entire product shelf-life (-18-24 months). An important point to note is that preservative effectiveness has to be demonstrated in the final formulation containing the active drug and all excipient components.

Some preservatives can cause injection site reactions, which is another factor that needs consideration when choosing a preservative. In clinical trials that focused on the evaluation of preservatives and buffers in Norditropin, pain perception was observed to be lower in formulations containing phenol and benzyl alcohol as compared to a formulation containing m-cresol (Kappelgaard A. M., Horm Res. 62 Suppl 3:98-103 (2004)). Interestingly, among the commonly used preservative, benzyl alcohol possesses anesthetic properties (Minogue S C, and Sun D A., AnesthAnalg., 100(3): 683-6 (2005)). In various aspects the use of preservatives provide a benefit that outweighs any side effects.

k. Methods of Preparation of Pharmaceutical Formulations

The present invention further contemplates methods for the preparation of pharmaceutical formulations.

The present methods further comprise one or more of the following steps: adding a stabilizing agent as described herein to said mixture prior to lyophilizing, adding at least one agent selected from a bulking agent, an osmolality regulating agent, and a surfactant, each of which as described herein, to said mixture prior to lyophilization.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration (Chen, Drug Development and Industrial Pharmacy, 18:1311-1354 (1992)). Accordingly, methods are provided for preparation of reconstituted rVWF compositions comprising the step of adding a diluent to a lyophilized rVWF composition of the invention.

The lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum acacia; dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example and without limitation, polyethylene sorbitan monooleate. In various aspects, the aqueous suspensions also contain one or more preservatives, for example and without limitation, ethyl, or n-propyl, p-hydroxybenzoate.

l. Exemplary rVWF Formulation for Administration

In some embodiments, the present methods provide for an enhanced formulation that allows a final product with high potency (high rVWF concentration and enhanced long term stability) in order to reduce the volume for the treatment (100 IU/ml to 10000 IU/ml). In some embodiments, the rVWF concentration in the formulation for administration is about 100 IU/ml to 10000 IU/ml. In some embodiments, the rVWF concentration in the formulation for administration is about 500 IU/ml to 10000 IU/ml. In some embodiments, the rVWF concentration in the formulation for administration is about 1000 IU/ml to 10000 IU/ml. In some embodiments, the rVWF concentration in the formulation for administration is about 2000 IU/ml to 10000 IU/ml. In some embodiments, the rVWF concentration in the formulation for administration is about 3000 IU/ml to 10000 IU/ml. In some embodiments, the rVWF concentration in the formulation for administration is about 4000 IU/ml to 10000 IU/ml. In some embodiments, the rVWF concentration in the formulation for administration is about 5000 IU/ml to 10000 IU/ml. In some embodiments, the rVWF concentration in the formulation for administration is about 6000 IU/ml to 10000 IU/ml. In some embodiments, the rVWF concentration in the formulation for administration is about 7000 IU/ml to 10000 IU/ml. In some embodiments, the rVWF concentration in the formulation for administration is about 8000 IU/ml to 10000 IU/ml. In some embodiments, the rVWF concentration in the formulation for administration is about 9000 IU/ml to 10000 IU/ml.

In some embodiments, the formulation for administration comprises one or more zwitterionic compounds, including for example, amino acids like Histidine, Glycine, Arginine. In some embodiments, the formulation for administration comprises a component with amphipathic characteristic having a minimum of one hydrophobic and one hydrophilic group, including for example polysorbate 80, octylpyranosid, dipeptides, and/or amphipathic peptides. In some embodiments, the formulation for administration comprises a non reducing sugar or sugar alcohol or disaccharides, including for example, sorbitol, mannitol, sucrose, or trehalose. In some embodiments, the formulation for administration comprises a nontoxic water soluble salt, including for example, sodium chloride, that results in a physiological osmolality. In some embodiments, the formulation for administration comprises a pH in a range from 6.0 to 8.0. In some embodiments, the formulation for administration comprises a pH of about 6.0, about 6.5, about 7, about 7.5 or about 8.0. In some embodiments, the formulation for administration comprises one or more bivalent cations that stabilize rVWF, including for example, Ca2+, Mg2+, Zn2+, Mn2+ and/or combinations thereof. In some embodiments, the formulation for administration comprises about 1 mM to about 50 mM Glycine, about 1 mM to about 50 mM Histidine, about zero to about 300 mM sodium chloride (e.g., less than 300 mM sodium), about 0.01% to about 0.05% polysorbate 20 (or polysorbate 80), and about 0.5% to about 20% (w/w) sucrose with a pH of about 7.0 and having a physiological osmolarity at the time point of administration.

In some embodiments, the formulation for administration can be freeze dried. In some embodiments, the formulation for administration is stable and can be stored in liquid state at about 2° C. to about 8° C., as well as at about 18° C. to about 25° C. In some embodiments, the formulation for administration is stable and can be stored in liquid state at about 2° C. to about 8° C. In some embodiments, the formulation for administration is stable and can be stored in liquid state at about 18° C. to about 25° C.

V. Administration of rVWF for Methods of Treating GI Bleeding in Patient with Severe VWD One of the advantages of administering rVWF to subjects with severe VWD to treat GI bleeding episodes is that the higher specific activity of rVWF as compared to pdVWF allows flexibility in the amount of rVWF administered and the number of times the subject is re-dosed. As will be appreciated and as is discussed in further detail herein, the co-administered FVIII may be recombinant or plasma derived.

To administer compositions to human or test animals, in one aspect, the compositions comprises one or more pharmaceutically acceptable carriers. The phrases "pharmaceutically" or "pharmacologically" acceptable refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

The pharmaceutical formulations are administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, and/or intrapulmonary injection at a particular site is contemplated as well. Generally, compositions are essentially free of pyrogens, as well as other impurities that could be harmful to the recipient.

Single or multiple administrations of rVWF are carried out with the dose levels and pattern being selected by the treating physician. For the prevention or treatment of disease, the appropriate dosage depends on the type of disease to be treated (e.g., von Willebrand disease), the severity and course of the disease, whether drug is administered for preventive or therapeutic purposes, previous therapy, the patient's clinical history and response to the drug, and the discretion of the attending physician.

In some aspects, rVWF is administered to a subject at a range from 40-100 IU/kg, e.g., 40, 45, 50, 55, 60, 65, 70, 75, 80, 90, 100, 40-100, 40-80, 50-80, 60-80, 70-80, 40-50, 40-60, 40-70, 40-50, 50-60, 60-70, 70-80, 80-90, or 90-100 IU/kg. In some embodiments, rVWF is administered at least once during a GI bleeding episode. In other embodiments, rVWF is administered two or more times, e.g., 2, 3, 4, 5, or more times, during a GI bleeding episode. In some instances, the subject is administered one or more infusions of rVWF. Each infusion can include a range from about 40-80 IU/kg rVWF, e.g., 40, 45, 50, 55, 60, 65, 70, 75, 80, 40-80, 50-80, 60-80, 70-80, 40-50, 40-60, 40-70, 40-50, 50-60, or 60-70 IU/kg rVWF. In some embodiments, the infusions can be substantially equal in amount. For instance, a first infusion and a second infusion can be substantially equal in amount. In some embodiments, the total dose of rVWF administered to the subject per bleeding episode is about 40-150 IU/kg, e.g., 40-150, 40-125, 40-100, 40-90, 40-75, 50-150, 50-100, 75-150, or 100-150 IU/kg.

In some embodiments, for minor and moderate bleeding events only 1-2 infusions more than estimated were required to control that bleeding episode and no additional VWF-containing product was required. In some embodiments, for major bleeding events <1.5 times more infusions than estimated were required to control that bleeding episode and no additional VWF-containing product was required. In some embodiments, minor, moderate, and major bleeding events the actual number of infusions was less than or equal to the estimated number required to treat the bleeding event, and no additional VWF-containing product was required.

In some embodiments, rVWF is administered at least once a day, at least twice a day, every 8-12 hours, and the like. In some instances, rVWF is administered for a total of 1 day, 2 days, 3 days, 4 days, 5 days, 6 days, 7 days, 8 days, 9 days, 10 days, 11 days, 12 days, 13 days, 14 days, and the like. In some embodiments, the rVWF is administered every 8 hours, every 9 hours, every 10 hours, every 11 hours, or every 12 hours. In some embodiments, rVWF is administered every 8 to 12 hours for about 3 days to about 7 days.

In some embodiments, recombinant Factor VIII (rFVIII) is also administered to the subject with severe VWD to treat a GI bleeding episode. In some cases, the treatment administered comprises rVWF and rFVIII. In other cases, the treatment administered does not include rFVIII. In some embodiments, rFVIII is administered to the subject at a range of about 10-70 IU/kg, e.g., 10-70, 10-60, 10-50, 10-40, 10-30, 10-20, 20-30, 30-40, 40-50, 50-60, or 60-70 IU/kg. In some instances, rFVIII is administered in the initial (first) dose or initial (first) infusion. In some cases, rFVIII is not administered as part of a second dose or second infusion. In some embodiments, a subject with VWD who is experiencing a GI bleeding episode is administered a single infusion of rVWF and rFVIII. In some embodiments, the second administration of rVWF is not administered with FVIII.

In some embodiments, of the method, when rVWF and FVIII are administered together, the rVWF to FVIII ratio is about 1.5:0.8. In some embodiments, of the method, when rVWF and FVIII are administered together, the rVWF to FVIII ratio is about 1.3:1. In some embodiments, of the method, when rVWF and FVIII are administered together, the rVWF to FVIII ratio is about 1.1:0.8. In some embodiments, of the method, when rVWF and FVIII are administered together, the rVWF to FVIII ratio is about 1.5:1. In some embodiments, of the method, when rVWF and FVIII are administered together, the rVWF to FVIII ratio is about 1.1:1.2.

In some embodiments, 40-60 IU/kg rVWF of the rVWF is administered when the gastrointestinal bleeding is minor or moderate gastrointestinal bleeding. In some embodiments, about 40 IU/kg rVWF of the rVWF is administered when the gastrointestinal bleeding is minor or moderate gastrointestinal bleeding. In some embodiments, about 45 IU/kg rVWF of the rVWF is administered when the gastrointestinal bleeding is minor or moderate gastrointestinal bleeding. In some embodiments, about 50 IU/kg rVWF of the rVWF is administered when the gastrointestinal bleeding is minor or moderate gastrointestinal bleeding. In some embodiments, about 55 IU/kg rVWF of the rVWF is administered when the gastrointestinal bleeding is minor or moderate gastrointestinal bleeding. In some embodiments, about 60 IU/kg rVWF of the rVWF is administered when the gastrointestinal bleeding is minor or moderate gastrointestinal bleeding. In some embodiments, 40-60 IU/kg rVWF of the rVWF is administered every 8 to 12 hours for about 3 days to about 7 days, wherein the gastrointestinal bleeding is minor or moderate gastrointestinal bleeding. In some embodiments, about 40 IU/kg rVWF of the rVWF is administered every 8 to 12 hours for about 3 days to about 7 days, when the gastrointestinal bleeding is minor or moderate gastrointestinal bleeding. In some embodiments, about 45 IU/kg rVWF of the rVWF is administered every 8 to 12 hours for about 3 days to about 7 days, when the gastrointestinal bleeding is minor or moderate gastrointestinal bleeding. In some embodiments, about 50 IU/kg rVWF of the rVWF is administered every 8 to 12 hours for about 3 days to about 7 days, when the gastrointestinal bleeding is minor or moderate gastrointestinal bleeding. In some embodiments, about 55 IU/kg rVWF of the rVWF is administered every 8 to 12 hours for about 3 days to about 7 days, when the gastrointestinal bleeding is minor or moderate gastrointestinal bleeding. In some embodiments, about 60 IU/kg rVWF of the rVWF is administered every 8 to 12 hours for about 3 days to about 7 days, when the gastrointestinal bleeding is minor or moderate gastrointestinal bleeding. In some embodiments, 40-60 IU/kg rVWF of the rVWF is administered every 8 hours for about 3 days to about 7 days, when the gastrointestinal bleeding is minor or moderate gastrointestinal bleeding. In some embodiments, 40-60 IU/kg rVWF of the rVWF is administered every 9 hours for about 3 days to about 7 days, when the gastrointestinal bleeding is minor or moderate gastrointestinal bleeding. In some embodiments, 40-60 IU/kg rVWF of the rVWF is administered every 10 hours for about 3 days to about 7 days, when the gastrointestinal bleeding is minor or moderate gastrointestinal bleeding. In some embodiments, 40-60 IU/kg rVWF of the rVWF is administered every 11 hours for about 3 days to about 7 days, when the gastrointestinal bleeding is minor or moderate gastrointestinal bleeding. In some embodiments, 40-60 IU/kg rVWF of the rVWF is administered every 12 hours for about 3 days to about 7 days, when the gastrointestinal bleeding is minor or moderate gastrointestinal bleeding. In some embodiments, 40-60 IU/kg rVWF of the rVWF is administered every 8 to 12 hours for about 3 days, when the gastrointestinal bleeding is minor or moderate gastrointestinal bleeding. In some embodiments, 40-60 IU/kg rVWF of the rVWF is administered every 8 to 12 hours for about 4 days, when the gastrointestinal bleeding is minor or moderate gastrointestinal bleeding. In some embodiments, 40-60 IU/kg rVWF of the rVWF is administered every 8 to 12 hours for about 5 days, when the gastrointestinal bleeding is minor or moderate gastrointestinal bleeding. In some embodiments, 40-60 IU/kg rVWF of the rVWF is administered every 8 to 12 hours for about 6 days, when the gastrointestinal bleeding is minor or moderate gastrointestinal bleeding. In some embodiments, 40-60 IU/kg rVWF of the rVWF is administered every 8 to 12 hours for about 7 days, when the gastrointestinal bleeding is minor or moderate gastrointestinal bleeding. In some embodiments, about 40, about 45, about 50, about 55, or about 60 IU/kg rVWF of the rVWF is administered every about 8 hours, about 9 hours, about 10 hours, about 11 hours, or about 12 hours for about 3 days, about 4 days, about 5 days, about 6 days, or about 7 days, when the gastrointestinal bleeding is minor or moderate gastrointestinal bleeding.

In some embodiments, about 40 IU/kg rVWF of said rVWF and when the gastrointestinal bleeding is major or severe gastrointestinal bleeding. In some embodiments, about 45 IU/kg rVWF of said rVWF and when the gastrointestinal bleeding is major or severe gastrointestinal bleeding. In some embodiments, about 50 IU/kg rVWF of said rVWF and when the gastrointestinal bleeding is major or severe gastrointestinal bleeding. In some embodiments, about 55 IU/kg rVWF of said rVWF and when the gastrointestinal bleeding is major or severe gastrointestinal bleeding. In some embodiments, about 60 IU/kg rVWF of said rVWF and when the gastrointestinal bleeding is major or severe gastrointestinal bleeding. In some embodiments, about 65 IU/kg rVWF of said rVWF and when the gastrointestinal bleeding is major or severe gastrointestinal bleeding. In some embodiments, about 70 IU/kg rVWF of said rVWF and when the gastrointestinal bleeding is major or severe gastrointestinal bleeding. In some embodiments, about 75 IU/kg rVWF of said rVWF and when the gastrointestinal bleeding is major or severe gastrointestinal bleeding. In some embodiments, about 80 IU/kg rVWF of said rVWF and when the gastrointestinal bleeding is major or severe gastrointestinal bleeding. In some embodiments, 40-80 IU/kg rVWF of said rVWF is administered every 8 to 12 hours for about 3 days to about 7 days when the gastrointestinal bleeding is major or severe gastrointestinal bleeding. In some embodiments, about 40 IU/kg rVWF of said rVWF is administered every 8 to 12 hours for about 3 days to about 7 days when the gastrointestinal bleeding is major or severe gastrointestinal bleeding. In some embodiments, about 45 IU/kg rVWF of said rVWF is administered every 8 to 12 hours for about 3 days to about 7 days when the gastrointestinal bleeding is major or severe gastrointestinal bleeding. In some embodiments, about 50 IU/kg rVWF of said rVWF is administered every 8 to 12 hours for about 3 days to about 7 days when the gastrointestinal bleeding is major or severe gastrointestinal bleeding. In some embodiments, about 55 IU/kg rVWF of said rVWF is administered every 8 to 12 hours for about 3 days to about 7 days when the gastrointestinal bleeding is major or severe gastrointestinal bleeding. In some embodiments, about 60 IU/kg rVWF of said rVWF is administered every 8 to 12 hours for about 3 days to about 7 days when the gastrointestinal bleeding is major or severe gastrointestinal bleeding. In some embodiments, about 65 IU/kg rVWF of said rVWF is administered every 8 to 12 hours for about 3 days to about 7 days when the gastrointestinal bleeding is major or severe gastrointestinal bleeding. In some embodiments, about 70 IU/kg rVWF of said rVWF is administered every 8 to 12 hours for about 3 days to about 7 days when the gastrointestinal bleeding is major or severe gastrointestinal bleeding. In some embodiments, about 75 IU/kg rVWF of said rVWF is administered every 8 to 12 hours for about 3 days to about 7 days when the gastrointestinal bleeding is major or severe gastrointestinal bleeding. In some embodiments, about 80 IU/kg rVWF of said rVWF is administered every 8 to 12 hours for about 3 days to about 7 days when the gastrointestinal bleeding is major or severe gastrointestinal bleeding. In some embodiments, 40-80 IU/kg rVWF of said rVWF is administered every 8 hours for about 3 days to about 7 days when the gastrointestinal bleeding is major or severe gastrointestinal bleeding. In some embodiments, 40-80 IU/kg rVWF of said rVWF is administered every 9 hours for about 3 days to about 7 days when the gastrointestinal bleeding is major or severe gastrointestinal bleeding. In some embodiments, 40-80 IU/kg rVWF of said rVWF is administered every 10 hours for about 3 days to about 7 days when the gastrointestinal bleeding is major or severe gastrointestinal bleeding. In some embodiments, 40-80 IU/kg rVWF of said rVWF is administered every 11 hours for about 3 days to about 7 days when the gastrointestinal bleeding is major or severe gastrointestinal bleeding. In some embodiments, 40-80 IU/kg rVWF of said rVWF is administered every 12 hours for about 3 days to about 7 days when the gastrointestinal bleeding is major or severe gastrointestinal bleeding. In some embodiments, 40-80 IU/kg rVWF of said rVWF is administered every 8 to 12 hours for about 3 days when the gastrointestinal bleeding is major or severe gastrointestinal bleeding. In some embodiments, 40-80 IU/kg rVWF of said rVWF is administered every 8 to 12 hours for about 4 days when the gastrointestinal bleeding is major or severe gastrointestinal bleeding. In some embodiments, 40-80 IU/kg rVWF of said rVWF is administered every 8 to 12 hours for about 5 days when the gastrointestinal bleeding is major or severe gastrointestinal bleeding. In some embodiments, 40-80 IU/kg rVWF of said rVWF is administered every 8 to 12 hours for about 6 days when the gastrointestinal bleeding is major or severe gastrointestinal bleeding. In some embodiments, 40-80 IU/kg rVWF of said rVWF is administered every 8 to 12 hours for about 7 days when the gastrointestinal bleeding is major or severe gastrointestinal bleeding. In some embodiments, about 40, about 45, about 50, about 55, about 60, about 65, about 70, about 75, or about 80 IU/kg rVWF of said rVWF is administered every about 8 hours, about 9 hours, about 10 hours, about 11 hours, or about 12 hours for about 3 days, about 4 days, about 5 days, about 6 days, or about 7 days when the gastrointestinal bleeding is major or severe gastrointestinal bleeding.

Generally, Type 1 VWD is indicated by <30 IU/dL VWF:RCo, <30 IU/dL VWF:Ag, low or normal FVIII, and >0.5-0.7 IU/dLVWF:RCo/VWF:Ag Ratio. Type 2A VWD is indicated by <30 IU/dL VWF:RCo, <30-200 IU/dL VWF:Ag, low or normal FVIII, and <0.5-0.7 IU/dLVWF:RCo/VWF:Ag Ratio. Type 2B VWD is indicated by <30-200 IU/dL VWF:RCo, <30 IU/dL VWF:Ag, low or normal FVIII, and usually <0.5-0.7 IU/dLVWF:RCo/VWF:Ag Ratio. Type 2M VWD is indicated by <30 IU/dL VWF:RCo, <30-200 IU/dL VWF:Ag, low or normal FVIII, and <0.5-0.7 IU/dLVWF:RCo/VWF:Ag Ratio. Type 2N VWD is indicated by 30-2000 IU/dL VWF:RCo, 30-200 IU/dL VWF:Ag, very low FVIII, and >0.5-0.7 IU/dLVWF:RCo/VWF:Ag Ratio. Type 3 VWD is indicated by <3 IU/dL VWF:RCo, <3 IU/dL VWF:Ag, extremely low (<10 IU/dL) FVIII, and the VWF:RCo/VWF:Ag Ratio is not applicable. Normal is indicated by 50-200 IU/dL VWF:RCo, 50-200 IU/dL VWF:Ag, normal FVIII, and >0.5-0.7 IU/dLVWF:RCo/VWF:Ag Ratio. In some embodiments, the subject has Type 3 VWD. In some embodiments, the subject has severe type 1 VWD. In some embodiments, the subject has severe type 2 VWD.

In some embodiments, the subject had been treated for at least 1 bleeding event within the previous 12 months. In some embodiments, the subject had been treated for more than 1 bleeding event within the previous 12 months.

Generally, minor bleeding is characterized by Acute or subacute clinically overt bleeding that did not satisfy the criteria for major bleeding and led to hospital admission for bleeding, physician-guided medical or surgical treatment for bleeding, or a change in antithrombotic therapy (including study drugs) for bleeding (Aristotle clinical definition); All other bleeding (except major and ICH) (RE-LY clinical definition); Overt bleeding not meeting the criteria for major bleeding but requiring medical intervention, unscheduled contact (visit or telephone) with a physician, temporary interruption of study drug (i.e., delayed dosing), pain, or impairment of daily activities) Rocket-AF clinical definition); Clinically relevant bleeding was defined as skin hematoma >25 cm$^2$, spontaneous nosebleed of >5 minutes duration, macroscopic hematuria, spontaneous rectal bleeding, gingival bleeding for >5 minutes, any bleeding leading to hospitalization, any bleeding leading to transfusion <2 U, or any other bleeding considered relevant by the investigator (Petro clinical definition); and/or CRNM (clinically relevant non-major bleeding) defined as acute or subacute, clinically overt, not major, and leading to hospital admission for bleeding, physician-guided medical or surgical treatment for bleeding, or a change in antithrombotic therapy as well as minor bleeding events defined as acute clinically overt events not meeting the criteria for either major or CRNM bleeding (Aristotle-J clinical definition). See, for example, Wells G, Coyle D, Cameron C, et al. Safety, Effectiveness, and Cost-Effectiveness of New Oral Anticoagulants Compared with Warfarin in Preventing Stroke and Other Cardiovascular Events in Patients with Atrial Fibrillation [Internet]. Ottawa (ON): Canadian Agency for Drugs and Technologies in Health; 2012 Apr. 9. 3, CLINICAL REVIEW. Available on the World Wide Web at www.ncbi.nlm.nih.gov/books/NBK169813/. Minor bleeding can include events were defined as those not fulfilling the criteria of major or clinically significant bleeding; minor bleeding from a wound (bleeding at the injection site, epistaxis, or wound hematoma not requiring operative decompression); overt bleeding that did not meet the criteria for major hemorrhage and associated with >1 of the following: epistaxis lasting more than 5 min or requiring intervention, ecchymosis or hematoma >5 cm at its greatest dimension, hematuria not associated with urinary catheter related trauma, GI hemorrhage not related to intubation or placement of a NG tube, wound hematoma or complications, subconjunctival hemorrhage necessitating cessation of medication; minor bleeding in the GI or urinary tract and hematoma at the site of an injection; and/or overt bleeding not meeting the criteria for major hemorrhage. See, for example, Sobieraj D M, Coleman C I, Tongbram V, et al. Venous Thromboembolism Prophylaxis in Orthopedic Surgery [Internet]. Rockville (Md.): Agency for Healthcare Research and Quality (US); 2012 March (Comparative Effectiveness Reviews, No. 49.) Appendix F, Additional Evidence Tables. Available from the World Wide Web at www.ncbi.nlm.nih.gov/books/NBK92309/.

Generally major bleeding is characterized by International Society on Thrombosis and Haemostasis (ISTH) standards, and includes, any life threatening and/or fatal bleeding; symptomatic bleeding into a critical area or organ and major bleeding was separated into intracranial (intracerebral, subdural) and extracranial (GI, non-GI) bleeding (RE-LY clinical definition); symptomatic bleeding into a critical anatomic site (Rocket-AF clinical definition); Life-threatening retroperitoneal, intracranial, intraocular, or intraspinal bleeding; or bleeding requiring surgery (Aristotle-J clinical definition). Major bleeing events can include those where there is fall in hemoglobin at least 20 g/L or transfusion of >2 units of whole blood (packed cells mentioned in life-threatening bleed definition; RE-LY definition of life-threatening bleeding: >1 of the following criteria: (1) fatal, symptomatic intracranial bleed; (2) reduction in hemoglobin level of at least 5.0 g/L; (3) transfusion of at least 4 U of blood or packed cells; (4) associated with hypotension requiring the use of intravenous inotropic agents; or (5) necessitated surgical intervention); fall in hemoglobin >2 g/dL or transfusion of >2 units of whole blood/red cells (ISTH or Rocket-AF clinical definition); and/or bleeding requiring surgery or transfusion of ≥2 U or associated with a decrease in hemoglobin of ≥2.0 g/L episodes. See, for example, Wells G, Coyle D, Cameron C, et al. Safety, Effectiveness, and Cost-Effectiveness of New Oral Anticoagulants Compared with Warfarin in Preventing Stroke and Other Cardiovascular Events in Patients with Atrial Fibrillation [Internet]. Ottawa (ON): Canadian Agency for Drugs and Technologies in Health; 2012 Apr. 9. 3, CLINICAL REVIEW. Available on the World Wide Web at www.ncbi.nlm.nih.gov/books/NBK169813/. Major bleeding can include clinically overt bleeding associated with >20 g/L fall in Hb; clinically overt leading to transfusion of >2U packed cells or whole blood; fatal, retroperitoneal, intracranial, intraocular or intraspinal bleeding; bleeding warranting treatment cessation or leading to reoperation; fatal, retroperitoneal, intracranial, or intraspinal bleeding; bleeding that involved any other critical organ; bleeding leading to reoperation; overt bleeding with a bleeding index ≥2; major bleeding from a wound (wound hematoma requiring operative decompression), or major bleeding not related to a wound (gastrointestinal or intracerebral hemorrhage); clinically overt bleeding associated with either a decrease in Hb≥2 g/dL or a need for a transfusion of ≥2 U RBC; intracranial or retroperitoneal (resulted in the permanent discontinuation of anticoagulation). See, for example, Sobieraj D M, Coleman C I, Tongbram V, et al. Venous Thromboembolism Prophylaxis in Orthopedic Surgery [Internet]. Rockville (Md.): Agency for Healthcare Research and Quality (US); 2012 March (Comparative Effectiveness Reviews, No. 49.) Appendix F, Additional Evidence Tables. Available from: the World Wide Web at www.ncbi.nlm.nih.gov/books/NBK92309/.

Compositions of rVWF can be contained in pharmaceutical formulations, as described herein. Such formulations can be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

In one aspect, formulations of the invention are administered by an initial bolus followed by a continuous infusion to maintain therapeutic circulating levels of drug product. As another example, the inventive compound is administered as a one-time dose. Those of ordinary skill in the art will readily optimize effective dosages and administration regimens as determined by good medical practice and the clinical condition of the individual patient. The route of administration can be, but is not limited to, by intravenous, intraperitoneal, subcutaneous, or intramuscular administration. The frequency of dosing depends on the pharmacokinetic parameters of the agents and the route of administration. The optimal pharmaceutical formulation is determined by one skilled in the art depending upon the route of administration and desired dosage. See for example, Remington's Pharmaceutical Sciences, 18th Ed., 1990, Mack Publishing Co., Easton, Pa. 18042 pages 1435-1712, the disclosure of which is hereby incorporated by reference in its entirety for all purposes and in particular for all teachings related to formulations, routes of administration and dosages for pharmaceutical products. Such formulations influence the physical state, stability, rate of in vivo release, and rate of in vivo clearance of the administered agents. Depending on the route of administration, a suitable dose is calculated according to body weight, body surface area or organ size. Appropriate dosages may be ascertained through use of established assays for determining blood level dosages in conjunction with appropriate dose-response data. The final dosage regimen is determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. By way of example, a typical dose of a recombinant VWF of the present invention is approximately 50 IU/kg, equal to 500 µg/kg. As studies are conducted, further information will emerge regarding the appropriate dosage levels and duration of treatment for various diseases and conditions.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, Highly stabilized York, Gait, "Oligonucleotide Synthesis: A Practical Approach" 1984, IRL Press, London, Nelson and Cox (2000), Lehninger, Principles of Biochemistry 3rd Ed., W. H. Freeman Pub., Highly stabilized York, N.Y. and Berg et al. (2002) Biochemistry, 5th Ed., W. H. Freeman Pub., Highly stabilized York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the above description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive method.

EXAMPLES

Example 1: Treatment of Gi Bleeding Episodes with Recombinant Von Willebrand Factor in Patients with Severe Von Willebrand Disease: Subanalysis from Pivotal Phase 3 on-Demand Study Introduction Gastrointestinal (GI) bleeding events occur in up to 20% of patients with von Willebrand disease (VWD) and have been observed in association with angiodysplastic lesions in 2%-4% of patients with VWD (1-3). GI bleeds are closely associated with the absence of higher molecular weight and ultra-large multimers (ULMs) of von Willebrand factor (VWF), which are most often seen in patients with type 2A and type 3 VWD (4). Higher doses and longer durations of therapy with plasma-derived VWF replacement concentrates are usually needed to resolve GI bleeds compared with bleeds at other sites, and treatment may still be unsuccessful (5). VONVENDI (von Willebrand factor [recombinant], Baxalta US Inc., Westlake Village, Calif.) is a recombinant VWF (rVWF) concentrate in which ULMs, the most hemostatically effective VWF multimers, are preserved because they are not exposed to ADAMTS13 during manufacturing (6).

Objectives

The pivotal phase 3 clinical trial of rVWF evaluated its efficacy and safety with and without recombinant factor VIII (rFVIII) (ADVATE [antihemophilic factor (recombinant)], Baxalta US Inc., Westlake Village, Calif.) for the treatment of bleeds in patients with severe VWD (7). This subanalysis was performed using data from patients who experienced GI bleeding events during participation in the pivotal clinical trial.

Methods

Phase 3, prospective, randomized clinical trial (NCT01410227) to assess patient demographics, GI bleed characteristics, hemostatic efficacy, timing of treatment and bleeding resolution, and dosages of rVWF±rFVIII. The study population included men and women aged 18-65 y, who had type 3 or severe type 1 or 2 VWD and had been treated for ≥1 bleeding event within 12 mo before enrollment. On-demand treatment of bleeds: Minor/moderate bleeds: 40-60 IU/kg rVWF; Major/severe bleeds: up to 80 IU/kg rVWF every 8-12 h for 3-7 d.

Initial dose of rVWF was coadministered with rFVIII at a ratio of 1.3:1±0.2 rVWF:rFVIII. rVWF was administered alone thereafter provided hemostatic FVIII:C levels were achieved.

Hemostatic efficacy was rated on a 4-point scale (none=4, moderate=3, good=2, excellent=1).

Adverse events were monitored throughout the study.

Results

A total of 192 bleeding events were treated with rVWF and assessed for hemostatic efficacy during the study; hemostatic efficacy was rated as either excellent (96.9%) or good (3.1%) in each case. 4 patients with type 3 VWD and a median age of 32.5 y experienced a total of 6 GI bleeding events (Table 1).

TABLE 1

Patient Demographics in GI Bleed Subgroup

| Patient | Age, y | Weight, kg | Sex | VWD Type | GI Bleeds During Study, n |
|---|---|---|---|---|---|
| 1 | 26 | 72 | Male | 3 | 1 |
| 2 | 42 | 85 | Male | 3 | 2 |
| 3 | 37 | 85 | Female | 3 | 2 |
| 4 | 28 | 77 | Female | 3 | 1 |

GI = gastrointestinal; VWD = von Willebrand disease.

TABLE 2

Bleed Characteristics and Efficacy in GI Bleed Subgroup

| Patient | Bleeds Treated During Study, n | Severity of GI Bleeds | Days to Treatment*, n | Clinical Efficacy Rating | Infusions to Resolution, n | Time to Resolution†, h |
|---|---|---|---|---|---|---|
| 1 | 4 | Major/Severe | 0 | Excellent | 1 | Unknown |
| 2 | 6 | Moderate | 3 | Excellent | 1 | 1.8 |
| 2 | 6 | Moderate | 7 | Excellent | 1 | 2.7 |
| 3 | 2 | Minor | 3 | Excellent | 1 | 18.6 |
| 3 | 2 | Minor | 0 | Good | 2 | Unknown |
| 4 | 1 | Major/Severe | 3 | Excellent | 2 | 14.0 |

GI = gastrointestinal.
*Days from bleeding onset to first infusion.
†Time from first infusion of rVWF to resolution of bleeding episode.

TABLE 3 rVWF and rFVIII Use in GI Bleed Subgroup

| Patient | Severity of GI Bleeds | Infusion 1 rVWF, IU/kg | Infusion 1 rFVIII, IU/kg | Infusion 2 rVWF, IU/kg | Hemostatic Efficacy Rating | Duration Between rVWF Infusions*, h |
|---|---|---|---|---|---|---|
| 1 | Major/Severe | 57.5 | 41.5 | — | Excellent | N/A |
| 2 | Moderate | 60.1 | 49.4 | — | Excellent | N/A |
| 2 | Moderate | 59.9 | 46.0 | — | Excellent | N/A |
| 3 | Minor | 53.6 | 19.4 | — | Excellent | N/A |
| 3 | Minor | 53.5 | 19.3 | 53.5 | Good | 50.6 |
| 4 | Major/Severe | 60.5 | 25.0 | 60.5 | Excellent | 22.1 |

GI = gastrointestinal;
rFVIII = recombinant factor VIII;
rVWF = recombinant von Willebrand factor.
*Time from end of rVWF infusion 1 to start of rVWF infusion 2.

TABLE 4

Adverse Events in GI Bleed Subgroup

| Adverse Events | Patients, n | Events, n |
|---|---|---|
| Total | 4 | 28 |
| Nonserious | 4 | 26 |
| Not related | 4 | 23 |
| Possibly related | 1 | 3* |
| Serious | 2 | 2 |
| Not related | 2 | 2 |
| Possibly related | 0 | 0 |

GI = gastrointestinal.
*Tachycardia, dysgeusia, and infusion site paresthesia.

Of the 6 GI bleeds, 2 each were reported as minor, moderate, and major/severe (Table 2). 67% of GI bleeds (4/6) required only 1 infusion of rVWF to successfully treat the bleed; 33% of GI bleeds (2/6) required 2 infusions to achieve hemostasis. Median time to resolution, which was known for 4/6 bleeds, was 8.3 h (range, 1.8-18.6 h). 100% of GI bleeds treated with rVWF had a hemostatic efficacy rating of excellent (83% [5/6]) or good (17% [1/6]; FIG. 1).

The 4 patients with GI bleeds experienced a total of 28 adverse events (Table 4). 3 possibly related nonserious adverse events occurred in 1 patient (tachycardia, dysgeusia, and infusion site paresthesia). Serious adverse events included GI hemorrhage and constipation in 1 patient each, and neither event was considered related to study drug.

The GI bleed resulted from 2 chronic ulcers with evidence of a recent hemorrhage and, per protocol, was considered a serious adverse event because the investigator thought it would have also occurred in a healthy individual under the same circumstances. rVWF and rFVIII use are shown in Table 3. The median dose per infusion was 58.7 IU/kg (range, 53.5-60.5 IU/kg) for rVWF and 33.3 IU/kg (range, 19.3-49.4 IU/kg) for rFVIII. The median total dose per bleed was 60.0 IU/kg (range, 53.6-121.0 IU/kg) for rVWF and 33.3 IU/kg (range, 19.3-49.4 IU/kg) for rFVIII.

Conclusions

In this subanalysis of the pivotal phase 3 clinical trial, rVWF was safe and effective for the on-demand treatment of GI bleeds in patients with severe VWD.

Of 6 GI bleeds (2 minor, 2 moderate, 2 major/severe), hemostatic efficacy was rated as excellent for 5 (83%) and good for 1 (17%). A single infusion of rVWF was successful in treating 4 (67%) of the GI bleeds (1 minor, 2 moderate, 1 major/severe). Time to resolution of the GI bleeds was available for 4 patients and ranged from 1.8-18.6 h (median, 8.3 h).

These findings from a small cohort of patients warrant further assessment of the role of rVWF in the treatment of GI bleeding and angiodysplasia in a larger population of patients with VWD.

The emerging association between angiodysplasia and a lack of higher molecular weight VWF multimers suggests that rVWF, with its higher ULM content, may be of particular benefit in this patient population (8,9).

REFERENCES

1. Randi A M. *Thromb Res.* 2016; 141 Suppl 2:S55-58.
2. Randi A M and Laffan M A. *J Thromb Haemost.* 2017; 15(1):13-20.
3. Franchini M and Mannucci P M. *Thromb Haemost.* 2014; 112(3):427-431.
4. Franchini M and Mannucci P M. *Br J Haematol.* 2013; 161(2):177-182.
5. Berntorp E, et al. *Haemophilia.* 2009; 15(1):122-130.
6. Turecek P L, et al. *Hamostaseologie.* 2009; 29(suppl 1):S32-38.
7. Gill J C, et al. *Blood.* 2015; 126(17):2038-2046.
8. Selvam S and James P. *Semin Thromb Hemost.* 2017.
9. Franchini M and Mannucci P M. *Expert Rev Hematol.* 2016; 9(9):825-830.

Example 2: Pharmacokinetics, Safety, and Efficacy of Recombinant Von Willebrand Factor (rVWF) in the Treatment of Bleeding Brief Summary The purpose of this Phase 3 study is to assess the pharmacokinetics of rVWF:rFVIII and rVWF, and to assess the safety and efficacy of rVWF:rFVIII and rVWF in the treatment of bleeding events in subjects with severe hereditary von Willebrand disease (VWD).

| Arm | Intervention/treatment |
|---|---|
| Experimental: PK 80 Arm (minimum of 22 subjects with severe VWD) PK assessment (80 IU/kg rVWF) + 12-month treatment period | Biological: Recombinant von Willebrand factor (rVWF) Intravenous administration Other Names: BAX 111 rVWF Biological: Recombinant factor VIIII (rFVIII) Intravenous administration Other Names: rFVIII ADVATE |
| Experimental: PK 50 Arm (14 subjects with type 3 VWD) Two single-blinded PK assessments (50 IU/kg rVWF + rFVIII/placebo) + 12-month treatment period | Biological: Recombinant von Willebrand factor (rVWF) Intravenous administration Other Names: BAX 111 rVWF Drug: Placebo Syringe supplied with physiologic saline solution for infusion Other Names: saline physiologic saline Biological: Recombinant factor VIIII (rFVIII) Intravenous administration |

-continued

| Arm | Intervention/treatment |
|---|---|
| | Other Names:<br>rFVIII<br>ADVATE |
| Experimental:<br>PK50<br>Only Arm (minimum of 7<br>subjects with type 3 VWD)<br>PK assessment (50 IU/kg<br>rVWF) only, no treatment<br>of bleeding episodes | Biological: Recombinant von Willebrand<br>factor (rVWF)<br>Intravenous administration<br>Other Names:<br>BAX 111<br>rVWF<br>Drug: Placebo<br>Syringe supplied with physiologic saline<br>solution for infusion<br>Other Names:<br>saline<br>physiologic saline<br>Biological: Recombinant factor VIIII<br>(rFVIII)<br>Intravenous administration<br>Other Names:<br>rFVIII<br>ADVATE |
| Experimental:<br>Treatment<br>Only (up to 7 subjects<br>independent of VWD<br>subtype)<br>Treatment of bleeding<br>episodes for a total of 12<br>months | Biological: Recombinant von Willebrand<br>factor (rVWF)<br>Intravenous administration<br>Other Names:<br>BAX 111<br>rVWF<br>Biological: Recombinant factor VIIII<br>(rFVIII)<br>Intravenous administration<br>Other Names:<br>rFVIII<br>ADVATE |

Primary Outcome Measures

Primary Outcome Measures: Primary Outcome #1

Percentage of Participants With Treatment Success for Treated Bleeding Episodes

[Time Frame: For 12 months after first infusion of rVWF:rFVIII or rVWF]

Treatment success was defined as the extent of control of bleeding episodes (BEs) using a mean efficacy rating score of <2.5 for a participant's BEs treated with study product (recombinant von Willebrand Factor [rVWF] with or without recombinant factor VIII [rFVIII]) during the study period. Scores used: Excellent=1—actual infusions 23 estimated number of infusions required to treat BE; no additional VWF required (all BEs); Good=2→1-2 infusions (minor/moderate BEs) or <1.5 infusions (major BEs) greater than estimated required to control BE; no additional VWF required (all BEs); Moderate=3≥3 infusions (minor/moderate BEs) or ≥1.5 infusions (major BEs) greater than estimated required to control BE; no additional VWF required (all BEs); None=4—severe uncontrolled bleeding or intensity of bleeding not changed; additional VWF required. Included participants with available primary efficacy rating (prospective-excluding gastrointestinal bleeds) in the Full Analysis Set.

Secondary Outcome Measures

Secondary Outcome Measures: Secondary Outcome #1

Percentage of Treated Bleeding Episodes With an Efficacy Rating of "Excellent" or "Good" [Time Frame: For 12 months after first infusion of rVWF:rFVIII or rVWF]

Efficacy ratings "excellent" or "good" for the control of bleeding episodes (BEs) with study product (recombinant von Willebrand Factor [rVWF] with or without recombinant factor VIII [rFVIII]) are defined as follows: Excellent— actual infusions ≤estimated number of infusions required to treat BE; no additional von Willebrand Factor (VWF) required (all BEs); Good→1-2 infusions (minor/moderate BEs) or <1.5 infusions (major BEs) greater than estimated required to control BE; no additional VWF required (all BEs). The data set included prospectively estimated BEs treated with study product with an available efficacy rating from participants in the Full Analysis Set Secondary Outcome Measures: Secondary Outcome #2

Percentage of Treated Bleeding Episodes With an Efficacy Rating of "Excellent" or "Good", Excluding Gastrointestinal Bleeds [Time Frame: For 12 months after first infusion of rVWF:rFVIII or rVWF]

Efficacy ratings of "excellent" or "good" for the control of bleeding episodes (BEs) with study product (recombinant von Willebrand Factor [rVWF] with or without recombinant factor VIII [rFVIII]) are defined as follows: Excellent— actual infusions ≤estimated number of infusions required to treat BE; no additional von Willebrand Factor (VWF) required (all BEs); Good→1-2 infusions (minor/moderate BEs) or <1.5 infusions (major BEs) greater than estimated required to control BE; no additional VWF required (all BEs). The data set included prospectively estimated BEs excluding gastrointestinal (GI) bleeds treated with study product with an available efficacy rating from participants in the Full Analysis Set.

Secondary Outcome Measures: Secondary Outcome #3

Number of Infusions of rVWF:rFVIII and/or rVWF Per Bleeding Episode [Time Frame: For 12 months after first infusion of rVWF:rFVIII or rVWF]

The actual number of infusions of recombinant von Willebrand factor:recombinant factor VIII (rVWF:rFVIII) and/or rVWF required to treat a bleeding episode (BE). BEs were to be initially treated with an infusion of rVWF:rFVIII and subsequently with rVWF with or without rFVIII, based on FVIII levels, if available. In cases, where no FVIII levels were available, the individual participant's PK data was used to determine the rFVIII dose. The data set included prospectively estimated BEs treated with study product with an available efficacy rating from participants in the Full Analysis Set.

Secondary Outcome Measures: Secondary Outcome #4

Number of Units of rVWF:rFVIII and/or rVWF Per Bleeding Episode [Time Frame: For 12 months after first infusion of rVWF:rFVIII or rVWF]

The number of units is provided as the actual dose [IU/kg] of recombinant von Willebrand factor:recombinant factor VIII (rVWF:rFVIII) and/or rVWF required to treat a bleeding episode (BE). BEs were to be initially treated with an infusion of rVWF:rFVIII and subsequently with rVWF with or without rFVIII, based on FVIII levels, if available. In cases, where no FVIII levels were available, the individual participant's PK data was used to determine the rFVIII dose. The data set included prospectively estimated BEs treated with study product of known lot number with an available efficacy rating from participants in the Full Analysis Set.

Secondary Outcome Measures: Secondary Outcome #5

Percentage of Participants Who Develop Inhibitory Antibodies to FVIII [Time Frame: For 12 months after first infusion of rVWF:rFVIII or rVWF].

Development of neutralizing antibodies (inhibitors) to factor VIII (FVIII) was assessed by the Nijmegen modification of the Bethesda assay. Positive FVIII inhibitor tests were defined as ≥0.4 Bethesda units/mL (BU/mL) by the Nijmegen-modified Bethesda assay that is confirmed by a second test performed on an independent sample obtained 2-4 weeks following the first test. Category title includes number of participants [N] who provided data for the category.

Secondary Outcome Measures: Secondary Outcome #6

Percentage of Participants Who Develop Inhibitory Antibodies to VWF [Time Frame: After signing informed consent until 12 months after first infusion of rVWF:rFVIII or rVWF].

Neutralizing antibodies (inhibitors) to Von Willebrand Factor Ristocetin cofactor (VWF:RCo), VWF collagen binding (VWF:CB) and VWF Factor VIII binding (VWF:FVIIIB) activities were measured using Nijmegen modification of the Bethesda assay. One Bethesda Unit (BU) is thereby defined as the amount of inhibitor that decreased the measured activity in the assays to 50% of that of the negative control samples. The assays were validated using human plasma samples from two type 3 VWD patients with low (1-2 BU/mL) and high (~10 BU/mL) titer inhibitors and plasma samples from non-human primates immunized with human rVWF (>100 BU/mL). Category title includes number of participants [N] who provided data for the category.

Secondary Outcome Measures: Secondary Outcome #7

Percentage of Participants Who Develop Binding Antibodies to VWF [Time Frame: After signing informed consent until 12 months after first infusion of rVWF:rFVIII or rVWF]

The presence of total binding anti-VWF antibodies was determined by an enzyme-linked immunosorbent assay (ELISA) employing polyclonal anti-human immunoglobulin (Ig) antibodies (IgG, IgM and IgA). Category title includes number of participants [N] who provided data for the category.

Secondary Outcome Measures: Secondary Outcome #8

Percentage of Participants Who Develop Binding Antibodies to CHO [Time Frame: After signing informed consent until 12 months after first infusion of rVWF:rFVIII or rVWF].

The presence of total binding anti-CHO antibodies was determined by measuring total immunoglobulin (Ig) antibodies (IgG, IgA, IgM) against Chinese Hamster Ovary (CHO) protein using an enzyme-linked immunosorbent assay (ELISA). Category title includes number of participants [N] who provided data for the category.

Secondary Outcome Measures: Secondary Outcome #9

Percentage of Participants Who Develop Binding Antibodies to rFurin [Time Frame: After signing informed consent until 12 months after first infusion of rVWF:rFVIII or rVWF].

The presence of total binding anti-rFurin antibodies was determined by measuring total immunoglobulin (Ig) antibodies (IgG, IgA, IgM) against rFurin protein using an enzyme-linked immunosorbent assay (ELISA). Category title includes number of participants [N] who provided data for the category.

Secondary Outcome Measures: Secondary Outcome #10

Percentage of Participants Who Develop Binding Antibodies to Mouse Immunoglobulin [Time Frame: After signing informed consent until 12 months after first infusion of rVWF:rFVIII or rVWF].

The presence of total binding anti-Murine immunoglobulin (IgG) antibodies was determined using an enzyme-linked immunosorbent assay (ELISA). Category title includes number of participants [N] who provided data for the category.

Secondary Outcome Measures: Secondary Outcome #11

Percentage of Participants Who Had an Occurrence of Thrombotic Events [Time Frame: After signing informed consent until 12 months after first infusion of rVWF:rFVIII or rVWF]

Secondary Outcome Measures: Secondary Outcome #12

Number of Adverse Events Related to Study Product Including Clinically Significant Changes in Laboratory Parameters and Vital Signs [Time Frame: For 12 months after first infusion of rVWF:rFVIII or rVWF].

Adverse Events (AEs) related to study product (recombinant von Willebrand Factor [rVWF] with or without recombinant factor VIII [rFVIII]) are described. Only laboratory parameters (hematology and clinical chemistry) and vital signs (physical examination, ECG) with clinically significant findings that are recorded as AEs are included. Categories presented as Severity-System Organ Class-Preferred Term Seriousness: serious adverse event (SAE); non serious adverse event (nsAE) System Organ Class: Cardiac disorders (CARD); General disorders and administration site conditions (GEN); Investigations (INV); Nervous system disorders (NERV); Skin and subcutaneous tissue disorders (SKN); Vascular disorders (VAS). Category title includes number of AEs [N] for the category.

Secondary Outcome Measures: Secondary Outcome #13

Number of Participants With Adverse Events Related to Study Product Including Clinically Significant Changes in Laboratory Parameters and Vital Signs [Time Frame: For 12 months after first infusion of rVWF:rFVIII or rVWF].

Number of participants with Adverse Events (AEs) related to study product (recombinant von Willebrand Factor [rVWF] with or without recombinant factor VIII [rFVIII]) are described. Only laboratory parameters (hematology and clinical chemistry) and vital signs (physical examination, ECG) with clinically significant findings that are recorded as AEs are included. Categories presented as Severity-System Organ Class-Preferred Term Seriousness: serious adverse event (SAE); non serious adverse event (nsAE) System Organ Class: Cardiac disorders (CARD); General disorders and administration site conditions (GEN); Investigations (INV); Nervous system disorders (NERV); Skin and subcutaneous tissue disorders (SKN); Vascular disorders (VAS).

Secondary Outcome Measures: Secondary Outcome #14

Number of Adverse Events by Infusion Related to Study Product Including Clinically Significant Changes in Laboratory Parameters and Vital Signs [Time Frame: For 12 months after first infusion of rVWF:rFVIII or rVWF].

Adverse Events (AEs) by infusion related to study product (recombinant von Willebrand Factor [rVWF] with or without recombinant factor VIII [rFVIII]) are described. Only laboratory parameters (hematology and clinical chemistry) and vital signs (physical examination, ECG) with clinically significant findings that are recorded as AEs are included. Categories presented as Severity-System Organ Class-Preferred Term Seriousness: serious adverse event (SAE); non serious adverse event (nsAE) System Organ Class: Cardiac disorders (CARD); General disorders and administration site conditions (GEN); Investigations (INV); Nervous system disorders (NERV); Skin and subcutaneous tissue disorders (SKN); Vascular disorders (VAS).

Secondary Outcome Measures: Secondary Outcome #15

PK50—Area Under the Plasma Concentration/Time Curve From Time 0 to Infinity (AUC0-∞/Dose) of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to infinity of von Willebrand Factor Ristocetin cofactor (VWF:RCo) after infusion of 50 IU/kg recombinant von Willebrand Factor:von Willebrand Factor Ristocetin cofactor (VWF:RCo rVWF) administered together with 38.5

IU/kg recombinant Factor VIII (rFVIII) (ratio of 1.3:1±0.2) [rVWF:rFVIII], or 50 IU/kg VWF:RCo rVWF administered together with saline (placebo) [rVWF] for subjects in the PK50 arms (Arm 1 and Arm 2). Category title includes number of participants [N] who provided data for the category.

Secondary Outcome Measures: Secondary Outcome #16

PK50—Area Under the Plasma Concentration/Time Curve From Time 0 to 96 Hours (AUC0-96 h/Dose) of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to 96 hours of von Willebrand Factor Ristocetin cofactor (VWF:RCo) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #17

PK50—Mean Residence Time of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Mean Residence Time (MRT) of von Willebrand Factor Ristocetin cofactor (VWF:RCo) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #18

PK50—Clearance of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Clearance (CL) of von Willebrand Factor Ristocetin cofactor (VWF:RCo) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #19

PK50—Incremental Recovery of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Incremental Recovery (IR) at the maximum plasma concentration of von Willebrand Factor Ristocetin cofactor (VWF:RCo) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #20

PK50—Elimination Phase Half-Life of VWF:Co [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Elimination Phase Half-Life (T1/2) of von Willebrand Factor Ristocetin cofactor (VWF:RCo) after infusion of 50 IU/kg recombinant von Willebrand Factor:von Willebrand Factor Ristocetin cofactor (VWF:RCo rVWF) administered together with 38.5 IU/kg recombinant FVIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #21

PK50—Volume of Distribution at Steady State of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Volume of Distribution at Steady State (Vss) of von Willebrand Factor Ristocetin cofactor (VWF:RCo) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #22

PK50—Area Under the Plasma Concentration/Time Curve From Time 0 to Infinity (AUC0-∞/Dose) of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to infinity of von Willebrand Factor Antigen (VWF:Ag) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #23

PK50—Area Under the Plasma Concentration/Time Curve From Time 0 to 96 Hours (AUC0-96 h/Dose) of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout].

Area under the plasma concentration curve (AUC) from time 0 to 96 hours of von Willebrand Factor Antigen (VWF:Ag) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #24

PK50—Mean Residence Time of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Mean Residence Time (MRT) of von Willebrand Factor Antigen (VWF:Ag) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII] or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #25

PK50—Clearance of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Clearance (CL) of von Willebrand Factor Antigen (VWF:Ag) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #26

PK50—Incremental Recovery of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Incremental Recovery (IR) at the maximum plasma concentration of von Willebrand Factor Antigen (VWF:Ag) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #27

PK50—Elimination Phase Half-Life of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Elimination Phase Half-Life (T1/2) of von Willebrand Factor Antigen (VWF:Ag) after infusion of 50 IU/kg recombinant von Willebrand Factor:von Willebrand Factor Ristocetin cofactor (VWF:RCo rVWF) administered together with 38.5 IU/kg recombinant FVIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category Secondary Outcome Measures: Secondary Outcome #28

PK50—Volume of Distribution at Steady State of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Volume of Distribution at Steady State (Vss) of von Willebrand Factor Antigen (VWF:Ag) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #29

PK50—Area Under the Plasma Concentration/Time Curve From Time 0 to Infinity (AUC0-∞/Dose) of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to infinity of von Willebrand Factor Collagen Binding (VWF:CB) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #30

PK50—Area Under the Plasma Concentration/Time Curve From Time 0 to 96 Hours (AUC0-96 h/Dose) of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to 96 hours of von Willebrand Factor Collagen Binding (VWF:CB) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #31

PK50—Mean Residence Time of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Mean Residence Time (MRT) of von Willebrand Factor Collagen Binding (VWF:CB) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #32

PK50—Clearance of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Clearance (CL) of von Willebrand Factor Collagen Binding (VWF:CB) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #33

PK50—Incremental Recovery of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Incremental Recovery (IR) at the maximum plasma concentration of von Willebrand Factor Collagen Binding (VWF:CB) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #34

PK50—Elimination Phase Half-Life of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Elimination Phase Half-Life (T1/2) of von Willebrand Factor Collagen Binding (VWF:CB) after infusion of 50 IU/kg recombinant von Willebrand Factor:von Willebrand Factor Ristocetin cofactor (VWF:RCo rVWF) administered together with 38.5 IU/kg recombinant FVIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #35

PK50—Volume of Distribution at Steady State of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Volume of Distribution at Steady State (Vss) of von Willebrand Factor Collagen Binding (VWF:CB) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #36

PK50—Area Under the Plasma Concentration/Time Curve From Time 0 to Infinity (AUC0-∞/Dose) of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to infinity of Factor VIII activity (FVIII:C) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #37

PK50—Area Under the Plasma Concentration/Time Curve From Time 0 to 96 Hours (AUC0-96 h/Dose) of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to 96 hours of Factor VIII activity (FVIII:C) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category.

Secondary Outcome Measures: Secondary Outcome #38

PK50—Mean Residence Time of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Mean Residence Time (MRT) of Factor VIII activity (FVIII:C) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII] for participants in the PK50 arms (Arm 1 and Arm 2).

Secondary Outcome Measures: Secondary Outcome #39

PK50—Clearance of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Clearance (CL) of Factor VIII activity (FVIII:C) after infusion of 50 IU/kg recombinant von Willebrand Factor: von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII] for participants in the PK50 arms (Arm 1 and Arm 2).

Secondary Outcome Measures: Secondary Outcome #40

PK50—Incremental Recovery of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Incremental Recovery (IR) at the maximum plasma concentration of Factor VIII activity (FVIII:C) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1±0.2) [rVWF:rFVIII] for participants in the PK50 arms (Arm 1 and Arm 2).

Secondary Outcome Measures: Secondary Outcome #41

PK50—Elimination Phase Half-Life of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Elimination Phase Half-Life (T1/2) of Factor VIII activity (FVIII:C) after infusion of 50 IU/kg recombinant von Willebrand Factor:von Willebrand Factor Ristocetin cofactor (VWF:RCo rVWF) administered together with 38.5 IU/kg recombinant FVIII (rFVIII) (ratio of 1.3:1±0.2) [rVWF: rFVIII] for participants in the PK50 arms (Arm 1 and Arm 2).

Secondary Outcome Measures: Secondary Outcome #42

PK50—Volume of Distribution at Steady State of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Volume of Distribution at Steady State (Vss) of Factor VIII activity (FVIII:C) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3: 1±0.2) [rVWF:rFVIII] for participants in the PK50 arms (Arm 1 and Arm 2).

Secondary Outcome Measures: Secondary Outcome #43

PK80—Area Under the Plasma Concentration/Time Curve From Time 0 to Infinity (AUC0-∞/Dose) of VWF: RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to infinity of von Willebrand Factor Ristocetin cofactor (VWF:RCo) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #44

PK80—Area Under the Plasma Concentration/Time Curve From Time 0 to 96 Hours (AUC0-96 h/Dose) of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to 96 hours of von Willebrand Factor Ristocetin cofactor (VWF:RCo) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #45

PK80—Mean Residence Time of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Mean Residence Time (MRT) of von Willebrand Factor Ristocetin cofactor (VWF:RCo) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #46

PK80—Clearance of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Clearance (CL) of von Willebrand Factor Ristocetin cofactor (VWF:RCo) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #47

PK80—Incremental Recovery of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Incremental Recovery (IR) at the maximum plasma concentration Area under the plasma concentration curve (AUC) from time 0 to infinity of von Willebrand Factor Ristocetin cofactor (VWF:RCo) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #48

PK80—Elimination Phase Half-Life of VWF:Co [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Elimination Phase Half-Life (T1/2) of von Willebrand Factor Ristocetin cofactor (VWF:RCo) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category Secondary Outcome Measures: Secondary Outcome #49

PK80—Volume of Distribution at Steady State of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Volume of Distribution at Steady State (Vss) of von Willebrand Factor Ristocetin cofactor (VWF:RCo) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study. PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #50

PK80—Area Under the Plasma Concentration/Time Curve From Time 0 to Infinity (AUC0-∞/Dose) of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to infinity of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #51

PK80—Area Under the Plasma Concentration/Time Curve From Time 0 to 96 Hours (AUC0-96 h/Dose) of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to 96 hours of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #52

PK80—Mean Residence Time of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Mean Residence Time (MRT) of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #53

PK80—Clearance of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Clearance (CL) of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #54

PK80—Incremental Recovery of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Incremental Recovery (IR) at the maximum plasma concentration Area under the plasma concentration curve (AUC) from time 0 to infinity of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #55

PK80—Elimination Phase Half-Life of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Elimination Phase Half-Life (T1/2) of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #56

PK80—Volume of Distribution at Steady State of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Volume of Distribution at Steady State (Vss) of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #57

PK80—Area Under the Plasma Concentration/Time Curve From Time 0 to Infinity (AUC0-∞/Dose) of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to infinity of von Willebrand Factor Collagen Binding (VWF:CB) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #58

PK80—Area Under the Plasma Concentration/Time Curve From Time 0 to 96 Hours (AUC0-96 h/Dose) of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to 96 hours of von Willebrand Factor Collagen Binding (VWF:CB) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #59

PK80—Mean Residence Time of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Mean Residence Time (MRT) of von Willebrand Factor Collagen Binding (VWF:CB) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #60

PK80—Clearance of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Clearance (CL) of von Willebrand Factor Collagen Binding (VWF:CB) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #61

PK80—Incremental Recovery of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Incremental Recovery (IR) at the maximum plasma concentration Area under the plasma concentration curve (AUC) from time 0 to infinity of von Willebrand Factor Collagen Binding (VWF:CB) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #62

PK80—Elimination Phase Half-Life of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Elimination Phase Half-Life (T1/2) of von Willebrand Factor Collagen Binding (VWF:CB) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #63

PK80—Volume of Distribution at Steady State of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Volume of Distribution at Steady State (Vss) of von Willebrand Factor Collagen Binding (VWF:CB) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #64

PK80—Area Under the Plasma Concentration/Time Curve From Time 0 to Infinity (AUC0-∞/Dose) of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to infinity of Factor VIII activity (FVIII:C) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #65

PK80—Area Under the Plasma Concentration/Time Curve From Time 0 to 96 Hours (AUC0-96 h/Dose) of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to 96 hours of Factor VIII activity (FVIII:C) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category.

Secondary Outcome Measures: Secondary Outcome #66

PK80—Ratio of Intra-participant PK of VWF:RCo, VWF:Ag and VWF:CB at Baseline and After 6 Months [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

Area under the plasma concentration curve (AUC) from time 0 to infinity per dose (AUC0-∞/dose) for von Willebrand Factor Ristocetin cofactor (VWF:RCo), von Willebrand Factor Antigen (VWF:Ag) and von Willebrand Factor Collagen Binding (VWF:CB). Each parameter was compared between the two PK assessments after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. 13 participants had data available for this endpoint i.e. data for PK1 and PK2.

Eligibility Criteria

18 Years to 65 Years (Adult, Older Adult); All sexes.

Inclusion Criteria:

Participant has been diagnosed with:

Type 1 (Von Willebrand factor: Ristocetin cofactor activity (VWF:RCo)<20 IU/dL) or, Type 2A (VWF:RCo <20 IU/dL), Type 2B (as diagnosed by genotype), Type 2N (Factor VIII activity (FVIII:C) <10% and historically documented genetics), Type 2M or, Type 3 (Von Willebrand factor antigen (VWF:Ag)≤3 IU/dL) or, Severe Von Willebrand disease (VWD) with a history of requiring substitution therapy with von Willebrand factor concentrate to control bleeding Participant, who participates in the treatment for bleeding episodes, has had a minimum of 1 documented bleed (medical history) requiring VWF coagulation factor replacement therapy during the previous 12 months prior to enrollment.

Participant has a Karnofsky score ≥60%

Participant is at least 18 and not older than 65 years of age at enrollment

If female of childbearing potential, participant presents with a negative pregnancy test Participant agrees to employ adequate birth control measures for the duration of the study Participant is willing and able to comply with the requirements of the protocol Exclusion Criteria:

Participant has been diagnosed with pseudo VWD or another hereditary or acquired coagulation disorder other than VWD (eg qualitative and quantitative platelet disorders or elevated PT/international normalized ratio [INR]>1.4).

Participant has a documented history of a VWF:RCo half-life of <6 hours.

Participant has a history or presence of a VWF inhibitor at screening.

Participant has a history or presence of a factor VIII (FVIII) inhibitor with a titer ≥0.4 BU (by Nijmegen assay) or ≥0.6 BU (by Bethesda assay).

Participant has a known hypersensitivity to any of the components of the study drugs, such as mouse or hamster proteins.

Participant has a medical history of immunological disorders, excluding seasonal allergic rhinitis/conjunctivitis, mild asthma, food allergies or animal allergies.

Participant has a medical history of a thromboembolic event.

Participant is HIV positive with an absolute CD4 count <200/mm3.

Participant has been diagnosed with cardiovascular disease (New York Heart Association [NYHA] classes 1-4.

Participant has an acute illness (eg, influenza, flu-like syndrome, allergic rhinitis/conjunctivitis, non-seasonal asthma) at screening.

Participant has been diagnosed with significant liver disease as evidenced by any of the following: serum alanine aminotransferase (ALT) 5 times the upper limit of normal; hypoalbuminemia; portal vein hypertension (eg, presence of otherwise unexplained splenomegaly, history of esophageal varices).

Participant has been diagnosed with renal disease, with a serum creatinine level ≥2 mg/dL.

In the judgment of the investigator, the participant has another clinically significant concomitant disease (eg, uncontrolled hypertension) that may pose additional risks for the participant.

Participant has been treated with an immunomodulatory drug, excluding topical treatment (e.g., ointments, nasal sprays), within 30 days prior to enrollment Participant is pregnant or lactating at the time of enrollment.

Participant has participated in another clinical study involving an IP or investigational device within 30 days prior to enrollment or is scheduled to participate in another clinical study involving an investigational product or investigational device during the course of this study.

Participant has a history of drug or alcohol abuse within the 2 years prior to enrollment.

Participant has a progressive fatal disease and/or life expectancy of less than 3 months.

Participant is identified by the investigator as being unable or unwilling to cooperate with study procedures.

Participant suffers from a mental condition rendering him/her unable to understand the nature, scope and possible consequences of the study and/or evidence of an uncooperative attitude.

Participant is in prison or compulsory detention by regulatory and/or juridical order Pre-Assignment Details 49 participants provided informed consent and were screened for the study, of which 37 were exposed to study product. Reasons for discontinuation were 6 screen failures, consent withdrawn by 3 participants, 1 physician decision, 1 participant received high doses of rFVIII for oral procedure and arm for which 1 participant was eligible was closed.

| Reporting Groups | |
|---|---|
| | Description |
| Arm 1: PK50 + Treatment | In Part A, (pharmacokinetic [PK] assessment followed by on-demand treatment for bleeding episodes [BEs] for 6 months) participants were initially infused either with 50 IU/kg recombinant von Willebrand Factor:von Willebrand Ristocetin cofactor (VWF:RCo rVWF) [rVWF] administered together with 38.5 IU/kg recombinant Factor VIII (rFVIII) [rVWF:rFVIII] or 50 IU/kg rVWF administered together with saline. Participants then crossed over to the alternate infusion after washout (PK). For on-demand treatment, participants received study product [VWF:rFVIII or rVWF], where BEs were initially treated with rVWF:rFVIII and subsequently with rVWF with or without rFVIII, based on FVIII levels (dose based on previous FVIII levels or if not available from the individual participant's PK data at discretion of investigator). In part, B participants continued to receive on- |

| | Reporting Groups |
|---|---|
| | demand treatment for BEs with study product [VWF:rFVIII or rVWF] for a further 6 months. |
| Arm 2: PK50 Only | In Part A, (pharmacokinetic [PK] assessment followed by on-demand treatment for bleeding episodes [BEs] for 6 months) participants were initially infused either with 50 IU/kg recombinant von Willebrand Factor:von Willebrand Ristocetin cofactor (VWF:RCo rVWF) [rVWF] administered together with 38.5 IU/kg recombinant Factor VIII (rFVIII) [rVWF:rFVIII] or 50 IU/kg rVWF administered together with saline. Participants then crossed over to the alternate infusion after washout (PK). For on-demand treatment, participants received study product [VWF:rFVIII or rVWF], where BEs were initially treated with rVWF:rFVIII and subsequently with rVWF with or without rFVIII, based on FVIII levels (dose based on previous FVIII levels or if not available from the individual participant's PK data at discretion of investigator). Participants then exited the study or could opt to sign informed consent to move to Arm 1 receive treatment for bleeding episodes with study product. |
| Arm 3: PK80 + Treatment | In Part A, participants initially underwent a first PK assessment of an infusion of 80 IU/kg recombinant von Willebrand Factor Ristocetin cofactor (VWF:RCo rVWF) [rVWF]. After the first PK assessment participants received on demand treatment for bleeding episodes (BEs) with study product [VWF:rFVIII or rVWF], where BEs were initially treated with rVWF:rFVIII and subsequently with rWVF with or without rFVIII, based on FVIII levels. If FVIII levels not available, the individual participant's PK data was used to determine rFVIII dose at discretion of investigator. Participants received on-demand treatment for 6 months after the first study product infusion. After 6 months participants underwent a second PK assessment of an infusion of 80 IU/kg rVWF. In part B, participants continued to receive on-demand treatment for BEs with study product [VWF:rFVIII or rVWF] for a further 6 months. |
| Arm 4: Treatment Only | In Part A, participants received on-demand treatment for bleeding episodes (BEs) with study product (recombinant von Willebrand Factor [rVWF] administered together with recombinant Factor VIII [rFVIII] (rVWF:rFVIII) or rVWF alone), where BEs were initially treated with rVWF:rFVIII and subsequently with rVWF with or without rFVIII, based on FVIII levels. If not available, the individual participant's PK data was used to determine rFVIII dose at discretion of investigator. Participants received on-demand treatment for 6 months after the first study product infusion. In part, B participants continued to receive on-demand treatment for BEs with study product [VWF:rFVIII or rVWF] for a further 6 months. No pharmacokinetic (PK) assessments were conducted in this arm. |

| Participant Flow: Overall Study | | | | |
|---|---|---|---|---|
| | Arm 1: PK50 + Treatment | Arm 2: PK50 Only | Arm 3: PK80 + Treatment | Arm 4: Treatment Only |
| STARTED | 8 | 8 | 15 | 6 |
| COMPLETED | 4 | 8 | 13 | 5 |
| NOT COMPLETED | 4 | 0 | 2 | 1 |
| Adverse Event | 1 | 0 | 0 | 0 |
| Withdrawal by Subject | 3 | 0 | 1 | 0 |
| Pregnancy | 0 | 0 | 0 | 1 |
| Met Excl. Criteria After Starting Study | 0 | 0 | 1 | 0 |

Baseline Characteristics

Baseline consists of all participants in study [N=37] so is a total of the four arms described in Participant Flow (Arm 1: PK50+Treatment [N=8]; Arm 2: PK50 Only [N=8]; Arm 3: PK80+Treatment [N=15]; Arm 4: Treatment Only [N=6]).

Results:

Outcome Measures

Primary Outcome Measures: Primary Outcome #1

1. Primary: Percentage of Participants With Treatment Success for Treated Bleeding Episodes [Time Frame: For 12 months after first infusion of rVWF:rFVIII or rVWF].

| | |
|---|---|
| Measure Type | Primary |
| Measure Title | Percentage of Participants With Treatment Success for Treated Bleeding Episodes |
| Measure Description | Treatment success was defined as the extent of control of bleeding episodes (BEs) using a mean efficacy rating score of <2.5 for a participant's BEs treated with study product (recombinant von Willebrand Factor [rVWF] with or without recombinant factor VIII [rFVIII]) during the study period. Scores used: Excellent = 1 - actual infusions ≤ estimated number of infusions required to treat BE; no additional VWF required (all BEs); Good = 2 - >1-2 infusions (minor/moderate BEs) or <1.5 infusions (major BEs) greater than estimated required to control BE; no additional VWF required (all BEs); Moderate = 3 ≥ 3 infusions (minor/moderate BEs) or ≥ 1.5 infusions (major BEs) greater than estimated required to control BE; no additional VWF required (all BEs); None = 4 - severe uncontrolled bleeding or intensity of bleeding not changed; additional VWF required. Included participants with available primary efficacy rating (prospective-excluding gastrointestinal bleeds) in the Full Analysis Set. |
| Time Frame | For 12 months after first infusion of rVWF:rFVIII or rVWF |

Reporting Groups

| | Description |
|---|---|
| Full Analysis Set | Comprises of participants treated with study product (recombinant von Willebrand Factor [rVWF] with or without recombinant factor VIII [rFVIII]) for whom at least one efficacy rating scale was available. |

Measured Values

| | Full Analysis Set |
|---|---|
| Participants Analyzed | 18 |
| Percentage of Participants With Treatment Success for Treated Bleeding Episodes [Units: Percent of participants] Number (90% Confidence Interval) | 100.0 (84.7 to 100.0) |

Statistical Analysis 1 for Percentage of Participants With Treatment Success for Treated Bleeding Episodes

| | |
|---|---|
| Groups [1] | Full Analysis Set |
| Statistical Test Type [2] | Non-Inferiority or Equivalence |
| Statistical Method [3] | Clopper-Pearson |
| Clopper-Pearson [4] | 100 |
| 90% Confidence Interval | 84.7 to 100 |

| | |
|---|---|
| [1] | Additional details about the analysis, such as null hypothesis and power calculation: No text entered. |
| [2] | Details of power calculation, definition of non-inferiority margin, and other key parameters: The null hypothesis of the rate of subjects with a treatment success of <= 0.65 (H0: p <= 0.65) versus an alternative hypothesis of > 0.65 (HA: p > 0.65) was tested at the 5% one-sided level of significance. The proportion of subjects with treatment success under the alternative hypothesis was expected to be approximately 0.90. If 20 subjects were treated, the study provided 86% power to reject the null hypothesis. |
| [3] | Other relevant method information, such as adjustments or degrees of freedom: No text entered. |
| [4] | Other relevant estimation information: No text entered. |

Secondary Outcome Measures: Secondary Outcome #1

2. Secondary: Percentage of Treated Bleeding Episodes With an Efficacy Rating of "Excellent" or "Good" [Time Frame: For 12 months after first infusion of rVWF:rFVIII or rVWF].

TABLE 10

Secondary Outcome #1

| | |
|---|---|
| Measure Type | Secondary |
| Measure Title | Percentage of Treated Bleeding Episodes With an Efficacy Rating of "Excellent" or "Good" |
| Measure Description | Efficacy ratings "excellent" or "good" for the control of bleeding episodes (BEs) with study product (recombinant von Willebrand Factor [rVWF] with or without recombinant factor VIII [rFVIII]) |

TABLE 10-continued

Secondary Outcome #1

| | |
|---|---|
| | are defined as follows: Excellent - actual infusions ≤ estimated number of infusions required to treat BE; no additional von Willebrand Factor (VWF) required (all BEs); Good - >1-2 infusions (minor/moderate BEs) or <1.5 infusions (major BEs) greater than estimated required to control BE; no additional VWF required (all BEs). The data set included prospectively estimated BEs treated with study product with an available efficacy rating from participants in the Full Analysis Set |
| Time Frame | For 12 months after first infusion of rVWF:rFVIII or rVWF |

TABLE 11

Reporting Groups

| | Description |
|---|---|
| Full Analysis Set | Comprised of participants treated with study product (recombinant von Willebrand Factor [rVWF] with or without recombinant factor VIII [rFVIII]) for whom at least one efficacy rating scale was available. |

TABLE 12

Measured Values

| | Full Analysis Set |
|---|---|
| Participants Analyzed | 22 |
| Units Analyzed (Bleeding episodes) | 130 |
| Percentage of Treated Bleeding Episodes With an Efficacy Rating of "Excellent" or "Good" [Units: Percent of bleeding episodes] Number (90% Confidence Interval) | 100.0 (97.7 to 100.0) |

No statistical analysis provided for Percentage of Treated Bleeding Episodes With an Efficacy Rating of "Excellent" or "Good"

Secondary Outcome Measures: Secondary Outcome #2

3. Secondary: Percentage of Treated Bleeding Episodes With an Efficacy Rating of "Excellent" or "Good", Excluding Gastrointestinal Bleeds [Time Frame: For 12 months after first infusion of rVWF:rFVIII or rVWF]

TABLE 13

Secondary Outcome #2

| Measure Type | Secondary |
|---|---|
| Measure Title | Percentage of Treated Bleeding Episodes With an Efficacy Rating of "Excellent" or "Good", Excluding Gastrointestinal Bleeds |
| Measure Description | Efficacy ratings of "excellent" or "good" for the control of bleeding episodes (BEs) with study product (recombinant von Willebrand Factor [rVWF] with or without recombinant factor VIII [rFVIII]) are defined as follows: Excellent—actual infusions ≤ estimated number of infusions required to treat BE; no additional von Willebrand Factor (VWF) required (all BEs); Good—>1-2 infusions (minor/moderate BEs) or <1.5 infusions (major BEs) greater than estimated required to control BE; no additional VWF required (all BEs). The data set included prospectively estimated BEs excluding gastrointestinal (GI) bleeds treated with study |

TABLE 13-continued

Secondary Outcome #2

| | |
|---|---|
| | product with an available efficacy rating from participants in the Full Analysis Set. |
| Time Frame | For 12 months after first infusion of rVWF:rFVIII or rVWF |

TABLE 14

Reporting Groups

| | Description |
|---|---|
| Full Analysis Set | Comprised of participants treated with study product (recombinant von Willebrand Factor [rVWF] with or without recombinant factor VIII [rFVIII]) for whom at least one efficacy rating scale was available. |

TABLE 15

Measured Values

| | Full Analysis Set |
|---|---|
| Participants Analyzed | 22 |
| Units Analyzed (Bleeding episodes) | 126 |
| Percentage of Treated Bleeding Episodes With an Efficacy Rating of "Excellent" or "Good", Excluding Gastrointestinal Bleeds [Units Percent of bleeding episodes] Geometric Mean (90% Confidence Interval) | 100.0 (97.7 to 100.0) |

No statistical analysis provided for Percentage of Treated Bleeding Episodes With an Efficacy Rating of "Excellent" or "Good", Excluding Gastrointestinal Bleeds Secondary Outcome Measures: Secondary Outcome #3

4. Secondary: Number of Infusions of rVWF:rFVIII and/or rVWF Per Bleeding Episode [Time Frame: For 12 months after first infusion of rVWF:rFVIII or rVWF]

TABLE 16

Secondary Outcome #3

| Measure Type | Secondary |
|---|---|
| Measure Title | Number of Infusions of rVWF:rFVIII and/or rVWF Per Bleeding Episode |
| Measure Description | The actual number of infusions of recombinant von Willebrand factor:recombinant factor VIII (rVWF:rFVIII) and/or rVWF required to treat a bleeding episode (BE). BEs were to be initially treated with an infusion of rVWF:rFVIII and subsequently with rVWF with or without rFVIII, based on FVIII levels, if available. In cases, where no FVIII levels were available, the individual participant's PK data was used to determine the rFVIII dose. The data set included prospectively estimated BEs treated with study product with an available efficacy rating from participants in the Full Analysis Set. |
| Time Frame | For 12 months after first infusion of rVWF:rFVIII or rVWF |

TABLE 17

Reporting Groups

| | Description |
|---|---|
| Full Analysis Set | Comprised of participants treated with study product (recombinant von Willebrand Factor [rVWF] with or without recombinant factor VIII [rFVIII]) for whom at least one efficacy rating scale was available. |

TABLE 18

Measured Values

| | Full Analysis Set |
|---|---|
| Participants Analyzed | 22 |
| Units Analyzed (Bleeding episodes) | 192 |
| Number of Infusions of rVWF:rFVIII and/or rWVF Per Bleeding Episode [Units: Number of infusions] Median (90% Confidence Interval) | 1.0 (1.0 to 1.0) |

No statistical analysis provided for Number of Infusions of rVWF:rFVIII and/or rVWF Per Bleeding Episode Secondary Outcome Measures: Secondary Outcome #4

5. Secondary: Number of Units of rVWF:rFVIII and/or rVWF Per Bleeding Episode [Time Frame: For 12 months after first infusion of rVWF:rFVIII or rVWF]

TABLE 19

| | Secondary Outcome #4 |
|---|---|
| Measure Type | Secondary |
| Measure Title | Number of Units of rVWF:rFVIII and/or rVWF Per Bleeding Episode |
| Measure Description | The number of units is provided as the actual dose [IU/kg] of recombinant von Willebrand factor:recombinant factor VIII (rVWF:rFVIII) and/or rVWF required to treat a bleeding episode (BE). BEs were to be initially treated with an infusion of rVWF:rFVIII and subsequently with rVWF with or without rFVIII, based on FVIII levels, if available. In cases, where no FVIII levels were available, the individual participant's PK data was used to determine the rFVIII dose. The data set included prospectively estimated BEs treated with study product of known lot number with an available efficacy rating from participants in the Full Analysis Set. |
| Time Frame | For 12 months after first infusion of rVWF:rFVIII or rVWF |

TABLE 20

Reporting Groups

| | Description |
|---|---|
| Full Analysis Set | Comprised of participants treated with study product (recombinant von Willebrand Factor [rVWF] with or without recombinant factor VIII [rFVIII]) for whom at least one efficacy rating scale was available. |

TABLE 21

Measured Values

| | Full Analysis Set |
|---|---|
| Participants Analyzed | 22 |
| Units Analyzed (Bleeding episodes) | 174 |
| Number of Units of rVWF:rFVIII and/or rVWF Per Bleeding Episode [Units: IU/kg] Median (90% Confidence Interval) | 48.2 (43.9 to 50.2) |

No statistical analysis provided for Number of Units of rVWF:rFVIII and/or rVWF Per Bleeding Episode Secondary Outcome Measures: Secondary Outcome #5

6. Secondary: Percentage of Participants Who Develop Inhibitory Antibodies to FVIII [Time Frame: For 12 months after first infusion of rVWF:rFVIII or rVWF]

TABLE 22

| | Secondary Outcome #5 |
|---|---|
| Measure Type | Secondary |
| Measure Title | Percentage of Participants Who Develop Inhibitory Antibodies to FVIII |
| Measure Description | Development of neutralizing antibodies (inhibitors) to factor VIII (FVIII) was assessed by the Nijmegen modification of the Bethesda assay. Positive FVIII inhibitor tests were defined as ≥0.4 Bethesda units/mL (BU/mL) by the Nijmegen-modified Bethesda assay that is confirmed by a second test performed on an independent sample obtained 2-4 weeks following the first test. Category title includes number of participants [N] who provided data for the category. |
| Time Frame | For 12 months after first infusion of rVWF:rFVIII or rVWF |

TABLE 23

Reporting Groups

| | Description |
|---|---|
| Safety Analysis Set | Comprised of participants who were treated with study product (recombinant von Willebrand Factor [rVWF] with or without recombinant factor VIII [rFVIII]) at least once during the study. |

TABLE 24

Measured Values

| | Safety Analysis Set |
|---|---|
| Participants Analyzed | 37 |
| Percentage of Participants Who Develop Inhibitory Antibodies to FVIII [Units: Percent of participants] | |
| Before 1st treatment with study product [N = 37] | 0 |
| During 1st treatment until study end [N = 27] | 0 |
| At final study visit [N = 24] | 0 |

No statistical analysis provided for Percentage of Participants Who Develop Inhibitory Antibodies to FVIII Secondary Outcome Measures: Secondary Outcome #6

7. Secondary: Percentage of Participants Who Develop Inhibitory Antibodies to VWF [Time Frame: After signing informed consent until 12 months after first infusion of rVWF:rFVIII or rVWF]

TABLE 25

Secondary Outcome #6

| | |
|---|---|
| Measure Type | Secondary |
| Measure Title | Percentage of Participants Who Develop Inhibitory Antibodies to VWF |
| Measure Description | Neutralizing antibodies (inhibitors) to Von Willebrand Factor Ristocetin cofactor (VWF:RCo), VWF collagen binding (VWF:CB) and VWF Factor VIII binding (VWF:FVIIIB) activities were measured using Nijmegen modification of the Bethesda assay. One Bethesda Unit (BU) is thereby defined as the amount of inhibitor that decreased the measured activity in the assays to 50% of that of the negative control samples. The assays were validated using human plasma samples from two type 3 VWD patients with low (1-2 BU/mL) and high (~10 BU/mL) titer inhibitors and plasma samples from non-human primates immunized with human rVWF (>100 BU/mL). Category title includes number of participants [N] who provided data for the category. |
| Time Frame | After signing informed consent until 12 months after first infusion of rVWF:rFVIII or rVWF |

TABLE 26

Reporting Groups

| | Description |
|---|---|
| Safety Analysis Set | Comprised of participants who were treated with study product (recombinant von Willebrand Factor [rVWF] with or without recombinant factor VIII [rFVIII]) at least once during the study. |

TABLE 27

Measured Values

| | Safety Analysis Set |
|---|---|
| Participants Analyzed | 37 |
| Percentage of Participants Who Develop Inhibitory Antibodies to VWF [Units: Percent of participants] | |
| Before 1st treatment with study product [N = 37] | 0 |
| During 1st treatment until study end [N = 27] | 0 |
| At final study visit [N = 24] | 0 |

No statistical analysis provided for Percentage of Participants Who Develop Inhibitory Antibodies to VWF Secondary Outcome Measures: Secondary Outcome #7

8. Secondary: Percentage of Participants Who Develop Binding Antibodies to VWF [Time Frame: After signing informed consent until 12 months after first infusion of rVWF:rFVIII or rVWF]

TABLE 28

Secondary Outcome #7

| | |
|---|---|
| Measure Type | Secondary |
| Measure Title | Percentage of Participants Who Develop Binding Antibodies to VWF |
| Measure Description | The presence of total binding anti-VWF antibodies was determined by an enzyme-linked immunosorbent assay (ELISA) employing polyclonal anti-human immunoglobulin (Ig) antibodies (IgG, IgM and IgA). Category title includes number of participants [N] who provided data for the category. |
| Time Frame | After signing informed consent until 12 months after first infusion of rVWF:rFVIII or rVWF |

TABLE 29

Reporting Groups

| | Description |
|---|---|
| Safety Analysis Set | Comprised of participants who were treated with study product (recombinant von Willebrand Factor [rVWF] with or without recombinant factor VIII [rFVIII]) at least once during the study. |

TABLE 30

Measured Values

| | Safety Analysis Set |
|---|---|
| Participants Analyzed | 37 |
| Percentage of Participants Who Develop Binding Antibodies to VWF [Units: Percent of participants] | |
| Before 1st treatment with study product [N = 37] | 0 |
| During 1st treatment until study end [N = 28] | 0 |
| At final study visit [N = 24] | 0 |

No statistical analysis provided for Percentage of Participants Who Develop Binding Antibodies to VWF Secondary Outcome Measures: Secondary Outcome #8

9. Secondary: Percentage of Participants Who Develop Binding Antibodies to CHO [Time Frame: After signing informed consent until 12 months after first infusion of rVWF:rFVIII or rVWF]

TABLE 30

Secondary Outcome #9

| | |
|---|---|
| Measure Type | Secondary |
| Measure Title | Percentage of Participants Who Develop Binding Antibodies to CHO |
| Measure Description | The presence of total binding anti-CHO antibodies was determined by measuring total immunoglobulin (Ig) antibodies (IgG, IgA, IgM) against Chinese Hamster Ovary (CHO) protein using an enzyme-linked immunosorbent assay (ELISA). Category title includes number of participants [N] who provided data for the category. |
| Time Frame | After signing informed consent until 12 months after first infusion of rVWF:rFVIII or rVWF |

TABLE 31

| Reporting Groups | |
|---|---|
| | Description |
| Safety Analysis Set | Comprised of participants who were treated with study product (recombinant von Willebrand Factor [rVWF] with or without recombinant factor VIII [rFVIII]) at least once during the study. |

TABLE 32

| Measured Values | |
|---|---|
| | Safety Analysis Set |
| Participants Analyzed | 37 |
| Percentage of Participants Who Develop Binding Antibodies to CHO [Units Percent of participants] | |
| Before 1st treatment with study product [N = 37] | 0 |
| During 1st treatment until study end [N = 28] | 0 |
| At final study visit [N = 24] | 0 |

No statistical analysis provided for Percentage of Participants Who Develop Binding Antibodies to CHO Secondary Outcome Measures: Secondary Outcome #9

10. Secondary: Percentage of Participants Who Develop Binding Antibodies to rFurin [Time Frame: After signing informed consent until 12 months after first infusion of rVWF:rFVIII or rVWF]

TABLE 33

| Secondary Outcome #9 | |
|---|---|
| Measure Type | Secondary |
| Measure Title | Percentage of Participants Who Develop Binding Antibodies to rFurin |
| Measure Description | The presence of total binding anti-rFurin antibodies was determined by measuring total immunoglobulin (Ig) antibodies (IgG, IgA, IgM) against rFurin protein using an enzyme-linked immunosorbent assay (ELISA). Category title includes number of participants [N] who provided data for the category. |
| Time Frame | After signing informed consent until 12 months after first infusion of rVWF:rFVIII or rVWF |

TABLE 34

| Reporting Groups | |
|---|---|
| | Description |
| Safety Analysis Set | Comprised of participants who were treated with study product (recombinant von Willebrand Factor [rVWF] with or without recombinant factor VIII [rFVIII]) at least once during the study. |

TABLE 35

| Measured Values | |
|---|---|
| | Safety Analysis Set |
| Participants Analyzed | 37 |
| Percentage of Participants Who Develop Binding Antibodies to rFurin [Units: Percent of participants] | |
| Before 1st treatment with study product [N = 37] | 0 |
| During 1st treatment until study end [N = 28] | 0 |
| At final study visit [N = 24] | 0 |

No statistical analysis provided for Percentage of Participants Who Develop Binding Antibodies to rFurin Secondary Outcome Measures: Secondary Outcome #10

11. Secondary: Percentage of Participants Who Develop Binding Antibodies to Mouse Immunoglobulin [Time Frame: After signing informed consent until 12 months after first infusion of rVWF:rFVIII or rVWF]

TABLE 36

| Secondary Outcome #10 | |
|---|---|
| Measure Type | Secondary |
| Measure Title | Percentage of Participants Who Develop Binding Antibodies to Mouse Immunoglobulin |
| Measure Description | The presence of total binding anti-Murine immunoglobulin (IgG) antibodies was determined using an enzyme-linked immunosorbent assay (ELISA). Category title includes number of participants [N] who provided data for the category. |
| Time Frame | After signing informed consent until 12 months after first infusion of rVWF:rFVIII or rVWF |

TABLE 37

| Reporting Groups | |
|---|---|
| | Description |
| Safety Analysis Set | Comprised of participants who were treated with study product (recombinant von Willebrand Factor [rVWF] with or without recombinant factor VIII [rFVIII]) at least once during the study. |

TABLE 38

| Measured Values | |
|---|---|
| | Safety Analysis Set |
| Participants Analyzed | 37 |
| Percentage of Participants Who Develop Binding Antibodies to Mouse Immunoglobulin [Units: Percent of participants] | |
| Before 1st treatment with study product [N = 37] | 2.8 |
| During 1st treatment until study end [N = 28] | 0 |
| At final study visit [N = 24] | 0 |

No statistical analysis provided for Percentage of Participants Who Develop Binding Antibodies to Mouse Immunoglobulin Secondary Outcome Measures: Secondary Outcome #11

12. Secondary: Percentage of Participants Who Had an Occurrence of Thrombotic Events [Time Frame: After signing informed consent until 12 months after first infusion of rVWF:rFVIII or rVWF]

TABLE 39

| Secondary Outcome #11 | |
| --- | --- |
| Measure Type | Secondary |
| Measure Title | Percentage of Participants Who Had an Occurrence of Thrombotic Events |
| Measure Description | No text entered. |
| Time Frame | After signing informed consent until 12 months after first infusion of rVWF:rFVIII or rVWF |

TABLE 40

| Reporting Groups | |
| --- | --- |
| | Description |
| Safety Analysis Set | Comprised of participants who were treated with study product (recombinant von Willebrand Factor [rVWF] with or without recombinant factor VIII [rFVIII]) at least once during the study. |

TABLE 41

| Measured Values | |
| --- | --- |
| | Safety Analysis Set |
| Participants Analyzed | 37 |
| Percentage of Participants Who Had an Occurrence of Thrombotic Events [Units: Percent of participants] | 0 |

No statistical analysis provided for Percentage of Participants Who Had an Occurrence of Thrombotic Events Secondary Outcome Measures: Secondary Outcome #12

13. Secondary: Number of Adverse Events Related to Study Product Including Clinically Significant Changes in Laboratory Parameters and Vital Signs [Time Frame: For 12 months after first infusion of rVWF:rFVIII or rVWF]

TABLE 42

| Secondary Outcome #12 | |
| --- | --- |
| Measure Type | Secondary |
| Measure Title | Number of Adverse Events Related to Study Product Including Clinically Significant Changes in Laboratory Parameters and Vital Signs |
| Measure Description | Adverse Events (AEs) related to study product (recombinant von Willebrand Factor [rVWF] with or without recombinant factor VIII [rFVIII]) are described. Only laboratory parameters (hematology and clinical chemistry) and vital signs (physical examination, ECG) with clinically significant findings that are recorded as AEs are included. Categories presented as Severity-System Organ Class-Preferred Term Seriousness: serious adverse event (SAE); non serious adverse event (nsAE) System Organ Class: Cardiac disorders (CARD); General disorders and administration site conditions (GEN); Investigations (INV); Nervous system disorders (NERV); Skin and subcutaneous tissue disorders (SKN); Vascular disorders (VAS). Category title includes number of AEs [N] for the category. |
| Time Frame | For 12 months after first infusion of rVWF:rFVIII or rVWF |

TABLE 43

| Reporting Groups | |
| --- | --- |
| | Description |
| Safety Analysis Set | Comprised of participants who were treated with study product (recombinant von Willebrand Factor [rVWF] with or without recombinant factor VIII [rFVIII]) at least once during the study. |

TABLE 44

| Measured Values | |
| --- | --- |
| | Safety Analysis Set |
| Participants Analyzed | 37 |
| Units Analyzed (Adverse Events) | 125 |
| Number of Adverse Events Related to Study Product Including Clinically Significant Changes in Laboratory Parameters and Vital Signs [Units: Number of Adverse Events] | |
| SAE-GEN-Chest discomfort [N = 1] | 1 |
| SAE-INV-Heart rate increased [N = 1] | 1 |
| nsAE-CARD-Tachycardia [N = 1] | 1 |
| nsAE-GEN-Infusion site paraesthesia [N = 1] | 1 |
| nsAE-INV-ECG T wave inversion [N = 1] | 1 |
| nsAE-NERV-Dysgeusia [N = 1] | 1 |
| nsAE-SKN-Pruritus generalized [N = 1] | 1 |
| nsAE-VAS-Hot flush [N = 1] | 1 |

No statistical analysis provided for Number of Adverse Events Related to Study Product Including Clinically Significant Changes in Laboratory Parameters and Vital Signs Secondary Outcome Measures: Secondary Outcome #13

14. Secondary: Number of Participants With Adverse Events Related to Study Product Including Clinically Significant Changes in Laboratory Parameters and Vital Signs [Time Frame: For 12 months after first infusion of rVWF:rFVIII or rVWF]

TABLE 45

| Secondary Outcome #13 | |
| --- | --- |
| Measure Type | Secondary |
| Measure Title | Number of Participants With Adverse Events Related to Study Product Including Clinically Significant Changes in Laboratory Parameters and Vital Signs |
| Measure Description | Number of participants with Adverse Events (AEs) related to study product (recombinant von Willebrand Factor [rVWF] with or without recombinant factor VIII [rFVIII]) are described. Only laboratory parameters (hematology and clinical chemistry) and |

TABLE 45-continued

Secondary Outcome #13

| | |
|---|---|
| | vital signs (physical examination, ECG) with clinically significant findings that are recorded as AEs are included. Categories presented as Severity-System Organ Class-Preferred Term Seriousness: serious adverse event (SAE); non serious adverse event (nsAE) System Organ Class: Cardiac disorders (CARD); General disorders and administration site conditions (GEN); Investigations (INV); Nervous system disorders (NERV); Skin and subcutaneous tissue disorders (SKN); Vascular disorders (VAS). |
| Time Frame | For 12 months after first infusion of rVWF:rFVIII or rVWF |

TABLE 46

Reporting Groups

| | Description |
|---|---|
| Safety Analysis Set | Comprised of participants who were treated with study product (recombinant von Willebrand Factor [rVWF] with or without recombinant factor VIII [rFVIII]) at least once during the study. |

TABLE 47

Measured Values

| | Safety Analysis Set |
|---|---|
| Participants Analyzed | 37 |
| Number of Participants With Adverse Events Related to Study Product Including Clinically Significant Changes in Laboratory Parameters and Vital Signs [Units: Number of participants] | |
| SAE-GEN-Chest discomfort | 1 |
| SAE-INV-Heart rate increased | 1 |
| nsAE-CARD-Tachycardia | 1 |
| nsAE-GEN-Infusion site paraesthesia | 1 |
| nsAE-INV-ECG T wave inversion | 1 |
| nsAE-NERV-Dysgeusia | 1 |
| nsAE-SKN-Pruritus generalized | 1 |
| nsAE-VAS-Hot flush | 1 |

No statistical analysis provided for Number of Participants With Adverse Events Related to Study Product Including Clinically Significant Changes in Laboratory Parameters and Vital Signs Secondary Outcome Measures: Secondary Outcome #14

15. Secondary: Number of Adverse Events by Infusion Related to Study Product Including Clinically Significant Changes in Laboratory Parameters and Vital Signs [Time Frame: For 12 months after first infusion of rVWF:rFVIII or rVWF]

TABLE 48

Secondary Outcome #14

| | |
|---|---|
| Measure Type | Secondary |
| Measure Title | Number of Adverse Events by Infusion Related to Study Product Including Clinically Significant Changes in Laboratory Parameters and Vital Signs |

TABLE 48-continued

Secondary Outcome #14

| | |
|---|---|
| Measure Description | Adverse Events (AEs) by infusion related to study product (recombinant von Willebrand Factor [rVWF] with or without recombinant factor VIII [rFVIII]) are described. Only laboratory parameters (hematology and clinical chemistry) and vital signs (physical examination, ECG) with clinically significant findings that are recorded as AEs are included. Categories presented as Severity-System Organ Class-Preferred Term Seriousness: serious adverse event (SAE); non serious adverse event (nsAE) System Organ Class: Cardiac disorders (CARD); General disorders and administration site conditions (GEN); Investigations (INV); Nervous system disorders (NERV); Skin and subcutaneous tissue disorders (SKN); Vascular disorders (VAS). |
| Time Frame | For 12 months after first infusion of rVWF:rFVIII or rVWF |

TABLE 49

Reporting Groups

| | Description |
|---|---|
| Safety Analysis Set | Comprised of participants who were treated with study product (recombinant von Willebrand Factor [rVWF] with or without recombinant factor VIII [rFVIII]) at least once during the study. |

TABLE 50

Measured Values

| | Safety Analysis Set |
|---|---|
| Participants Analyzed | 37 |
| Units Analyzed (Infusions) | 318 |
| Number of Adverse Events by Infusion Related to Study Product Including Clinically Significant Changes in Laboratory Parameters and Vital Signs [Units: Number of Adverse Events] | |
| SAE-GEN-Chest discomfort | 1 |
| SAE-INV-Heart rate increased | 1 |
| nsAE-CARD-Tachycardia | 1 |
| nsAE-GEN-Infusion site paraesthesia | 1 |
| nsAE-INV-ECG T wave inversion | 1 |
| nsAE-NERV-Dysgeusia | 1 |
| nsAE-SKN-Pruritus generalized | 1 |
| nsAE-VAS-Hot flush | 1 |

No statistical analysis provided for Number of Adverse Events by Infusion Related to Study Product Including Clinically Significant Changes in Laboratory Parameters and Vital Signs Secondary Outcome Measures: Secondary Outcome #15

16. Secondary: PK50—Area Under the Plasma Concentration/Time Curve From Time 0 to Infinity (AUC0-∞/Dose) of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 51

Secondary Outcome #15

| | |
|---|---|
| Measure Type | Secondary |
| Measure Title | PK50-Area Under the Plasma Concentration/Time Curve From Time 0 to Infinity (AUC0-∞/Dose) of VWF:RCo |
| Measure Description | Area under the plasma concentration curve (AUC) from time 0 to infinity of von Willebrand Factor Ristocetin cofactor (VWF:RCo) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for subjects in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 52

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total of participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 53

Measured Values

| | PK50 Arms |
|---|---|
| Participants Analyzed | 16 |
| PK50-Area Under the Plasma Concentration/Time Curve From Time 0 to Infinity (AUC0-∞/Dose) of VVVF:RCo [Units (hours*U/dL)/(U VWF: RCo/kg)] Median (95% Confidence Interval) | |
| rVWF:rFVIII [N = 16] | 32.4 (27.5 to 40.1) |
| rVWF [N = 14] | 32.7 (29.0 to 47.8) |

No statistical analysis provided for PK50—Area Under the Plasma Concentration/Time Curve From Time 0 to Infinity (AUC0-∞/Dose) of VWF:RCo
Secondary Outcome Measures: Secondary Outcome #16

17. Secondary: PK50—Area Under the Plasma Concentration/Time Curve From Time 0 to 96 Hours (AUC0-96 h/Dose) of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 54

Secondary Outcome #16

| | |
|---|---|
| Measure Type | Secondary |
| Measure Title | PK50-Area Under the Plasma Concentration/Time Curve From Time 0 to 96 Hours (AUC0-96 h/Dose) of VWF:RCo |
| Measure Description | Area under the plasma concentration curve (AUC) from time 0 to 96 hours of von Willebrand Factor Ristocetin cofactor (VWF:RCo) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 55

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 56

Measured Values

| | PK50 Arms |
|---|---|
| Participants Analyzed | 16 |
| PK50-Area Under the Plasma Concentration/Time Curve From Time 0 to 96 Hours (AUC0-96 h/Dose) of VWF:RCo [Units: (hours*U/dL)/(U VWF: RCo/kg)] Median (95% Confidence Interval) | |
| rVWF:rFVIII [N = 16] | 31.6 (27.3 to 37.3) |
| rVWF [N = 14] | 31.3 (28.4 to 43.7) |

No statistical analysis provided for PK50—Area Under the Plasma Concentration/Time Curve From Time 0 to 96 Hours (AUC0-96 h/Dose) of VWF:RCo
Secondary Outcome Measures: Secondary Outcome #17

18. Secondary: PK50—Mean Residence Time of VWF: RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 57

Secondary Outcome #17

| | |
|---|---|
| Measure Type | Secondary |
| Measure Title | PK50—Mean Residence Time of VWF:RCo |
| Measure Description | Mean Residence Time (MRT) of von Willebrand Factor Ristocetin cofactor (VWF:RCo) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 58

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 59

Measured Values

| | PK50 Arms |
|---|---|
| Participants Analyzed | 16 |
| PK50—Mean Residence Time of VWF:RCo | |
| [Units: Hours] | |
| Median (95% Confidence Interval) | |
| rVWF:rFVIII [N = 16] | 25.2 |
| | (20.0 to 30.1) |
| rVWF [N = 14] | 26.7 |
| | (22.7 to 36.0) |

No statistical analysis provided for PK50—Mean Residence Time of VWF:RCo

Secondary Outcome Measures: Secondary Outcome #18

19. Secondary: PK50—Clearance of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 60

Secondary Outcome #18

| | |
|---|---|
| Measure Type | Secondary |
| Measure Title | PK50—Clearance of VWF:RCo |
| Measure Description | Clearance (CL) of von Willebrand Factor Ristocetin cofactor (VWF:RCo) after infusion of 50 IU/kg recombinant von Willebrand Factor: von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 61

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 62

Measured Values

| | PK50 Arms |
|---|---|
| Participants Analyzed | 16 |
| PK50—Clearance of VWF:RCo | |
| [Units: dL/kg/hours] | |
| Median (95% Confidence Interval) | |
| rVWF:rFVIII [N = 16] | 0.031 |
| | (0.025 to 0.041) |
| rVWF [N = 14] | 0.031 |
| | (0.021 to 0.035) |

No statistical analysis provided for PK50—Clearance of VWF:RCo

Secondary Outcome Measures: Secondary Outcome #19

20. Secondary: PK50—Incremental Recovery of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 63

Secondary Outcome #19

| | |
|---|---|
| Measure Type | Secondary |
| Measure Title | PK50—Incremental Recovery of VWF:RCo |
| Measure Description | Incremental Recovery (IR) at the maximum plasma concentration of von Willebrand Factor Ristocetin cofactor (VWF:RCo) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) |

TABLE 63-continued

Secondary Outcome #19

| | |
|---|---|
| | [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 64

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 65

Measured Values

| | PK50 Arms |
|---|---|
| Participants Analyzed | 16 |
| PK50—Incremental Recovery of VWF:RCo [Units: (U/dL)/(U VWF: RCo/kg)] Median (95% Confidence Interval) | |
| rVWF:rFVIII [N = 16] | 1.8 (1.6 to 2.4) |
| rVWF [N = 14] | 1.8 (1.5 to 2.2) |

No statistical analysis provided for PK50—Incremental Recovery of VWF:RCo

Secondary Outcome Measures: Secondary Outcome #20

21. Secondary: PK50—Elimination Phase Half-Life of VWF:Co [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 66

Secondary Outcome #20

| | |
|---|---|
| Measure Type | Secondary |
| Measure Title | PK50—Elimination Phase Half-Life of VWF:Co |
| Measure Description | Elimination Phase Half-Life (T1/2) of von Willebrand Factor Ristocetin cofactor (VWF:RCo) after infusion of 50 IU/kg recombinant von Willebrand Factor:von Willebrand Factor Ristocetin cofactor (VWF:RCo rVWF) administered together with 38.5 IU/kg recombinant FVIII (rFVIII) (ratio of 1.3:1 ± 0.2) [rVWF:rFVIII], or 50 IU/kg VWF:RCo rVWF |

TABLE 66-continued

Secondary Outcome #20

| | |
|---|---|
| | administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 67

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 68

Measured Values

| | PK50 Arms |
|---|---|
| Participants Analyzed | 16 |
| PK50—Elimination Phase Half-Life of VWF:Co [Units: Hours] Median (95% Confidence Interval) | |
| rVWF:rFVIII [N = 16] | 16.6 (14.7 to 20.4) |
| rVWF [N = 14] | 19.4 (15.5 to 31.3) |

No statistical analysis provided for PK50—Elimination Phase Half-Life of VWF:Co

Secondary Outcome Measures: Secondary Outcome #21

22. Secondary: PK50—Volume of Distribution at Steady State of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 69

Secondary Outcome #21

| | |
|---|---|
| Measure Type | Secondary |
| Measure Title | PK50—Volume of Distribution at Steady State of VWF:RCo |
| Measure Description | Volume of Distribution at Steady State (Vss) of von Willebrand Factor Ristocetin cofactor (VWF:RCo) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |

TABLE 69-continued

Secondary Outcome #21

| | |
|---|---|
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 70

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 71

Measured Values

| | PK50 Arms |
|---|---|
| Participants Analyzed | 16 |
| PK50—Volume of Distribution at Steady State of VWF:RCo [Units: dL/kg] Median (95% Confidence Interval) | |
| rVWF:rFVIII [N = 16] | 0.70 (0.66 to 0.93) |
| rVWF [N = 14] | 0.83 (0.70 to 0.97) |

No statistical analysis provided for PK50—Volume of Distribution at Steady State of VWF:RCo Secondary Outcome Measures: Secondary Outcome #22

23. Secondary: PK50—Area Under the Plasma Concentration/Time Curve From Time 0 to Infinity (AUC0-∞/Dose) of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 72

Secondary Outcome #23

| | |
|---|---|
| Measure Type | Secondary |
| Measure Title | PK50—Area Under the Plasma Concentration/Time Curve From Time 0 to Infinity (AUC0-∞/Dose) of VWF:Ag |
| Measure Description | Area under the plasma concentration curve (AUC) from time 0 to infinity of von Willebrand Factor Antigen (VWF:Ag) after infusion of 50 IU/kg recombinant von Willebrand Factor:von Willebrand Factor Ristocetin cofactor (VWF:RCo rVWF) administered together with 38.5IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |

TABLE 72-continued

Secondary Outcome #23

| | |
|---|---|
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 73

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 74

Measured Values

| | PK50 Arms |
|---|---|
| Participants Analyzed | 16 |
| PK50—Area Under the Plasma Concentration/Time Curve From Time 0 to Infinity (AUC0-∞/Dose) of VWF:Ag [Units: (hours*U/dL)/(U VWF: RCo/kg)] Median (95% Confidence Interval) | |
| rVWF:rFVIII [N = 16] | 67.8 (55.1 to 81.7) |
| rVWF [N = 14] | 67.1 (55.6 to 80.5) |

No statistical analysis provided for PK50—Area Under the Plasma Concentration/Time Curve From Time 0 to Infinity (AUC0-∞/Dose) of VWF:Ag Secondary Outcome Measures: Secondary Outcome #23

24. Secondary: PK50—Area Under the Plasma Concentration/Time Curve From Time 0 to 96 Hours (AUC0-96 h/Dose) of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout]

TABLE 75

Secondary Outcome #24

| | |
|---|---|
| Measure Type | Secondary |
| Measure Title | PK50—Area Under the Plasma Concentration/Time Curve From Time 0 to 96 Hours (AUC0-96 h/Dose) of VWF:Ag |
| Measure Description | Area under the plasma concentration curve (AUC) from time 0 to 96 hours of von Willebrand Factor Antigen (VWF:Ag) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and |

TABLE 75-continued

Secondary Outcome #24

| | |
|---|---|
| Time Frame | Arm 2). Category title includes number of participants [N] who provided data for the category. PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout |

TABLE 76

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 77

Measured Values

| | PK50 Arms |
|---|---|
| Participants Analyzed | 16 |
| PK50—Area Under the Plasma Concentration/Time Curve From Time 0 to 96 Hours (AUC0-96 h/Dose) of VWF:Ag [Units: (hours*U/dL)/(U VWF: RCo/kg)] Median (95% Confidence Interval) | |
| rVWF:rFVIII [N = 16] | 62.1 (52.8 to 74.9) |
| rVWF [N = 14] | 62.2 (54.7 to 74.5) |

No statistical analysis provided for PK50—Area Under the Plasma Concentration/Time Curve From Time 0 to 96 Hours (AUC0-96 h/Dose) of VWF:Ag Secondary Outcome Measures: Secondary Outcome #24

25. Secondary: PK50—Mean Residence Time of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 78

Secondary Outcome #24

| | |
|---|---|
| Measure Type | Secondary |
| Measure Title | PK50—Mean Residence Time of VWF:Ag |
| Measure Description | Mean Residence Time (MRT) of von Willebrand Factor Antigen (VWF:Ag) after infusion of 50 IU/kg recombinant von Willebrand Factor: von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII] or 50 IU/kg VWF:RCo rVWF administered together with saline (placebo) [rVWF] for participants in the |

TABLE 78-continued

Secondary Outcome #24

| | |
|---|---|
| Time Frame | PK50 arms (Arm 1 and Arm 2). Category title includes number of participants [N] who provided data for the category. PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 79

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 80

Measured Values

| | PK50 Arms |
|---|---|
| Participants Analyzed | 16 |
| PK50—Mean Residence Time of VWF:Ag [Units Hours] Median (95% Confidence Interval) | |
| rVWF:rFVIII [N = 16] | 32.1 (29.8 to 41.1) |
| rVWF [N = 14] | 34.3 (30.4 to 41.4) |

No statistical analysis provided for PK50—Mean Residence Time of VWF:Ag

Secondary Outcome Measures: Secondary Outcome #25

26. Secondary: PK50—Clearance of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 81

Secondary Outcome #25

| | |
|---|---|
| Measure Type | Secondary |
| Measure Title | PK50—Clearance of VWF:Ag |
| Measure Description | Clearance (CL) of von Willebrand Factor Antigen (VWF:Ag) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post- |

TABLE 81-continued

Secondary Outcome #25 infusion. PK evaluation timeframe for 28 ± 3 days after first infusion of study product which includes PK evaluation for both infusions and washout.

TABLE 82

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only. Participants in the PK50 arms have received at least one PK infusion and have provided data suitable for PK analysis. Only PK data included from the PK50 arms. |

TABLE 83

Measured Values

| | PK50 Arms |
|---|---|
| Participants Analyzed | 16 |
| PK50—Clearance of VWF:Ag [Units: dL/kg/hours] Median (95% Confidence Interval) | |
| rVWF:rFVIII [N = 16] | 0.015 (0.013 to 0.018) |
| rVWF [N = 14] | 0.015 (0.013 to 0.018) |

No statistical analysis provided for PK50—Clearance of VWF:Ag

Secondary Outcome Measures: Secondary Outcome #26

27. Secondary: PK50—Incremental Recovery of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 84

Secondary Outcome #26

| Measure Type | Secondary |
|---|---|
| Measure Title | PK50—Incremental Recovery of VWF:Ag |
| Measure Description | Incremental Recovery (IR) at the maximum plasma concentration of von Willebrand Factor Antigen (VWF:Ag) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 85

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 86

Measured Values

| | PK50 Arms |
|---|---|
| Participants Analyzed | 16 |
| PK50—Incremental Recovery of VWF:Ag [Units: (U/dL)/(U VWF: RCo/kg)] Median (95% Confidence Interval) | |
| rVWF:rFVIII [N = 16] | 2.3 (2.0 to 2.5) |
| rVWF [N = 14] | 2.2 (1.9 to 2.5) |

No statistical analysis provided for PK50—Incremental Recovery of VWF:Ag

Secondary Outcome Measures: Secondary Outcome #27

28. Secondary: PK50—Elimination Phase Half-Life of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 87

Secondary Outcome #27

| Measure Type | Secondary |
|---|---|
| Measure Title | PK50-Elimination Phase Half-Life of VWF:Ag |
| Measure Description | Elimination Phase Half-Life (T1/2) of von Willebrand Factor Antigen (VWF:Ag) after infusion of 50 IU/kg recombinant von Willebrand Factor:von Willebrand Factor Ristocetin cofactor (VWF:RCo rVWF) administered together with 38.5 IU/kg recombinant FVIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 88

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 89

Measured Values

| | PK50 Arms |
|---|---|
| Participants Analyzed | 16 |
| PK50-Elimination Phase Half-Life of VWF:Ag [Units: Hours] Median (95% Confidence Interval) | |
| rVWF:rFVIII [N = 16] | 21.8 (19.5 to 27.2) |
| rVWF [N = 14] | 25.2 (21.9 to 30.3) |

No statistical analysis provided for PK50—Elimination Phase Half-Life of VWF:Ag

Secondary Outcome Measures: Secondary Outcome #28

29. Secondary: PK50—Volume of Distribution at Steady State of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 90

Secondary Outcome #28

| Measure Type | Secondary |
|---|---|
| Measure Title | PK50-Volume of Distribution at Steady State of VWF:Ag |
| Measure Description | Volume of Distribution at Steady State (Vss) of von Willebrand Factor Antigen (VWF:Ag) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 91

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 92

Measured Values

| | PK50 Arms |
|---|---|
| Participants Analyzed | 16 |
| PK50-Volume of Distribution at Steady State of VWF:Ag [Units: dL/kg] Median (95% Confidence Interval) | |
| rVWF:rFVIII [N = 16] | 0.50 (0.45 to 0.56) |
| rVWF [N = 14] | 0.49 (0.45 to 0.58) |

No statistical analysis provided for PK50—Volume of Distribution at Steady State of VWF:Ag Secondary Outcome Measures: Secondary Outcome #29

30. Secondary: PK50—Area Under the Plasma Concentration/Time Curve From Time 0 to Infinity (AUC0-∞/Dose) of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 93

Secondary Outcome #30

| Measure Type | Secondary |
|---|---|
| Measure Title | PK50-Area Under the Plasma Concentration/Time Curve From Time 0 to Infinity (AUC0-∞/Dose) of VWF:CB |
| Measure Description | Area under the plasma concentration curve (AUC) from time 0 to infinity of von Willebrand Factor Collagen Binding (VWF:CB) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) |

TABLE 93-continued

Secondary Outcome #30

| | |
|---|---|
| Measure Type | Secondary |
| | [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 94

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 95

Measured Values

| | PK50 Arms |
|---|---|
| Participants Analyzed | 16 |
| PK50-Area Under the Plasma Concentration/Time Curve From Time 0 to Infinity (AUC0-∞/Dose) of VWF:CB [Units: (hours*U/dL)/(U VWF: RCo/kg)] Median (95% Confidence Interval) | |
| rVWF:rFVIII [N = 16] | 80.1 |
| | (68.4 to 95.0) |
| rVWF [N = 14] | 81.3 |
| | (71.2 to 99.8) |

No statistical analysis provided for PK50—Area Under the Plasma Concentration/Time Curve From Time 0 to Infinity (AUC0-∞/Dose) of VWF:CB Secondary Outcome Measures: Secondary Outcome #30

31. Secondary: PK50—Area Under the Plasma Concentration/Time Curve From Time 0 to 96 Hours (AUC0-96 h/Dose) of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 26

Secondary Outcome #30

| | |
|---|---|
| Measure Type | Secondary |
| Measure Title | PK50-Area Under the Plasma Concentration/Time Curve From Time 0 to 96 Hours (AUCO-96h/Dose) of VWF:CB |
| Measure Description | Area under the plasma concentration curve (AUC) from time 0 to 96 hours of von Willebrand Factor Collagen Binding (VWF:CB) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 97

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII]or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 98

Measured Values

| | PK50 Arms |
|---|---|
| Participants Analyzed | 16 |
| PK50-Area Under the Plasma Concentration/Time Curve From Time 0 to 96 Hours (AUC0-96h/Dose) of VWF:CB [Units: (hours*U/dL)/(U VWF: RCo/kg)] Median (95% Confidence Interval) | |
| rVWF:rFVIII [N = 16] | 78.7 |
| | (66.5 to 90.5) |
| rVWF [N = 14] | 75.1 |
| | (69.2 to 97.0) |

No statistical analysis provided for PK50—Area Under the Plasma Concentration/Time Curve From Time 0 to 96 Hours (AUC0-96 h/Dose) of VWF:CB Secondary Outcome Measures: Secondary Outcome #31

32. Secondary: PK50—Mean Residence Time of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 99

| Secondary Outcome #31 | |
|---|---|
| Measure Type | Secondary |
| Measure Title | PK50-Mean Residence Time of VWF:CB |
| Measure Description | Mean Residence Time (MRT) of von Willebrand Factor Collagen Binding (VWF:CB) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 100

| Reporting Groups | |
|---|---|
| | Description |
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 101

| Measured Values | |
|---|---|
| | PK50 Arms |
| Participants Analyzed | 16 |
| PK50-Mean Residence Time of VWF:CB [Units: Hours] Median (95% Confidence Interval) | |

TABLE 101-continued

| Measured Values | |
|---|---|
| | PK50 Arms |
| rVWF:rFVIII [N = 16] | 27.5 |
| | (22.7 to 32.1) |
| rVWF [N = 14] | 26.1 |
| | (25.1 to 33.2) |

No statistical analysis provided for PK50—Mean Residence Time of VWF:CB

Secondary Outcome Measures: Secondary Outcome #32

33. Secondary: PK50—Clearance of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 102

| Secondary Outcome #32 | |
|---|---|
| Measure Type | Secondary |
| Measure Title | PK50-Clearance of VWF:CB |
| Measure Description | Clearance (CL) of von Willebrand Factor Collagen Binding (VWF:CB) after infusion of 50 IU/kg recombinant von Willebrand Factor: von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 103

| Reporting Groups | |
|---|---|
| | Description |
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 104

Measured Values

| | PK50 Arms |
|---|---|
| Participants Analyzed | 16 |
| PK50—Clearance of VWF:CB | |
| [Units: dL/kg/hours] | |
| Median (95% Confidence Interval) | |
| rVWF:rFVIII [N = 16] | 0.012 |
| | (0.011 to 0.015) |
| rVWF [N = 14] | 0.012 |
| | (0.011 to 0.015) |

No statistical analysis provided for PK50—Clearance of VWF:CB

Secondary Outcome Measures: Secondary Outcome #33

34. Secondary: PK50—Incremental Recovery of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 105

Secondary Outcome #33

| | |
|---|---|
| Measure Type | Secondary |
| Measure Title | PK50—Incremental Recovery of VWF:CB |
| Measure Description | Incremental Recovery (IR) at the maximum plasma concentration of von Willebrand Factor Collagen Binding (VWF:CB) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 106

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 107

Measured Values

| | PK50 Arms |
|---|---|
| Participants Analyzed | 16 |
| PK50—Incremental Recovery of VWF:CB | |
| [Units: (U/dL)/(U VWF:RCo/kg)] | |
| Median (95% Confidence Interval) | |
| rVWF:rFVIII [N = 16] | 3.4 |
| | (3.0 to 3.7) |
| rVWF [N = 14] | 3.2 |
| | (2.8 to 3.7) |

No statistical analysis provided for PK50—Incremental Recovery of VWF:CB

Secondary Outcome Measures: Secondary Outcome #34

35. Secondary: PK50—Elimination Phase Half-Life of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 108

Secondary Outcome #34

| | |
|---|---|
| Measure Type | Secondary |
| Measure Title | PK50—Elimination Phase Half-Life of VWF:CB |
| Measure Description | Elimination Phase Half-Life (T1/2) of von Willebrand Factor Collagen Binding (VWF:CB) after infusion of 50 IU/kg recombinant von Willebrand Factor:von Willebrand Factor Ristocetin cofactor (VWF:RCo rVWF) administered together with 38.5 IU/kg recombinant FVIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 109

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 110

| Measured Values | |
|---|---|
| | PK50 Arms |
| Participants Analyzed | 16 |
| PK50—Elimination Phase Half-Life of VWF:CB | |
| [Units: Hours] | |
| Median (95% Confidence Interval) | |
| rVWF:rFVIII [N = 16] | 19.3 |
| | (14.9 to 23.4) |
| rVWF [N = 14] | 18.3 |
| | (17.4 to 24.8) |

No statistical analysis provided for PK50—Elimination Phase Half-Life of VWF:CB

Secondary Outcome Measures: Secondary Outcome #35

36. Secondary: PK50—Volume of Distribution at Steady State of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 111

| Secondary Outcome #35 | |
|---|---|
| Measure Type | Secondary |
| Measure Title | PK50—Volume of Distribution at Steady State of VWF:CB |
| Measure Description | Volume of Distribution at Steady State (Vss) of von Willebrand Factor Collagen Binding (VWF:CB) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants[N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 112

| Reporting Groups | |
|---|---|
| | Description |
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 113

| Measured Values | |
|---|---|
| | PK50 Arms |
| Participants Analyzed | 16 |
| PK50—Volume of Distribution at Steady State of VWF:CB | |
| [Units: dL/kg] | |
| Median (95% Confidence Interval) | |
| rVWF:rFVIII [N = 16] | 0.35 |
| | (0.31 to 0.40) |
| rVWF [N = 14] | 0.36 |
| | (0.28 to 0.42) |

No statistical analysis provided for PK50—Volume of Distribution at Steady State of VWF:CB Secondary Outcome Measures: Secondary Outcome #36

37. Secondary: PK50—Area Under the Plasma Concentration/Time Curve From Time 0 to Infinity (AUC0-∞/Dose) of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 114

| Secondary Outcome #36 | |
|---|---|
| Measure Type | Secondary |
| Measure Title | PK50—Area Under the Plasma Concentration/Time Curve From Time 0 to Infinity (AUC0-∞/Dose) of FVIII:C |
| Measure Description | Area under the plasma concentration curve (AUC) from time 0 to infinity of Factor VIII activity (FVIII:C) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) |

TABLE 114-continued

Secondary Outcome #36

| | |
|---|---|
| | (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 115

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABEL 116

| Measured Values | |
|---|---|
| | PK50 Arms |
| Participants Analyzed | 16 |
| PK50—Area Under the Plasma Concentration/Time Curve From Time 0 to Infinity (AUC0-∞/Dose) of FVIII:C [Units hours*U/dL]/(U VWF:RCo/kg)] Median (95% Confidence Interval) | |
| rVWF:rFVIII [N = 16] | 145.4 (118.8 to 189.5) |
| rVWF [N = 14] | 113.0 (93.0 to 167.4) |

No statistical analysis provided for PK50—Area Under the Plasma Concentration/Time Curve From Time 0 to Infinity (AUC0-∞/Dose) of FVIII:C
Secondary Outcome Measures: Secondary Outcome #37
38. Secondary: PK50—Area Under the Plasma Concentration/Time Curve From Time 0 to 96 Hours (AUC0-96 h/Dose) of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 116

Secondary Outcome #37

| | |
|---|---|
| Measure Type | Secondary |
| Measure Title | PK50—Area Under the Plasma Concentration/Time Curve From Time 0 to 96 Hours (AUC0-96 h/Dose) of FVIII:C |
| Measure Description | Area under the plasma concentration curve (AUC) from time 0 to 96 hours of Factor VIII activity (FVIII:C) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII], or 50 IU/kg VWF:RCo rVWF administered together with saline (placebo) [rVWF] for participants in the PK50 arms (Arm 1 and Arm 2). Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 117

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 118

| Measured Values | |
| --- | --- |
| | PK50 Arms |
| Participants Analyzed | 16 |
| PK50-Area Under the Plasma Concentration/Time Curve From Time 0 to 96 Hours (AUC0-96h/Dose) of FVIII:C [Units: hours*U/dL)/(U VWF: RCo/kg)] Median (95% Confidence Interval) | |
| rVWF:rFVIII [N = 16] | 127.8 (112.3 to 145.1) |
| rVWF [N = 14] | 101.8 (74.4 to 124.4) |

No statistical analysis provided for PK50—Area Under the Plasma Concentration/Time Curve From Time 0 to 96 Hours (AUC0-96 h/Dose) of FVIII:C Secondary Outcome Measures: Secondary Outcome #38

39. Secondary: PK50—Mean Residence Time of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 119

| Secondary Outcome #38 | |
| --- | --- |
| Measure Type | Secondary |
| Measure Title | PK50-Mean Residence Time of FVIII:C |
| Measure Description | Mean Residence Time (MRT) of Factor VIII activity (FVIII:C) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII] for participants in the PK50 arms (Arm 1 and Arm 2). |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 120

| Reporting Groups | |
| --- | --- |
| | Description |
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII]or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 121

| Measured Values | |
| --- | --- |
| | PK50 Arms |
| Participants Analyzed | 16 |
| PK50-Mean Residence Time of FVIII:C [Units: Hours] Median (95% Confidence Interval) | 44.0 (38.0 to 75.0) |

No statistical analysis provided for PK50—Mean Residence Time of FVIII:C

Secondary Outcome Measures: Secondary Outcome #39

40. Secondary: PK50—Clearance of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 122

Secondary Outcome #39

| | |
|---|---|
| Measure Type | Secondary |
| Measure Title | PK50-Clearance of FVIII:C |
| Measure Description | Clearance (CL) of Factor VIII activity (FVIII:C) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII] for participants in the PK50 arms (Arm 1 and Arm 2). |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 123

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 124

Measured Values

| | PK50 Arms |
|---|---|
| Participants Analyzed | 16 |
| PK50-Clearance of FVIII:C [Units: dL/kg/hours] Median (95% Confidence Interval) | 0.007 (0.006 to 0.009) |

No statistical analysis provided for PK50—Clearance of FVIII:C

Secondary Outcome Measures: Secondary Outcome #40

41. Secondary: PK50—Incremental Recovery of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 125

Secondary Outcome #40

| | |
|---|---|
| Measure Type | Secondary |
| Measure Title | PK50-Incremental Recovery of FVIII:C |
| Measure Description | Incremental Recovery (IR) at the maximum plasma concentration of Factor VIII activity (FVIII:C) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII] for participants in the PK50 arms (Arm 1 and Arm 2). |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 126

| Reporting Groups | |
|---|---|
| | Description |
| Overall Study Arm | No text entered. |

TABLE 127

| Measured Values | |
|---|---|
| | Overall Study Arm |
| Participants Analyzed | 16 |
| PK50-Incremental Recovery of FVIII:C [Units: (U/dL)/(U VWF: RCo/kg)] Median (95% Confidence Interval) | 2.3 (1.9 to 2.7) |

No statistical analysis provided for PK50—Incremental Recovery of FVIII:C
Secondary Outcome Measures: Secondary Outcome #41

42. Secondary: PK50—Elimination Phase Half-Life of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 128

| Secondary Outcome #41 | |
|---|---|
| Measure Type | Secondary |
| Measure Title | PK50-Elimination Phase Half-Life of FVIII:C |
| Measure Description | Elimination Phase Half-Life (T1/2) of Factor VIII activity (FVIII:C) after infusion of 50 IU/kg recombinant von Willebrand Factor:von Willebrand Factor Ristocetin cofactor (VWF:RCo rVWF) administered together with 38.5 IU/kg recombinant VIII (rFVIII) (ratio of 1.3:1 ± 0.2) [rVWF:rFVIII] for participants in the PK50 arms (Arm 1 and Arm 2). |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 129

| Reporting Groups | |
|---|---|
| | Description |
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 130

| Measured Values | |
|---|---|
| | PK50 Arms |
| Participants Analyzed | 16 |
| PK50-Elimination Phase Half-Life of FVIII:C [Units: Hours] Median (95% Confidence Interval) | 24.8 (20.1 to 50.5) |

No statistical analysis provided for PK50—Elimination Phase Half-Life of FVIII:C Secondary Outcome Measures: Secondary Outcome #42

43. Secondary: PK50—Volume of Distribution at Steady State of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 131

Secondary Outcome #42

| | |
|---|---|
| Measure Type | Secondary |
| Measure Title | PK50-Volume of Distribution at Steady State of FVIII:C |
| Measure Description | Volume of Distribution of Steady State (Vss) of Factor VIII activity (FVIII:C) after infusion of 50 IU/kg recombinant von Willebrand Factor:von Willebrand Factor Ristocetin cofactor (VWF:RCo rVWF) administered together with 38.5 IU/kg recombinant Factor VIII (rFVIII) (ratio of 1.3:1 ± 0.2) [rVWF:rFVIII] for participants in the PK50 arms (Arm 1 and Arm 2). |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 132

Reporting Groups

| | Description |
|---|---|
| PK50 Arms | Comprised of participants who underwent PK analysis of study product (50 IU/kg recombinant von Willebrand Factor (rVWF) administered together with 38.5 IU/kg recombinant Factor VIII (rFVIII) [rVWF:rFVIII] or 50 IU/kg rVWF administered together with saline [rVWF]) i.e. a total participants from Arm 1 [PK50 + Treatment] and Arm 2 [PK50 only]. Participants in the PK50 arms have received at least one PK infusion and have provided data suitable for PK analysis. Only PK data included from the PK50 arms. |

TABLE 133

Measured Values

| | PK50 Arms |
|---|---|
| Participants Analyzed PK50-Volume of Distribution at Steady State of FVIII:C | 16 |
| [Units: dL/kg] Median (95% Confidence Interval) | 0.32 (0.29 to 0.44) |

No statistical analysis provided for PK50—Volume of Distribution at Steady State of FVIII:C Secondary Outcome Measures: Secondary Outcome #43

44. Secondary: PK80—Area Under the Plasma Concentration/Time Curve From Time 0 to Infinity (AUC0-∞/Dose) of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 134

Secondary Outcome #43

| | |
|---|---|
| Measure Type | Secondary |
| Measure Title | PK80-Area Under the Plasma Concentration/Time Curve From Time 0 to Infinity (AUC0-∞/Dose) of VWF:RCo |
| Measure Description | Area under the plasma concentration curve (AUC) from time 0 to infinity of von Willebrand Factor Ristocetin cofactor (VWF:RCo) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |

TABLE 134-continued

Secondary Outcome #43

| | |
|---|---|
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 135

Reporting Groups

| | Description |
|---|---|
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 136

Measured Values

| Participants Analyzed PK80-Area Under the Plasma Concentration/ Time Curve From Time 0 to Infinity (AUC0-∞/Dose) of VWF:RCo | PK80 Arm 15 |
|---|---|
| [Units: (hours*U/dL)/(U VWF: RCo/kg)] Median (95% Confidence Interval) | |
| PK1 of rVWF [N = 15] | 36.9 (29.2 to 41.7) |
| PK2 of rVWF [N = 13] | 38.9 (28.1 to 43.3) |

No statistical analysis provided for PK80—Area Under the Plasma Concentration/Time Curve From Time 0 to Infinity (AUC0-∞/Dose) of VWF:RCo Secondary Outcome Measures: Secondary Outcome #44

45. Secondary: PK80—Area Under the Plasma Concentration/Time Curve From Time 0 to 96 Hours (AUC0-96 h/Dose) of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 137

Secondary Outcome #44

| | |
|---|---|
| Measure Type | Secondary |
| Measure Title | PK80-Area Under the Plasma Concentration/Time Curve From Time 0 to 96 Hours (AUC0-96h/Dose) of VWF:RCo |
| Measure Description | Area under the plasma concentration curve (AUC) from time 0 to 96 hours of von Willebrand Factor Ristocetin cofactor (VWF:RCo) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 136

Reporting Groups

| | Description |
|---|---|
| PK80 Arm | Comprised of participants who underwent PK analysis of study product (80 IU/kg recombinant von Willebrand Factor [rVWF]) i.e. participants from Arm |

TABLE 136-continued

| Reporting Groups | |
|---|---|
| Description | |
| 3 [PK80 + Treatment]. Participants in this arm have received at least one PK infusion and have provided data suitable for PK analysis. Only PK data included in this arm. | |

TABLE 13

| Measured Values | |
|---|---|
| Participants Analyzed<br>PK80-Area Under the Plasma Concentration/<br>Time Curve From Time 0<br>to 96 Hours (AUC0-96h/Dose) of VWF:RCo | PK80<br>Arm<br>15 |
| [Units (hours*U/dL)/(U VWF RCo/kg)]<br>Median (95% Confidence Interval) | |
| PK1 of rVWF [N = 15] | 35.6<br>(28.9 to 41.2) |
| PK2 of rVWF [N = 13] | 37.9<br>(25.9 to 41.8) |

No statistical analysis provided for PK80—Area Under the Plasma Concentration/Time Curve From Time 0 to 96 Hours (AUC0-96 h/Dose) of VWF:RCo Secondary Outcome Measures: Secondary Outcome #45

46. Secondary: PK80—Mean Residence Time of VWF: RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 138

| | Secondary Outcome #45 |
|---|---|
| Measure Type | Secondary |
| Measure Title | PK80-Mean Residence Time of VWF:RCo |
| Measure Description | Mean Residence Time (MRT) of von Willebrand Factor Ristocetin cofactor (VWF:RCo) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 139

| Reporting Groups | |
|---|---|
| Description | |
| PK80<br>Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 140

| Measured Values | |
|---|---|
| Participants Analyzed | PK80 Arm |
| PK80-Mean Residence Time of VWF:RCo | 15 |

| [Units: Hours] Median (95% Confidence Interval) | |
|---|---|
| PK1 of rVWF [N = 15] | 26.4 (20.9 to 31.1) |
| PK2 of rVWF [N = 13] | 26.4 (23.7 to 32.8) |

No statistical analysis provided for PK80—Mean Residence Time of VWF:RCo
Secondary Outcome Measures: Secondary Outcome #46

47. Secondary: PK80—Clearance of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 141

| Secondary Outcome #47 | |
|---|---|
| Measure Type | Secondary |
| Measure Title | PK80-Clearance of VWF:RCo |
| Measure Description | Clearance (CL) of von Willebrand Factor Ristocetin cofactor (VWF:RCo) after infusion of 80 IU/kg recombinant von Willebrand Factor: von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 142

| Reporting Groups | |
|---|---|
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 143

| Measured Values | |
|---|---|
| Participants Analyzed | PK80 Arm |
| PK80-Clearance of VWF:RCo | 15 |

| [Units: dL/kg/hours] Median (95% Confidence Interval) | |
|---|---|
| PK1 of rVWF [N = 15] | 0.027 (0.024 to 0.034) |
| PK2 of rVWF [N = 13] | 0.026 (0.023 to 0.036) |

No statistical analysis provided for PK80—Clearance of VWF:RCo

Secondary Outcome Measures: Secondary Outcome #47

48. Secondary: PK80—Incremental Recovery of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 144

| | Secondary Outcome #47 |
|---|---|
| Measure Type | Secondary |
| Measure Title | PK80-Incremental Recovery of VWF:RCo |
| Measure Description | Incremental Recovery (IR) at the maximum plasma concentration Area under the plasma concentration curve (AUC) from time 0 to infinity of von Willebrand Factor Ristocetin cofactor (VWF:RCo) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 145

| Reporting Groups | |
|---|---|
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 146

| Measured Values | |
|---|---|
| | PK80 Arm |
| Participants Analyzed | 15 |
| PK80-Incremental Recovery of VVVF:RCo [Units: (U/dL)/(U VWF: RCo/kg)] Median (95% Confidence Interval) | |
| PK1 of rVWF [N = 15] | 1.8 (1.7 to 2.2) |
| PK2 of rVWF [N = 13] | 1.8 (1.6 to 2.0) |

No statistical analysis provided for PK80—Incremental Recovery of VWF:RCo

Secondary Outcome Measures: Secondary Outcome #48

49. Secondary: PK80—Elimination Phase Half-Life of VWF:Co [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 147

| | Secondary Outcome #48 |
|---|---|
| Measure Type | Secondary |
| Measure Title | PK80-Elimination Phase Half-Life of VWF:Co |
| Measure Description | Elimination Phase Half-Life (T½) of von Willebrand Factor Ristocetin cofactor (VWF:RCo) after infusion of 80 IU/kg |

TABLE 147-continued

| | Secondary Outcome #48 |
|---|---|
| | recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 148

| Reporting Groups | |
|---|---|
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 149

| Measured Values | |
| --- | --- |
| | PK80 Arm |
| Participants Analyzed | 15 |
| PK80-Elimination Phase Half-Life of VWF:Co | |
| [Units: Hours] | |
| Median (95% Confidence Interval) | |
| PK1 of rVWF [N = 15] | 18.4 |
| | (16.4 to 22.1) |
| PK2 of rVWF [N = 13] | 19.8 |
| | (15.2 to 23.6) |

No statistical analysis provided for PK80—Elimination Phase Half-Life of VWF:Co

Secondary Outcome Measures: Secondary Outcome #49

50. Secondary: PK80—Volume of Distribution at Steady State of VWF:RCo [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 150

| Secondary Outcome #50 | |
| --- | --- |
| Measure Type | Secondary |
| Measure Title | PK80-Volume of Distribution at Steady State of VWF:RCo |
| Measure Description | Volume of Distribution at Steady State (Vss) of von Willebrand Factor Ristocetin cofactor (VWF:RCo) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 151

| Reporting Groups | |
| --- | --- |
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 152

| Measured Values | |
| --- | --- |
| | PK80 Arm |
| Participants Analyzed | 15 |
| PK80-Volume of Distribution at Steady State of VWF:RCo | |
| [Units: dL/kg] | |
| Median (95% Confidence Interval) | |
| PK1 of rVWF [N = 15] | 0.78 |
| | (0.58 to 0.86) |
| PK2 of rVWF [N = 13] | 0.75 |
| | (0.58 to 1.01) |

No statistical analysis provided for PK80—Volume of Distribution at Steady State of VWF:RCo Secondary Outcome Measures: Secondary Outcome #50

51. Secondary: PK80—Area Under the Plasma Concentration/Time Curve From Time 0 to Infinity (AUC0-∞/Dose) of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 153

| Secondary Outcome #50 | |
| --- | --- |
| Measure Type | Secondary |
| Measure Title | PK80-Area Under the Plasma Concentration/Time Curve From Time 0 to Infinity (AUC0-∞/Dose) of VWF:Ag |
| Measure Description | Area under the plasma concentration curve (AUC) from time 0 to infinity of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 154

| Reporting Groups | |
| --- | --- |
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 155

| Measured Values | |
| --- | --- |
| | PK80 Arm |
| Participants Analyzed | 15 |
| PK80-Area Under the Plasma Concentration/Time Curve From Time 0 to Infinity (AUC0-∞/Dose) of VVVF:Ag [Units: (hours*U/dL)/(U VWF: RCo/kg)] Median (95% Confidence Interval) | |
| PK1 of rVWF [N = 15] | 66.6 (50.4 to 89.4) |
| PK2 of rVWF [N = 13] | 86.9 (54.9 to 100.5) |

No statistical analysis provided for PK80—Area Under the Plasma Concentration/Time Curve From Time 0 to Infinity (AUC0-∞/Dose) of VWF:Ag Secondary Outcome Measures: Secondary Outcome #51

52. Secondary: PK80—Area Under the Plasma Concentration/Time Curve From Time 0 to 96 Hours (AUC0-96 h/Dose) of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 156

| Secondary Outcome #51 | |
| --- | --- |
| Measure Type | Secondary |
| Measure Title | PK80-Area Under the Plasma Concentration/Time Curve From Time 0 to 96 Hours (AUC0-96 h/Dose) of VWF:Ag |
| Measure Description | Area under the plasma concentration curve (AUC) from time 0 to 96 hours of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 157

| Reporting Groups | |
| --- | --- |
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 158

| Measured Values | |
| --- | --- |
| | PK80 Arm |
| Participants Analyzed | 15 |
| PK80-Area Under the Plasma Concentration/Time Curve From Time 0 to 96 Hours (AUC0-96 h/Dose) of VWF:Ag [Units: (hours*U/dL)/(U VWF: RCo/kg)] Median (95% Confidence Interval) | |
| PK1 of rVWF [N = 15] | 61.3 (48.8 to 73.7) |
| PK2 of rVWF [N = 13] | 77.4 (53.0 to 87.6) |

No statistical analysis provided for PK80—Area Under the Plasma Concentration/Time Curve From Time 0 to 96 Hours (AUC0-96 h/Dose) of VWF:Ag Secondary Outcome Measures: Secondary Outcome #52

53. Secondary: PK80—Mean Residence Time of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 159

| Secondary Outcome #52 | |
| --- | --- |
| Measure Type | Secondary |
| Measure Title | PK80-Mean Residence Time of VWF:Ag |
| Measure Description | Mean Residence Time (MRT) of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 160

| Reporting Groups | |
| --- | --- |
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 161

| Measured Values | |
|---|---|
| | PK80 Arm |
| Participants Analyzed | 15 |
| PK80-Mean Residence Time of VWF:Ag | |
| [Units: Hours] | |
| Median (95% Confidence Interval) | |
| PK1 of rVWF [N = 15] | 38.4 |
| | (31.9 to 48.1) |
| PK2 of rVWF [N = 13] | 36.9 |
| | (30.0 to 50.8) |

No statistical analysis provided for PK80—Mean Residence Time of VWF:Ag

Secondary Outcome Measures: Secondary Outcome #53

54. Secondary: PK80—Clearance of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 162

| Secondary Outcome #54 | |
|---|---|
| Measure Type | Secondary |
| Measure Title | PK80-Clearance of VWF:Ag |
| Measure Description | Clearance (CL) of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 163

| Reporting Groups | |
|---|---|
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 164

| Measured Values | |
|---|---|
| | PK80 Arm |
| Participants Analyzed | 15 |
| PK80-Clearance of VWF:Ag | |
| [Units: dL/kg/hours] | |
| Median (95% Confidence Interval) | |
| PK1 of rVWF [N = 15] | 0.015 |
| | (0.011 to 0.020) |
| PK2 of rVWF [N = 13] | 0.012 |
| | (0.010 to 0.018) |

No statistical analysis provided for PK80—Clearance of VWF:Ag

Secondary Outcome Measures: Secondary Outcome #54

55. Secondary: PK80—Incremental Recovery of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 165

| Secondary Outcome #54 | |
|---|---|
| Measure Type | Secondary |
| Measure Title | PK80-Incremental Recovery of VWF:Ag |
| Measure Description | Incremental Recovery (IR) at the maximum plasma concentration Area under the plasma concentration curve (AUC) from time 0 to infinity of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 166

| Reporting Groups | |
|---|---|
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 167

Measured Values

| | PK80 Arm |
|---|---|
| Participants Analyzed | 15 |
| PK80-Incremental Recovery of VVVF:Ag | |
| [Units: (U/dL)/(U VWF: RCo/kg)] | |
| Median (95% Confidence Interval) | |
| PK1 of rVWF [N = 15] | 2.2 |
| | (1.9 to 2.6) |
| PK2 of rVWF [N = 13] | 2.4 |
| | (2.0 to 2.9) |

No statistical analysis provided for PK80—Incremental Recovery of VWF:Ag

Secondary Outcome Measures: Secondary Outcome #55

56. Secondary: PK80—Elimination Phase Half-Life of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 168

Secondary Outcome #56

| | |
|---|---|
| Measure Type | Secondary |
| Measure Title | PK80-Elimination Phase Half-Life of VWF:Ag |
| Measure Description | Elimination Phase Half-Life (T½) of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 169

Reporting Groups

| | Description |
|---|---|
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 170

Measured Values

| | PK80 Arm |
|---|---|
| Participants Analyzed | 15 |
| PK80-Elimination Phase Half-Life of VWF:Ag | |
| [Units: Hours] | |
| Median (95% Confidence Interval) | |
| PK1 of rVWF [N = 15] | 27.5 |
| | (22.5 to 34.0) |
| PK2 of rVWF [N = 13] | 24.8 |
| | (21.1 to 37.7) |

No statistical analysis provided for PK80—Elimination Phase Half-Life of VWF:Ag

Secondary Outcome Measures: Secondary Outcome #56

57. Secondary: PK80—Volume of Distribution at Steady State of VWF:Ag [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 171

Secondary Outcome #57

| | |
|---|---|
| Measure Type | Secondary |
| Measure Title | PK80-Volume of Distribution at Steady State of VWF:Ag |
| Measure Description | Volume of Distribution at Steady State (Vss) of von Willebrand Factor Antigen (VWF:Ag) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 172

Reporting Groups

| | Description |
|---|---|
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 173

| Measured Values | |
|---|---|
| | PK80 Arm |
| Participants Analyzed | 15 |
| PK80-Volume of Distribution at Steady State of VWF:Ag [Units: dL/kg] Median (95% Confidence Interval) | |
| PK1 of rVWF [N = 15] | 0.55 (0.46 to 0.61) |
| PK2 of rVWF [N = 13] | 0.50 (0.41 to 0.57) |

No statistical analysis provided for PK80—Volume of Distribution at Steady State of VWF:Ag Secondary Outcome Measures: Secondary Outcome #57

58. Secondary: PK80—Area Under the Plasma Concentration/Time Curve From Time 0 to Infinity (AUC0-∞/Dose) of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 174

| Secondary Outcome #57 | |
|---|---|
| Measure Type | Secondary |
| Measure Title | PK80-Area Under the Plasma Concentration/ Time Curve From Time 0 to Infinity (AUC0-∞/Dose) of VWF:CB |
| Measure Description | Area under the plasma concentration curve (AUC) from time 0 to infinity of von Willebrand Factor Collagen Binding (VWF:CB) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 175

| Reporting Groups | |
|---|---|
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 176

| Measured Values | |
|---|---|
| | PK80 Arm |
| Participants Analyzed | 15 |
| PK80 - Area Under the Plasma Concentration/ Time Curve From Time 0 to Infinity (AUC0-∞/Dose) of VWF:CB [Units: (hours*U/dL)/(U VWF: RCo/kg)] Median (95% Confidence Interval) | |
| PK1 of rVWF [N = 15] | 73.9 (57.3 to 96.2) |
| PK2 of rVWF [N = 13] | 90.8 (66.0 to 105.2) |

No statistical analysis provided for PK80—Area Under the Plasma Concentration/Time Curve From Time 0 to Infinity (AUC0-∞/Dose) of VWF:CB Secondary Outcome Measures: Secondary Outcome #58

59. Secondary: PK80—Area Under the Plasma Concentration/Time Curve From Time 0 to 96 Hours (AUC0-96 h/Dose) of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 177

| Secondary Outcome #58 | |
|---|---|
| Measure Type | Secondary |
| Measure Title | PK80 - Area Under the Plasma Concentration/Time Curve From Time 0 to 96 Hours (AUC0-96 h/Dose) of VWF:CB |
| Measure Description | Area under the plasma concentration curve (AUC) from time 0 to 96 hours of von Willebrand Factor Collagen Binding (VWF:CB) after infusion of 80 IU/kg recombinant von Willebrand Factor:von Willebrand Factor Ristocetin cofactor (VWF:RCo rVWF) [rVWF] for participants in the PK80 arm (participatns from Arm 3 with PK80 data only). PK assessment conducted at first infusion of 80 IU/kg rWVF [PK1] and the second infusion [of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 178

| Reporting Groups | |
|---|---|
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 188

| Measured Values | |
| --- | --- |
| | PK80 Arm |
| Participants Analyzed | 15 |
| PK80 - Area Under the Plasma Concentration/Time Curve From Time 0 to 96 Hours (AUC0-96 h/Dose) of VWF:CB [Units: (hours*U/dL)/(U VWF: RCo/kg)] Median (95% Confidence Interval) | |
| PK1 of rVWF [N = 15] | 71.9 (57.0 to 89.8) |
| PK2 of rVWF [N = 13] | 88.1 (63.8 to 96.3) |

No statistical analysis provided for PK80—Area Under the Plasma Concentration/Time Curve From Time 0 to 96 Hours (AUC0-96 h/Dose) of VWF:CB Secondary Outcome Measures: Secondary Outcome #59

60. Secondary: PK80—Mean Residence Time of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 189

| Secondary Outcome #59 | |
| --- | --- |
| Measure Type | Secondary |
| Measure Title | PK80 - Mean Residence Time of VWF:CB |
| Measure Description | Mean Residence Time (MRT) of von Willebrand Factor Collagen Binding (VWF:CB) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number ofparticipants[N] who provided data for the category. PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |
| Time Frame | |

TABLE 190

| Reporting Groups | |
| --- | --- |
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 191

| Measured Values | |
| --- | --- |
| | PK80 Arm |
| Participants Analyzed | 15 |
| PK80 - Mean Residence Time of VWF:CB [Units: Hours] Median (95% Confidence Interval) | |
| PK1 of rVWF [N = 15] | 30.9 (24.3 to 35.0) |
| PK2 of rVWF [N = 13] | 28.7 (25.6 to 37.2) |

No statistical analysis provided for PK80—Mean Residence Time of VWF:CB

Secondary Outcome Measures: Secondary Outcome #60

61. Secondary: PK80—Clearance of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 192

| Secondary Outcome #60 | |
| --- | --- |
| Measure Type | Secondary |
| Measure Title | PK80 - Clearance of VWF:CB |
| Measure Description | Clearance (CL) of von Willebrand Factor Collagen Binding (VWF:CB) after infusion of 80 IU/kg recombinant von Willebrand Factor: von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 193

| Reporting Groups | |
| --- | --- |
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have provided data suitable for PK analysis. Only PK data included in this arm. |

TABLE 194

| Measured Values | |
| --- | --- |
| | PK80 Arm |
| Participants Analyzed | 15 |
| PK80 - Clearance of VWF:CB [Units: dL/kg/hours] | |

TABLE 194-continued

| Measured Values | |
|---|---|
| | PK80 Arm |
| Median (95% Confidence Interval) | |
| PK1 of rVWF [N = 15] | 0.014 |
| | (0.010 to 0.017) |
| PK2 of rVWF [N = 13] | 0.011 |
| | (0.010 to 0.015) |

No statistical analysis provided for PK80—Clearance of VWF:CB

Secondary Outcome Measures: Secondary Outcome #61

62. Secondary: PK80—Incremental Recovery of VWF: CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 195

| | Secondary Outcome #61 |
|---|---|
| Measure Type | Secondary |
| Measure Title | PK80 - Incremental Recovery of VWF:CB |
| Measure Description | Incremental Recovery (IR) at the maximum plasma concentration Area under the plasma concentration curve (AUC) from time 0 to infinity of von Willebrand Factor Collagen Binding (VWF:CB) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 196

| | Reporting Groups |
|---|---|
| | Description |
| PK80 Arm | Comprised of participants who underwent PK analysis of study product (80 IU/kg recombinant von Willebrand Factor [rVWF]) i.e. participants from Arm 3 [PK80 + Treatment]. Participants in this arm have received at least one PK infusion and have |

TABLE 196-continued

| | Reporting Groups |
|---|---|
| | Description |
| | provided data suitable for PK analysis. Only PK data included in this arm. |

TABLE 197

| Measured Values | |
|---|---|
| | PK80 Arm |
| Participants Analyzed | 15 |
| PK80 - Incremental Recovery of VWF:CB [Units: (U/dL)/(U VWF: RCo/kg)] Median (95% Confidence Interval) | |
| PK1 of rVWF [N = 15] | 3.1 |
| | (2.8 to 3.6) |
| PK2 of rVWF [N = 13] | 3.7 |
| | (2.7 to 4.0) |

No statistical analysis provided for PK80—Incremental Recovery of VWF:CB

Secondary Outcome Measures: Secondary Outcome #62

63. Secondary: PK80—Elimination Phase Half-Life of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 198

| | Secondary Outcome #62 |
|---|---|
| Measure Type | Secondary |
| Measure Title | PK80 - Elimination Phase Half-Life of VWF:CB |
| Measure Description | Elimination Phase Half-Life (T1/2) of von Willebrand Factor Collagen Binding (VWF:CB) after infusion of 80 recombinant von Willebrand Factor:von Willebrand Factor Ristocetin cofactor (VWF:RCo rVWF) [rVWF] for participants in the PK80 arm (participants from Arm 3 IU/kg with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 199

| | Reporting Groups |
|---|---|
| | Description |
| PK80 Arm | Comprised of participants who underwent PK analysis of study product (80 IU/kg recombinant von Willebrand Factor [rVWF]) i.e. participants from Arm 3 [PK80+ Treatment]. Participants in this arm have received at least one PK infusion and have provided data suitable for PK analysis. Only PK data included in this arm. |

TABLE 200

| Measured Values | |
| --- | --- |
| | PK80 Arm |
| Participants Analyzed | 15 |
| PK80 - Elimination Phase Half-Life of VWF:CB [Units: Hours] Median (95% Confidence Interval) | |
| PK1 of rVWF [N = 15] | 18.8 (16.6 to 24.9) |
| PK2 of rVWF [N = 13] | 20.9 (17.8 to 23.5) |

No statistical analysis provided for PK80—Elimination Phase Half-Life of VWF:CB

Secondary Outcome Measures: Secondary Outcome #63

64. Secondary: PK80—Volume of Distribution at Steady State of VWF:CB [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 201

| Secondary Outcome #63 | |
| --- | --- |
| Measure Type | Secondary |
| Measure Title | PK80 - Volume of Distribution at Steady State of VWF:CB |
| Measure Description | Volume of Distribution at Steady State (Vss) of von Willebrand Factor Collagen Binding (VWF:CB) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 202

| Reporting Groups | |
| --- | --- |
| | Description |
| PK80 Arm | Comprised of participants who underwent PK analysis of study product (80 IU/kg recombinant von Willebrand Factor [rVWF]) i.e. participants from Arm 3 [PK80+ Treatment]. Participants in this arm have received at least one PK infusion and have provided data suitable for PK analysis. Only PK data included in this arm. |

TABLE 203

| Measured Values | |
| --- | --- |
| | PK80 Arm |
| Participants Analyzed | 15 |
| PK80 - Volume of Distribution at Steady State of VWF:CB [Units: dL/kg] Median (95% Confidence Interval) | |
| PK1 of rVWF [N = 15] | 0.39 (0.34 to 0.46) |
| PK2 of rVWF [N = 13] | 0.36 (0.33 to 0.40) |

No statistical analysis provided for PK80—Volume of Distribution at Steady State of VWF:CB Secondary Outcome Measures: Secondary Outcome #64

65. Secondary: PK80—Area Under the Plasma Concentration/Time Curve From Time 0 to Infinity (AUC0-∞/Dose) of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 204

| Secondary Outcome #65 | |
|---|---|
| Measure Type | Secondary |
| Measure Title | PK80 - Area Under the Plasma Concentration/Time Curve From Time 0 to Infinity (AUC0-∞/Dose) of FVIII:C |
| Measure Description | Area under the plasma concentration curve (AUC) from time 0 to infinity of Factor VIII activity (FVIII:C) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 205

| Reporting Groups | |
|---|---|
| | Description |
| PK80 Arm | Comprised of participants who underwent PK analysis of study product (80 IU/kg recombinant von Willebrand Factor [rVWF]) i.e. participants from Arm 3 [PK80+ Treatment]. Participants in this arm have received at least one PK infusion and have provided data suitable for PK analysis. Only PK data included in this arm. |

TABLE 206

| Measured Values | |
|---|---|
| | PK80 Arm |
| Participants Analyzed | 15 |
| PK80 - Area Under the Plasma Concentration/Time Curve From Time 0 to Infinity (AUC0-∞/Dose) of FVIII:C [Units: (hours * U/dL)/(U VWF: RCo/kg)] Median (95% Confidence Interval) | |
| PK1 of rVWF [N = 15] | 96.8 (64.0 to 126.5) |
| PK2 of rVWF [N = 13] | 94.8 (60.4 to 106.5) |

No statistical analysis provided for PK80—Area Under the Plasma Concentration/Time Curve From Time 0 to Infinity (AUC0-∞/Dose) of FVIII:C Secondary Outcome Measures: Secondary Outcome #65

66. Secondary: PK80—Area Under the Plasma Concentration/Time Curve From Time 0 to 96 Hours (AUC0-96 h/Dose) of FVIII:C [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 207

Secondary Outcomes #65

| | |
|---|---|
| Measure Type | Secondary |
| Measure Title | PK80 - Area Under the Plasma Concentration/Time Curve From Time 0 to 96 Hours (AUC0-96h/Dose) of FVIII:C |
| Measure Description | Area under the plasma concentration curve (AUC) from time 0 to 96 hours of Factor VIII activity (FVIII:C) after infusion of 80 IU/kg recombinant von Willebrand Factor:von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. Category title includes number of participants [N] who provided data for the category. |
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 208

Reporting Groups

| | Description |
|---|---|
| PK80 Arm | Comprised of participants who underwent PK analysis of study product (80 IU/kg recombinant von Willebrand Factor [rVWF]) i.e. participants from Arm 3 [PK80+ Treatment]. Participants in this arm have received at least one PK infusion and have provided data suitable for PK analysis. Only PK data included in this arm. |

TABLE 209

Measured Values

| | PK80 Arm |
|---|---|
| Participants Analyzed | 15 |
| PK80 - Area Under the Plasma Concentration/Time Curve From Time 0 to 96 Hours (AUC0-96h/Dose) of FVIII:C [Units: (hours * U/dL)/(U VWF: RCo/kg)] Median (95% Confidence Interval) | |
| PK1 of rVWF [N = 15] | 81.7 (54.7 to 104.3) |
| PK2 of rVWF [N = 13] | 71.8 (49.6 to 89.2) |

No statistical analysis provided for PK80—Area Under the Plasma Concentration/Time Curve From Time 0 to 96 Hours (AUC0-96 h/Dose) of FVIII:C Secondary Outcome Measures: Secondary Outcome #66

67. Secondary: PK80—Ratio of Intra-participant PK of VWF:RCo, VWF:Ag and VWF:CB at Baseline and After 6 Months [Time Frame: PK evaluations at pre-infusion, then at 15, 30 and 60 mins, and 3, 6, 12, 24, 30, 48, 72 and 96 hrs post-infusion. PK evaluation timeframe for 28±3 days after first infusion of study product which includes PK evaluation for both infusions and washout.]

TABLE 210

Secondary Outcome #66

| | |
|---|---|
| Measure Type | Secondary |
| Measure Title | PK80- Ratio of Intra-participant PK of VWF:RCo, VWF:Ag and VWF:CB at Baseline and After 6 Months |
| Measure Description | Area under the plasma concentration curve (AUC) from time 0 to infinity per dose (AUC0-∞/dose) for von Willebrand Factor Ristocetin cofactor (VWF:RCo), von Willebrand Factor Antigen (VWF:Ag) and von Willebrand Factor Collagen Binding (VWF:CB). Each parameter was compared between the two PK assessments after infusion of 80 IU/kg recombinant von Willebrand Factor: von Willebrand Factor Ristocetin cofactor (VWF:RCo rVWF) [rVWF] for participants in the PK80 arm (participants from Arm 3 with PK80 data only). PK assessment conducted at first infusion of 80 IU/kg rWVF [PK1] and the second infusion of 80 IU/kg rVWF after participants were treated on demand for bleeding episodes for at least 6 months since their first infusion of study product [PK2]. 13 participants had data available for this endpoint i.e. data for PK1 and PK2. |

TABLE 210-continued

Secondary Outcome #66

| Measure Type | Secondary |
|---|---|
| Time Frame | PK evaluations at pre-infusion, then at 15, 30 and 60 mins, and 3, 6, 12, 24, 30, 48, 72 and 96 hrs post-infusion. PK evaluation timeframe for 28 ± 3 days after first infusion of study product which includes PK evaluation for both infusions and washout. |

TABLE 211

Population Description

Participants from the PK80 Arm who had pharmacokinetic (PK) data available after both the first infusion of 80 IU/kg recombinant von Willebrand Factor:von Willebrand Factor Ristocetin cofactor (VWF:RCo rVWF) [rVWF] [PK1] and the second infusion of 80 IU/kg rVW [PK2].

TABLE 212

Reporting Groups

| | Description |
|---|---|
| PK80 Arm | Comprised of participants who underwent PK analysis of study product (80 IU/kg recombinant von Willebrand Factor [rVWF]) i.e. participants from Arm 3 [PK80+ Treatment]. Participants in this arm have received at least one PK infusion and have provided data suitable for PK analysis. Only PK data included in this arm. |

TABLE 213

Measured Values

| | PK80 Arm |
|---|---|
| Participants Analyzed | 13 |
| PK80- Ratio of Intra-participant PK of VWF:RCo, VWF:Ag and VWF:CB at Baseline and After 6 Months [Units Ratio of AUC0-∞/dose] Geometric Mean (90% Confidence Interval) | |
| AUC0-∞/dose - VWF:RCo | 0.9587 (0.8466 to 1.0857) |
| AUC0-∞/dose - VWF:Ag | 1.0914 (1.0132 to 1.1757) |
| AUC0-∞/dose - VWF:CB | 1.0666 (1.0004 to 1.1372) |

No statistical analysis provided for PK80—Ratio of Intra-participant PK of VWF:RCo, VWF:Ag and VWF:CB at Baseline and After 6 Months The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method for treating mild or moderate gastrointestinal bleeding in a subject with severe von Willebrand Disease (VWD) comprising administering to the subject at least one dose of recombinant von Willebrand Factor (rVWF) each ranging from about 40 IU/kg to about 60 IU/kg, wherein the first dose further comprises recombinant Factor VIII (rFVIII) ranging from about 20 to about 50 IU/kg.

2. The method of treatment of claim 1, wherein the second dose of rVWF does not comprise rFVIII.

3. The method of treatment of claim 1, wherein said rVWF is administered every 8 to 12 hours.

4. The method of claim 1, wherein the subject is administered one dose of rVWF.

5. The method of treatment of claim 1, wherein said subject has Type 3 VWD.

6. The method of treatment of claim 1, wherein said subject has severe Type 1 VWD.

7. The method of treatment of claim 1, wherein said subject has severe Type 2 VWD.

8. The method of claim 1, wherein the subject had been treated for at least 1 bleeding event within the previous 12 months.

9. The method of claim 1, wherein the subject had been treated for more than 1 bleeding event within the previous 12 months.

10. The method of treatment of claim 1, wherein said rVWF and said rFVIII are administered sequentially.

11. A method for treating major or severe gastrointestinal bleeding in a subject with severe von Willebrand Disease (VWD) comprising administering to the subject at least one dose of recombinant von Willebrand Factor (rVWF) each ranging from up to about 80 IU/kg, wherein the first dose further comprises recombinant Factor VIII (rFVIII) ranging from about 20 to about 40 IU/kg.

12. The method of treatment of claim 11, wherein the second dose of rVWF does not comprise rFVIII.

13. The method of treatment of claim 11, wherein said rVWF is administered every 8 to 12 hours.

14. The method of claim 11, wherein the subject is administered a single dose of rVWF.

15. The method of treatment of claim 11, wherein said subject has Type 3 VWD.

16. The method of treatment of claim 11, wherein said subject has severe Type 1 VWD.

17. The method of treatment of claim 11, wherein said subject has severe Type 2 VWD.

18. The method of claim 11, wherein the subject had been treated for at least 1 bleeding event within the previous 12 months.

19. The method of claim 11, wherein the subject had been treated for more than 1 bleeding event within the previous 12 months.

20. The method of treatment of claim 11, wherein said rVWF and said rFVIII are administered sequentially.

* * * * *

SEQUENCE LISTING

<160> NUMBER OF SEQ ID NOS: 4

<210> SEQ ID NO 1
<211> LENGTH: 8833
<212> TYPE: DNA

<213> ORGANISM: Artificial Sequence
<220> FEATURE:
<223> OTHER INFORMATION: Synthetic prepro-VWF

<400> SEQUENCE: 1

```
agctcacagc tattgtggtg ggaaagggag ggtggttggt ggatgtcaca gcttgggctt    60
tatctccccc agcagtgggg actccacagc ccctgggcta cataacagca agacagtccg   120
gagctgtagc agacctgatt gagcctttgc agcagctgag agcatggcct agggtgggcg   180
gcaccattgt ccagcagctg agtttcccag ggaccttgga gatagccgca gccctcattt   240
gcagggggaag atgattcctg ccagatttgc cggggtgctg cttgctctgg ccctcatttt   300
gccagggacc ctttgtgcag aaggaactcg cggcaggtca tccacggccc gatgcagcct   360
tttcggaagt gacttcgtca acacctttga tgggagcatg tacagctttg cgggatactg   420
cagttacctc ctggcagggg gctgccagaa acgctccttc tcgattattg gggacttcca   480
gaatggcaag agagtgagcc tctccgtgta tcttggggaa tttttttgaca tccatttgtt   540
tgtcaatggt accgtgacac aggggggacca aagagtctcc atgccctatg cctccaaagg   600
gctgtatcta gaaactgagg ctgggtacta caagctgtcc ggtgaggcct atggctttgt   660
ggccaggatc gatggcagcg gcaactttca gtcctgctgt cagacagat acttcaacaa   720
gacctgcggg ctgtgtggca actttaacat cttttgctgaa gatgacttta tgacccaaga   780
agggacccttg acctcggacc cttatgactt tgccaactca tgggctctga gcagtggaga   840
acagtggtgt gaacgggcat ctcctcccag cagctcatgc aacatctcct ctggggaaat   900
gcagaagggc ctgtgggagc agtgccagct tctgaagagc acctcggtgt ttgcccgctg   960
ccacccctctg gtggaccccg agccttttgt ggccctgtgt gagaagactt tgtgtgagtg  1020
tgctgggggg ctggagtgcg cctgccctgc cctcctggag tacgcccgga cctgtgccca  1080
ggagggaatg gtgctgtacg gctggaccga ccacagcgcg tgcagcccag tgtgccctgc  1140
tggtatggag tataggcagt gtgtgtcccc ttgcgccagg acctgccaga gcctgcacat  1200
caatgaaatg tgtcaggagc gatgcgtgga tggctgcagc tgccctgagg acagctcct   1260
ggatgaaggc ctctgcgtgg agagcaccga gtgtcctgc gtgcattccg aaagcgcta   1320
ccctcccggc acctccctct ctcgagactg caacacctgc atttgccgaa acagccagtg  1380
gatctgcagc aatgaagaat gtccagggga gtgcctttgc acaggtcaat cacacttcaa  1440
gagctttgac aacagatact tcaccttcag tgggatctgc cagtacctgc tggcccggga  1500
ttgccagggac cactccttct ccattgtcat tgagactgtc cagtgtgctg atgaccgcga  1560
cgctgtgtgc acccgctccg tcaccgtccg gctgcctggc ctgcacaaca gccttgtgaa  1620
actgaagcat ggggcaggag ttgccatgga tggccaggac gtccagctcc cctcctgaa   1680
aggtgacctc cgcatccagc atacagtgac ggcctccgtg cgcctcagct acgggggagga  1740
cctgcagatg gactgggatg gccgcggag gctgctggtg aagctgtccc ccgtctatgc  1800
cgggaagacc tgcggcctgt gtgggaatta caatggcaac cagggcgacg acttccttac  1860
ccctctgggg ctggcggagc ccgggtgga ggacttcggg aacgctggaa gctgcacgg   1920
ggactgccag gacctgcaga agcagcacag cgatccctgc gccctcaacc cgcgcatgac  1980
caggttctcc gaggaggcgt gcgcggtcct gacgtccccc acattcgagg cctgccatcg  2040
tgccgtcagc ccgctgccct acctgcggaa ctgccgctac gacgtgtgct cctgctcgga  2100
cggccgcgag tgcctgtgcg gcgccctggc cagctatgcc gcggcctgcg cggggagagg  2160
cgtgcgcgtc gcgtggcgcg agccaggccg ctgtgagctg aactgcccga aaggccaggt  2220
```

-continued

```
gtacctgcag tgcgggaccc cctgcaacct gacctgccgc tctctctctt acccggatga      2280
ggaatgcaat gaggcctgcc tggagggctg cttctgcccc ccagggctct acatggatga      2340 gagggggggac tgcgtgccca aggcccagtg ccctgttac tatgacggtg agatcttcca      2400
gccagaagac atcttctcag accatcacac catgtgctac tgtgaggatg gcttcatgca      2460
ctgtaccatg agtggagtcc ccggaagctt gctgcctgac gctgtcctca gcagtcccct      2520
gtctcatcgc agcaaaagga gcctatcctg tcggcccccc atggtcaagc tggtgtgtcc      2580
cgctgacaac ctgcgggctg aagggctcga gtgtaccaaa acgtgccaga actatgacct      2640
ggagtgcatg agcatgggct gtgtctctgg ctgcctctgc cccccgggca tggtccggca      2700
tgagaacaga tgtgtggccc tggaaaggtg tccctgcttc catcagggca aggagtatgc      2760
ccctggagaa acagtgaaga ttggctgcaa cacttgtgtc tgtcgggacc ggaagtggaa      2820
ctgcacagac catgtgtgtg atgccacgtg ctccacgatc ggcatggccc actacctcac      2880
cttcgacggg ctcaaatacc tgttccccgg ggagtgccag tacgttctgg tgcaggatta      2940
ctgcggcagt aaccctggga cctttcggat cctagtgggg aataagggat gcagccaccc      3000
ctcagtgaaa tgcaagaaac gggtcaccat cctggtggag ggaggagaga ttgagctgtt      3060
tgacggggag gtgaatgtga agaggcccat gaaggatgag actcactttg aggtggtgga      3120
gtctggccgg tacatcattc tgctgctggg caaagccctc tccgtggtct gggaccgcca      3180
cctgagcatc tccgtggtcc tgaagcagac ataccaggag aaagtgtgtg gcctgtgtgg      3240
gaattttgat ggcatccaga caatgacct caccagcagc aacctccaag tggaggaaga      3300
ccctgtggac tttgggaact cctggaaagt gagctcgcag tgtgctgaca ccagaaaagt      3360
gcctctggac tcatcccctg ccacctgcca taacaacatc atgaagcaga cgatggtgga      3420
ttcctcctgt agaatcctta ccagtgacgt cttccaggac tgcaacaagc tggtggaccc      3480
cgagccatat ctggatgtct gcatttacga cacctgctcc tgtgagtcca ttggggactg      3540
cgcctgcttc tgcgacacca ttgctgccta tgcccacgtg tgtgcccagc atggcaaggt      3600
ggtgacctgg aggacggcca cattgtgccc ccagagctgc gaggagagga atctccggga      3660
gaacgggtat gagtgtgagt ggcgctataa cagctgtgca cctgcctgtc aagtcacgtg      3720
tcagcaccct gagccactgg cctgccctgt gcagtgtgtg gagggctgcc atgcccactg      3780
ccctccaggg aaaatcctgg atgagctttt gcagacctgc gttgaccctg aagactgtcc      3840
agtgtgtgag gtggctggcc ggcgttttgc ctcaggaaag aaagtcacct tgaatcccag      3900
tgaccctgag cactgccaga tttgccactg tgatgttgtc aacctcacct gtgaagcctg      3960
ccaggagccg ggaggcctgg tggtgcctcc cacagatgcc ccggtgagcc ccaccactct      4020
gtatgtggag gacatctcgg aaccgccgtt gcacgatttc tactgcagca ggctactgga      4080
cctggtcttc ctgctggatg gctcctccag gctgtccgag gctgagtttg aagtgctgaa      4140
ggcctttgtg gtggacatga tggagcggct gcgcatctcc cagaagtggg tccgcgtggc      4200
cgtggtggag taccacgacg gctcccacgc ctacatcggg ctcaaggacc ggaagcgacc      4260
gtcagagctg cggcgcattg ccagccaggt gaagtatgcg ggcagccagg tggcctccac      4320
cagcgaggtc ttgaaataca cactgttcca aatcttcagc aagatcgacc gccctgaagc      4380
ctcccgcatc accctgctcc tgatggccag ccaggagccc caacggatgt cccggaactt      4440
tgtccgctac gtccagggcc tgaagaagaa gaaggtcatt gtgatcccgg tgggcattgg      4500
gccccatgcc aacctcaagc agatccgcct catcgagaag caggcccctg agaacaaggc      4560
```

```
cttcgtgctg agcagtgtgg atgagctgga gcagcaaagg gacgagatcg ttagctacct    4620
ctgtgacctt gccctgaag ccctcctcc tactctgccc cccgacatgg cacaagtcac     4680
tgtgggcccg gggctcttgg gggtttcgac cctggggccc aagaggaact ccatggttct   4740
ggatgtggcg ttcgtcctgg aaggatcgga caaaattggt gaagccgact tcaacaggag   4800
caaggagttc atggaggagg tgattcagcg gatggatgtg ggccaggaca gcatccacgt   4860
cacggtgctg cagtactcct acatggtgac tgtggagtac cccttcagcg aggcacagtc   4920
caaaggggac atcctgcagc gggtgcgaga gatccgctac cagggcggca acaggaccaa   4980
cactgggctg gccctgcggt acctctctga ccacagcttc ttggtcagcc agggtgaccg   5040
ggagcaggcg cccaacctgg tctacatggt caccggaaat cctgcctctg atgagatcaa   5100
gaggctgcct ggagacatcc aggtggtgcc cattggagtg ggccctaatg ccaacgtgca   5160
ggagctggag aggattggct ggcccaatgc ccctatcctc atccaggact ttgagacgct   5220
cccccgagag gctcctgacc tggtgctgca gaggtgctgc tccggagagg ggctgcagat   5280
ccccacctc tccctgcac ctgactgcag ccagcccctg gacgtgatcc ttctcctgga    5340
tggctcctcc agtttcccag cttcttattt tgatgaaatg aagagtttcg ccaaggcttt   5400
catttcaaaa gccaatatag ggcctcgtct cactcaggtg tcagtgctgc agtatggaag   5460
catcaccacc attgacgtgc catggaacgt ggtcccggag aaagcccatt tgctgagcct   5520
tgtggacgtc atgcagcggg agggaggccc cagccaaatc ggggatgcct gggctttgc    5580
tgtgcgatac ttgacttcag aaatgcatgg tgccaggccg ggagcctcaa aggcggtggt   5640
catcctggtc acggacgtct ctgtggattc agtggatgca gcagctgatg ccgccaggtc   5700
caacagagtg acagtgttcc ctattggaat tggagatcgc tacgatgcag cccagctacg   5760
gatcttggca ggcccagcag gcgactccaa cgtggtgaag ctccagcgaa tcgaagacct   5820
ccctaccatg gtcaccttgg gcaattcctt cctccacaaa ctgtgctctg gatttgttag   5880
gatttgcatg gatgaggatg ggaatgagaa gaggcccggg gacgtctgga ccttgccaga   5940
ccagtgccac accgtgactt gccagccaga tggccagacc ttgctgaaga gtcatcgggt   6000
caactgtgac cggggggctga ggccttcgtg ccctaacagc cagtcccctg ttaaagtgga   6060
agagacctgt ggctgccgct ggacctgccc ctgcgtgtgc acaggcagct ccactcggca   6120
catcgtgacc tttgatgggc agaatttcaa gctgactggc agctgttctt atgtcctatt   6180
tcaaaacaag gagcaggacc tggaggtgat tctccataat ggtgcctgca gccctggagc   6240
aaggcagggc tgcatgaaat ccatcgaggt gaagcacagt gccctctccg tcgagctgca   6300
cagtgacatg gaggtgacgg tgaatgggag actggtctct gttccttacg tgggtgggaa   6360
catggaagtc aacgttttatg gtgccatcat gcatgaggtc agattcaatc accttggtca   6420
catcttcaca ttcactccac aaaacaatga gttccaactg cagctcagcc ccaagacttt   6480
tgcttcaaag acgtatggtc tgtgtgggat ctgtgatgag aacggagcca atgacttcat   6540
gctgagggat ggcacagtca ccacagactg gaaaacactt gttcaggaat ggactgtgca   6600
gcggccaggg cagacgtgcc agcccatcct ggaggagcag tgtcttgtcc ccgacagctc   6660
ccactgccag gtcctcctct taccactgtt tgctgaatgc cacaaggtcc tggctccagc   6720
cacattctat gccatctgcc agcaggacag ttgccaccag gagcaagtgt gtgaggtgat   6780
cgcctcttat gcccacctct gtcggaccaa cggggtctgc gttgactgga ggacacctga   6840
tttctgtgct atgtcatgcc caccatctct ggtctacaac cactgtgagc atggctgtcc   6900
ccggcactgt gatggcaacg tgagctcctg tggggaccat ccctccgaag gctgtttctg   6960
```

```
cccctccagat aaagtcatgt tggaaggcag ctgtgtccct gaagaggcct gcactcagtg    7020
cattggtgag gatggagtcc agcaccagtt cctggaagcc tgggtcccgg accaccagcc    7080
ctgtcagatc tgcacatgcc tcagcgggcg aaggtcaac tgcacaacgc agccctgccc     7140
cacggccaaa gctcccacgt gtggcctgtg tgaagtagcc cgcctccgcc agaatgcaga    7200
ccagtgctgc cccgagtatg agtgtgtgtg tgacccagtg agctgtgacc tgccccccagt   7260 gcctcactgt gaacgtggcc tccagcccac actgaccaac cctggcgagt gcagacccaa    7320
cttcacctgc gcctgcagga aggaggagtg caaaagagtg tccccaccct cctgcccccc    7380
gcaccgtttg cccacccttc ggaagaccca gtgctgtgat gagtatgagt gtgcctgcaa    7440
ctgtgtcaac tccacagtga gctgtcccct gggtacttg gcctcaactg ccaccaatga     7500
ctgtggctgt accacaacca cctgccttcc cgacaaggtg tgtgtccacc gaagcaccat    7560
ctaccctgtg ggccagttct ggaggaggg ctgcgatgtg tgcacctgca ccgacatgga     7620
ggatgccgtg atgggcctcc gcgtggccca gtgctcccag aagccctgtg aggacagctg    7680
tcggtcgggc ttcacttacg ttctgcatga aggcgagtgc tgtggaaggt gcctgccatc    7740
tgcctgtgag gtggtgactg gctcaccgcg ggggactcc cagtcttcct ggaagagtgt     7800
cggctcccag tgggcctccc cggagaaccc ctgcctcatc aatgagtgtg tccgagtgaa    7860
ggaggaggtc tttatacaac aaaggaacgt ctcctgcccc cagctggagg tccctgtctg    7920
cccctcgggc tttcagctga gctgtaagac ctcagcgtgc tgcccaagct gtcgctgtga    7980
gcgcatggag gcctgcatgc tcaatggcac tgtcattggg cccgggaaga ctgtgatgat    8040
cgatgtgtgc acgacctgcc gctgcatggt gcaggtgggg gtcatctctg gattcaagct    8100
ggagtgcagg aagaccacct gcaaccctg ccccctgggt acaaggaag aaaataacac      8160 aggtgaatgt tgtgggagat gtttgcctac ggcttgcacc attcagctaa gaggaggaca    8220
gatcatgaca ctgaagcgtg atgagacgct ccaggatggc tgtgatactc acttctgcaa    8280
ggtcaatgag agaggagagt acttctggga agaggggtc acaggctgcc cacccttga     8340 tgaacacaag tgtctggctg agggaggtaa aattatgaaa attccaggca cctgctgtga    8400
cacatgtgag gagcctgagt gcaacgacat cactgccagg ctgcagtatg tcaaggtggg    8460
aagctgtaag tctgaagtag aggtggatat ccactactgc caggggcaaat gtgccagcaa   8520 agccatgtac tccattgaca tcaacgatgt gcaggaccag tgctcctgct gctccgac     8580 acggacggag cccatgcagg tggccctgca ctgcaccaat ggctctgttg tgtaccatga    8640
ggttctcaat gccatggagt gcaaatgctc ccccaggaag tgcagcaagt gaggctgctg    8700
cagctgcatg ggtgcctgct gctgcctgcc ttggcctgat ggccaggcca gagtgctgcc    8760
agtcctctgc atgttctgct cttgtgccct tctgagccca caataaaggc tgagctctta    8820
tcttgcaaaa ggc                                                       8833
```

<210> SEQ ID NO 2
<211> LENGTH: 2783
<212> TYPE: PRT
<213> ORGANISM: Artificial Sequence
<220> FEATURE:
<223> OTHER INFORMATION: Synthetic prepro-VWF

<400> SEQUENCE: 2

```
Met Ile Pro Ala Arg Phe Ala Gly Val Leu Leu Leu Ile Leu Pro Gly
1               5                   10                  15

Thr Leu Cys Ala Glu Gly Thr Arg Gly Arg Ser Ser Thr Ala Arg Cys
```

```
            20                  25                  30
Ser Leu Phe Gly Ser Asp Phe Val Asn Thr Phe Asp Gly Ser Met Tyr
        35                  40                  45

Ser Phe Ala Gly Tyr Cys Ser Tyr Leu Leu Ala Gly Gly Cys Gln Lys
        50                  55                  60

Arg Ser Phe Ser Ile Ile Gly Asp Phe Gln Asn Gly Lys Arg Val Ser
 65                  70                  75                  80

Leu Ser Val Tyr Leu Gly Glu Phe Phe Asp Ile His Leu Phe Val Asn
                85                  90                  95

Gly Thr Val Thr Gln Gly Asp Gln Arg Val Ser Met Pro Tyr Ala Ser
               100                 105                 110

Lys Leu Glu Thr Glu Ala Gly Tyr Tyr Lys Leu Ser Gly Glu Ala Tyr
               115                 120                 125

Gly Phe Val Ala Arg Ile Asp Gly Ser Gly Asn Phe Gln Val Leu Leu
               130                 135                 140

Ser Asp Arg Tyr Phe Asn Lys Thr Cys Gly Leu Cys Gly Asn Phe Asn
145                 150                 155                 160

Ile Phe Ala Glu Asp Asp Phe Met Thr Gln Glu Gly Thr Leu Thr Ser
               165                 170                 175

Asp Pro Tyr Asp Phe Ala Asn Ser Trp Ala Leu Ser Ser Gly Glu Gln
               180                 185                 190

Trp Cys Glu Arg Pro Ser Ser Cys Asn Ile Ser Ser Gly Glu Met
               195                 200                 205

Gln Lys Gly Leu Trp Glu Gln Cys Gln Leu Leu Lys Ser Thr Ser Val
               210                 215                 220

Phe Ala Arg Cys His Pro Leu Val Asp Pro Glu Pro Phe Cys Glu Lys
225                 230                 235                 240

Thr Leu Cys Glu Cys Ala Gly Gly Leu Glu Cys Ala Cys Pro Ala Leu
               245                 250                 255

Leu Glu Tyr Ala Arg Thr Cys Ala Gln Glu Gly Met Val Leu Tyr Gly
               260                 265                 270

Trp Thr Asp His Ser Ala Cys Ser Pro Val Cys Pro Ala Gly Met Glu
               275                 280                 285

Tyr Arg Gln Cys Val Ser Pro Cys Ala Arg Thr Cys Gln Ser Leu His
               290                 295                 300

Ile Asn Glu Met Cys Gln Glu Arg Cys Val Asp Gly Cys Ser Cys Pro
305                 310                 315                 320

Glu Gly Gln Leu Leu Asp Glu Gly Leu Cys Val Glu Ser Thr Glu Cys
               325                 330                 335

Pro Cys Val His Ser Gly Lys Arg Tyr Pro Pro Gly Thr Ser Leu Ser
               340                 345                 350

Arg Asp Cys Asn Thr Cys Ile Cys Arg Asn Ser Gln Trp Ile Cys Ser
               355                 360                 365

Asn Glu Glu Cys Pro Gly Glu Cys Leu Val Thr Gly Gln Ser His Phe
               370                 375                 380

Lys Ser Phe Asp Asn Arg Tyr Phe Thr Phe Ser Gly Ile Cys Gln Tyr
385                 390                 395                 400

Leu Leu Ala Arg Asp Cys Gln Asp His Ser Phe Ser Ile Val Ile Glu
               405                 410                 415

Thr Val Gln Cys Ala Asp Asp Arg Asp Ala Val Cys Thr Arg Ser Val
               420                 425                 430

Thr Val Arg Leu Pro Gly Leu His Asn Ser Leu Val Lys Leu Lys His
               435                 440                 445
```

```
Gly Ala Gly Val Ala Met Asp Gly Gln Asp Val Gln Leu Pro Leu Leu
            450                 455                 460

Lys Gly Asp Leu Arg Ile Gln His Thr Val Thr Ala Ser Val Arg Leu
465                 470                 475                 480

Ser Tyr Gly Glu Asp Leu Gln Met Asp Trp Asp Gly Arg Gly Arg Leu
                485                 490                 495

Leu Val Lys Leu Ser Pro Val Tyr Ala Gly Lys Thr Cys Gly Leu Cys
                500                 505                 510

Gly Asn Tyr Asn Gly Asn Gln Gly Asp Asp Phe Leu Thr Pro Ser Gly
            515                 520                 525

Leu Ala Glu Pro Arg Val Glu Asp Phe Gly Asn Ala Trp Lys Leu His
530                 535                 540

Gly Asp Cys Gln Asp Leu Gln Lys Gln His Ser Asp Pro Cys Ala Leu
545                 550                 555                 560

Asn Pro Arg Met Thr Arg Phe Ser Glu Glu Ala Cys Ala Val Leu Thr
                565                 570                 575

Ser Pro Thr Phe Glu Ala Cys His Arg Ala Val Ser Pro Leu Pro Tyr
                580                 585                 590

Leu Arg Asn Cys Arg Tyr Asp Val Cys Ser Cys Ser Asp Gly Arg Glu
            595                 600                 605

Cys Leu Cys Gly Ser Tyr Ala Ala Ala Cys Ala Gly Arg Gly Val Arg
        610                 615                 620

Val Ala Trp Arg Glu Pro Gly Arg Cys Glu Leu Asn Cys Pro Lys Gly
625                 630                 635                 640

Gln Val Tyr Leu Gln Cys Gly Thr Pro Cys Asn Leu Thr Cys Arg Ser
                645                 650                 655

Leu Ser Tyr Pro Asp Glu Glu Cys Asn Glu Ala Cys Leu Glu Gly Cys
                660                 665                 670

Phe Cys Pro Pro Met Asp Glu Arg Gly Asp Cys Val Pro Lys Ala Gln
        675                 680                 685

Cys Pro Cys Tyr Tyr Asp Gly Glu Ile Phe Gln Pro Glu Asp Ile Phe
        690                 695                 700

Ser Asp His His Thr Met Cys Tyr Cys Glu Asp Gly Phe Met His Cys
705                 710                 715                 720

Thr Met Ser Gly Val Pro Gly Ser Leu Leu Pro Asp Ala Val Leu Ser
                725                 730                 735

Ser Pro Leu Ser His Arg Ser Lys Arg Ser Leu Ser Cys Arg Pro Pro
                740                 745                 750

Met Val Lys Leu Val Cys Pro Ala Asp Asn Leu Arg Ala Glu Gly Leu
        755                 760                 765

Glu Cys Thr Lys Thr Cys Gln Asn Tyr Asp Leu Glu Cys Met Ser Met
770                 775                 780

Gly Cys Val Ser Gly Cys Leu Cys Pro Pro Gly Met Val Arg His Glu
785                 790                 795                 800

Asn Arg Cys Glu Arg Cys Pro Cys Phe His Gln Gly Lys Glu Tyr Ala
                805                 810                 815

Pro Gly Glu Thr Val Lys Ile Gly Cys Asn Thr Cys Val Cys Arg Asp
                820                 825                 830

Arg Lys Trp Asn Cys Thr Asp His Val Cys Asp Ala Thr Cys Ser Thr
            835                 840                 845

Ile Gly Met Ala His Tyr Leu Thr Phe Asp Gly Leu Lys Tyr Leu Phe
        850                 855                 860
```

-continued

Pro Gly Glu Cys Gln Tyr Val Leu Val Gln Asp Tyr Cys Gly Ser Asn
865                 870                 875                 880

Pro Gly Thr Phe Arg Ile Leu Val Gly Asn Lys Gly Cys Ser His Pro
            885                 890                 895

Ser Val Lys Cys Lys Lys Arg Val Thr Ile Leu Val Glu Gly Gly Glu
        900                 905                 910

Ile Glu Leu Phe Asp Gly Glu Val Asn Val Lys Arg Pro Met Lys Asp
            915                 920                 925

Glu Thr His Phe Glu Val Val Glu Ser Gly Arg Tyr Ile Ile Leu Leu
        930                 935                 940

Leu Gly Lys Ala Leu Ser Val Val Trp Asp Arg His Leu Ser Ile Ser
945                 950                 955                 960

Val Val Leu Lys Gln Thr Tyr Gln Glu Lys Val Cys Gly Leu Cys Gly
                965                 970                 975

Asn Phe Asp Gly Ile Gln Asn Asn Asp Leu Thr Ser Ser Asn Leu Gln
            980                 985                 990

Val Glu Glu Asp Pro Val Asp Phe Gly Asn Ser Trp Lys Val Ser Ser
        995                 1000                1005

Gln Cys Ala Asp Thr Arg Lys Val Pro Leu Asp Ser Ser Pro Ala
    1010                1015                1020

Thr Cys His Asn Asn Ile Met Lys Gln Thr Met Val Asp Ser Ser
    1025                1030                1035

Cys Arg Ile Leu Thr Ser Asp Val Phe Gln Asp Cys Asn Lys Leu
    1040                1045                1050

Val Asp Pro Glu Pro Tyr Leu Asp Val Cys Ile Tyr Asp Thr Cys
    1055                1060                1065

Ser Cys Glu Ser Ile Gly Asp Cys Ala Cys Phe Cys Asp Thr Ile
    1070                1075                1080

Ala Ala Tyr Ala His Val Cys Ala Gln His Gly Lys Val Val Thr
    1085                1090                1095

Trp Arg Thr Ala Thr Leu Cys Pro Gln Ser Cys Glu Glu Arg Asn
    1100                1105                1110

Leu Arg Glu Asn Gly Tyr Glu Cys Glu Trp Arg Tyr Asn Ser Cys
    1115                1120                1125

Ala Pro Ala Cys Gln Val Thr Cys Gln His Pro Glu Pro Leu Ala
    1130                1135                1140

Cys Pro Val Gln Cys Val Glu Gly Cys His Ala His Cys Pro Pro
    1145                1150                1155

Gly Lys Ile Leu Asp Glu Leu Leu Gln Thr Cys Val Asp Pro Glu
    1160                1165                1170

Asp Cys Pro Val Cys Glu Val Ala Gly Arg Arg Phe Ala Ser Gly
    1175                1180                1185

Lys Lys Val Thr Leu Asn Pro Ser Asp Pro Glu His Cys Gln Ile
    1190                1195                1200

Cys His Cys Asp Val Val Asn Leu Thr Cys Glu Ala Cys Gln Glu
    1205                1210                1215

Pro Gly Gly Leu Val Val Pro Pro Thr Asp Ala Pro Val Ser Pro
    1220                1225                1230

Thr Thr Leu Tyr Val Glu Asp Ile Ser Glu Pro Pro Leu His Asp
    1235                1240                1245

Phe Tyr Cys Ser Arg Leu Leu Asp Leu Val Phe Leu Leu Asp Gly
    1250                1255                1260

Ser Ser Arg Leu Ser Glu Ala Glu Phe Glu Val Leu Lys Ala Phe

```
            1265                1270                1275
Val Val Asp Met Met Glu Arg Leu Arg Ile Ser Gln Lys Trp Val
        1280                1285                1290
Arg Val Ala Val Val Glu Tyr His Asp Gly Ser His Ala Tyr Ile
        1295                1300                1305
Gly Leu Lys Asp Arg Lys Arg Pro Ser Glu Leu Arg Arg Ile Ala
        1310                1315                1320
Ser Gln Val Lys Tyr Ala Gly Ser Gln Val Ala Ser Thr Ser Glu
        1325                1330                1335
Val Leu Lys Tyr Thr Leu Phe Gln Ile Phe Ser Lys Ile Asp Arg
        1340                1345                1350
Pro Glu Ala Ser Arg Ile Thr Leu Leu Leu Met Ala Ser Gln Glu
        1355                1360                1365
Pro Gln Arg Met Ser Arg Asn Phe Val Arg Tyr Val Gln Gly Leu
        1370                1375                1380
Lys Lys Lys Val Ile Val Ile Pro Val Gly Ile Gly Pro His
        1385                1390                1395
Ala Asn Leu Lys Gln Ile Arg Leu Ile Glu Lys Gln Ala Pro Glu
        1400                1405                1410
Asn Lys Ala Phe Val Leu Ser Ser Val Asp Glu Leu Glu Gln Gln
        1415                1420                1425
Arg Asp Glu Ile Val Ser Tyr Leu Cys Asp Leu Ala Pro Glu Ala
        1430                1435                1440
Pro Pro Pro Thr Leu Pro Pro Asp Met Ala Gln Val Thr Val Gly
        1445                1450                1455
Pro Gly Leu Leu Gly Val Ser Thr Leu Gly Pro Lys Arg Asn Ser
        1460                1465                1470
Met Val Leu Asp Val Ala Phe Val Leu Glu Gly Ser Asp Lys Ile
        1475                1480                1485
Gly Glu Ala Asp Phe Asn Arg Ser Lys Glu Phe Met Glu Glu Val
        1490                1495                1500
Ile Gln Arg Met Asp Val Gly Gln Asp Ser Ile His Val Thr Val
        1505                1510                1515
Leu Gln Tyr Ser Tyr Met Val Thr Val Glu Tyr Pro Phe Ser Glu
        1520                1525                1530
Ala Gln Ser Lys Gly Asp Ile Leu Gln Arg Val Arg Glu Ile Arg
        1535                1540                1545
Tyr Gln Gly Gly Asn Arg Thr Asn Thr Gly Leu Ala Leu Arg Tyr
        1550                1555                1560
Leu Ser Asp His Ser Phe Leu Val Ser Gln Gly Asp Arg Glu Gln
        1565                1570                1575
Ala Pro Asn Leu Val Tyr Met Val Thr Gly Asn Pro Ala Ser Asp
        1580                1585                1590
Glu Ile Lys Arg Leu Pro Gly Asp Ile Gln Val Val Pro Ile Gly
        1595                1600                1605
Val Gly Pro Asn Ala Asn Val Gln Glu Leu Glu Arg Ile Gly Trp
        1610                1615                1620
Pro Asn Ala Pro Ile Leu Ile Gln Asp Phe Glu Thr Leu Pro Arg
        1625                1630                1635
Glu Ala Pro Asp Leu Val Leu Gln Arg Cys Cys Ser Gly Glu Gly
        1640                1645                1650
Leu Gln Ile Pro Thr Leu Ser Pro Ala Pro Asp Cys Ser Gln Pro
        1655                1660                1665
```

```
Leu Asp Val Ile Leu Leu Leu Asp Gly Ser Ser  Phe Pro Ala
    1670            1675            1680

Ser Tyr Phe Asp Glu Met Lys Ser Phe Ala Lys  Ala Phe Ile Ser
    1685            1690            1695

Lys Ala Asn Ile Gly Pro Arg Leu Thr Gln Val  Ser Val Leu Gln
    1700            1705            1710

Tyr Gly Ser Ile Thr Thr Ile Asp Val Pro Trp  Asn Val Val Pro
    1715            1720            1725

Glu Lys Ala His Leu Leu Ser Leu Val Asp Val  Met Gln Arg Glu
    1730            1735            1740

Gly Gly Pro Ser Gln Ile Gly Asp Ala Leu Gly  Phe Ala Val Arg
    1745            1750            1755

Tyr Leu Thr Ser Glu Met His Gly Ala Arg Pro  Gly Ala Ser Lys
    1760            1765            1770

Ala Val Val Ile Leu Val Thr Asp Val Ser Val  Asp Ser Val Asp
    1775            1780            1785

Ala Ala Ala Asp Ala Ala Arg Ser Asn Arg Val  Thr Val Phe Pro
    1790            1795            1800

Ile Gly Ile Gly Asp Arg Tyr Asp Ala Ala Gln  Leu Arg Ile Leu
    1805            1810            1815

Ala Gly Pro Ala Gly Asp Ser Asn Val Val Lys  Leu Gln Arg Ile
    1820            1825            1830

Glu Asp Leu Pro Thr Met Val Thr Leu Gly Asn  Ser Phe Leu His
    1835            1840            1845

Lys Leu Cys Ser Gly Phe Val Arg Ile Cys Met  Asp Glu Asp Gly
    1850            1855            1860

Asn Glu Lys Arg Pro Gly Asp Val Trp Thr Leu  Pro Asp Gln Cys
    1865            1870            1875

His Thr Val Thr Cys Gln Pro Asp Gly Gln Thr  Leu Leu Lys Ser
    1880            1885            1890

His Arg Val Asn Cys Asp Arg Gly Leu Arg Pro  Ser Cys Pro Asn
    1895            1900            1905

Ser Gln Ser Pro Val Lys Val Glu Glu Thr Cys  Gly Cys Arg Trp
    1910            1915            1920

Thr Cys Pro Cys Val Cys Thr Gly Ser Ser Thr  Arg His Ile Val
    1925            1930            1935

Thr Phe Asp Gly Gln Asn Phe Lys Leu Thr Gly  Ser Cys Ser Tyr
    1940            1945            1950

Val Leu Phe Gln Asn Lys Glu Gln Asp Leu Glu  Val Ile Leu His
    1955            1960            1965

Asn Gly Ala Cys Ser Pro Gly Ala Arg Gln Gly  Cys Met Lys Ser
    1970            1975            1980

Ile Glu Val Lys His Ser Ala Leu Ser Val Glu  Leu His Ser Asp
    1985            1990            1995

Met Glu Val Thr Val Asn Gly Arg Leu Val Ser  Val Pro Tyr Val
    2000            2005            2010

Gly Gly Asn Met Glu Val Asn Val Tyr Gly Ala  Ile Met His Glu
    2015            2020            2025

Val Arg Phe Asn His Leu Gly His Ile Phe Thr  Phe Thr Pro Gln
    2030            2035            2040

Asn Asn Glu Phe Gln Leu Gln Leu Ser Pro Lys  Thr Phe Ala Ser
    2045            2050            2055
```

```
Lys Thr Tyr Gly Leu Cys Gly Ile Cys Asp Glu Asn Gly Ala Asn
    2060                2065                2070

Asp Phe Met Leu Arg Asp Gly Thr Val Thr Thr Asp Trp Lys Thr
    2075                2080                2085

Leu Val Gln Glu Trp Thr Val Gln Arg Pro Gly Gln Thr Cys Gln
    2090                2095                2100

Pro Glu Gln Cys Leu Val Pro Asp Ser Ser His Cys Gln Val Leu
    2105                2110                2115

Leu Leu Pro Leu Phe Ala Glu Cys His Lys Val Leu Ala Pro Ala
    2120                2125                2130

Thr Phe Tyr Ala Ile Cys Gln Gln Asp Ser Cys His Gln Glu Gln
    2135                2140                2145

Val Cys Glu Val Ile Ala Ser Tyr Ala His Leu Cys Arg Thr Asn
    2150                2155                2160

Gly Val Cys Val Asp Trp Arg Thr Pro Asp Phe Cys Ala Met Ser
    2165                2170                2175

Cys Pro Pro Ser Leu Val Tyr Asn His Cys Glu His Gly Cys Pro
    2180                2185                2190

Arg His Cys Asp Gly Asn Val Ser Ser Cys Gly Asp His Pro Ser
    2195                2200                2205

Glu Gly Cys Phe Cys Pro Pro Asp Lys Val Met Leu Glu Gly Ser
    2210                2215                2220

Cys Val Pro Glu Glu Ala Cys Thr Gln Cys Ile Gly Glu Asp Gly
    2225                2230                2235

Val Gln His Gln Phe Leu Glu Ala Trp Val Pro Asp His Gln Pro
    2240                2245                2250

Cys Gln Ile Cys Thr Cys Leu Ser Gly Arg Lys Val Asn Cys Thr
    2255                2260                2265

Thr Gln Pro Cys Pro Thr Ala Lys Ala Pro Thr Cys Gly Leu Cys
    2270                2275                2280

Glu Val Ala Arg Leu Arg Gln Asn Ala Asp Gln Cys Cys Pro Glu
    2285                2290                2295

Tyr Glu Cys Val Cys Asp Pro Val Ser Cys Asp Leu Pro Pro Val
    2300                2305                2310

Pro His Cys Glu Arg Gly Leu Gln Pro Thr Leu Thr Asn Pro Gly
    2315                2320                2325

Glu Cys Arg Pro Asn Phe Thr Cys Ala Cys Arg Lys Glu Glu Cys
    2330                2335                2340

Lys Arg Val Ser Pro Pro Ser Cys Pro Pro His Arg Leu Pro Thr
    2345                2350                2355

Leu Arg Lys Thr Gln Cys Cys Asp Glu Tyr Glu Cys Ala Cys Asn
    2360                2365                2370

Cys Val Asn Ser Thr Val Ser Cys Pro Leu Gly Tyr Leu Ala Ser
    2375                2380                2385

Thr Ala Thr Asn Asp Cys Gly Cys Thr Thr Thr Cys Leu Pro
    2390                2395                2400

Asp Lys Val Cys Val His Arg Ser Thr Ile Tyr Pro Val Gly Gln
    2405                2410                2415

Phe Trp Glu Glu Gly Cys Asp Val Cys Thr Cys Thr Asp Met Glu
    2420                2425                2430

Asp Ala Val Met Gly Leu Arg Val Ala Gln Cys Ser Gln Lys Pro
    2435                2440                2445

Cys Glu Asp Ser Cys Arg Ser Gly Phe Thr Tyr Val Leu His Glu
```

Gly Glu Cys Cys Gly Arg Cys Leu Pro Ser Ala Cys Glu Val Val
         2465                2470                2475

Thr Gly Ser Pro Arg Gly Asp Ser Gln Ser Ser Trp Lys Ser Val
         2480                2485                2490

Gly Ser Gln Trp Glu Asn Pro Cys Leu Ile Asn Glu Cys Val Arg
         2495                2500                2505

Val Lys Glu Glu Val Phe Ile Gln Gln Arg Asn Val Ser Cys Pro
         2510                2515                2520

Gln Leu Glu Val Pro Val Cys Pro Ser Gly Phe Gln Leu Ser Cys
         2525                2530                2535

Lys Thr Ser Ala Cys Cys Pro Ser Cys Arg Cys Glu Arg Met Glu
         2540                2545                2550

Ala Cys Met Leu Asn Gly Thr Val Ile Gly Pro Gly Lys Thr Val
         2555                2560                2565

Met Ile Asp Val Cys Thr Thr Cys Arg Cys Met Val Gln Val Gly
         2570                2575                2580

Val Ile Ser Gly Phe Lys Leu Glu Cys Arg Lys Thr Thr Cys Asn
         2585                2590                2595

Pro Cys Pro Leu Gly Tyr Lys Glu Glu Asn Asn Thr Gly Glu Cys
         2600                2605                2610

Cys Gly Arg Cys Leu Pro Thr Ala Cys Thr Ile Gln Leu Arg Gly
         2615                2620                2625

Gly Gln Ile Met Thr Leu Lys Arg Asp Glu Thr Leu Gln Asp Gly
         2630                2635                2640

Cys Asp Thr His Phe Cys Lys Val Asn Glu Arg Gly Glu Tyr Phe
         2645                2650                2655

Trp Glu Lys Arg Val Thr Gly Cys Pro Pro Phe Asp Glu His Lys
         2660                2665                2670

Cys Leu Ala Glu Gly Gly Lys Ile Met Lys Ile Pro Gly Thr Cys
         2675                2680                2685

Cys Asp Thr Cys Glu Glu Pro Glu Cys Asn Asp Ile Thr Ala Arg
         2690                2695                2700

Leu Gln Tyr Val Lys Val Gly Ser Cys Lys Ser Glu Val Glu Val
         2705                2710                2715

Asp Ile His Tyr Cys Gln Gly Lys Cys Ala Ser Lys Ala Met Tyr
         2720                2725                2730

Ser Ile Asp Ile Asn Asp Val Gln Asp Gln Cys Ser Cys Cys Ser
         2735                2740                2745

Pro Thr Arg Thr Glu Pro Met Gln His Cys Thr Asn Gly Ser Val
         2750                2755                2760

Val Tyr His Glu Val Leu Asn Ala Met Glu Cys Lys Cys Ser Pro
         2765                2770                2775

Arg Lys Cys Ser Lys
         2780

<210> SEQ ID NO 3
<211> LENGTH: 2783
<212> TYPE: PRT
<213> ORGANISM: Artificial Sequence
<220> FEATURE:
<223> OTHER INFORMATION: Synthetic mature VWF

<400> SEQUENCE: 3

Met Ile Pro Ala Arg Phe Ala Gly Val Leu Leu Leu Ile Leu Pro Gly

-continued

```
1               5                   10                  15
Thr Leu Cys Ala Glu Gly Thr Arg Gly Arg Ser Ser Thr Ala Arg Cys
                20                  25                  30

Ser Leu Phe Gly Ser Asp Phe Val Asn Thr Phe Asp Gly Ser Met Tyr
                35                  40                  45

Ser Phe Ala Gly Tyr Cys Ser Tyr Leu Leu Ala Gly Cys Gln Lys
                50                  55                  60

Arg Ser Phe Ser Ile Ile Gly Asp Phe Gln Asn Gly Lys Arg Val Ser
65                  70                  75                  80

Leu Ser Val Tyr Leu Gly Glu Phe Phe Asp Ile His Leu Phe Val Asn
                85                  90                  95

Gly Thr Val Thr Gln Gly Asp Gln Arg Val Ser Met Pro Tyr Ala Ser
                100                 105                 110

Lys Leu Glu Thr Glu Ala Gly Tyr Tyr Lys Leu Ser Gly Glu Ala Tyr
                115                 120                 125

Gly Phe Val Ala Arg Ile Asp Gly Ser Gly Asn Phe Gln Val Leu Leu
                130                 135                 140

Ser Asp Arg Tyr Phe Asn Lys Thr Cys Gly Leu Cys Gly Asn Phe Asn
145                 150                 155                 160

Ile Phe Ala Glu Asp Asp Phe Met Thr Gln Glu Gly Thr Leu Thr Ser
                165                 170                 175

Asp Pro Tyr Asp Phe Ala Asn Ser Trp Ala Leu Ser Ser Gly Glu Gln
                180                 185                 190

Trp Cys Glu Arg Pro Ser Ser Cys Asn Ile Ser Ser Gly Glu Met
                195                 200                 205

Gln Lys Gly Leu Trp Glu Gln Cys Gln Leu Leu Lys Ser Thr Ser Val
    210                 215                 220

Phe Ala Arg Cys His Pro Leu Val Asp Pro Glu Pro Phe Cys Glu Lys
225                 230                 235                 240

Thr Leu Cys Glu Cys Ala Gly Gly Leu Glu Cys Ala Cys Pro Ala Leu
                245                 250                 255

Leu Glu Tyr Ala Arg Thr Cys Ala Gln Glu Gly Met Val Leu Tyr Gly
                260                 265                 270

Trp Thr Asp His Ser Ala Cys Ser Pro Val Cys Pro Ala Gly Met Glu
    275                 280                 285

Tyr Arg Gln Cys Val Ser Pro Cys Ala Arg Thr Cys Gln Ser Leu His
    290                 295                 300

Ile Asn Glu Met Cys Gln Glu Arg Cys Val Asp Gly Cys Ser Cys Pro
305                 310                 315                 320

Glu Gly Gln Leu Leu Asp Glu Gly Leu Cys Val Glu Ser Thr Glu Cys
                325                 330                 335

Pro Cys Val His Ser Gly Lys Arg Tyr Pro Pro Gly Thr Ser Leu Ser
                340                 345                 350

Arg Asp Cys Asn Thr Cys Ile Cys Arg Asn Ser Gln Trp Ile Cys Ser
                355                 360                 365

Asn Glu Glu Cys Pro Gly Glu Cys Leu Val Thr Gly Gln Ser His Phe
370                 375                 380

Lys Ser Phe Asp Asn Arg Tyr Phe Thr Phe Ser Gly Ile Cys Gln Tyr
385                 390                 395                 400

Leu Leu Ala Arg Asp Cys Gln Asp His Ser Phe Ser Ile Val Ile Glu
                405                 410                 415

Thr Val Gln Cys Ala Asp Asp Arg Asp Ala Val Cys Thr Arg Ser Val
                420                 425                 430
```

```
Thr Val Arg Leu Pro Gly Leu His Asn Ser Leu Val Lys Leu Lys His
        435                 440                 445

Gly Ala Gly Val Ala Met Asp Gly Gln Asp Val Gln Leu Pro Leu Leu
        450                 455                 460

Lys Gly Asp Leu Arg Ile Gln His Thr Val Thr Ala Ser Val Arg Leu
465                 470                 475                 480

Ser Tyr Gly Glu Asp Leu Gln Met Asp Trp Asp Gly Arg Gly Arg Leu
                485                 490                 495

Leu Val Lys Leu Ser Pro Val Tyr Ala Gly Lys Thr Cys Gly Leu Cys
                500                 505                 510

Gly Asn Tyr Asn Gly Asn Gln Gly Asp Asp Phe Leu Thr Pro Ser Gly
                515                 520                 525

Leu Ala Glu Pro Arg Val Glu Asp Phe Gly Asn Ala Trp Lys Leu His
        530                 535                 540

Gly Asp Cys Gln Asp Leu Gln Lys Gln His Ser Asp Pro Cys Ala Leu
545                 550                 555                 560

Asn Pro Arg Met Thr Arg Phe Ser Glu Glu Ala Cys Ala Val Leu Thr
                565                 570                 575

Ser Pro Thr Phe Glu Ala Cys His Arg Ala Val Ser Pro Leu Pro Tyr
                580                 585                 590

Leu Arg Asn Cys Arg Tyr Asp Val Cys Ser Cys Ser Asp Gly Arg Glu
        595                 600                 605

Cys Leu Cys Gly Ser Tyr Ala Ala Ala Cys Ala Gly Arg Gly Val Arg
        610                 615                 620

Val Ala Trp Arg Glu Pro Gly Arg Cys Glu Leu Asn Cys Pro Lys Gly
625                 630                 635                 640

Gln Val Tyr Leu Gln Cys Gly Thr Pro Cys Asn Leu Thr Cys Arg Ser
                645                 650                 655

Leu Ser Tyr Pro Asp Glu Glu Cys Asn Glu Ala Cys Leu Glu Gly Cys
                660                 665                 670

Phe Cys Pro Pro Met Asp Glu Arg Gly Asp Cys Val Pro Lys Ala Gln
        675                 680                 685

Cys Pro Cys Tyr Tyr Asp Gly Glu Ile Phe Gln Pro Glu Asp Ile Phe
        690                 695                 700

Ser Asp His His Thr Met Cys Tyr Cys Glu Asp Gly Phe Met His Cys
705                 710                 715                 720

Thr Met Ser Gly Val Pro Gly Ser Leu Leu Pro Asp Ala Val Leu Ser
                725                 730                 735

Ser Pro Leu Ser His Arg Ser Lys Arg Ser Leu Ser Cys Arg Pro Pro
                740                 745                 750

Met Val Lys Leu Val Cys Pro Ala Asp Asn Leu Arg Ala Glu Gly Leu
        755                 760                 765

Glu Cys Thr Lys Thr Cys Gln Asn Tyr Asp Leu Glu Cys Met Ser Met
        770                 775                 780

Gly Cys Val Ser Gly Cys Leu Cys Pro Pro Gly Met Val Arg His Glu
785                 790                 795                 800

Asn Arg Cys Glu Arg Cys Pro Cys Phe His Gln Gly Lys Glu Tyr Ala
                805                 810                 815

Pro Gly Glu Thr Val Lys Ile Gly Cys Asn Thr Cys Val Cys Arg Asp
                820                 825                 830

Arg Lys Trp Asn Cys Thr Asp His Val Cys Asp Ala Thr Cys Ser Thr
        835                 840                 845
```

```
Ile Gly Met Ala His Tyr Leu Thr Phe Asp Gly Leu Lys Tyr Leu Phe
850                 855                 860

Pro Gly Glu Cys Gln Tyr Val Leu Val Gln Asp Tyr Cys Gly Ser Asn
865                 870                 875                 880

Pro Gly Thr Phe Arg Ile Leu Val Gly Asn Lys Gly Cys Ser His Pro
                885                 890                 895

Ser Val Lys Cys Lys Arg Val Thr Ile Leu Val Glu Gly Gly Glu
                900                 905                 910

Ile Glu Leu Phe Asp Gly Glu Val Asn Val Lys Arg Pro Met Lys Asp
                915                 920                 925

Glu Thr His Phe Glu Val Val Glu Ser Gly Arg Tyr Ile Ile Leu Leu
930                 935                 940

Leu Gly Lys Ala Leu Ser Val Val Trp Asp Arg His Leu Ser Ile Ser
945                 950                 955                 960

Val Val Leu Lys Gln Thr Tyr Gln Glu Lys Val Cys Gly Leu Cys Gly
                965                 970                 975

Asn Phe Asp Gly Ile Gln Asn Asn Asp Leu Thr Ser Ser Asn Leu Gln
                980                 985                 990

Val Glu Glu Asp Pro Val Asp Phe Gly Asn Ser Trp Lys Val Ser Ser
                995                 1000                1005

Gln Cys Ala Asp Thr Arg Lys Val Pro Leu Asp Ser Ser Pro Ala
    1010                1015                1020

Thr Cys His Asn Asn Ile Met Lys Gln Thr Met Val Asp Ser Ser
    1025                1030                1035

Cys Arg Ile Leu Thr Ser Asp Val Phe Gln Asp Cys Asn Lys Leu
    1040                1045                1050

Val Asp Pro Glu Pro Tyr Leu Asp Val Cys Ile Tyr Asp Thr Cys
    1055                1060                1065

Ser Cys Glu Ser Ile Gly Asp Cys Ala Cys Phe Cys Asp Thr Ile
    1070                1075                1080

Ala Ala Tyr Ala His Val Cys Ala Gln His Gly Lys Val Val Thr
    1085                1090                1095

Trp Arg Thr Ala Thr Leu Cys Pro Gln Ser Cys Glu Glu Arg Asn
    1100                1105                1110

Leu Arg Glu Asn Gly Tyr Glu Cys Glu Trp Arg Tyr Asn Ser Cys
    1115                1120                1125

Ala Pro Ala Cys Gln Val Thr Cys Gln His Pro Glu Pro Leu Ala
    1130                1135                1140

Cys Pro Val Gln Cys Val Glu Gly Cys His Ala His Cys Pro Pro
    1145                1150                1155

Gly Lys Ile Leu Asp Glu Leu Leu Gln Thr Cys Val Asp Pro Glu
    1160                1165                1170

Asp Cys Pro Val Cys Glu Val Ala Gly Arg Arg Phe Ala Ser Gly
    1175                1180                1185

Lys Lys Val Thr Leu Asn Pro Ser Asp Pro Glu His Cys Gln Ile
    1190                1195                1200

Cys His Cys Asp Val Val Asn Leu Thr Cys Glu Ala Cys Gln Glu
    1205                1210                1215

Pro Gly Gly Leu Val Val Pro Pro Thr Asp Ala Pro Val Ser Pro
    1220                1225                1230

Thr Thr Leu Tyr Val Glu Asp Ile Ser Glu Pro Pro Leu His Asp
    1235                1240                1245

Phe Tyr Cys Ser Arg Leu Leu Asp Leu Val Phe Leu Leu Asp Gly
```

```
            1250                1255                1260

Ser  Ser  Arg  Leu  Ser  Glu  Ala  Glu  Phe  Glu  Val  Leu  Lys  Ala  Phe
     1265                1270                1275

Val  Val  Asp  Met  Met  Glu  Arg  Leu  Arg  Ile  Ser  Gln  Lys  Trp  Val
     1280                1285                1290

Arg  Val  Ala  Val  Val  Glu  Tyr  His  Asp  Gly  Ser  His  Ala  Tyr  Ile
     1295                1300                1305

Gly  Leu  Lys  Asp  Arg  Lys  Arg  Pro  Ser  Glu  Leu  Arg  Arg  Ile  Ala
     1310                1315                1320

Ser  Gln  Val  Lys  Tyr  Ala  Gly  Ser  Gln  Val  Ala  Ser  Thr  Ser  Glu
     1325                1330                1335

Val  Leu  Lys  Tyr  Thr  Leu  Phe  Gln  Ile  Phe  Ser  Lys  Ile  Asp  Arg
     1340                1345                1350

Pro  Glu  Ala  Ser  Arg  Ile  Thr  Leu  Leu  Leu  Met  Ala  Ser  Gln  Glu
     1355                1360                1365

Pro  Gln  Arg  Met  Ser  Arg  Asn  Phe  Val  Arg  Tyr  Val  Gln  Gly  Leu
     1370                1375                1380

Lys  Lys  Lys  Lys  Val  Ile  Val  Ile  Pro  Val  Gly  Ile  Gly  Pro  His
     1385                1390                1395

Ala  Asn  Leu  Lys  Gln  Ile  Arg  Leu  Ile  Glu  Lys  Gln  Ala  Pro  Glu
     1400                1405                1410

Asn  Lys  Ala  Phe  Val  Leu  Ser  Ser  Val  Asp  Glu  Leu  Glu  Gln  Gln
     1415                1420                1425

Arg  Asp  Glu  Ile  Val  Ser  Tyr  Leu  Cys  Asp  Leu  Ala  Pro  Glu  Ala
     1430                1435                1440

Pro  Pro  Pro  Thr  Leu  Pro  Pro  Asp  Met  Ala  Gln  Val  Thr  Val  Gly
     1445                1450                1455

Pro  Gly  Leu  Leu  Gly  Val  Ser  Thr  Leu  Gly  Pro  Lys  Arg  Asn  Ser
     1460                1465                1470

Met  Val  Leu  Asp  Val  Ala  Phe  Val  Leu  Glu  Gly  Ser  Asp  Lys  Ile
     1475                1480                1485

Gly  Glu  Ala  Asp  Phe  Asn  Arg  Ser  Lys  Glu  Phe  Met  Glu  Glu  Val
     1490                1495                1500

Ile  Gln  Arg  Met  Asp  Val  Gly  Gln  Asp  Ser  Ile  His  Val  Thr  Val
     1505                1510                1515

Leu  Gln  Tyr  Ser  Tyr  Met  Val  Thr  Val  Glu  Tyr  Pro  Phe  Ser  Glu
     1520                1525                1530

Ala  Gln  Ser  Lys  Gly  Asp  Ile  Leu  Gln  Arg  Val  Arg  Glu  Ile  Arg
     1535                1540                1545

Tyr  Gln  Gly  Gly  Asn  Arg  Thr  Asn  Thr  Gly  Leu  Ala  Leu  Arg  Tyr
     1550                1555                1560

Leu  Ser  Asp  His  Ser  Phe  Leu  Val  Ser  Gln  Gly  Asp  Arg  Glu  Gln
     1565                1570                1575

Ala  Pro  Asn  Leu  Val  Tyr  Met  Val  Thr  Gly  Asn  Pro  Ala  Ser  Asp
     1580                1585                1590

Glu  Ile  Lys  Arg  Leu  Pro  Gly  Asp  Ile  Gln  Val  Val  Pro  Ile  Gly
     1595                1600                1605

Val  Gly  Pro  Asn  Ala  Asn  Val  Gln  Glu  Leu  Glu  Arg  Ile  Gly  Trp
     1610                1615                1620

Pro  Asn  Ala  Pro  Ile  Leu  Ile  Gln  Asp  Phe  Glu  Thr  Leu  Pro  Arg
     1625                1630                1635

Glu  Ala  Pro  Asp  Leu  Val  Leu  Gln  Arg  Cys  Cys  Ser  Gly  Glu  Gly
     1640                1645                1650
```

```
Leu Gln Ile Pro Thr Leu Ser Pro Ala Pro Asp Cys Ser Gln Pro
1655                1660                1665

Leu Asp Val Ile Leu Leu Leu Asp Gly Ser Ser Phe Pro Ala
1670                1675                1680

Ser Tyr Phe Asp Glu Met Lys Ser Phe Ala Lys Ala Phe Ile Ser
1685                1690                1695

Lys Ala Asn Ile Gly Pro Arg Leu Thr Gln Val Ser Val Leu Gln
1700                1705                1710

Tyr Gly Ser Ile Thr Thr Ile Asp Val Pro Trp Asn Val Val Pro
1715                1720                1725

Glu Lys Ala His Leu Leu Ser Leu Val Asp Val Met Gln Arg Glu
1730                1735                1740

Gly Gly Pro Ser Gln Ile Gly Asp Ala Leu Gly Phe Ala Val Arg
1745                1750                1755

Tyr Leu Thr Ser Glu Met His Gly Ala Arg Pro Gly Ala Ser Lys
1760                1765                1770

Ala Val Val Ile Leu Val Thr Asp Val Ser Val Asp Ser Val Asp
1775                1780                1785

Ala Ala Ala Asp Ala Ala Arg Ser Asn Arg Val Thr Val Phe Pro
1790                1795                1800

Ile Gly Ile Gly Asp Arg Tyr Asp Ala Ala Gln Leu Arg Ile Leu
1805                1810                1815

Ala Gly Pro Ala Gly Asp Ser Asn Val Val Lys Leu Gln Arg Ile
1820                1825                1830

Glu Asp Leu Pro Thr Met Val Thr Leu Gly Asn Ser Phe Leu His
1835                1840                1845

Lys Leu Cys Ser Gly Phe Val Arg Ile Cys Met Asp Glu Asp Gly
1850                1855                1860

Asn Glu Lys Arg Pro Gly Asp Val Trp Thr Leu Pro Asp Gln Cys
1865                1870                1875

His Thr Val Thr Cys Gln Pro Asp Gly Gln Thr Leu Leu Lys Ser
1880                1885                1890

His Arg Val Asn Cys Asp Arg Gly Leu Arg Pro Ser Cys Pro Asn
1895                1900                1905

Ser Gln Ser Pro Val Lys Val Glu Glu Thr Cys Gly Cys Arg Trp
1910                1915                1920

Thr Cys Pro Cys Val Cys Thr Gly Ser Ser Thr Arg His Ile Val
1925                1930                1935

Thr Phe Asp Gly Gln Asn Phe Lys Leu Thr Gly Ser Cys Ser Tyr
1940                1945                1950

Val Leu Phe Gln Asn Lys Glu Gln Asp Leu Glu Val Ile Leu His
1955                1960                1965

Asn Gly Ala Cys Ser Pro Gly Ala Arg Gln Gly Cys Met Lys Ser
1970                1975                1980

Ile Glu Val Lys His Ser Ala Leu Ser Val Glu Leu His Ser Asp
1985                1990                1995

Met Glu Val Thr Val Asn Gly Arg Leu Val Ser Val Pro Tyr Val
2000                2005                2010

Gly Gly Asn Met Glu Val Asn Val Tyr Gly Ala Ile Met His Glu
2015                2020                2025

Val Arg Phe Asn His Leu Gly His Ile Phe Thr Phe Thr Pro Gln
2030                2035                2040
```

```
Asn Asn Glu Phe Gln Leu Gln Leu Ser Pro Lys Thr Phe Ala Ser
    2045            2050            2055
Lys Thr Tyr Gly Leu Cys Gly Ile Cys Asp Glu Asn Gly Ala Asn
    2060            2065            2070
Asp Phe Met Leu Arg Asp Gly Thr Val Thr Thr Asp Trp Lys Thr
    2075            2080            2085
Leu Val Gln Glu Trp Thr Val Gln Arg Pro Gly Gln Thr Cys Gln
    2090            2095            2100
Pro Glu Gln Cys Leu Val Pro Asp Ser Ser His Cys Gln Val Leu
    2105            2110            2115
Leu Leu Pro Leu Phe Ala Glu Cys His Lys Val Leu Ala Pro Ala
    2120            2125            2130
Thr Phe Tyr Ala Ile Cys Gln Gln Asp Ser Cys His Gln Glu Gln
    2135            2140            2145
Val Cys Glu Val Ile Ala Ser Tyr Ala His Leu Cys Arg Thr Asn
    2150            2155            2160
Gly Val Cys Val Asp Trp Arg Thr Pro Asp Phe Cys Ala Met Ser
    2165            2170            2175
Cys Pro Pro Ser Leu Val Tyr Asn His Cys Glu His Gly Cys Pro
    2180            2185            2190
Arg His Cys Asp Gly Asn Val Ser Ser Cys Gly Asp His Pro Ser
    2195            2200            2205
Glu Gly Cys Phe Cys Pro Pro Asp Lys Val Met Leu Glu Gly Ser
    2210            2215            2220
Cys Val Pro Glu Glu Ala Cys Thr Gln Cys Ile Gly Glu Asp Gly
    2225            2230            2235
Val Gln His Gln Phe Leu Glu Ala Trp Val Pro Asp His Gln Pro
    2240            2245            2250
Cys Gln Ile Cys Thr Cys Leu Ser Gly Arg Lys Val Asn Cys Thr
    2255            2260            2265
Thr Gln Pro Cys Pro Thr Ala Lys Ala Pro Thr Cys Gly Leu Cys
    2270            2275            2280
Glu Val Ala Arg Leu Arg Gln Asn Ala Asp Gln Cys Cys Pro Glu
    2285            2290            2295
Tyr Glu Cys Val Cys Asp Pro Val Ser Cys Asp Leu Pro Pro Val
    2300            2305            2310
Pro His Cys Glu Arg Gly Leu Gln Pro Thr Leu Thr Asn Pro Gly
    2315            2320            2325
Glu Cys Arg Pro Asn Phe Thr Cys Ala Cys Arg Lys Glu Glu Cys
    2330            2335            2340
Lys Arg Val Ser Pro Pro Ser Cys Pro Pro His Arg Leu Pro Thr
    2345            2350            2355
Leu Arg Lys Thr Gln Cys Cys Asp Glu Tyr Glu Cys Ala Cys Asn
    2360            2365            2370
Cys Val Asn Ser Thr Val Ser Cys Pro Leu Gly Tyr Leu Ala Ser
    2375            2380            2385
Thr Ala Thr Asn Asp Cys Gly Cys Thr Thr Thr Cys Leu Pro
    2390            2395            2400
Asp Lys Val Cys Val His Arg Ser Thr Ile Tyr Pro Val Gly Gln
    2405            2410            2415
Phe Trp Glu Glu Gly Cys Asp Val Cys Thr Cys Thr Asp Met Glu
    2420            2425            2430
Asp Ala Val Met Gly Leu Arg Val Ala Gln Cys Ser Gln Lys Pro
```

2435                2440                2445

Cys Glu Asp Ser Cys Arg Ser Gly Phe Thr Tyr Val Leu His Glu
        2450                2455                2460

Gly Glu Cys Cys Gly Arg Cys Leu Pro Ser Ala Cys Glu Val Val
    2465                2470                2475

Thr Gly Ser Pro Arg Gly Asp Ser Gln Ser Ser Trp Lys Ser Val
2480                2485                2490

Gly Ser Gln Trp Glu Asn Pro Cys Leu Ile Asn Glu Cys Val Arg
    2495                2500                2505

Val Lys Glu Glu Val Phe Ile Gln Gln Arg Asn Val Ser Cys Pro
2510                2515                2520

Gln Leu Glu Val Pro Val Cys Pro Ser Gly Phe Gln Leu Ser Cys
    2525                2530                2535

Lys Thr Ser Ala Cys Cys Pro Ser Cys Arg Cys Glu Arg Met Glu
    2540                2545                2550

Ala Cys Met Leu Asn Gly Thr Val Ile Gly Pro Gly Lys Thr Val
    2555                2560                2565

Met Ile Asp Val Cys Thr Thr Cys Arg Cys Met Val Gln Val Gly
    2570                2575                2580

Val Ile Ser Gly Phe Lys Leu Glu Cys Arg Lys Thr Thr Cys Asn
    2585                2590                2595

Pro Cys Pro Leu Gly Tyr Lys Glu Glu Asn Asn Thr Gly Glu Cys
    2600                2605                2610

Cys Gly Arg Cys Leu Pro Thr Ala Cys Thr Ile Gln Leu Arg Gly
    2615                2620                2625

Gly Gln Ile Met Thr Leu Lys Arg Asp Glu Thr Leu Gln Asp Gly
    2630                2635                2640

Cys Asp Thr His Phe Cys Lys Val Asn Glu Arg Gly Glu Tyr Phe
    2645                2650                2655

Trp Glu Lys Arg Val Thr Gly Cys Pro Pro Phe Asp Glu His Lys
    2660                2665                2670

Cys Leu Ala Glu Gly Gly Lys Ile Met Lys Ile Pro Gly Thr Cys
    2675                2680                2685

Cys Asp Thr Cys Glu Glu Pro Glu Cys Asn Asp Ile Thr Ala Arg
    2690                2695                2700

Leu Gln Tyr Val Lys Val Gly Ser Cys Lys Ser Glu Val Glu Val
    2705                2710                2715

Asp Ile His Tyr Cys Gln Gly Lys Cys Ala Ser Lys Ala Met Tyr
    2720                2725                2730

Ser Ile Asp Ile Asn Asp Val Gln Asp Gln Cys Ser Cys Cys Ser
    2735                2740                2745

Pro Thr Arg Thr Glu Pro Met Gln His Cys Thr Asn Gly Ser Val
    2750                2755                2760

Val Tyr His Glu Val Leu Asn Ala Met Glu Cys Lys Cys Ser Pro
    2765                2770                2775

Arg Lys Cys Ser Lys
    2780

<210> SEQ ID NO 4
<211> LENGTH: 2050
<212> TYPE: PRT
<213> ORGANISM: Artificial Sequence
<220> FEATURE:
<223> OTHER INFORMATION: Synthetic mature VWF

```
<400> SEQUENCE: 4

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415
```

```
Gly Lys Ile Leu Asp Glu Leu Leu Gln Thr Cys Val Asp Pro Glu Asp
        420             425                 430
Cys Pro Val Cys Glu Val Ala Gly Arg Arg Phe Ala Ser Gly Lys Lys
        435             440                 445
Val Thr Leu Asn Pro Ser Asp Pro Glu His Cys Gln Ile Cys His Cys
        450             455                 460
Asp Val Val Asn Leu Thr Cys Glu Ala Cys Gln Glu Pro Gly Gly Leu
465             470             475                 480
Val Val Pro Pro Thr Asp Ala Pro Val Ser Pro Thr Leu Tyr Val
                485             490                 495
Glu Asp Ile Ser Glu Pro Pro Leu His Asp Phe Tyr Cys Ser Arg Leu
        500             505                 510
Leu Asp Leu Val Phe Leu Leu Asp Gly Ser Ser Arg Leu Ser Glu Ala
        515             520                 525
Glu Phe Glu Val Leu Lys Ala Phe Val Val Asp Met Met Glu Arg Leu
        530             535                 540
Arg Ile Ser Gln Lys Trp Val Arg Val Ala Val Val Glu Tyr His Asp
545             550             555                 560
Gly Ser His Ala Tyr Ile Gly Leu Lys Asp Arg Lys Arg Pro Ser Glu
                565             570                 575
Leu Arg Arg Ile Ala Ser Gln Val Lys Tyr Ala Gly Ser Gln Val Ala
        580             585                 590
Ser Thr Ser Glu Val Leu Lys Tyr Thr Leu Phe Gln Ile Phe Ser Lys
        595             600                 605
Ile Asp Arg Pro Glu Ala Ser Arg Ile Thr Leu Leu Leu Met Ala Ser
610             615                 620
Gln Glu Pro Gln Arg Met Ser Arg Asn Phe Val Arg Tyr Val Gln Gly
625             630             635                 640
Leu Lys Lys Lys Lys Val Ile Val Ile Pro Val Gly Ile Gly Pro His
                645             650                 655
Ala Asn Leu Lys Gln Ile Arg Leu Ile Glu Lys Gln Ala Pro Glu Asn
        660             665                 670
Lys Ala Phe Val Leu Ser Ser Val Asp Glu Leu Glu Gln Gln Arg Asp
        675             680                 685
Glu Ile Val Ser Tyr Leu Cys Asp Leu Ala Pro Glu Ala Pro Pro Pro
        690             695                 700
Thr Leu Pro Pro Asp Met Ala Gln Val Thr Val Gly Pro Gly Leu Leu
705             710             715                 720
Gly Val Ser Thr Leu Gly Pro Lys Arg Asn Ser Met Val Leu Asp Val
                725             730                 735
Ala Phe Val Leu Glu Gly Ser Asp Lys Ile Gly Glu Ala Asp Phe Asn
        740             745                 750
Arg Ser Lys Glu Phe Met Glu Glu Val Ile Gln Arg Met Asp Val Gly
        755             760                 765
Gln Asp Ser Ile His Val Thr Val Leu Gln Tyr Ser Tyr Met Val Thr
        770             775                 780
Val Glu Tyr Pro Phe Ser Glu Ala Gln Ser Lys Gly Asp Ile Leu Gln
785             790             795                 800
Arg Val Arg Glu Ile Arg Tyr Gln Gly Gly Asn Arg Thr Asn Thr Gly
                805             810                 815
Leu Ala Leu Arg Tyr Leu Ser Asp His Ser Phe Leu Val Ser Gln Gly
        820             825                 830
```

```
Asp Arg Glu Gln Ala Pro Asn Leu Val Tyr Met Val Thr Gly Asn Pro
            835                 840                 845
Ala Ser Asp Glu Ile Lys Arg Leu Pro Gly Asp Ile Gln Val Val Pro
850                 855                 860
Ile Gly Val Gly Pro Asn Ala Asn Val Gln Glu Leu Glu Arg Ile Gly
865                 870                 875                 880
Trp Pro Asn Ala Pro Ile Leu Ile Gln Asp Phe Glu Thr Leu Pro Arg
                885                 890                 895
Glu Ala Pro Asp Leu Val Leu Gln Arg Cys Cys Ser Gly Glu Gly Leu
            900                 905                 910
Gln Ile Pro Thr Leu Ser Pro Ala Pro Asp Cys Ser Gln Pro Leu Asp
            915                 920                 925
Val Ile Leu Leu Leu Asp Gly Ser Ser Ser Phe Pro Ala Ser Tyr Phe
930                 935                 940
Asp Glu Met Lys Ser Phe Ala Lys Ala Phe Ile Ser Lys Ala Asn Ile
945                 950                 955                 960
Gly Pro Arg Leu Thr Gln Val Ser Val Leu Gln Tyr Gly Ser Ile Thr
                965                 970                 975
Thr Ile Asp Val Pro Trp Asn Val Val Pro Glu Lys Ala His Leu Leu
            980                 985                 990
Ser Leu Val Asp Val Met Gln Arg Glu Gly Gly Pro Ser Gln Ile Gly
        995                 1000                1005
Asp Ala  Leu Gly Phe Ala Val Arg Tyr Leu Thr  Ser Glu Met His
    1010                 1015                  1020
Gly Ala  Arg Pro Gly Ala Ser  Lys Ala Val Val Ile  Leu Val Thr
    1025                 1030                 1035
Asp Val  Ser Val Asp Ser Val  Asp Ala Ala Ala Asp  Ala Ala Arg
    1040                 1045                 1050
Ser Asn  Arg Val Thr Val Phe  Pro Ile Gly Ile Gly  Asp Arg Tyr
    1055                 1060                 1065
Asp Ala  Ala Gln Leu Arg Ile  Leu Ala Gly Pro Ala  Gly Asp Ser
    1070                 1075                 1080
Asn Val  Val Lys Leu Gln Arg  Ile Glu Asp Leu Pro  Thr Met Val
    1085                 1090                 1095
Thr Leu  Gly Asn Ser Phe Leu  His Lys Leu Cys Ser  Gly Phe Val
    1100                 1105                 1110
Arg Ile  Cys Met Asp Glu Asp  Gly Asn Glu Lys Arg  Pro Gly Asp
    1115                 1120                 1125
Val Trp  Thr Leu Pro Asp Gln  Cys His Thr Val Thr  Cys Gln Pro
    1130                 1135                 1140
Asp Gly  Gln Thr Leu Leu Lys  Ser His Arg Val Asn  Cys Asp Arg
    1145                 1150                 1155
Gly Leu  Arg Pro Ser Cys Pro  Asn Ser Gln Ser Pro  Val Lys Val
    1160                 1165                 1170
Glu Glu  Thr Cys Gly Cys Arg  Trp Thr Cys Pro Cys  Val Cys Thr
    1175                 1180                 1185
Gly Ser  Ser Thr Arg His Ile  Val Thr Phe Asp Gly  Gln Asn Phe
    1190                 1195                 1200
Lys Leu  Thr Gly Ser Cys Ser  Tyr Val Leu Phe Gln  Asn Lys Glu
    1205                 1210                 1215
Gln Asp  Leu Glu Val Ile Leu  His Asn Gly Ala Cys  Ser Pro Gly
    1220                 1225                 1230
Ala Arg  Gln Gly Cys Met Lys  Ser Ile Glu Val Lys  His Ser Ala
```

-continued

```
            1235                1240                1245

Leu Ser Val Glu Leu His Ser Asp Met Glu Val Thr Val Asn Gly
        1250                1255                1260

Arg Leu Val Ser Val Pro Tyr Val Gly Gly Asn Met Glu Val Asn
        1265                1270                1275

Val Tyr Gly Ala Ile Met His Glu Val Arg Phe Asn His Leu Gly
        1280                1285                1290

His Ile Phe Thr Phe Thr Pro Gln Asn Asn Glu Phe Gln Leu Gln
        1295                1300                1305

Leu Ser Pro Lys Thr Phe Ala Ser Lys Thr Tyr Gly Leu Cys Gly
        1310                1315                1320

Ile Cys Asp Glu Asn Gly Ala Asn Asp Phe Met Leu Arg Asp Gly
        1325                1330                1335

Thr Val Thr Thr Asp Trp Lys Thr Leu Val Gln Glu Trp Thr Val
        1340                1345                1350

Gln Arg Pro Gly Gln Thr Cys Gln Pro Ile Leu Glu Glu Gln Cys
        1355                1360                1365

Leu Val Pro Asp Ser Ser His Cys Gln Val Leu Leu Leu Pro Leu
        1370                1375                1380

Phe Ala Glu Cys His Lys Val Leu Ala Pro Ala Thr Phe Tyr Ala
        1385                1390                1395

Ile Cys Gln Gln Asp Ser Cys His Gln Glu Gln Val Cys Glu Val
        1400                1405                1410

Ile Ala Ser Tyr Ala His Leu Cys Arg Thr Asn Gly Val Cys Val
        1415                1420                1425

Asp Trp Arg Thr Pro Asp Phe Cys Ala Met Ser Cys Pro Pro Ser
        1430                1435                1440

Leu Val Tyr Asn His Cys Glu His Gly Cys Pro Arg His Cys Asp
        1445                1450                1455

Gly Asn Val Ser Ser Cys Gly Asp His Pro Ser Glu Gly Cys Phe
        1460                1465                1470

Cys Pro Pro Asp Lys Val Met Leu Glu Gly Ser Cys Val Pro Glu
        1475                1480                1485

Glu Ala Cys Thr Gln Cys Ile Gly Glu Asp Gly Val Gln His Gln
        1490                1495                1500

Phe Leu Glu Ala Trp Val Pro Asp His Gln Pro Cys Gln Ile Cys
        1505                1510                1515

Thr Cys Leu Ser Gly Arg Lys Val Asn Cys Thr Thr Gln Pro Cys
        1520                1525                1530

Pro Thr Ala Lys Ala Pro Thr Cys Gly Leu Cys Glu Val Ala Arg
        1535                1540                1545

Leu Arg Gln Asn Ala Asp Gln Cys Cys Pro Glu Tyr Glu Cys Val
        1550                1555                1560

Cys Asp Pro Val Ser Cys Asp Leu Pro Pro Val Pro His Cys Glu
        1565                1570                1575

Arg Gly Leu Gln Pro Thr Leu Thr Asn Pro Gly Glu Cys Arg Pro
        1580                1585                1590

Asn Phe Thr Cys Ala Cys Arg Lys Glu Glu Cys Lys Arg Val Ser
        1595                1600                1605

Pro Pro Ser Cys Pro Pro His Arg Leu Pro Thr Leu Arg Lys Thr
        1610                1615                1620

Gln Cys Cys Asp Glu Tyr Glu Cys Ala Cys Asn Cys Val Asn Ser
        1625                1630                1635
```

```
Thr Val Ser Cys Pro Leu Gly Tyr Leu Ala Ser Thr Ala Thr Asn
1640                1645                1650

Asp Cys Gly Cys Thr Thr Thr Thr Cys Leu Pro Asp Lys Val Cys
1655                1660                1665

Val His Arg Ser Thr Ile Tyr Pro Val Gly Gln Phe Trp Glu Glu
1670                1675                1680

Gly Cys Asp Val Cys Thr Cys Thr Asp Met Glu Asp Ala Val Met
1685                1690                1695

Gly Leu Arg Val Ala Gln Cys Ser Gln Lys Pro Cys Glu Asp Ser
1700                1705                1710

Cys Arg Ser Gly Phe Thr Tyr Val Leu His Glu Gly Glu Cys Cys
1715                1720                1725

Gly Arg Cys Leu Pro Ser Ala Cys Glu Val Val Thr Gly Ser Pro
1730                1735                1740

Arg Gly Asp Ser Gln Ser Ser Trp Lys Ser Val Gly Ser Gln Trp
1745                1750                1755

Ala Ser Pro Glu Asn Pro Cys Leu Ile Asn Glu Cys Val Arg Val
1760                1765                1770

Lys Glu Glu Val Phe Ile Gln Gln Arg Asn Val Ser Cys Pro Gln
1775                1780                1785

Leu Glu Val Pro Val Cys Pro Ser Gly Phe Gln Leu Ser Cys Lys
1790                1795                1800

Thr Ser Ala Cys Cys Pro Ser Cys Arg Cys Glu Arg Met Glu Ala
1805                1810                1815

Cys Met Leu Asn Gly Thr Val Ile Gly Pro Gly Lys Thr Val Met
1820                1825                1830

Ile Asp Val Cys Thr Thr Cys Arg Cys Met Val Gln Val Gly Val
1835                1840                1845

Ile Ser Gly Phe Lys Leu Glu Cys Arg Lys Thr Thr Cys Asn Pro
1850                1855                1860

Cys Pro Leu Gly Tyr Lys Glu Glu Asn Asn Thr Gly Glu Cys Cys
1865                1870                1875

Gly Arg Cys Leu Pro Thr Ala Cys Thr Ile Gln Leu Arg Gly Gly
1880                1885                1890

Gln Ile Met Thr Leu Lys Arg Asp Glu Thr Leu Gln Asp Gly Cys
1895                1900                1905

Asp Thr His Phe Cys Lys Val Asn Glu Arg Gly Glu Tyr Phe Trp
1910                1915                1920

Glu Lys Arg Val Thr Gly Cys Pro Pro Phe Asp Glu His Lys Cys
1925                1930                1935

Leu Ala Glu Gly Gly Lys Ile Met Lys Ile Pro Gly Thr Cys Cys
1940                1945                1950

Asp Thr Cys Glu Glu Pro Glu Cys Asn Asp Ile Thr Ala Arg Leu
1955                1960                1965

Gln Tyr Val Lys Val Gly Ser Cys Lys Ser Glu Val Glu Val Asp
1970                1975                1980

Ile His Tyr Cys Gln Gly Lys Cys Ala Ser Lys Ala Met Tyr Ser
1985                1990                1995

Ile Asp Ile Asn Asp Val Gln Asp Gln Cys Ser Cys Cys Ser Pro
2000                2005                2010

Thr Arg Thr Glu Pro Met Gln Val Ala Leu His Cys Thr Asn Gly
2015                2020                2025
```

```
Ser Val Val Tyr His Glu Val Leu Asn Ala Met Glu Cys Lys Cys
    2030            2035            2040

Ser Pro Arg Lys Cys Ser Lys
    2045            2050
```